(12) United States Patent
Basch et al.

(10) Patent No.: US 7,214,527 B2
(45) Date of Patent: May 8, 2007

(54) COMPOSITIONS AND METHODS FOR HYDROXYLATING EPOTHILONES

(75) Inventors: Jonathan David Basch, DeWitt, NY (US); Shu-Jen David Chiang, Manlius, NY (US); Suo-Win Liu, Manlius, NY (US); Akbar Nayeem, Newtown, PA (US); Yuhua Sun, East Syracuse, NY (US); Li You, Jamesville, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 403 days.

(21) Appl. No.: 10/915,172

(22) Filed: Aug. 9, 2004

(65) Prior Publication Data

US 2005/0208620 A1 Sep. 22, 2005

Related U.S. Application Data

(62) Division of application No. 10/321,188, filed on Dec. 17, 2002, now Pat. No. 6,884,608.

(60) Provisional application No. 60/344,271, filed on Dec. 26, 2001.

(51) Int. Cl.
    *C12N 1/20* (2006.01)
    *C12N 15/74* (2006.01)
    *C07H 21/04* (2006.01)

(52) U.S. Cl. .............................. 435/252.35; 536/23.1; 536/23.2; 435/189; 435/471; 435/320.1; 435/252.3

(58) Field of Classification Search ....................... None
    See application file for complete search history.

(56) References Cited

U.S. PATENT DOCUMENTS

| 5,942,423 A | 8/1999 | Demain et al. |
| 5,976,830 A | 11/1999 | Strohl et al. |
| 6,274,360 B1 | 8/2001 | Demain et al. |
| 2001/0034046 A1 | 10/2001 | McDaniel |
| 2003/0219877 A1 | 11/2003 | Tang et al. |

FOREIGN PATENT DOCUMENTS

| WO | WO 93/10121 | 5/1993 |
| WO | WO 93/12236 | 6/1993 |

(Continued)

OTHER PUBLICATIONS

Aussel, Claude et al., "Imidazole antimycotics inhibitors of cytochrome P450 increase phosphatidylserine synthesis similarly to K+-channel blockers in Jurkat T cells", FEBS Letters, vol. 319, No. 1-2, pp. 155-158 (1993).

(Continued)

*Primary Examiner*—Nashaat T. Nashed
(74) *Attorney, Agent, or Firm*—Paul D. Golian

(57) ABSTRACT

Isolated nucleic acid sequences and polypeptides encoded thereby for epothilone B hydroxylase and mutants and variants thereof and a ferredoxin located downstream from the epothilone B hydroxylase gene are provided. Also provided are vectors and cells containing these vectors. In addition, methods for producing recombinant microorganisms, methods for using these recombinant microorganism to produce hydroxyalkyl-bearing epothilones and an epothilone analog produced by a mutant of epothilone B hydroxylase are provided.

21 Claims, 5 Drawing Sheets

Biotransformation of epothilone B to epothilone F epothilone B    SC15847 biotransformation    epothilone F

FOREIGN PATENT DOCUMENTS

| | | |
|---|---|---|
| WO | WO 98/22461 | 5/1998 |
| WO | WO 98/25929 | 6/1998 |
| WO | WO 00/39276 | 7/2000 |

OTHER PUBLICATIONS

Gerth, Klaus et al., "Studies on the Biosynthesis of Epothilones: The PKS and Epothilone C/D Monooxygenase", Journal of Antibiotics, vol. 54, No. 2, Feb. (2001).

Gerth, Klaus et al., "Studies on the Biosynthesis of Epotilones: Hydroxylation of Epo A and B to Epothilones E and F", Journal of Antibiotics, vol. 55, No. 1, Jan. (2002).

Bruntner, C. et al., "Molecular Characterization of Co-Transcribed Genes from Streptomyces Tendae Tu901 Involved in the Biosynthesis of the Peptidyl moiety of the Peptidyl Nucleoside Antibiotic Nikkomycin", Mol. Gen. Genet., vol. 262, pp. 102-225 (1999).

Dickens, M. et al., "Isolation and Characterization of a Gene From *Streptomyces* sp. Strain C5 That Confers the Ability To Convert Daunomycin to Doxorubicin on *Streptomyces lividans* TK24", Journal of Bacteriology, vol. 78, No. 11, pp. 3389-3395 (1996).

Julien, B. et al., "Isolation and Characterization of the Epothilone Biosynthetic Gene Cluster From *Sorangium cellulosum*", Gene, vol. 249, pp. 153-160 (2000).

Schinzer, D. et al., "Total Synthesis of (-) -Epothilone A", Chem. Eur. J. , vol. 5, No. 9, pp. 2483-2491 (1999).

Watanabe, I. et al., "Molecular Approaches For Production of Pravastatin, a HMG-CoA reductase Inhibitor", Gene, vol. 210, pp. 109-116 (1998).

O'Keefe, D. et al., "Ferredoxins From Two Sulfonylurea Herbicide Monooxygenase Systems in *Streptomyces griseolus*", Biochemistry, vol. 30, pp. 447-455 (1991).

Motamedi, H. et al., "Characterization of Methyltransferase and Hydroxylase Genes Involved in the Biosynthesis of the Immunosuppressants FK506 and FK520", Journal of Bacteriology, vol. 178, No. 17, pp. 5243-5248 (1996).

Rodriguez, A. "A Cytochrome P450-like Gene Possibly Involved in Oleandomycin Biosynthesis by *Streptomyces antibioticus*", FEMS Microbiology Letters , vol. 127, pp. 117-120 (1995).

Jennewein, S. et al., "Taxol Biosynthesis: Taxane 13 beta-Hydroxylase is a Cytochrome P450-Dependent Monooxygenase", PNAS, vol. 98, No. 24, pp. 13595-13600 (2001).

Brautaset, T. et al., "Biosynthesis of the Polyene Antifungal Antibiotic Nystatin in *Streptomyces noursei* ATCC 11455:Analysis of the Gene Cluster and Dedcution of the Biosynthetic Pathway", Chemistry & Biology, vol. 7, No. 6, pp. 395-403 (2000).

Gietz, R.D. et al., "New Yeast-*Escherichia coli* Shuttle Vectors Constructed With In Vitro Mutagenized Yeast Genes Lacking Six-Base Pair Restriction Sites", Gene, vol. 74, pp. 527-534 (1988).

Betlach, M. et al., "Characterization of the Macrolide P*450 Hydroxylase From *Streptomyces venezuelae* Which Converts Narbomycin to Picromycin", Biochemistry, vol. 37, pp. 14937-14942 (1998).

Halpert, J. et al., "Structure-Function of Cytochromes P450 and Flavin-Containing Monooxygenases", Drug Metabolism and Disposition, vol. 26, No. 12, pp. 1223-1231 (1998).

Tang, Li, et al., "Cloning and Heterologous Expression of the Epothilone Gene Cluster", Science, vol. 287, pp. 640-642 (2000).

Watanabe, I. et al., "Cloning, Characterization and Expression of the Gene Encoding Cytochrome P-450$_{sca-2}$ From *Streptomyces carbophilus* Involved in Production of Pravastatin, a Specifid HMG-CoA Reductase Inhibitor", Gene, vol. 163, pp. 81-85 (1995).

Leung, D. et al., "A Method For Random Mutagenesis of A Defined DNA Segment Using A Modified Polymerase Chain Reaction", Technique—A Journal of Methods in Cell and Molecular Biology, vol. 1, No. 1, pp. 11-15 (1989).

Chang, Y et al., "Construction of a 3D Model of Cytochrome P450 2B4", Protein Engineering, vol. 10, No. 2, pp. 119-129 (1997).

Lesk, A. et al., "Homology Modelling: Inferences From Tables of Aligned Sequences", Current Opinion in Structural Biology, vol. 2, pp. 242-247 (1992).

Greer, J., "Comparative Modeling of Homologous Proteins", Methods in Enzymology, vol. 202, pp. 239-252 (1991).

Lewis, D. et al., "Interactions Between Redox Partners in Various Cytochrome P450 Systems: Functional and Structural Aspects", Biochimica et Biophysica Acta 1460, pp. 353-374 (2000).

Matsuoka, T. et al., Purification and Characterization of Cytochrome P-450 sca From *Streptomyces carbophilus*, Eur. J. Biochem. , vol. 184, pp. 707-713 (1989).

Cardozo, T. et al., "Homology Modeling by the ICM Method", Proteins: Structure, Function and Genetics, vol. 23, pp. 403-414 (1995).

Ueda, K. et al., "Overexpression of a Gene Cluster Encoding a Chalcone Synthase-like Protein Confers Redbrown Pigment Production in *Streptomyces griseus*", Journal of Antibiotics, vol. 48, No. 7, pp. 638-646 (1995).

Anderson, J. et al., "Characterization of *Saccharopolyspora erythraea* Cytochrome P-450 Genes and Enzymes, Including 6-Deoxyerythronolide B Hydroxylase", Journal of Bacteriology, vol. 174, No. 3, pp. 725-735 (1992).

Cupp-Vickery, J. et al., "Structure of Cytochrome P450eryF Involved in Erythromycin Biosynthesis", Structural Biology, vol. 2, No. 2, pp. 144-153 (1995).

Meng, D. et al., "Total Synthesis of Epothilones A and B", J. Am. Chem. Soc., vol. 119, pp. 10073-10092 (1997).

Yang, Z. et al., "Total Synthesis of Epothilone A: The Olefin Metathesis Approach", Angew. Chem. Int. Ed. Eng., vol. 36, No. 1/2, pp. 166-168 (1997).

Nicolaou, K.C. et al., "Total Synthesis of Epothilones A and B Via a Macrolactonization-Based Strategy", J. Am. Chem. Soc., vol. 119, pp. 7974-7991 (1997).

Gerth, K. et al., "Epothilones A and B: Antifungal and Cytotoxic Compounds From *Sorangium cellulosum* (Myxobacteria)", The Journal of Antibiotics, vol. 49, No. 6, pp. 560-563 (1996).

Hofle, G. et al., "Epothilone A and B—Novel 16-Membered Macrolides With Cytotoxic Activity: Isolation, Crystal Structure, and Conformation in Solution", Angew. Chem. Int. Ed. Engl., vol. 35, Nos. 13/14, pp. 1567-1569 (1996).

Balog, A et al., "Total Synthesis of (-)-Epothilone A", Angew. Chem. Int. Ed. Engl. , vol. 35, Nos. 23/24, pp. 2801-2803 (1996).

Schinzer, D. et al., "Total Synthesis of (-)-Epothilone A", Angew. Chem. Int. Ed. Engl., vol. 36, No. 5, pp. 523-524 (1997).

Huynh, H. et al., "Tumor Suppressor Activity of the Gene Encoding Mammary-Derived Growth Inhibitor", Cancer Research, vol. 55, pp. 2225-2231 (1995).

Omer, C. et al., "Genes for Two Herbicide-Inducible Cytochromes P-450 From *Streptomyces griseolus*", Journal of Bacteriology, vol. 172, No. 6, pp. 3335-3345 (1990).

Nucleotide sequence alignments used to design the PCR Primers:

Alignment used to design primers P450-1+ and P450-1a+

| | | |
|---|---|---|
| STMSUACB NO:5) | tcctcatcgccggccacgagac | (SEQ ID |
| STMSUBCB NO:6) | tgctggtcgccggccacgagac | (SEQ ID |
| 3702259 NO:7) | tgctcatcaccggccaggacac | (SEQ ID |
| SSU65940 NO:8) | --ctgttcgccgggcacgactc | (SEQ ID |
| STMOLEP NO:9) | tgctcatcgcgggccacgagac | (SEQ ID |
| SERCP450A NO:10) | tgctggtcgccgggcacgagac | (SEQ ID |

Alignment used to design primers P450-2+ and P450-2−

| | | |
|---|---|---|
| STMSUACB NO:11) | cggcgcggtggaggaactgct | (SEQ ID |
| STMSUBCB NO:12) | gggcgccgtcgaggagctgct | (SEQ ID |
| 3702259 NO:13) | ccgcaccctggaggagctgct | (SEQ ID |
| SSU65940 NO:14) | cggcgcggtcgaggagatgct | (SEQ ID |
| STMOLEP NO:15) | cgcggcggtggaggagatgct | (SEQ ID |
| SERCP450A NO:16) | cggcgcgatcgaggagaccct | (SEQ ID |

Alignment used to design primer P450-3−

| | | |
|---|---|---|
| STMSUACB NO:17) | ttcggcttcggcgtgcaccagtgcctgggc | (SEQ ID |
| STMSUBCB NO:18) | ttcggcttcggcgtccaccagtgcctggga | (SEQ ID |
| 3702259 NO:19) | ttcggctggggcccccaccactgcctgggc | (SEQ ID |
| SSU65940 NO:20) | ttcggtcacggcgtccacaagtgtcctggc | (SEQ ID |
| STMOLEP NO:21) | ttcgggcacggagcgcaccactgcatcggc | (SEQ ID |
| SERCP450A NO:22) | ttcggccacggcatccacttctgcgtgggc | (SEQ ID |

FIG. 2

Sequence alignment between Epo-B hydroxylase and EryF (PDB code 1JIN chain A)

```
EPO-B    MTDVEETTATLPLARKCPFSPP--PEYERLRRESPVSRVGLPSGQTAWALTRLEDIREML
1JINA    --------ATVPDLESDSFHVDWYSTYAELRETAPVTPVRFL-GQDAWLVTGYDEAKAAL
                 **:*  .. .*     . * .**. :**: * :  ** ** :*  :: :  *

EPO-B    SSPHFSSD--RQSPSFPLMVARQI--RREDKP-FRPSLIAMDPPEHGKARRDVVGEFTVK
1JINA    SDLRLSSDPKKKYPGVEVEFPAYLGFPEDVRNYFATNMGTSDPPTHTRLRKLVSQEFTVR
         *. ::***  :: *.. : ..  :    .: :  * ..: : *** * : *: *  ****:

EPO-B    RMKALQPRIQQIVDEHIDALLAGPKPADLVQALSLPVPSLVICELLGVPYSDHEFFQSCS
1JINA    RVEAMRPRVEQITAELLDEV-GDSGVVDIVDRFAHPLPIKVICELLGVDEAARGAFGRWS
         *::*::**::**. * :* : ...  .*:*: :: *:*  ********  : :  *   *

EPO-B    SRMLSREVT-AEERMTAFESLENYLDELVTKKEANATEDDLLGRQILKQRESGEADHGEL
1JINA    SEILVMDPERAEQRGQAAREVVNFILDLVERRRTEPGDDLLSALISVQDDDDGRLSADEL
         *.:*  :   **:*  * ..: *:: :** ::.::. :* * .   ::: :.*. . .**

EPO-B    VGLAFLLLIAGHETTANMISLGTVTLLENPDQLAKIKADPGKTLAAIEELLRIFTIAETA
1JINA    TSIALVLLLAGFEASVSLIGIGTYLLLTHPDQLALVRADPSALPNAVEEILRYIAPPETT
         ..:*::**:**.*:..:*.:**  ** :***** ::***.    *:**:** :: .**:

EPO-B    TSRFATADVEIGGTLIRAGEGVVGLSNAGNHDPDGFENPDTFDIERGARHHVAFGFGVHQ
1JINA    T-RFAAEEVEIGGVAIPQYSTVLVANGAANRDPSQFPDPHRFDVTRDTRGHLSFGQGIHF
         * ***: :*****. *   . *:  ..*.*:**. * :*. **: *.:* *::** *:*

EPO-B    CLGQNLARLELQIVFDTLFRRVPGIRIAVPVDELPFKHDSTIYGLHALPVTW--
1JINA    CMGRPLAKLEGEVALRALFGRFPALSLGIDADDVVWRRSLLLRGIDHLPVRLDG
         *:*: **:** ::.: :** *.*.: :.: .*:: :::.  : *:. ***
```

COMPOSITIONS AND METHODS FOR HYDROXYLATING EPOTHILONES

BASIS FOR PRIORITY CLAIM

This application is a divisional application of U.S. application Ser. No. 10/321,188 filed Dec. 17, 2002 now U.S. Pat. No. 6,884,608, and claims the benefit of U.S. Provisional Application No. 60/344,271, filed December 26, 2001, which is herein incorporated by reference in its entirety.

FIELD OF THE INVENTION

The present invention relates to isolated nucleic acids sequences and polypeptides encoded thereby for epothilone B hydroxylase and mutants and variants thereof, and a ferredoxin located downstream from the epothilone B hydroxylase gene. The present invention also relates to recombinant microorganisms expressing epothilone B hydroxylase or a mutant or variant thereof and/or ferredoxin which are capable of hydroxylating small organic molecule compounds, such as epothilones, having a terminal alkyl group to produce compounds having a terminal hydroxyalkyl group. Also provided are methods for recombinantly producing such microorganisms as well as methods for using these recombinant microorganisms in the synthesis of compounds having a terminal hydroxylalkyl group. The compositions and methods of the present invention are useful in preparation of epothilones having a variety of utilities in the pharmaceutical field. A novel epothilone analog produced using a mutant of epothilone B hydroxylase of the present invention is also described.

BACKGROUND OF THE INVENTION

Epothilones are macrolide compounds that find utility in the pharmaceutical field. For example, epothilones A and B having the structures:

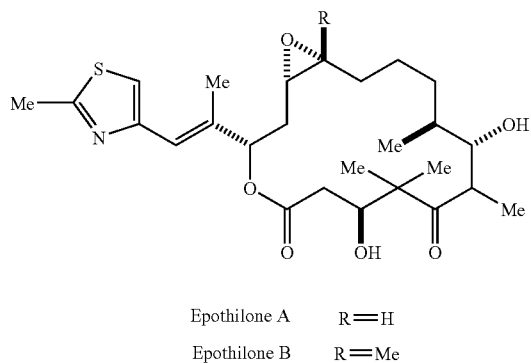

Epothilone A R=H
Epothilone B R=Me have been found to exert microtubule-stabilizing effects similar to paclitaxel (TAXOL®) and hence cytotoxic activity against rapidly proliferating cells, such as, tumor cells or cells associated with other hyperproliferative cellular diseases, see Bollag et al., *Cancer Res.*, Vol. 55, No. 11, 2325–2333 (1995).

Epothilones A and B are natural anticancer agents produced by *Sorangium cellulosum* that were first isolated and characterized by Hofle et al., DE 4138042; WO 93/10121; *Angew. Chem. Int. Ed. Engl.* Vol. 35, No13/14, 1567–1569 (1996); and *J. Antibiot.*, Vol. 49, No. 6, 560–563 (1996). Subsequently, the total syntheses of epothilones A and B have been published by Balog et al., *Angew. Chem. Int. Ed. Engl.*, Vol. 35, No. 23/24, 2801–2803, 1996; Meng et al., *J. Am. Chem. Soc.*, Vol. 119, No. 42, 10073–10092 (1997); Nicolaou et al., *J. Am. Chem. Soc.*, Vol. 119, No. 34, 7974–7991 (1997); Schinzer et al., *Angew. Chem. Int. Ed. Eng.*, Vol. 36, No. 5, 523–524 (1997); and Yang et al., *Angew. Chem. Int. Ed. Engl.*, Vol. 36, No. 1/2, 166–168, 1997. WO 98/25929 disclosed the methods for chemical synthesis of epothilone A, epothilone B, analogs of epothilone and libraries of epothilone analogs. The structure and production from *Sorangium cellulosum* DSM 6773 of epothilones C, D, E, and F was disclosed in WO 98/22461. FIG. 1 provides a diagram of the biotransformation as described in WO 00/39276 of epothilone B to epothilone F in *Actinomycetes* species strain SC15847 (ATCC PT-1043), subsequently identified as *Amycolatopsis orientalis*.

Cytochrome P450 enzymes are found in prokaryotes and eukaryotic cells and have in common a heme binding domain which can be distinguished by an absorbance peak at 450 nm when complexed with carbon monoxide. Cytochrome P450 enzymes perform a broad spectrum of oxidative reactions on primarily hydrophobic substrates including aromatic and benzylic rings, and alkanes. In prokaryotes they are found as detoxifying systems and as a first enzymatic step in metabolizing substrates such as toluene, benzene and camphor. Cytochrome P450 genes have also been found in biosynthetic pathways of secondary metabolites such as nikkomycin in *Streptomyces tendae* (Bruntner, C. et al, 1999, Mol. Gen. Genet. 262: 102–114), doxorubicin (Dickens, M. L, Strohl, W. R., 1996, J. Bacteriol, 178: 3389-3395) and in the epothilone biosynthetic cluster of *Sorangium cellulosum* (Julien, B. et al., 2000, Gene, 249: 153–160). With a few exceptions, the cytochrome P450 systems in prokaryotes are composed of three proteins; a ferredoxin NADH or NADPH dependent reductase, an iron-sulfur ferredoxin and the cytochrome P450 enzyme (Lewis, D. F., Hlavica, P., 2000, Biochim. Biophys. Acta., 1460: 353–374). Electrons are transferred from ferredoxin reductase to the ferredoxin and finally to the cytochrome P450 enzyme for the splitting of molecular oxygen.

SUMMARY OF THE INVENTION

An object of the present invention is to provide isolated nucleic acid sequences encoding epothilone B hydroxylase and variants or mutants thereof and isolated nucleic acid sequences encoding ferredoxin or variants or mutants thereof.

Another object of the present invention is to provide isolated polypeptides comprising amino acid sequences of epothilone B hydroxylase and variants or mutants thereof and isolated polypeptides comprising amino acid sequences of ferredoxin and variants or mutants thereof.

Another object of the present invention is to provide structure coordinates of the homology model of the epothilone B hydroxylase. The structure coordinates are listed in Appendix 1. This model of the present invention provides a means for designing modulators of a biological function of epothilone B hydroxylase as well as additional mutants of epothilone B hydroxylase with altered specificities.

Another object of the present invention is to provide vectors comprising nucleic acid sequences encoding epothilone B hydroxylase or a variant or mutant thereof and/or ferredoxin or a variant or mutant thereof. In a preferred embodiment, these vectors further comprise a nucleic acid sequence encoding ferredoxin.

Another object of the present invention is to provide host cells comprising a vector containing a nucleic acid sequence encoding epothilone B hydroxylase or a variant or mutant thereof and/or ferredoxin or a variant or mutant thereof.

Another object of the present invention is to provide a method for producing recombinant microorganisms that are capable of hydroxylating compounds, and in particular epothilones, having a terminal alkyl group to produce compounds having a terminal hydroxyalkyl group.

Another object of the present invention is to provide microorganisms produced recombinantly which are capable of hydroxylating compounds, and in particular epothilones, having a terminal alkyl group to produce compounds having a terminal hydroxyalkyl group.

Another object of the present invention is to provide methods for hydroxylating compounds in these recombinant microorganisms. In particular, the present invention provides a method for the preparation of hydroxyalkyl-bearing epothilones, which compounds find utility as antitumor agents and as starting materials in the preparation of other epothilone analogs.

Yet another object of the present invention is to provide a compound of Formula A:

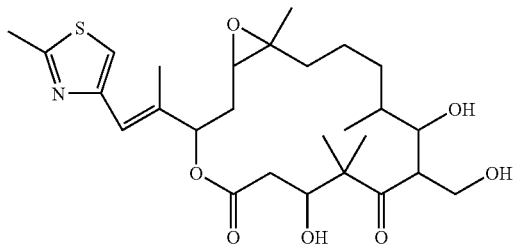

referred to herein as 24-OH epothilone B or 24-OH EpoB, as well as compositions and methods for production of compositions comprising the compound of Formula A.

BRIEF DESCRIPTION OF THE FIGURES

FIG. 2 shows the nucleic acid sequence alignments of SEQ ID NO:5 through SEQ ID NO:22 used to design the PCR primers for cloning of the nucleic acid sequence encoding epothilone B hydroxylase.

FIG. 3 shows the sequence alignment between epothilone B hydroxylase (SEQ ID NO:2) and EryF (PDB code 1JIN chain A; SEQ ID NO:76). The asterisks indicate sequence identities, the colons (:) similar residues.

DETAILED DESCRIPTION OF THE INVENTION

Figure 1:
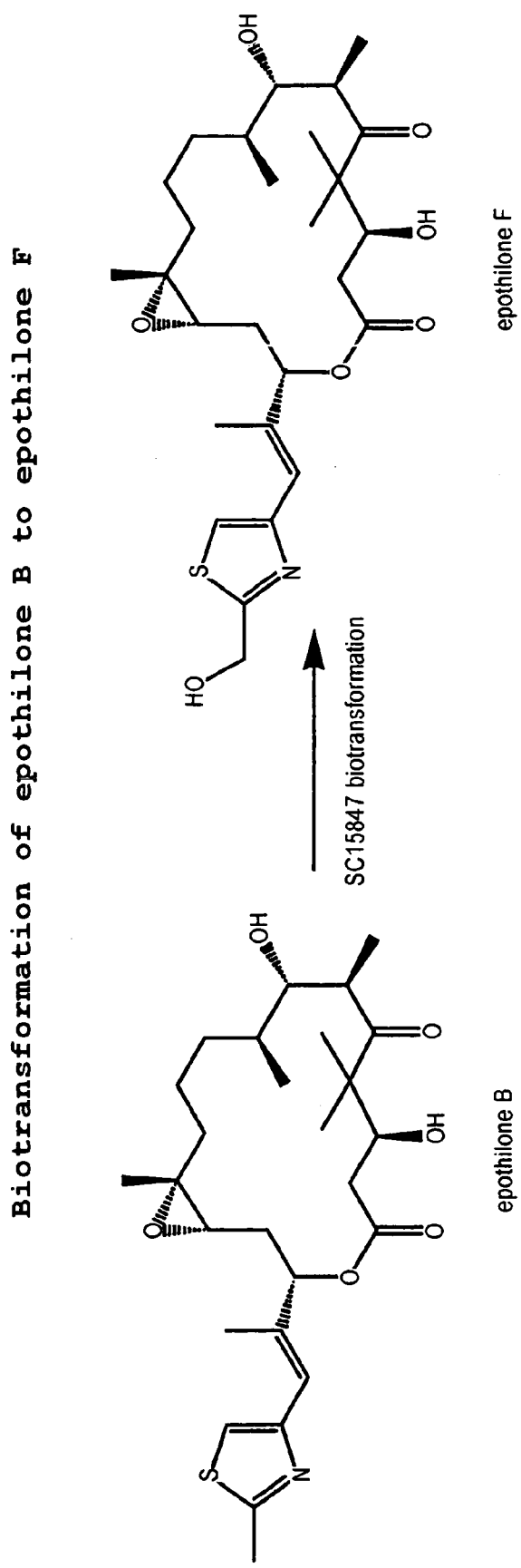
FIG. 1 provides a schematic of the biotransformation as set forth in WO 00/39276, U.S. application Ser. No. 09/468,854, filed Dec. 21, 1999, of epothilone B to epothilone F by *Amycolatopsis orientalis* strain SC 15847 (PTA 1043).

The present invention relates to isolated nucleic acid sequences and polypeptides and methods for obtaining compounds with desired substituents at a terminal carbon position. In particular, the present invention provides compositions and methods for the preparation of hydroxyalkyl-bearing epothilones, which compounds find utility as antitumor agents and as starting materials in the preparation of other epothilone analogs.

The term "epothilone," as used herein, denotes compounds containing an epothilone core and a side chain group as defined herein. The term "epothilone core," as used herein, denotes a moiety containing the core structure (with the numbering of ring system positions used herein shown):

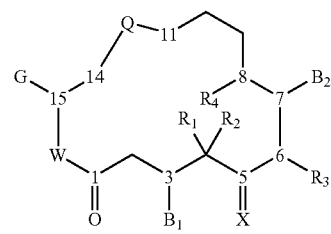

wherein the substituents are as follows:

Q is selected from the group consisting of

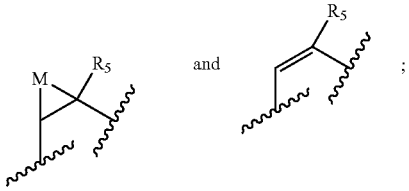

W is O or $NR_6$;

X is selected from the group consisting of O, H and $OR_7$;

M is O, S, $NR_8$, $CR_9R_{10}$;

$B_1$ and $B_2$ are selected from the group consisting of $OR_{11}$, $OCOR_{12}$;

$R_1$–$R_5$ and $R_{12}$–$R_{17}$ are selected from the group consisting of H, alkyl, substituted alkyl, aryl, and heterocyclo, and wherein $R_1$ and $R_2$ are alkyl they can be joined to form a cycloalkyl;

$R_6$ is selected from the group consisting of H, alkyl, and substituted alkyl;

$R_7$ and $R_{11}$ are selected from the group consisting of H, alkyl, substituted alkyl, trialkylsilyl, alkyldiarylsilyl and dialkylarylsilyl;

$R_8$ is selected from the group consisting of H, alkyl, substituted alkyl, $R_{13}C=O$, $R_{14}OC=O$ and $R_{15}SO_2$; and $R_9$ and $R_{10}$ are selected from the group consisting of H, halogen, alkyl, substituted alkyl, aryl, heterocyclo, hydroxy, $R_{16}C=O$, and $R_{17}OC=O$.

The term "side chain group" refers to substituent G as defined above for Epothilone A or B or $G_1$ and $G_2$ as shown below.

$G_1$ is the following formula V $$HO-CH_2-(A_1)_n-(Q)_m-(A_2)_o \qquad (V),$$

and

G$_2$ is the following formula VI

$$CH_3\text{-}(A_1)_n\text{-}(Q)_m\text{-}(A_2)_o \tag{VI},$$

where

A$_1$ and A$_2$ are independently selected from the group of optionally substituted C$_1$–C$_3$ alkyl and alkenyl;

Q is optionally substituted ring system containing one to three rings and at least one carbon to carbon double bond in at least one ring; and n, m, and o are integers independently selected from the group consisting of zero and 1, where at least one of m, n or o is 1.

The term "terminal carbon" or "terminal alkyl group" refers to the terminal carbon or terminal methyl group of the moiety either directly bonded to the epothilone core at position 15 or to the terminal carbon or terminal alkyl group of the side chain group bonded at position 15. It is understood that the term "alkyl group" includes alkyl and substituted alkyl as defined herein.

The term "alkyl" refers to optionally substituted, straight or branched chain saturated hydrocarbon groups of 1 to 20 carbon atoms, preferably 1 to 7 carbon atoms. The expression "lower alkyl" refers to optionally substituted alkyl groups of 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkyloxy, heterocyclooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. SO$_2$NH$_2$), substituted sulfonamido, nitro, cyano, carboxy, carbamyl (e.g. CONH$_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

In accordance with one aspect of the present invention there are provided isolated polynucleotides that encode epothilone B hydroxylase, an enzyme capable of hydroxylating epothilones having a terminal alkyl group to produce epothilones having a terminal hydroxyalkyl group.

In accordance with another aspect of the present invention there are provided isolated polynucleotides that encode a ferredoxin, the gene for which is located downstream from the epothilone B hydroxylase gene. Ferredoxin is a protein of the cytochrome P450 system.

By "polynucleotides", as used herein, it is meant to include any form of DNA or RNA such as cDNA or genomic DNA or mRNA, respectively, encoding these enzymes or an active fragment thereof which are obtained by cloning or produced synthetically by well known chemical techniques. DNA may be double- or single-stranded. Single-stranded DNA may comprise the coding or sense strand or the non-coding or antisense strand. Thus, the term polynucleotide also includes polynucleotides exhibiting at least 60% or more, preferably at least 80%, homology to sequences disclosed herein, and which hybridize under stringent conditions to the above-described polynucleotides. As used herein, the term "stringent conditions" means hybridization conditions of 60° C. at 2×SSC buffer. More preferred are isolated nucleic acid molecules capable of hybridizing to the nucleic acid sequence set forth in 1, 30, 32, 34, 36, 37, 38, 39, 40, 41, 42, 60, 62, 64, 66, 68, 70, 72, or 74 or SEQ ID NO:3, or to the complementary sequence of the nucleic acid sequence set forth in SEQ ID NO:1, 30, 32, 34, 36, 37, 38, 39, 40, 41, 42, 60, 62, 64, 66, 68, 70, 72, or 74 or SEQ ID NO:3, under hybridization conditions of 3×SSC at 65° C. for 16 hours, and which are capable of remaining hybridized to the nucleic acid sequence set forth in SEQ ID NO:1, 30, 32, 34, 36, 37, 38, 39, 40, 41, 42, 60, 62, 64, 66, 68, 70, 72 or 74 or SEQ ID NO:3, or to the complementary sequence of the nucleic acid sequence set forth in SEQ ID NO:1, 30, 32, 34, 36, 37, 38, 39, 40, 41 or 42, 60, 62, 64, 66, 68, 70, 72 or 74 or SEQ ID NO:3, under wash conditions of 0.5×SSC, 55° C. for 30 minutes.

In one embodiment, a polynucleotide of the present invention comprises the genomic DNA depicted in SEQ ID NO:1 or a homologous sequence or fragment thereof which encodes a polypeptide having similar activity to that of this epothilone B hydroxylase. Alternatively, a polynucleotide of the present invention may comprise the genomic DNA depicted in SEQ ID NO:3 or a homologous sequence or fragment thereof which encodes a polypeptide having similar activity to this ferredoxin. Due to the degeneracy of the genetic code, polynucleotides of the present invention may also comprise other nucleic acid sequences encoding this enzyme and derivatives, variants or active fragments thereof.

The present invention also relates to variants of these polynucleotides which may be naturally occurring, i.e., present in microorganisms such as *Amycolatopsis orientalis* and *Amycolata autotrophica*, or in soil or other sources from which nucleic acids can be isolated, or mutants prepared by well known mutagenesis techniques. Exemplary variants polynucleotides of the present invention are depicted in SEQ ID NO: 36–42.

By "mutants" as used herein it is meant to be inclusive of nucleic acid sequences with one or more point mutations, or deletions or additions of nucleic acids as compared to SEQ ID NO: 1 or 3, but which still encode a polypeptide or fragment with similar activity to the polypeptides encoded by SEQ ID NO: 1 or 3. In a preferred embodiment, mutations are made which alter the substrate specificity and/or yield of the enzyme. A preferred region of mutation with respect to the epothilone B hydroxylase gene is that region of the nucleic acid sequence coding for the approximately 113 amino acids residues comprising the active site of the enzyme. Also preferred are mutants encoding a polypeptide with at least one amino acid substitution at amino acid position GLU31, ARG67, ARG88, ILE92, ALA93, VAL106, ILE130, ALA140, MET176, PHE190, GLU 231, SER294, PHE237, or ILE365 of SEQ ID NO:1. Exemplary polynucleotide mutants of the present invention are depicted in SEQ ID NO: 30, 32, 34, 60, 62, 64, 66, 68, 70, 72 and 74.

Cloning of the nucleic acid sequence of SEQ ID NO:1 encoding epothilone B hydroxylase was performed using PCR primers designed by aligning the nucleic acid sequences of six cytochrome P450 genes from bacteria. The following cytochrome P450 genes were aligned:

Sequence: Locus: STMSUACB; Accession number: M32238; Reference: Omer, C. A., J. Bacteriol. 172: 3335–3345 (1990)

Sequence: Locus: STMSUBCB; Accession number: M32239; Reference: Omer, C. A., J. Bacteriol. 172: 3335–3345 (1990)

Sequence: Locus: AB018074 (formerly STMORFA); Accession number: AB018074; Reference: Ueda, K., J. Antibiot. 48: 638–646 (1995)

Sequence: Locus: SSU65940; Accession number: U65940; Reference: Motamedi, H., J. Bacteriol. 178: 5243–5248 (1996)

Sequence: Locus: STMOLEP; Accession number: L37200; Reference: Rodriguez, A. M., FEMS Microbiol. Lett. 127: 117–120 (1995)

Sequence: Locus: SERCP450A; Accession number: M83110; Reference: Andersen, J. F. and Hutchinson, C. R., J. Bacteriol. 174: 725–735 (1992)

Alignments were performed using an implementation of the algorithm of Myers, E. W. and W. Miller. 1988. *CABIOS* 4:1, 11–17., the Align program from Scientific and Educational Software (Durham, N.C., USA). Three highly conserved regions were identified in the I-helix, containing the oxygen binding domain, in the K-helix, and spanning the B-bulge and L-helix containing the conserved heme binding domain. Primers were designed to the three conserved regions identified in the alignment. Primers P450-1$^+$ (SEQ ID NO:23) and P450-1a$^+$ (SEQ ID NO:24) were designed from the I helix, Primer P450-2$^+$ (SEQ ID NO:25) was designed from the B-Bulge and L-helix region and Primer P450-3$^-$ (SEQ ID NO:27) was designed as the reverse complement to the heme binding protein.

Genomic fragments were then amplified via polymerase chain reaction (PCR). After PCR amplification, the reaction products were separated by gel electrophoresis and fragments of the expected size were excised. The DNA was extracted from the agarose gel slices using the Qiaquick gel extraction procedure (Qiagen, Santa Clarita, Calif., USA). The fragments were then cloned into the PCRscript vector (Stratagene, La Jolla, Calif., USA) using the PCRscript Amp cloning kit (Stratagene). Colonies containing inserts were picked to 1–2 ml of LB broth with 100 μg/ml ampicillin, 30–37° C., 16–24 hours, 230–300 rpm. Plasmid isolation was performed using the Mo Bio miniplasmid prep kit (Mo Bio, Solano Beach, Calif., USA). This plasmid DNA was used as a PCR and sequencing template and for restriction digest analysis.

The cloned PCR products were sequenced using the Big-Dye sequencing kit from Applied Biosystems, (Foster City, Calif., USA) and were analyzed using the ABI310 sequencer (Applied Biosystems, Foster City, Calif., USA). The sequence of the inserts was used to perform a TblastX search, using the protocol of Altschul, S. F, et al., *Mol. Biol.* 215:403–410 (1990), of the non-redundant protein database. Unique sequences having a significant similarity to known cytochrome P450 proteins were retained. Using this approach, a total of nine different P450 sequences were identified from SC15847, seven from the genomic DNA template and two from the cDNA. Two P450 sequences were found in common between the DNA and cDNA templates. Of the fifty cDNA clones analyzed, two sequences were predominant, with twenty clones each. These two genes were then cloned from the genomic DNA.

The nucleic acid sequence of the genomic DNA was determined using the Big-Dye sequencing system (Applied Biosystems) and analyzed using an ABI310 sequencer. This sequence is depicted in SEQ ID NO:1. An open reading frame coding for a protein of 404 amino acids and a predicted molecular weight of 44.7 kDa was found within the cloned BglII fragment. The deduced amino acid sequence of this polypeptide is depicted in SEQ ID NO: 2. The amino acid sequence of this polypeptide was found to share 51% identity with the NikF protein of *Streptomyces tendae* (Bruntner, C. et al, 1999, Mol. Gen. Genet. 262: 102–114) and 48% identity with the Sca-2 protein of *S. carbophilus* (Watanabe, I. Et al, 1995, Gene 163: 81–85). Both of these enzymes belong to the cytochrome P450 family 105. The invariable cysteine found in the heme-binding domain of all cytochrome P450 enzymes is found at residue 356. This gene for epothilone B hydroxylase has been named ebh. The ATG start codon of a putative ferredoxin gene of 64 amino acids is found nine basepairs downstream from the stop codon of ebh. This enzyme was found to share 50% identity with ferredoxin genes of *S. griseoulus* (O'Keefe, D. P., et al, 1991, Biochemistry 30: 447–455) and *S. noursei* (Brautaset, T., et al, 2000, Chem. Biol. 7: 395–403). The nucleic acid sequence encoding this ferredoxin is depicted in SEQ ID NO:3 and the amino acid sequence for this ferredoxin polypeptide is depicted in SEQ ID NO:4.

The ebh gene sequence was also used to isolate variant cytochrome P450 genes from other microorganisms. Exemplary variant polynucleotides ebh43491, ebh14930, ebh53630, ebh53550, ebh39444, ebh43333 and ebh35165 of the present invention and the species from which they were isolated are depicted in Table 1 below. The nucleic acid sequences for these variants are depicted in SEQ ID NO:36-42, respectively.

TABLE 1

Variant polynucleotides

| ATCC ID | Species | ebh gene designation |
|---|---|---|
| 43491 | *Amycolatopsis orientalis* | ebh43491 |
| 14930 | *Amycolatopsis orientalis* | ebh14930 |
| 53630 | *Amycolatopsis orientalis* | ebh53630 |
| 53550 | *Amycolatopsis orientalis* | ebh53550 |
| 39444 | *Amycolatopsis orientalis* | ebh39444 |
| 43333 | *Amycolatopsis orientalis* | ebh43333 |
| 35165 | *Amycolatopsis orientalis* | ebh35165 |

The amino acid sequences encoded by the exemplary variants ebh43491, ebh14930, ebh53630, ebh53550, ebh39444, ebh43333 and ebh35165 are depicted in SEQ ID NO:43-49, respectively. Table 2 provides a summary of the amino acid substitutions of these exemplary variants.

TABLE 2

Amino acid Substitutions

| Position | ebh | Substitution | ebh variant |
|---|---|---|---|
| 100 | Gly | Ser | ebh14930, ebh43333, ebh53550, ebh43491 |
| 101 | Lys | Arg | ebh14930 |
| 130 | Ile | Leu | ebh14930 |
| 192 | Ser | Gln | ebh14930 |
| 224 | Ser | Thr | ebh14930, ebh43333, ebh53550, ebh43491 |
| 285 | Ile | Val | ebh14930, ebh43333, ebh53550, ebh43491 |
| 69 | Ser | Asn | ebh43333 |
| 256 | Val | Ala | ebh43333, ebh53550, ebh43491 |
| 93 | Ala | Ser | ebh53550 |
| 326 | Asp | Glu | ebh53550, ebh43491 |
| 333 | Thr | Ala | ebh53550, ebh43491 |
| 133 | Leu | Met | ebh43491 |
| 398 | His | Arg | ebh39444 |

Mutations were also introduced into the coding region of the ebh gene to identify mutants with improved yield, and/or rate of bioconversion and/or altered substrate specificity. Exemplary mutant nucleic acid sequences of the present invention are depicted in SEQ ID NO:30, 32, 34, 60, 62, 64, 66, 68, 70, 72 and 74.

The nucleic acid sequence of SEQ ID NO:30 encodes a mutant ebh25-1 which exhibits altered substrate specificity. Plasmid pANT849ebh25-1 containing this mutant gene was deposited and accepted by an International Depository Authority under the provisions of the Budapest Treaty. The deposit was made on Nov. 21, 2002 to the American Type Culture Collection at 10801 University Boulevard in Manassas, Va. 20110-2209. The ATCC Accession Number is PTA-4809. All restrictions upon public access to this plasmid will be irrevocably removed upon granting of this patent application. The Deposit will be maintained in a public depository for a period of thirty years after the date of deposit or five years after the last request for a sample or for the enforceable life of the patent, whichever is longer. The above-referenced plasmid was viable at the time of the deposit. The deposit will be replaced if viable samples cannot be dispensed by the depository.

This S. lividans transformant identified in the screening of mutation 25 (primers NPB29-mut25f (SEQ ID NO:58) and NPB29-mut25r (SEQ ID NO:59)) was found to produce a product with a different HPLC elution time than epothilone B or epothilone F. A sample of this unknown was analyzed by LC-MS and was found to have a molecular weight of 523 (M.W.), consistent with a single hydroxylation of epothilone B. Plasmid DNA was isolated from the S. lividans culture and used as a template for PCR amplification using primers NPB29-6f (SEQ ID NO:28) and NPB29-7r (SEQ ID NO:29) (see Example 17). The expected fragment was obtained and sequenced using the Big-Dye sequencing system. The ebh25-1 mutant was found to have two mutations resulting in changes in the amino acid sequence of the protein, asparagine 195 is changed to serine and serine 294 is changed to proline. The position targeted for mutation at codon 238 was found to have a two nucleotide change, which did not result in a change of the amino acid sequence of the protein. The amino acid sequence of the mutant polypeptide encoded by SEQ ID NO:30 is depicted in SEQ ID NO:31.

The nucleic acid sequence of SEQ ID NO:32 encodes a mutant ebh10-53, which exhibits improved bioconversion yield. This S. lividans transformant identified in the screening of mutation 10 (primers NPB29-mut10f (SEQ ID NO:54) and NPB29-mut10r (SEQ ID NO:55)) produced a greater yield of epothilone F. Plasmid DNA was isolated from the S. lividans culture and used as a template for PCR amplification using primers NPB29-6f (SEQ ID NO:28) and NPB29-7r (SEQ ID NO:29)(see Example 16). The expected fragment was obtained and sequenced using the Big-Dye sequencing system. The ebh10-53 mutant was found to have two mutations resulting in changes in the amino acid sequence of the protein, glutamic acid 231 is changed to arginine and phenylalanine 190 is changed to tyrosine. The position 231 was the target of the mutagenesis, the change at residue 190 is an inadvertent change that is an artifact of the mutagenesis procedure. The amino acid sequence of the mutant polypeptide encoded by SEQ ID NO:32 is depicted in SEQ ID NO:33.

The nucleic acid sequence of SEQ ID NO:34 encodes a mutant ebh24-16, which also exhibits improved bioconversion yield. This S. lividans transformant, ebh24-16 identified in the screening of mutation 24 (primers NPB29-mut24f (SEQ ID NO:56) and NPB29-mut24r (SEQ ID NO:57) also produced a greater yield of epothilone F. Plasmid DNA was isolated from the S. lividans culture and used as a template for PCR amplification using primers NPB29-6f (SEQ ID NO:28) and NPB29-7r (SEQ ID NO:29). The expected fragment was obtained and sequenced using the Big-Dye sequencing system. The ebh24-16 mutant was found to have two mutations resulting in changes in the amino acid sequence of the protein, phenylalanine 237 is changed to alanine and isoleucine 92 is changed to valine. The position 237 was the target of the mutagenesis, the change at residue 92 is an inadvertent change that is an artifact of the mutagenesis procedure. The amino acid sequence of the mutant polypeptide encoded by SEQ ID NO:34 is depicted in SEQ ID NO:35.

The nucleic acid sequence of SEQ ID NO:60 encodes a mutant ebh24-16d8, which also exhibits improved bioconversion yield. This S. rimosus transformant, ebh24-16d8 identified in the screening of mutation 59 (primer NPB29mut59 (SEQ ID NO:70)) also produced a greater yield of epothilone F. Plasmid DNA was isolated from the S. rimosus culture and used as a template for PCR amplification using primers NPB29-6f (SEQ ID NO:28) and NPB29-7r (SEQ ID NO:29). The expected fragment was obtained and sequenced using the Big-Dye sequencing system. The ebh24-16d8 mutant was found to have one mutation resulting in a change in the amino acid sequence of the protein, arginine 67 is changed to glutamine. This change is an artifact of the mutagenesis procedure. The amino acid sequence of the mutant polypeptide encoded by SEQ ID NO:60 is SEQ ID NO:61.

The nucleic acid sequence of SEQ ID NO:62 encodes a mutant ebh24-16c11, which also exhibits improved bioconversion yield. This S. rimosus transformant, ebh24-16c11 identified in the screening of mutation 59 (primer NPB29mut59 (SEQ ID NO:70)) also produced a greater yield of epothilone F. Plasmid DNA was isolated from the S. rimosus culture and used as a template for PCR amplification using primers NPB29-6f (SEQ ID NO:28) and NPB29-7r (SEQ ID NO:29). The expected fragment was obtained and sequenced using the Big-Dye sequencing system. The ebh24-16c11 mutant was found to have two additional mutations resulting in changes in the amino acid sequence of the protein, alanine 93 is changed to glycine and isoleucine 365 is changed to threonine. The position 93 is the target of the mutagenesis, the change at 365 is an artifact of the mutagenesis procedure. The amino acid sequence of the mutant polypeptide encoded by SEQ ID NO:62 is depicted in SEQ ID NO:63.

The nucleic acid sequence of SEQ ID NO:64 encodes a mutant ebh24-16-16, which also exhibits improved bioconversion yield. This S. rimosus transformant, ebh24-16-16 identified in the screening of random mutants of ebh24-16 also produced a greater yield of epothilone F. Plasmid DNA was isolated from the S. rimosus culture and used as a template for PCR amplification using primers NPB29-6f (SEQ ID NO:28) and NPB29-7r (SEQ ID NO:29). The expected fragment was obtained and sequenced using the Big-Dye sequencing system. The ebh24-16-16 mutant was found to have one additional mutation resulting in changes in the amino acid sequence of the protein, valine 106 is changed to alanine. The amino acid sequence of the mutant polypeptide encoded by SEQ ID NO:64 is depicted in SEQ ID NO:65.

The nucleic acid sequence of SEQ ID NO:66 encodes a mutant ebh24-16-74, which also exhibits improved bioconversion yield. This S. rimosus transformant, ebh24-16-74 identified in the screening of random mutants of ebh24-16 also produced a greater yield of epothilone F. Plasmid DNA was isolated from the *S. rimosus* culture and used as a template for PCR amplification using primers NPB29-6f (SEQ ID NO:28) and NPB29-7r (SEQ ID NO:29). The expected fragment was obtained and sequenced using the Big-Dye sequencing system. The ebh24-16-74 mutant was found to have one additional mutation resulting in changes in the amino acid sequence of the protein, arginine 88 is changed to histidine. The amino acid sequence of the mutant polypeptide encoded by SEQ ID NO:66 is SEQ ID NO:67.

The nucleic acid sequence of SEQ ID NO:68 encodes a mutant ebh24-M18, which also exhibits improved bioconversion yield. This *S. rimosus* transformant, ebhM-18 identified in the screening of random mutants of ebh also produced a greater yield of epothilone F. Plasmid DNA was isolated from the *S. rimosus* culture and used as a template for PCR amplification using primers NPB29-6f (SEQ ID NO:28) and NPB29-7r (SEQ ID NO:29). The expected fragment was obtained and sequenced using the Big-Dye sequencing system. The ebhM-18 mutant was found to have two mutations resulting in changes in the amino acid sequence of the protein, glutamic acid 31 is changed to lysine and methionine 176 is changed to valine. The amino acid sequence of the mutant polypeptide encoded by SEQ ID NO:68 is depicted in SEQ ID NO:69.

The nucleic acid sequence of SEQ ID NO:72 encodes a mutant ebh24-16g8, which also exhibits improved bioconversion yield. This *S. rimosus* transformant, ebh24-16g8 identified in the screening of mutation 50 (primer NPB29mut50 (SEQ ID NO:71)) also produced a greater yield of epothilone F. Plasmid DNA was isolated from the *S. rimosus* culture and used as a template for PCR amplification using primers NPB29-6f (SEQ ID NO:28) and NPB29-7r (SEQ ID NO:29). The expected fragment was obtained and sequenced using the Big-Dye sequencing system. The ebh24-16g8 mutant was found to have two additional mutations resulting in changes in the amino acid sequence of the protein, methionine 176 is changed to alanine and isoleucine 130 is changed to threonine. The position 176 is the target of the mutagenesis, the change at 130 is an artifact of the mutagenesis procedure. The amino acid sequence of the mutant polypeptide encoded by SEQ ID NO:72 is depicted in SEQ ID NO:73.

The nucleic acid sequence of SEQ ID NO:74 encodes a mutant ebh24-16b9, which also exhibits improved bioconversion yield. This *S. rimosus* transformant, ebh24-16b9 identified in the screening of mutation 50 (primer NPB29mut50 (SEQ ID NO:71)) also produced a greater yield of epothilone F. Plasmid DNA was isolated from the *S. rimosus* culture and used as a template for PCR amplification using primers NPB29-6f (SEQ ID NO:28) and NPB29-7r (SEQ ID NO:29). The expected fragment was obtained and sequenced using the Big-Dye sequencing system. The ebh24-16b9 mutant was found to have two additional mutations resulting in changes in the amino acid sequence of the protein, methionine 176 is changed to serine and alanine 140 is changed to threonine. The position 176 is the target of the mutagenesis, the change at 140 is an artifact of the mutagenesis procedure. The amino acid sequence of the mutant polypeptide encoded by SEQ ID NO:74 is depicted in SEQ ID NO:75.

A mixture composed of the plasmids pANT849ebh-24-16, pANT849ebh-10-53, pANT849ebh-24-16d8, pANT849ebh-24-16c11, pANT849ebh-24-16-16, pant849ebh-24-16-74, pANT849ebh-24-16b9, pANT849ebh-M18 and pANT849ebh-24-16g8 for these nine mutant genes was deposited and accepted by an International Depository Authority under the provisions of the Budapest Treaty. The deposit was made on Nov. 21, 2002 to the American Type Culture Collection at 10801 University Boulevard in Manassas, Va. 20110-2209. The ATCC Accession Number is PTA-4808. All restrictions upon public access to this mixture of plasmids will be irrevocably removed upon granting of this patent application. The deposit will be maintained in a public depository for a period of thirty years after the date of deposit or five years after the last request for a sample or for the enforceable life of the patent, whichever is longer. The above-referenced mixture of plasmids was viable at the time of the deposit. The deposit will be replaced if viable samples cannot be dispensed by the depository.

Thus, in accordance with another aspect of the present invention, there are provided isolated polypeptides of epothilone B hydroxylase and variants and mutants thereof and isolated polypeptides of ferredoxin or variants thereof. In one embodiment of the present invention, by "polypeptide" it is meant to include the amino acid sequence of SEQ ID NO: 2, and fragments or variants, which retain essentially the same biological activity and/or function as this epothilone B hydroxylase. In another embodiment of the present invention, by "polypeptide" it is meant to include the amino acid sequence of SEQ ID NO:4, and fragments and/or variants, which retain essentially the same biological activity and/or function as this ferredoxin.

By "variants" as used herein it is meant to include polypeptides with amino acid sequences with conservative amino acid substitutions as compared to SEQ ID NO: 2 or 4 which are demonstrated to exhibit similar biological activity and/or function to SEQ ID NO:2 or 4. By "conservative amino acid substitutions" it is meant to include replacement, one for another, of the aliphatic amino acids such as Ala, Val, Leu and Ile, the hydroxyl residues Ser and Thr, the acidic residues Asp and Glu, and the amide residues Asn and Gln. Exemplary variant amino acid sequences of the present invention are depicted in SEQ ID NO:43–49 and the amino acid substitutions of these exemplary variants are described in Table 2, supra.

By "mutants" as used herein it is meant to include polypeptides encoded by nucleic acid sequences with one or more point mutations, or deletions or additions of nucleic acids as compared to SEQ ID NO: 1 or 3, but which still have similar activity to the polypeptides encoded by SEQ ID NO: 1 or 3. In a preferred embodiment, mutations are made to the nucleic acid that alter the substrate specificity and/or yield from the polypeptide encoded thereby. A preferred region of mutation with respect to the epothilone B hydroxylase gene is that region of the nucleic acid sequence coding for the approximately 113 amino acid residues comprising the active site of the enzyme. Also preferred are mutants with at least one amino acid substitution at amino acid position GLU31, ARG67, ARG88, ILE92, ALA93, VAL106, ILE130, ALA140, MET176, PHE190, GLU 231, SER294, PHE237, or ILE365 of SEQ ID NO:1 Exemplary mutants ebh25-1, ebh10-53, ebh24-16, ebh24-16d8, ebh24-16c11, ebh24-16-16, ebh24-16-74, ebh24-16g8, ebh24-16b9 and the nucleic acid sequences encoding such mutants of the present invention are depicted in SEQ ID NO:31, 33, 35, 61, 63, 65, 67, 69, 71, 73 and 75, and SEQ ID NO:30, 32, 34, 60, 62, 64, 66, 68, 70, 72 and 74, respectively.

A 3-dimensional model of epothilone B hydroxylase has also been constructed in accordance with general teachings of Greer et al. (Comparative modeling of homologous proteins. Methods In Enzymology 202239-52, 1991), Lesk et al. (Homology Modeling: Inferences from Tables of Aligned Sequences. Curr. Op. Struc. Biol. (2) 242–247, 1992), and Cardozo et al. (Homology modeling by the ICM method. Proteins 23, 403–14, 1995) on the basis of the known structure of a homologous protein EryF (PDB Code 1KIN chain A). Homology between these sequences is 34%. Alignment of the sequences of epothilone B hydroxylase (SEQ ID NO:2) and EryF (PDB Code 1KIN chain A; SEQ ID NO:76) is depicted in FIG. 3. A homology model of epothilone B hydroxylase based upon sequence alignment with EryF is depicted in FIG. 4.

Figure 4:
FIG. 4 provides a homology model of epothilone B hydroxylase based upon sequence alignment with EryF as shown in FIG. 3.
Figure 5:
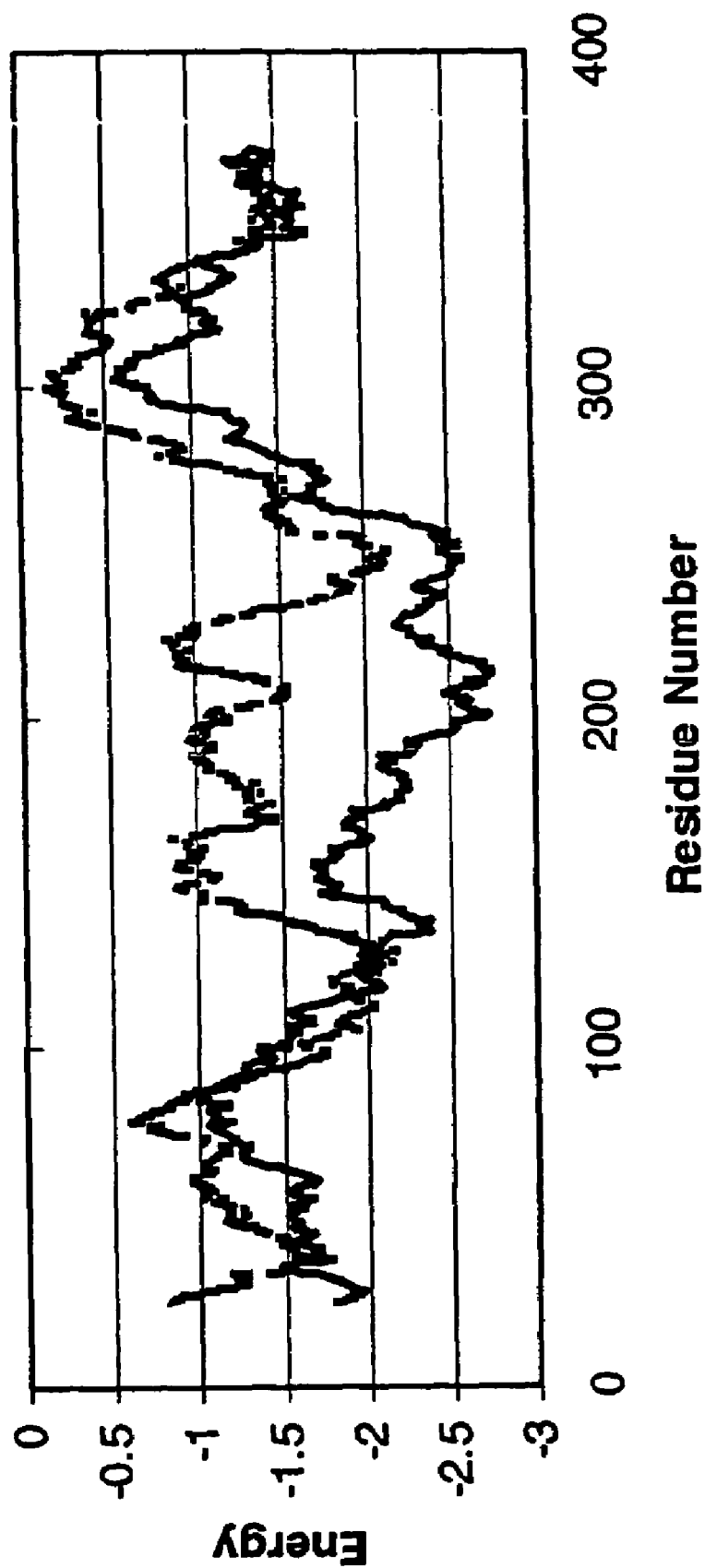
FIG. 5 shows an energy plot of the epothilone B hydroxylase model (indicated by dashed line) relative to EryF (PDB code 1JIN; indicated by solid line). An averaging window size of 51 residues was used, i.e., the energy at a given residue position is calculated as the average of the energies of the 51 residues in the sequence that lie with the given residue at the central positions.

An energy plot of the epothilone B hydroxylase model relative to EryF (PDB code 1JIN) was also prepared and is depicted in FIG. 5. An averaging window size of 51 residues was used at a given residue position to calculate the average of the energies of the 51 residues in the sequence that lie with the given residue at the central position. As shown in FIG. 5, all energies along the sequence lie below zero thus indicating that the modeled structure as set forth in FIG. 4 and Appendix 1 is reasonable.

The three-dimensional structure represented in the homology model of epothilone B hydroxylase of FIG. 4 is defined by a set of structure coordinates as set forth in Appendix 1. The term "structure coordinates" refers to Cartesian coordinates generated from the building of a homology model. As will be understood by those of skill in the art, however, a set of structure coordinates for a protein is a relative set of points that define a shape in three dimensions. Thus, it is possible that an entirely different set of coordinates could define a similar or identical shape. Moreover, slight variations in the individual coordinates, as emanate from generation of similar homology models using different alignment templates and/or using different methods in generating the homology model, will have minor effects on the overall shape. Variations in coordinates may also be generated because of mathematical manipulations of the structure coordinates. For example, the structure coordinates set forth in Appendix 1 could be manipulated by fractionalization of the structure coordinates; integer additions or subtractions to sets of the structure coordinates, inversion of the structure coordinates or any combination of the above.

Various computational analyses are therefore necessary to determine whether a molecule or a portion thereof is sufficiently similar to all or parts of epothilone B hydroxylase described above as to be considered the same. Such analyses may be carried out in current software applications, such as SYBYL version 6.7 or INSIGHTII (Molecular Simulations Inc., San Diego, Calif.) version 2000 and as described in the accompanying User's Guides.

For example, the superimposition tool in the program SYBYL allows comparisons to be made between different structures and different conformations of the same structure. The procedure used in SYBYL to compare structures is divided into four steps: 1) load the structures to be compared; 2) define the atom equivalencies in these structures; 3) perform a fitting operation; and 4) analyze the results. Each structure is identified by a name. One structure is identified as the target (i.e., the fixed structure); the second structure (i.e., moving structure) is identified as the source structure. Since atom equivalency within SYBYL is defined by user input, for the purpose of this aspect of the present invention equivalent atoms are defined as protein backbone atoms (N, C$\alpha$, C and O) for all conserved residues between the two structures being compared. Further, only rigid fitting operations are considered. When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atoms is an absolute minimum. This number, given in angstroms, is reported by SYBYL.

For the purposes of the present invention, any homology model of epothilone B hydroxylase that has a root mean square deviation of conserved residue backbone atoms (N, C$\alpha$, C, O) of less than about 4.0 Å when superimposed on the corresponding backbone atoms described by structure coordinates listed in Appendix 1 are considered identical. More preferably, the root mean square deviation is less than about 3.0 Å. More preferably the root mean square deviation is less than about 2.0 Å.

For the purpose of this invention, any homology model of epothilone B hydroxylase that has a root mean square deviation of conserved residue backbone atoms (N, C$\alpha$, C, O) of less than about 2.0 Å when superimposed on the corresponding backbone atoms described by structure coordinates listed in Appendix 1 are considered identical. More preferably, the root mean square deviation is less than about 1.0 Å.

In another embodiment of the present invention, structural models wherein backbone atoms have been substituted with other elements which when superimposed on the corresponding backbone atoms have low root mean square deviations are considered to be identical. For example, an homology model where the original backbone carbon, and/or nitrogen and/or oxygen atoms are replaced with other elements having a root mean square deviation of about 4.0 Å, more preferably about 3.0 Å, even more preferably less than about 2 Å, when superimposed on the corresponding backbone atoms described by structure coordinates listed in Appendix 1 is considered identical.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the relevant portion of the backbone of the epothilone B hydroxylase portion of the complex as defined by the structure coordinates described herein.

The present invention as embodied by the homology model enables the structure-based design of additional mutants of epothilone B hydroxylase. For example, using the homology model of the present invention, residues lying within 10 Å of the binding site of epothilone B hydroxylase have now been defined. These residues include LEU39, GLN43, ALA45, MET57, LEU58, HIS62, PHE63, SER64, SER65, ASP66, ARG67, GLN68, SER69, LEU74, MET75, VAL76, ALA77, ARG78, GLN79, ILE80, ASP84, LYS85, PRO86, PHE87, ARG88, PRO89, SER90, LEU91, ILE92, ALA93, MET94, ASP95, HIS99, ARG103, PHE110, ILE155, PHE169, GLN170, CYS172, SER173, SER174, ARG175, MET176, LEU177, SER178, ARG179, ARG186, PHE190, LEU193, VAL233, GLY234, LEU235, ALA236, PHE237, LEU238, LEU239, LEU240, ILE241, ALA242, GLY243, HIS244, GLU245, THR246, THR247, ALA248, ASN249, MET250, LEU283, THR287, ILE288, ALA289, GLU290, THR291, ALA292, THR293, SER294, ARG295, PHE296, ALA297, THR298, GLU312, GLY313, VAL314, VAL315, GLY316, VAL344, ALA345, PHE346, GLY347, PHE348, VAL350, HIS351, GLN352, CYS353, LEU354, GLY355, GLN356, LEU358, ALA359, GLU362, LYS389, ASP391, SER392, THR393, ILE394 and TYR395 as set forth in Appendix 1. Mutants with mutations at one or more of these positions are expected to exhibit altered biological function and/or specificity and thus comprise another embodiment of preferred mutants of the present invention. Another embodiment of preferred mutants are molecules that have a root mean square deviation from the backbone atoms of said epothilone B hydroxylase of not more than about 4.0 Å.

The structure coordinates of an epothilone B hydroxylase homology model or portions thereof are stored in a machine-readable storage medium. Such data may be used for a variety of purposes, such as drug discovery.

Accordingly, another aspect of the present invention relates to machine-readable data storage medium comprising a data storage material encoded with the structure coordinates set forth in Appendix 1.

The three-dimensional model structure of epothilone B hydroxylase can also be used to identify modulators of biological function and potential substrates of the enzyme. Various methods or combinations thereof can be used to identify such modulators.

For example, a test compound can be modeled that fits spatially into a binding site in epothilone B hydroxylase, according to Appendix 1. Structure coordinates of amino acids within 10 Å of the binding region of epothilone B hydroxylase defined by amino acids LEU39, GLN43, ALA45, MET57, LEU58, HIS62, PHE63, SER64, SER65, ASP66, ARG67, GLN68, SER69, LEU74, MET75, VAL76, ALA77, ARG78, GLN79, ILE80, ASP84, LYS85, PRO86, PHE87, ARG88, PRO89, SER90, LEU91, ILE92, ALA93, MET94, ASP95, HIS99, ARG103, PHE110, ILE155, PHE169, GLN170, CYS172, SER173, SER174, ARG175, MET176, LEU177, SER178, ARG179, ARG186, PHE190, LEU193, VAL233, GLY234, LEU235, ALA236, PHE237, LEU238, LEU239, LEU240, ILE241, ALA242, GLY243, HIS244, GLU245, THR246, THR247, ALA248, ASN249, MET250, LEU283, THR287, ILE288, ALA289, GLU290, THR291, ALA292, THR293, SER294, ARG295, PHE296, ALA297, THR298, GLU312, GLY313, VAL314, VAL315, GLY316, VAL344, ALA345, PHE346, GLY347, PHE348, VAL350, HIS351, GLN352, CYS353, LEU354, GLY355, GLN356, LEU358, ALA359, GLU362, LYS389, ASP391, SER392, THR393, ILE394 and TYR395, and the coordinated heme group, HEM1 can also be used to identify desirable structural and chemical features of such modulators. Identified structural or chemical features can then be employed to design or select compounds as potential epothilone B hydroxylase ligands. By structural and chemical features it is meant to include, but is not limited to, covalent bonding, van der Waals interactions, hydrogen bonding interactions, charge interaction, hydrophobic bonding interaction, and dipole interaction. Compounds identified as potential epothilone B hydroxylase ligands can then be synthesized and screened in an assay characterized by binding of a test compound to epothilone B hydroxylase, or in characterizing the ability of epothilone B hydroxylase to modulate a protease target in the presence of a small molecule. Examples of assays useful in screening of potential epothilone B hydroxylase ligands include, but are not limited to, screening in silico, in vitro assays and high throughput assays.

As will be understood by those of skill in the art upon this disclosure, other structure-based design methods can be used. Various computational structure-based design methods have been disclosed in the art. For example, a number of computer modeling systems are available in which the sequence of epothilone B hydroxylase and the epothilone B hydroxylase structure (i.e., atomic coordinates of epothilone B hydroxylase as provided in Appendix 1 and/or the atomic coordinates within 10 Å of the binding region as provided above) can be input. This computer system then generates the structural details of one or more these regions in which a potential epothilone B hydroxylase modulator binds so that complementary structural details of the potential modulators can be determined. Design in these modeling systems is generally based upon the compound being capable of physically and structurally associating with epothilone B hydroxylase. In addition, the compound must be able to assume a conformation that allows it to associate with epothilone B hydroxylase. Some modeling systems estimate the potential inhibitory or binding effect of a potential epothilone B hydroxylase substrate or modulator prior to actual synthesis and testing.

Methods for screening chemical entities or fragments for their ability to associate with a given protein target are also well known. Often these methods begin by visual inspection of the binding site on the computer screen. Selected fragments or chemical entities are then positioned in a binding region of epothilone B hydroxylase. Docking is accomplished using software such as INSIGHTII, QUANTA and SYBYL, following by energy minimization and molecular dynamics with standard molecular mechanic force fields such as, MMFF, CHARMM and AMBER. Examples of computer programs which assist in the selection of chemical fragment or chemical entities useful in the present invention include, but are not limited to, GRID (Goodford, 1985), AUTODOCK (Goodsell, 1990), and DOCK (Kuntz et al. 1982).

Upon selection of preferred chemical entities or fragments, their relationship to each other and epothilone B hydroxylase can be visualized and then assembled into a single potential modulator. Programs useful in assembling the individual chemical entities include, but are not limited to CAVEAT (Bartlett et al. 1989) and 3D Database systems (Martin 1992).

Alternatively, compounds may be designed de novo using either an empty active site or optionally including some portion of a known inhibitor. Methods of this type of design include, but are not limited to LUDI (Bohm 1992) and LeapFrog (Tripos Inc., St. Louis Mo.).

Programs such as DOCK (Kuntz et al. 1982) can be used with the atomic coordinates from the homology model to identify potential ligands from databases or virtual databases which potentially bind the in the active site binding region which may therefore be suitable candidates for synthesis and testing.

Also provided in the present invention are vectors comprising polynucleotides of the present invention and host cells which are genetically engineered with vectors of the present invention to produce epothilone B hydroxylase or active fragments and variants or mutants of this enzyme and/or ferredoxin or active fragments thereof. Generally, any vector suitable to maintain, propagate or express polynucleotides to produce these polypeptides in the host cell may be used for expression in this regard. In accordance with this aspect of the invention the vector may be, for example, a plasmid vector, a single- or double-stranded phage vector, or a single- or double-stranded RNA or DNA viral vector. Vectors may be extra-chromosomal or designed for integration into the host chromosome. Such vectors include, but are not limited to, chromosomal, episomal and virus-derived vectors e.g., vectors derived from bacterial plasmids, bacteriophages, yeast episomes, yeast chromosomal elements, and viruses such as baculoviruses, papova viruses, SV40, vaccinia viruses, adenoviruses, fowl pox viruses, pseudorabies viruses and retroviruses, and vectors derived from combinations thereof, such as those derived from plasmid and bacteriophage genetic elements, cosmids and phagemids.

Useful expression vectors for prokaryotic hosts include, but are not limited to, bacterial plasmids, such as those from *E. coli, Bacillus* or *Streptomyces*, including pBluescript, pGEX-2T, pUC vectors, pET vectors, ColE1, pCR1, pBR322, pMB9, pCW, pBMS200, pBMS2020, PIJ101, PIJ702, pANT849, pOJ260, pOJ446, pSET152, pKC1139, pKC1218, pFD666 and their derivatives, wider host range plasmids, such as RP4, phage DNAs, e.g., the numerous derivatives of phage lambda, e.g., NM989, λGT10 and λGT11, and other phages, e.g., M13 and filamentous single stranded phage DNA.

Vectors of the present invention for use in yeast will typically contain an origin of replication suitable for use in yeast and a selectable marker that is functional in yeast. Examples of yeast vectors useful in the present invention include, but are not limited to, Yeast Integrating plasmids (e.g., YIp5) and Yeast Replicating plasmids (the YRp and YEp series plasmids), Yeast Centromere plasmids (the YCp series plasmids), Yeast Artificial Chromosomes (YACs) which are based on yeast linear plasmids, denoted YLp, pGPD-2, 2μ plasmids and derivatives thereof, and improved shuttle vectors such as those described in Gietz et al., *Gene*, 74: 527–34 (1988) (YIplac, YEplac and YCplac).

Mammalian vectors useful for recombinant expression may include a viral origin, such as the SV40 origin (for replication in cell lines expressing the large T-antigen, such as COS1 and COS7 cells), the papillomavirus origin, or the EBV origin for long term episomal replication (for use, e.g., in 293-EBNA cells, which constitutively express the EBV EBNA-1 gene product and adenovirus E1A). Expression in mammalian cells can be achieved using a variety of plasmids, including, but not limited to, pSV2, pBC12BI, and p91023, pCDNA vectors as well as lytic virus vectors (e.g., vaccinia virus, adeno virus, and baculovirus), episomal virus vectors (e.g., bovine papillomavirus), and retroviral vectors (e.g., murine retroviruses). Useful vectors for insect cells include baculoviral vectors and pVL941.

Selection of an appropriate promoter to direct mRNA transcription and construction of expression vectors are well known. In general, however, expression constructs will contain sites for transcription initiation and termination, and, in the transcribed region, a ribosome binding site for translation. The coding portion of the mature transcripts expressed by the constructs will include a translation initiating codon at the beginning and a termination codon appropriately positioned at the end of the polypeptide to be translated.

Examples of useful promoters for prokaryotes include, but are not limited to phage promoters such as phage lambda pL promoter, the trc promoter, a hybrid derived from the trp and lac promoters, the bacteriophage T7 promoter, the TAC or TRC system, the major operator and promoter regions of phage lambda, the control regions of fd coat protein, snpA promoter, melC promotor, ermE* promoter or the araBAD operon. Examples of useful promoters for yeast include, but are not limited to, the CYC1 promoter, the GAL1 promoter, the GAL10 promoter, ADH1 promoter, the promoters of the yeast α-mating system, and the GPD promoter. Examples of promoters routinely used in mammalian expression vectors include, but are not limited to, the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

Vectors comprising the polynucleotides can be introduced into host cells using any number of well known techniques including infection, transduction, transfection, transvection and transformation. The polynucleotides may be introduced into a host alone or with additional polynucleotides encoding, for example, a selectable marker or ferredoxin reductase. In a preferred embodiment of the present invention the polynucleotide for epothilone B hydroxylase and ferredoxin are introduced into the host cell. Host cells for the various expression constructs are well known, and those of skill can routinely select a host cell for expressing the epothilone B hydroxylase and/or ferredoxin in accordance with this aspect of the present invention. Examples of mammalian expression systems useful in the present invention include, but are not limited to, the C127, 3T3, CHO, HeLa, human kidney 293 and BHK cell lines, and the COS-7 line of monkey kidney fibroblasts.

Alternatively, as exemplified herein, epothilone B hydroxylase and ferredoxin can be expressed recombinantly in microorganisms.

Accordingly, another aspect of the present invention relates to recombinantly produced microorganisms which express epothilone B hydroxylase alone or in conjunction with the ferredoxin and which are capable of hydroxylating a compound, and in particular an epothilone, having a terminal alkyl group to produce ones having a terminal hydroxyalkyl group. The recombinantly produced microorganisms are produced by transforming cells such as bacterial cells with a plasmid comprising a nucleic acid sequence encoding epothilone B hydroxylase. In a preferred embodiment, the cells are transformed with a plasmid comprising a nucleic acid encoding epothilone B hydroxylase or mutants or variants thereof as well as the nucleic acid sequence encoding ferredoxin located downstream of the epothilone B hydroxylase gene. Examples of microorganisms which can be transformed with these plasmids to produce the recombinant microorganisms of the present invention include, but are not limited, *Escherichia coli, Bacillus megaterium, Amycolatopsis orientalis, Sorangium cellulosum, Rhodococcus erythropolis*, and *Streptomyces* species such as *Streptomyces lividans, Streptomyces virginiae, Streptomyces venezuelae, Streptomyces albus, Streptomyces coelicolor, Streptomyces rimosus* and *Streptomyces griseus*.

The recombinantly produced microorganisms of the present invention are useful in microbial processes or methods for production of compounds, and in particular epothilones, containing a terminal hydroxyalkyl group. In general, the hydroxyalkyl-bearing product can be produced by culturing the recombinantly produced microorganism or enzyme derived therefrom, capable of selectively hydroxylating a terminal carbon or alkyl, in the presence of a suitable substrate in an aqueous nutrient medium containing sources of assimilable carbon and nitrogen, under submerged aerobic conditions.

Suitable epothilones employed as substrate for the method of the present invention may be any such compound having a terminal carbon or terminal alkyl group capable of undergoing the enzymatic hydroxylation of the present invention. The starting material, or substrate, can be isolated from natural sources, such as *Sorangium cellulosum*, or they can be synthetically formed epothilones. Other substrates having a terminal carbon or terminal alkyl group capable of undergoing an enzymatic hydroxylation can be employed by the methods herein. For example, compactin can be used as a substrate, which upon hydroxylation forms the compound pravastatin. Methods for hydroxylating compactin to pravastatin via an *Actinomadura* strain are set forth in U.S. Pat. No. 5,942,423 and U.S. Pat. No. 6,274,360.

For example, using the recombinant microorganisms of the present invention at least one epothilone can be prepared as described in WO 00/39276, U.S. Ser. No. 09/468,854, filed Dec. 21, 1999, the text of which is incorporated herein as if set forth at length. An epothilone of the following Formula I

$$HO-CH_2-(A_1)_n-(Q)_m-(A_2)_o-E \qquad (I)$$

where $A_1$ and $A_2$ are independently selected from the group of optionally substituted $C_1$–$C_3$ alkyl and alkenyl;

Q is an optionally substituted ring system containing one to three rings and at least one carbon to carbon double bond in at least one ring;

n, m, and o are integers selected from the group consisting of zero and 1, where at least one of m or n or o is 1; and E is an epothilone core; can be prepared.

This method comprises the steps of contacting at least one epothilone of the following formula II

$$CH_3-(A_1)_n-(Q)_m-(A_2)_o-E \qquad (II)$$

where $A_1$, Q, $A_2$, E, n, m, and o are defined as above;

with a recombinantly produced microorganism, or an enzyme derived therefrom, which is capable of selectively catalyzing the hydroxylation of formula II, and effecting said hydroxylation.

In a preferred embodiment, the starting material is epothilone B. Epothilone B can be obtained from the fermentation of *Sorangium cellulosum* So ce90, as described in DE 41 38 042 and WO 93/10121. The strain has been deposited at the Deutsche Sammlung von Mikroorganismen (German Collection of Microorganisms) (DSM) under No. 6773. The process of fermentation is also described in Hofle, G., et al., *Angew. Chem. Int. Ed. Engl.*, Vol 35, No. 13/14, 1567–1569 (1996). Epothilone B can also be obtained by chemical means, such as those disclosed by Meng, D., et al., *J. Am. Chem. Soc.*, Vol. 119, No. 42, 10073–10092 (1996); Nicolaou, K., et al., *J. Am. Chem. Soc.*, Vol. 119, No. 34, 7974–7991 (1997) and Schinzer, D., et al., *Chem. Eur. J.*, Vol. 5, No. 9, 2483–2491 (1999).

Growth of the recombinantly produced microorganism selected for use in the process may be achieved by one of ordinary skill in the art by the use of appropriate nutrient medium. Appropriate media for the growing of the recombinantly produced microorganisms include those that provide nutrients necessary for the growth of microbial cells. See, for example, T. Nagodawithana and J. M. Wasileski, Chapter 2: "Media Design for Industrial Fermentations," *Nutritional Requirements of Commercially Important Microorganism*, edited by T. W. Nagodawithana and G. Reed, Esteekay Associates, Inc., Milwaukee, Wis., 18–45 (1998); T. L. Miller and B. W. Churchill, Chapter 10: "Substrates for Large-Scale Fermentations," *Manual of Industrial Microbiology and Biotechnology*, edited by A. L. Demain and N. A. Solomon, American Society for Microbiology, Washington, D.C., 122–136 (1986). A typical medium for growth includes necessary carbon sources, nitrogen sources, and trace elements. Inducers may also be added to the medium. The term inducer as used herein, includes any compound enhancing formation of the desired enzymatic activity within the recombinantly produced microbial cell. Typical inducers as used herein may include solvents used to dissolve substrates, such as dimethyl sulfoxide, dimethyl formamide, dioxane, ethanol and acetone. Further, some substrates, such as epothilone B, may also be considered to be inducers.

Carbon sources may include sugars such as glucose, fructose, galactose, maltose, sucrose, mannitol, sorbital, glycerol starch and the like; organic acids such as sodium acetate, sodium citrate, and the like; and alcohols such as ethanol, propanol and the like. Preferred carbon sources include, but are not limited to, glucose, fructose, sucrose, glycerol and starch.

Nitrogen sources may include an N-Z amine A, corn steeped liquor, soybean meal, beef extract, yeast extract, tryptone, peptone, cottonseed meal, peanut meal, amino acids such as sodium glutamate and the like, sodium nitrate, ammonium sulfate and the like.

Trace elements may include magnesium, manganese, calcium, cobalt, nickel, iron, sodium and potassium salts. Phosphates may also be added in trace or preferably, greater than trace amounts.

The medium employed for the fermentation may include more than one carbon or nitrogen source or other nutrient.

For growth of the recombinantly produced microorganisms and/or hydroxylation according to the method of the present invention, the pH of the medium is preferably from about 5 to about 8 and the temperature is from about 14° C. to about 37° C., preferably the temperature is 28° C. The duration of the reaction is 1 to 100 hours, preferably 8 to 72 hours.

The medium is incubated for a period of time necessary to complete the biotransformation as monitored by high performance liquid chromatography (HPLC). Typically, the period of time needed to complete the transformation is twelve to one hundred hours and preferably about 72 hours after the addition of the substrate. The medium is placed on a rotary shaker (New Brunswick Scientific Innova 5000) operating at 150 to 300 rpm and preferably about 250 rpm with a throw of 2 inches.

The hydroxyalkyl-bearing product can be recovered from the fermentation broth by conventional means that are commonly used for the recovery of other known biologically active substances. Examples of such recovery means include, but are not limited to, isolation and purification by extraction with a conventional solvent, such as ethyl acetate and the like; by pH adjustment; by treatment with a conventional resin, for example, by treatment with an anion or cation exchange resin or a non-ionic adsorption resin; by treatment with a conventional adsorbent, for example, by distillation, by crystallization; or by recrystallization, and the like.

The extract obtained above from the biotransformation reaction mixture can be further isolated and purified by column chromatography and analytical thin layer chromatography.

The ability of a recombinantly produced microorganism of the present invention to biotransform an epothilone having a terminal alkyl group to an epothilone having a terminal hydroxyalkyl group was demonstrated. In these experiments, a culture comprising a *Streptomyces lividans* clone containing a plasmid with the ebh gene as described in more detail in Example 11 was incubated with an epothilone B suspension for 3 days at 30° with agitation. A sample of the incubate was extracted with an equal volume of 25% methanol: 75% n-butanol, vortexed and allowed to settle for 5 minutes. Two hundred μl of the organic phase was transferred to an HPLC vial and analyzed by HPLC/MS (Example 12). A product peak of epothilone F eluted at a retention time of 15.9 minutes and had a protonated molecular weight of 524. The epothilone B substrate eluted at 19.0 minutes and had a protonated molecular weight of 508. The peak retention times and molecular weights were confirmed using known standards.

Rates of biotransformation of epothilone B by cells expressing ebh were also compared to rates of biotransformation by ebh mutants. Cells expressing ebh comprised a frozen spore preparation of. S. lividans (pANT849-ebh). Cells expressing mutants comprises frozen spore preparations of S. lividans (pANT849-ebh10-53) and S. lividans (pANT849-ebh24-16). A frozen spore preparation of S. lividans TK24 was used as the control. The cells were pre-incubated for several days at 30° C. Following this pre-incubation, epothilone B in 100% EtOH was added to each culture to a final concentration of 0.05% weight/volume. Samples were then taken at 0, 24, 48 and 72 hours with the exception of the S. lividans (pANT849-ebh24-16) culture, in which the epothilone B had been completely converted to epothilone F at 48 hours. The samples were analyzed by HPLC. The results are calculated as a percentage of the epothilone B at time 0 hours.

| Time (hours) | TK24 | pANT849-ebh | pANT849-ebh10-53 | pANT849-ebh24-16 |
|---|---|---|---|---|
| 0 | 100% | 100% | 100% | 100% |
| 24 | 99% | 78% | 69% | 56% |
| 48 | 87% | 19% | 39% | 0% |
| 72 | 87% | 0% | 3% | — |

| Time (hours) | TK24 | pANT849-ebh | pANT849-ebh10-53 | pANT849-ebh24-16 |
|---|---|---|---|---|
| 0 | 0% | 0% | 0% | 0% |
| 24 | 0% | 4% | 9% | 23% |
| 48 | 0% | 21% | 29% | 52% |
| 72 | 0% | 14% | 41% | — |

The ability of cells expressing ebh to biotransform compactin to pravastatin was also examined. In these experiments, frozen spore preparations of S. lividans (pANT849) or S. lividans (pANT849-ebh) were grown for several days at 30° C. Following the pre-incubation, an aliquot of each cell culture was transferred to a polypropylene culture tube, compactin was added to each culture tube, and the tubes were incubated for 24 hours, 30° C., 250 rpm. An aliquot of the culture broth was then extracted and compactin and pravastatin values relative to the control S. lividans (pANT849) culture were measured via HPLC.

Compactin and pravastatin as a percentage of starting compactin concentration:

|  | S. lividans (pANT849) | S. lividans (pANT849-ebh) |
|---|---|---|
| Compactin | 36% | 11% |
| Pravastatin | 11% | 53% |

As discussed supra, mutant ebh25-1 (SEQ ID NO:30) exhibits altered substrate specificity and biotransformation of epothilone B by this mutant resulted in a product with a different HPLC elution time than epothilone B or epothilone F. A sample of this unknown was analyzed by LC-MS and was found to have a molecular weight of 523 (M.W.), consistent with a single hydroxylation of epothilone B. The structure of the biotransformation product was determined as 24-hydroxyl-epothilone B, based on MS and NMR data (compared with data of epothilone B):

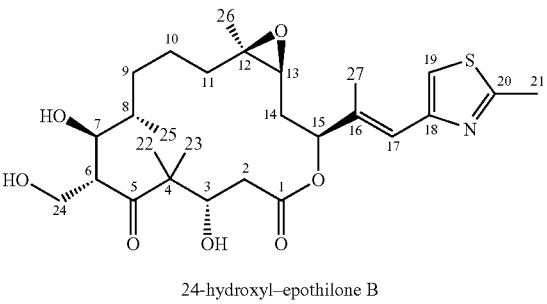

Formula A 24-hydroxyl–epothilone B

Molecular Formula: $C_{27}H_{41}NO_7S$ Molecular Weight: 523 Mass Spectrum: ES+ (m/z): 524([M+H]$^+$), 506. LC/MS/MS: +ESI (m/z): 524, 506, 476, 436, 320 HRMS: Calculated for [M+H]$^+$: 524.2682; Found: 524.2701 HPLC (Rt) 7.3 minutes (on the analytical HPLC system) LC/NMR Observed Chemical Shifts Varian AS-600 (Proton: 599.624 MHz), Solvent $D_2O/CD_3CN$ (δ 1.94): ~4/6 Proton: δ7.30 (s, 1H), 6.43 (s, 1H), 5.30 (m, 1H), 4.35 (m, 1H), 3.81 (m, 1H), 3.74 (m, 1H), 3.68 (m, 1H), 3.43 (m, 1H), 2.87 (m, 1H), 2.66 (s, 3H), 2.40 (m, 2H), 1.58 (b, 1H), 1.48 (b, 1H), 1.35 (m, 3H), 1.18 (s, 3H), 1.13 (s, 3H), 0.87 (m, 6H) *Peaks between 1.8–2.1 ppm were not observed due to solvent suppression.

The proton chemical shift was assigned as follows:

| Position | Proton | Pattern |
|---|---|---|
| 1 | — |  |
| 2 | 2.40 | m |
| 3 | 4.35 | m |
| 4 | — |  |
| 5 | — |  |
| 6 | 3.43 | m |
| 7 | 3.68 | m |
| 8 | 1.58 | m |
| 9 | 1.35 | b |
| 10 | 1.48 | b |
| 10 | 1.35 | b |
| 11 | SSP |  |
| 12 | — |  |
| 13 | 2.87 | m |
| 14 | SSP |  |
| 15 | 5.30 | m |
| 16 | — |  |
| 17 | 6.43 | s |
| 18 | — |  |
| 19 | 7.30 | s |
| 20 | — |  |
| 21 | 2.66 | s |
| 22 | 1.18 | s |
| 23 | 0.87 | m |
| 24 | 3.81 | m |
| 24 | 3.74 | m |
| 25 | 0.87 | m |
| 26 | 1.13 | s |
| 27 | SSP |  |

*SSP: no observed due to solvent suppression.

Accordingly, the compositions and methods of the present invention are useful in producing known compounds that are microtubule-stabilizing agents as well as new compounds comprising epothilone analogs such as 24-hydroxyl-epothilone B (Formula A) and pharmaceutically acceptable salts thereof expected to be useful as microtubule-stabilizing agents. The microtubule stabilizing agents produced using these compositions and methods are useful in the treatment of a variety of cancers and other proliferative diseases including, but not limited to, the following:

carcinoma, including that of the bladder, breast, colon, kidney, liver, lung, ovary, pancreas, stomach, cervix, thyroid and skin; including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyoscarcoma;

other tumors, including melanoma, seminoma, tetratocarcinoma, neuroblastoma and glioma;

tumors of the central and peripheral nervous system, including astrocytoma, neuroblastoma, glioma, and schwannomas;

tumors of mesenchymal origin, including fibrosarcoma, rhabdomyosarcoma, and osteosarcoma; and other tumors, including melanoma, xenoderma pigmentosum, keratoactanthoma, seminoma, thyroid follicular cancer and teratocarcinoma.

Microtubule stabilizing agents produced using the compositions and methods of the present invention will also inhibit angiogenesis, thereby affecting the growth of tumors and providing treatment of tumors and tumor-related disorders. Such anti-angiogenesis properties of these compounds will also be useful in the treatment of other conditions responsive to anti-angiogenesis agents including, but not limited to, certain forms of blindness related to retinal vascularization, arthritis, especially inflammatory arthritis, multiple sclerosis, restinosis and psoriasis.

Microtubule stabilizing agents produced using the compositions and methods of the present invention will induce or inhibit apoptosis, a physiological cell death process critical for normal development and homeostasis. Alterations of apoptotic pathways contribute to the pathogenesis of a variety of human diseases. Compounds of the present invention such as those set forth in formula I and II and Formula A, as modulators of apoptosis, will be useful in the treatment of a variety of human diseases with aberrations in apoptosis including, but not limited to, cancer and precancerous lesions, immune response related diseases, viral infections, degenerative diseases of the musculoskeletal system and kidney disease.

Without wishing to be bound to any mechanism or morphology, microtubule stabilizing agents produced using the compositions and methods of the present invention may also be used to treat conditions other than cancer or other proliferative diseases. Such conditions include, but are not limited to viral infections such as herpesvirus, poxvirus, Epstein-Barr virus, Sindbis virus and adenovirus; autoimmune diseases such as systemic lupus erythematosus, immune mediated glomerulonephritis, rheumatoid arthritis, psoriasis, inflammatory bowel diseases and autoimmune diabetes mellitus; neurodegenerative disorders such as Alzheimer's disease, AIDS-related dementia, Parkinson's disease, amyotrophic lateral sclerosis, retinitis pigmentosa, spinal muscular atrophy and cerebellar degeneration; AIDS; myelodysplastic syndromes; aplastic anemia; ischemic injury associated myocardial infarctions; stroke and reperfusion injury; restenosis; arrhythmia; atherosclerosis; toxin-induced or alcohol induced liver diseases; hematological diseases such as chronic anemia and aplastic anemia; degenerative diseases of the musculoskeletal system such as osteoporosis and arthritis; aspirin-sensitive rhinosinusitis; cystic fibrosis; multiple sclerosis; kidney diseases; and cancer pain.

The following nonlimiting examples are provided to further illustrate the present invention.

EXAMPLES

Example 1

Reagents

R2 Medium was prepared as follows:

A solution containing sucrose (103 grams), $K_2SO_4$ (0.25 grams) $MgCl_2 \cdot 6H_2O$ (10.12 grams), glucose (10 grams), Difco Casaminoacids (0.1 grams) and distilled water (800 ml) was prepared. Eighty ml of this solution was then poured into a 200 ml screw capped bottle containing 2.2 grams Difco Bacto agar. The bottle was capped and autoclaved. At time of use, the medium was remelted and the following autoclaved solutions were added in the order listed:

1 ml $KH_2PO_4$ (0.5%)
8 ml $CaCl_2 \cdot 2H_2O$ (3.68%)
1.5 ml L-proline (20%)
10 ml TES buffer (5.73%, adjusted to pH 7.2)
0.2 ml Trace element solution containing $ZnCl_2$ (40 mg), $FeCl_3 \cdot 6H_2O$ (200 mg), $CuCl_2 \cdot 2H_2O$ (10 mg), $MnCl_2 \cdot 4H_2O$ (10 mg), $Na_2B_4O_7 \cdot 10H_2O$ (10 mg), and $(NH_4)_6Mo_7O_{24} \cdot H_2O$
0.5 ml NaOH (1N)(sterilization not required)
0.5 ml Required growth factors for auxotrophs (Histidine (50 μg/ml); Cysteine (37 μg/ml); adenine, guanine, thymidine and uracil (7.5 μg/ml); and Vitamins (0.5 μg/ml).

R2YE medium was prepared in the same fashion as R2 medium. However, 5 ml of Difco yeast extract (10%) was added to each 100 ml flask at time of use.

P (protoplast) buffer was prepared as follows:
A basal solution made up of the following was prepared:
Sucrose (103 grams)
$K_2SO_4$ (0.25 grams)
$MgCl_2 \cdot 6H_2O$ (2.02 grams)
Trace Element Solution as described for R2 medium (2 ml)
Distilled water to 800 ml Eighty ml aliquots of the basal solution were then dispensed and autoclaved. Before use, the following was added to each flask in the order listed:
1 ml $KH_2PO_4$ (0.5%)
10 ml $CaCl_2 \cdot 2H_2O$ (3.68%)
TES buffer (5.75%, adjusted to pH 7.2)

T (transformation) buffer was prepared by mixing the following sterile solutions:
25 ml Sucrose (10.3%)
75 ml distilled water
1 ml Trace Element Solution as described for R2 medium
1 ml $K_2SO_4$ (2.5%)

The following are then added to 9.3 mls of this solution:
0.2 ml $CaCl_2$ (5M)

0.5 ml Tris maleic acid buffer prepared from 1 M solution of Tris adjusted to pH 8.0 by adding maleic acid.

For use, 3 parts by volume of the above solution are added to 1 part by weight of PEG 1000, previously sterilized by autoclaving.

L (lysis) buffer was prepared by mixing the following sterile solutions:
100 ml Sucrose (10.3%)
10 ml TES buffer (5.73%, adjusted to pH 7.2)
1 ml $K_2SO_4$ (2.5%)
1 ml Trace Element Solution as described for R2 medium
1 ml $KH_2PO_4$ (0.5%)
0.1 ml $MgCl_2.6H_2O$ (2.5 M)
1 ml $CaCl_2$ (0.25 M)

CRM Medium

A solution containing the following components was prepared in 1 liter of $dH_2O$: glucose (10 grams), sucrose (103 grams), $MgCl_2.6H_2O$ (10.12 grams), BBL™ trypticase soy broth (15 grams) (Becton Dickinson Microbiology Systems, Sparks, Md., USA), and BBL™ yeast extract (5 grams) (Becton Dickinson Microbiology Systems). The solution was autoclaved for 30 minutes. Thiostrepton was added to a concentration of 10 µg/ml for cultures propagated with plasmids.

Electroporation Buffer

A solution containing 30% (wt/vol) PEG 1000, 10% glycerol, and 6.5% sucrose was prepared in $dH_2O$. The solution was sterilized by vacuum filtration through a 0.22 µm cellulose acetate filter.

Example 2

Extraction of Chromosomal DNA from Strain SC15847

Genomic DNA was isolated from an *Amycolatopsis orientalis* soil isolate strain designation SC15847 (ATCC PT-1043) using a guanidine-detergent lysis method, DNAzol reagent (Invitrogen, Carlsbad, Calif., USA). The SC15847 culture was grown 24 hours at 28° C. in F7 medium (glucose 2.2%, yeast extract 1.0%, malt extract 1.0%, peptone 0.1%, pH 7.0). Twenty ml of culture was harvested by centrifugation and resuspended in 20 ml of DNAzol, mixed by pipetting and centrifuged 10 minutes in the Beckman TJ6 centrifuge. Ten ml of 100% ethanol was added, inverted several times and stored at room temperature 3 minutes. The DNA was spooled on a glass pipette washed in 100% ethanol and allowed to air dry 10 minutes. The pellet was resuspended in 500 µl of 8 mM NaOH and once dissolved it was neutralized with 30 µl of 1M HEPES pH7.2.

Example 3

PCR Reactions

PCR reactions were prepared in a volume of 50 µl, containing 200–500 ng of genomic DNA or 1.0 µl of the cDNA, a forward and reverse primer, and the forward primer being either P450-1$^+$ (SEQ ID NO:23) or P450-1a$^+$ (SEQ ID NO:24) or P450-2$^+$ (SEQ ID NO:25) and the reverse primer P450-3$^-$ (SEQ ID NO:27) or P450-2$^-$ (SEQ ID NO:26). All primers were added to a final concentration of 1.4–2.0 µM. The PCR reaction was prepared with 1 µl of Taq enzyme (2.5 units) (Stratagene), 5 µl of Taq buffer and 4 µl of 2.5 mM of dNTPs with $dH_2O$ to 50 µl. The cycling reactions were performed on a Geneamp® PCR system with the following protocol: 95° C. for 5 minutes, 5 cycles [95° C. 30 seconds, 37° C. 15 seconds (30% ramp), 72° C. 30 seconds], 35 cycles (94° C. 30 seconds, 65° C. 15 seconds, 72° C. 30 seconds), 72° C. 7 minutes. The expected sizes for the reactions are 340 bp for the P450-1$^+$ (SEQ ID NO:23) or P450-1a$^+$ (SEQ ID NO:24) and P450-3$^-$ (SEQ ID NO:27) primer pairs, 240 bp for the P450-1$^+$ (SEQ ID NO:23) and P450-2$^-$ (SEQ ID NO:26) primer pairs and 130 bp for the P450-2$^+$ (SEQ ID NO:25) and P450-3$^-$ (SEQ ID NO:27) primer pairs.

Example 4

Cloning of Epothilone B Hydroxylase and Ferredoxin Genes

Twenty µg of SC15847 genomic DNA was digested with BglII restriction enzyme for 6 hours at 37° C. A 30k nanosep column (Gelman Sciences, Ann Arbor, Mich., USA) was used to concentrate the DNA and remove the enzyme and buffer. The reactions were concentrated to 40 µl and washed with 200 µl of TE. The digestion products were then separated a 0.7% agarose gel and genomic DNA in the range of 12~15 kb was excised from the gel and purified using the Qiagen gel extraction method. The genomic DNA was then ligated to plasmid pWB19N (U.S. Pat. No. 5,516,679), which had been digested with BamHI and dephosphorylated using the SAP I enzyme (Roche Molecular Biochemicals, Indianapolis, Ind., catalog#1 758 250). Ligation reactions were performed in a 15 µl volume with 1 U of T4 DNA ligase (Invitrogen) for 1 hour at room temperature. One µl of the ligation was transformed to 100 µl of chemically competent DH10B cells (Invitrogen) and 100 µl plated to five LB agar plates with 30 µg/ml of neomycin, 37° C. overnight.

Five nylon membrane circles (Roche Molecular Biochemicals, Indianapolis, Ind.) were numbered and marked for orientation. The membranes were placed on the plates 2 minutes and then allowed to dry for 5 minutes. The membranes were then placed on Whatman filter disks saturated with 10% SDS for 5 minutes, 0.5N NaOH with 1.5 M NaCl for 5 minutes, 1.5 M NaCl with 1.0 M Tris pH 8.0 for 5 minutes, and 15 minutes on 2×SSC. The filters were hybridized as described previously for the Southern hybridization. Hybridizing colonies were picked to 2 ml of TB with 30 µg/ml neomycin and grown overnight at 37° C. Plasmid DNA was isolated using a miniprep column procedure (Mo Bio). This plasmid was named NPB29-1.

Example 5

DNA Sequencing and Analysis

The cloned PCR products were sequenced using fluorescent-dye-labeled terminator cycle sequencing, Big-Dye sequencing kit (Applied Biosystems, Foster city, Calif., USA) and were analyzed using laser-induced fluorescence capillary electrophoresis, ABI Prism 310 sequencer (Applied Biosystems).

Example 6

Extraction of Total RNA

Total RNA was isolated from the SC15847 culture using a modification of the Chomczynski and Sacchi method with a mono-phasic solution of phenol and guanidine isothiocyanate, Trizol reagent (Invitrogen). Five ml of an SC15847 frozen stock culture was thawed and used to inoculate 100 ml of F7 media in a 500 ml Erlenmeyer flask. The culture was grown in a shaker incubator at 230 rpm, 30° C. for 20 hours to an optical density at 600 nm ($OD_{600}$) of 9.0. The culture was placed in a 16° C. shaker incubator at 230 rpm for 20 minutes. Fifty-five milligrams of epothilone B was dissolved in 1 ml of 100% ethanol and added to the culture. A second ml of ethanol was used to rinse the residual epothilone B from the tube and added to the culture. The culture was incubated at 16° C., 230 rpm for 30 hours. Thirty ml of the culture was transferred to a 50 ml tube, 150 mg of lysozyme was added to the culture and the culture was incubated 5 minutes at room temperature. Ten ml of the culture was placed in a 50 ml Falcon tube and centrifuged 5 minutes, 4° C. in a TJ6 centrifuge. Two ml of chloroform was added and the tube was mixed vigorously for 15 seconds. The tube was incubated 2 minutes at room temperature and centrifuged 10 minutes, top speed in the TJ6 centrifuge. The aqueous layer was transferred to a fresh tube and 2.5 ml of isopropanol was added to precipitate the RNA. The tube was incubated 10 minutes at room temperature and centrifuged 10 minutes, 4° C. The supernatant was removed, the pellet was rinsed with 70% ethanol and dried briefly under vacuum. The pellet was resuspended in 150 µl of RNase-free $dH_2O$. Fifty µl of 7.5M LiCl was added to the RNA and incubated at −20° C. for 30 minutes. The RNA was pelleted by centrifugation 10 minutes, 4° C. in a microcentrifuge. The pellet was rinsed with 200 µl of 70% ethanol, dried briefly under vacuum and resuspended in 150 µl of RNase free $dH_2O$.

The RNA was treated with DNaseI (Ambion, Austin, Tex., USA). Twenty-five µl of total RNA (5.3 µg/µl), 2.5 µl of DNaseI buffer, 1.0 µl of DNase I added and incubated at 37° C. for 25 minutes. Five µl of DNase I inactivation buffer added, incubated 2 minutes, centrifuged 1 minute, the supernatant was transferred to a fresh tube.

Example 7 cDNA Synthesis cDNA was synthesized from the total RNA using the Superscript II enzyme (Invitrogen). The reaction was prepared with 1 µl of total RNA (5.3 µg/µl), 9 µl of $dH_2O$, 1 µl of dNTP mix (10 mM), and 1 µl of random hexamers. The reaction was incubated at 65° C. for 5 minutes then placed on ice. The following components were then added: 4 µl of $1^{st}$ strand buffer, 1 µl of RNase Inhibitor, 2.0 µl of 0.1 M DTT, and 1 µl of Superscript II enzyme. The reaction was incubated at room temperature 10 minutes, 42° C. for 50 minutes and 70° C. for 15 minutes. One µl of RNaseH was added and incubated 20 minutes at 37° C., 15 minutes at 70° C. and stored at 4° C.

Example 8

DNA Labeling

The PCR conditions used to amplify the P450 specific products from genomic DNA and cDNA were used to amplify the insert of plasmid pCRscript-29. Plasmid pCRscript-29 contains a 340 bp PCR fragment amplified from SC15847 genomic DNA using primers P450 $1^+$ (SEQ ID NO:23) and P450 $3^-$ (SEQ ID NO:27). Two µl of the plasmid prep was used as a template, with a total of 25 cycles. The amplified product was gel purified using the Qiaquick gel extraction system (Qiagen). The extracted DNA was ethanol precipitated and resuspended in 5 µl of TE, the yield was estimated to be 500 ng. This fragment was labeled with digoxigenin using the chem link labeling reagent (Roche Molecular Biochemicals, Indianapolis, Ind. catalog #1 836 463). Five µl of the PCR product was mixed with 0.5 µl of Dig-chem link and $dH_2O$ added to 20 µl. The reaction was incubated 30 minutes at 85° C. and 5 µl of stop solution added. The probe concentration was estimated at 20 ng/µl.

Example 9

Southern DNA Hybridization

Ten µl of genomic DNA (0.5 µg/l) was digested with BamHI, BglII, EcoRI, HindIII or NotI and separated at 12 volts for 16 hours. The gel was depurinated 10 minutes in 0.25 N HCl and transferred by vacuum to a nylon membrane (Roche Molecular Biochemicals) in 0.4 N NaOH 5" Hg, 90 minutes using a vacuum blotter (Bio-Rad Laboratories, Inc. Hercules, Calif., USA catalog # 165-5000). The membrane was rinsed in 1 M ammonium acetate and UV-crosslinked using the Stratalinker UV Crosslinker (Stratagene). The membrane was rinsed in 2×SSC and stored at room temperature.

The membrane was prehybridized 1 hour at 42° C. in 20 ml of Dig Easy Hyb buffer (Roche Molecular Biochemicals). The probe was denatured 10 minutes at 65° C. and then placed on ice. Five ml of probe in Dig-Easy Hyb at an approximate concentration on 20 ng/ml was incubated with the membrane at 42° C. overnight. The membrane was washed 2 times in 2×SCC with 0.1% SDS at room temperature, then 2 times in 0.5×SSC with 0.1% SDS at 65° C. The membrane was equilibrated in Genius buffer 1 (10 mM maleic acid, 15 mM NaCl; pH 7.5; 0.3% v/v Tween 20) (Roche Molecular Biochemicals, Indianapolis, Ind.) for 2 minutes, then incubated with 2% blocking solution (2% Blocking reagent in Genius Buffer 1)(Roche Molecular Biochemicals Indianapolis, Ind.) for 1 hour at room temperature. The membrane was incubated with a 1:20,000 dilution of anti-dig antibody in 50 ml of blocking solution for 30 minutes. The membrane was washed 2 times, 15 minutes each in 50 ml of Genius buffer 1. The membrane was equilibrated for two minutes in Genius Buffer 3 (10 mM Tris-HCl, 10 mM NaCl; pH 9.5). One ml of a 1:100 dilution of CSPD (disodium 3-(4-methoxyspiro{1,2-dioxetane-3,2'-(5'-chloro)tricyclo[$3.3.1.1^{3,7}$]decan}-4-yl)phenyl phosphate) (Roche Molecular Biochemicals) in Genius buffer 3 was added to the membrane and incubated 5 minutes at room temperature, then placed at 37° C. for 15 minutes. The membrane was exposed to Biomax ML film (Kodak, Rochester, N.Y., USA) for 1 hour.

Example 10

E. coli Transformation

Competent cells were purchased from Invitrogen. E. coli strain DH10B was used as a host for genomic cloning. The chemically competent cells were thawed on ice and 100 µl aliquoted to a 17×100-mm polypropylene tube on ice. One µl of the ligation mixture was added to the cells and incubated on ice for 30 minutes. The cells were incubated at 42° C. for 45 seconds, then placed on ice 1–2 minutes. 0.9 ml pf SOC. medium (Invitrogen) was added and the cells were incubated one hour at 30–37° C. at 200–240 rpm. Cells were plated on a selective medium (Luria agar with neomycin or ampicillin at a concentration of 30 µg/ml or 100 µg/ml respectively).

Example 11

Transformation of Streptomyces lividans TK24

Plasmid pWB19N849 was constructed by digesting plasmid pWB19N with HindIII and treating with SAP I and digesting plasmid pANT849 (Keiser, et al., 2000, Practical *Streptomyces* Genetics, John Innes) with HindIII. The two linearized fragments were ligated 1 hour at room temperature with 1 U of T4 DNA ligase. One µl of the ligation reaction was used to transform XL-1 Blue electrocompetent cells (Stratagene). The recovered cells were plated to LB neomycin (30 µg/ml) overnight at 37° C. Colonies were picked to 2 ml of LB with 30 µg/ml neomycin and incubated overnight at 30° C. MoBio plasmid minipreps were performed on all cultures. Plasmids constructed from the ligation of pWB19N and pANT849 were determined by electrophoretic mobility on 0.7% agarose. The plasmid pWB19N849 was digested with HindIII and BglII to excise a 5.3 kb fragment equivalent to plasmid pANT849 digested with BglII and HindIII. This 5.3 kb fragment was purified on an agarose gel and extracted using the Qiaquick gel extraction system.

A 1.469 kb DNA fragment containing the epothilone B hydroxylase gene and the downstream ferredoxin gene was amplified using PCR. The 50 µl PCR reaction was composed of 5 µl of Taq buffer, 2.5 µl glycerol, 1 µl of 20 ng/µl NPB29-1 plasmid, 0.4 µl of 25 mM dNTPs, 1.0 µl each of primers NPB29-6F (SEQ ID NO:28) and NPB29-7R (SEQ ID NO:29) (5 pmole/µl), 38.1 µl of dH$_2$O and 0.5 µl of Taq enzyme (Stratagene). The reactions were performed on a Perkin Elmer 9700, 95° C. for 5 minutes, then 30 cycles (96° C. for 30 seconds, 60° C. 30 seconds, 72° C. for 2 minutes), and 72° C. for 7 minutes. The PCR product was purified using a Qiagen minielute column with the PCR cleanup procedure. The purified product was digested with BglII and HindIII and purified on a 0.7% agarose gel. A 1.469 kb band was excised from the gel and eluted using a Qiagen minielute column. Five µl of this PCR product was ligated with 2 µl of the BglII, HindIII digested pANT849 vector in a 10 µl ligation reaction. The reaction was incubated at room temperature for 24 hours and then transformed to *S. lividans* TK24 protoplasts.

Twenty ml of YEME media was inoculated with a frozen spore suspension of *S. lividans* TK24 and grown 48 hours in a 125 ml bi-indent flask. Protoplasts were prepared as described in Practical *Streptomyces* Genetics. The ligation reaction was mixed with protoplasts, then 500 µl of transformation buffer was added, followed immediately by 5 ml of P buffer. The transformation reactions were spun down 7 minutes at 2,750 rpm, resuspended in 100 µl of P buffer and plated to one R2YE plate. The plate was incubated at 28° C. for 20 hours then overlaid with 5 ml of LB 0.7% agar with 250 µg/ml thiostrepton. After 7 days colonies were picked to an R2YE grid plate with 50 µg/ml of thiostrepton. The colonies were grown an additional 5 days at 28° C., then stored at 4° C.

This recombinant microorganism has been deposited with the ATCC and designated PTA-4022.

Example 12

Transformation of Streptomyces rimosus

The procedure of Pigac and Schrempf Appl. Environ Microb., Vol. 61, No. 1, 352–356 (1995) was used to transform *S. rimosus*. *S. rimosus* strain R6 593 was cultivated in 20 ml of CRM medium at 30° C. on a rotary shaker (250 rpm). The cells were harvested at 24 hrs by centrifugation for 5 minutes, 5,000 rpm, 4° C., and resuspended in 20 ml of 10% sucrose, 4° C., and centrifuged for 5 minutes, 5,000 rpm, 4° C. The pellet was resuspended in 10 ml of 15% glycerol, 4° C. and centrifuged for 5 minutes, 5,000 rpm, 4° C. The pellet was resuspended in 2 ml of 15% glycerol, 4° C. with 100 µg/ml lysozyme and incubated at 37° C. for 30 minutes, centrifuged for 5 minutes, 5,000 rpm, 4° C. and resuspended in 2 ml of 15% glycerol, 4° C. The 15% glycerol wash was repeated once and the pellet was resuspended in 1 to 2 ml of Electroporation Buffer. The cells were stored at −80° C. in 50–200 µl aliquots.

The ligations were prepared as described for the *S. lividans* transformation. After the incubation of the ligation reaction, the volume was brought to 100 µl with dH$_2$O, NaCl was added to 0.3M, and the reaction extracted with an equal volume of 24:1:1 phenol:choroform isoamyl alcohol. Twenty µg of glycogen was added and the ligated DNA was precipitated with 2 volumes of 100% ethanol at −20° C. for 30 minutes. The DNA was pelleted 10 minutes in a microcentrifuge, washed once with 70% ethanol, dried 5 minutes in a speed-vac concentrator and resuspended in 5 µl of dH$_2$O.

One frozen aliquot of cells was thawed at room temperature and divided, 50 µl/tube for each DNA sample for electroporation. The cells were stored on ice until use. DNA in 1 to 2 µl of dH$_2$O was added and mixed. The cell and DNA mixture was transferred to a 2 mm gapped electrocuvette (Bio-Rad Laboratories, Richmond Calif. USA) that was pre-chilled on ice. The cells were electroporated at a setting of 2 kV (10 kV/cm), 25 µF, 400 Ω using a Gene Pulser™ (Bio-Rad Laboratories). The cells were diluted with 0.75 to 1.0 ml of CRM (0–4° C.), transferred to 15 ml culture tubes and incubated with agitation 3 hrs at 30° C. The cells were plated on trypticase soy broth agar plates with 10–30 µg/ml of thiostrepton.

Example 13

High Performance Liquid Chromatography

The liquid chromatography separation was performed using a Waters 2690 Separation Module system (Waters Corp., Milford, Mass., USA) and a column, 4.6×150 mm, filled with SymmetryShield RP$_8$, particle size 3.5 µm (Waters Corp., Milford, Mass., USA). The gradient mobile phase programming was used with a flow rate of 1.0 ml/minute. Eluent A was water/acetonitrile (20:1)+10 mM ammonium acetate. Eluent B was acetonitrile/water (20:1). The mobile phase was a linear gradient from 12% B to 28% B over 6 minutes and held isocratic at 28% B over 4 minutes. This was followed by a 28% B to 100% B linear gradient over 20 minutes and a linear gradient to 12% B over two minutes with a 3 minute hold at 12% B.

Example 14

Mass Spectrometry

The column effluent was introduced directly into the electrospray ion source of a ZMD mass spectrometer (Micromass, Manchester, UK). The instrument was calibrated-using Test Juice reference standard (Waters Corp, Milford, Mass., USA) and was delivered at a flow of 10 µl/minute from a syringe pump (Harvard Apparatus, Holliston, Mass., USA). The mass spectrometer was operated at a low mass resolution of 13.2 and a high mass resolution of 11.2. Spectra were acquired from using a scan range of m/z 100 to 600 at an acquisition rate of 10 spectra/second. The ionization technique employed was positive electrospray (ES). The sprayer voltage was kept at 2900 V and the cone voltage of the ion source was kept at a potential of 17 V.

Example 15

Use of the ebh Gene Sequence (SEQ ID NO:1) to Isolate Cytochrome P450 Genes from Other Microorganisms Genomic DNA was isolated from a set of cultures (ATCC43491, ATCC14930, ATCC53630, ATCC53550, ATCC39444, ATCC43333, ATCC35165) using the DNAzol reagent. The DNA was used as a template for PCR reactions using primers designed to the sequence of the ebh gene. Three sets of primers were used for amplification; NPB29-6f (SEQ ID NO:28) and NPB29-7r (SEQ ID NO:29), NPB29-16f (SEQ ID NO:50) and NPB29-17r (SEQ ID NO:51), and NPB29-19f (SEQ ID NO:52) and NPB29-20r (SEQ ID NO:53).

PCR reactions were prepared in a volume of 20 µl, containing 200–500 ng of genomic DNA and a forward and reverse primer. All primers were added to a final concentration of 1.4–2.0 µM. The PCR reaction was prepared with 0.2 µl of Advantage™ 2 Taq enzyme (BD Biosciences Clontech, Palo Alto, Calif., USA), 2 µl of Advantage™ 2 Taq buffer and 0.2 µl of 2.5 mM of dNTPs with dH$_2$O to 20 µl. The cycling reactions were performed on a Geneamp® 9700 PCR system or a Mastercycler® gradient (Eppendorf, Westbury, N.Y., USA) with the following protocol: 95° C. for 5 minutes, 35 cycles (96° C. 20 seconds, 54–69° C. 30 seconds, 72° C. 2 minutes), 72° C. for 7 minutes. The expected size of the PCR products is approximately 1469 bp for the NPB29-6f (SEQ ID NO:28) and NPB29-7r (SEQ ID NO:29) primer pair, 1034 bp for the NPB29-16f (SEQ ID NO:50) and NPB29-17r (SEQ ID NO:51) primer pair and 1318 bp for the NPB29-19f (SEQ ID NO:52) and NPB29-20r (SEQ ID NO:53) primer pair. The PCR reactions were analyzed on 0.7% agarose gels. PCR products of the expected size were excised from the gel and purified using the Qiagen gel extraction method. The purified products were sequenced using the Big-Dye sequencing kit and analyzed using an AB1310 sequencer.

Example 16

Construction of Plasmid pPCRscript-ebh

A 1.469 kb DNA fragment containing the epothilone B hydroxylase gene and the downstream ferredoxin gene was amplified using PCR. The 50 µl PCR reaction was composed of 5 µl of Taq buffer, 2.5 µl glycerol, 1 µl of 20 ng/µl NPB29-1 plasmid, 0.4 µl of 25 mM dNTPs, 1.0 µl each of primers NPB29-6f (SEQ ID NO:28) and NPB29-7r (SEQ ID NO:29) (5 pmole/µl), 38.1 µl of dH$_2$O and 0.5 µl of Taq enzyme (Stratagene). The reactions were performed on a Geneamp® 9700 PCR system, with the following conditions; 95° C. for 5 minutes, then 30 cycles (96° C. for 30 seconds, 60° C. 30 seconds, 72° C. for 2 minutes), and 72° C. for 7 minutes. The PCR product was purified using a Qiagen Qiaquick column with the PCR cleanup procedure. The purified product was digested with BglII and HindIII and purified on a 0.7% agarose gel. A 1.469 kb band was excised from the gel and eluted using a Qiagen Qiaquick gel extraction procedure. The fragments were then cloned into the pPCRscript Amp vector using the PCRscript Amp cloning kit. Colonies containing inserts were picked to 1–2 ml of LB (Luria Broth) with 100 µg/ml ampicillin, 30–37° C., 16–24 hours, 230–300 rpm. Plasmid isolation was performed using the Mo Bio miniplasmid prep kit. The sequence of the insert was confirmed by cycle sequencing with the Big-Dye sequencing kit. This plasmid was named pPCRscript-ebh.

Example 17

Mutagenesis of the ebh Gene for Improved Yield or Altered Specificity

The Quikchange® XL Site-Directed Mutagenesis Kit and the Quikchange® Multi Site-Directed Mutagenesis kit, both from Stratagene were used to introduce mutations in the coding region of the ebh gene. Both of these methods employ DNA primers 35–45 bases in length containing the desired mutation (SEQ ID NO:54–59 and 70), a methylated circular plasmid template and PfuTurbo® DNA Polymerase (U.S. Pat. Nos. 5,545,552 and 5,866,395 and 5,948,663) to generate copies of the plasmid template incorporating the mutation carried on the mutagenic primers. Subsequent digestion of the reaction with the restriction endonuclease enzyme DpnI, selectively digests the methylated plasmid template, but leaves the non-methylated mutated plasmid intact. The manufacturer's instructions were followed for all procedures with the exception of the DpnI digestion step in which the incubation time was increased from 1 hr to 3 hrs. The pPCRscript-ebh vector was used as the template for mutagenesis.

One to two µl of the reaction was transformed to either XL1-Blue® electrocompetent or XL10-Gold® ultracompetent cells (Stratagene). Cells were plated to a density of greater than 100 colonies per plate on LA (Luria Agar) 100 µg/ml ampicillin plates, and incubated 24–48 hrs at 30–37° C. The entire plate was resuspended in 5 ml of LB containing 100 µg/ml ampicillin. Plasmid was isolated directly from the resuspended cells by centrifuging the cells and then purifying the plasmid using the Mo Bio miniprep procedure. This plasmid was then used as a template for PCR with primers NPB29-6f (SEQ ID NO:28) and NPB29-7r (SEQ ID NO:29) to amplify a mutated expression cassette. Digestion of the 1.469 kb PCR product with the restriction enzymes BglII and HindIII was used to prepare this fragment for ligation to vector pANT849 also digested with BglII and HindIII. Alternatively, the resuspended cells were used to inoculate 20–50 ml of LB containing 100 µg/ml ampicillin and grown 18–24 hrs at 30–37° C. Qiagen midi-preps were performed on the cultures to isolate plasmid DNA containing the desired mutation. Digestion with the restriction enzymes BglII and HindIII was used to excise the mutated expression cassette for ligation to BglII and HindIII digested plasmid pANT849. Screening of mutants was performed in S. lividans or S. rimosus as described.

Alternatively, the method of Leung et al., Technique—A Journal of Methods in Cell and Molecular Biology, Vol. 1, No. 1, 11–15 (1989) was used to generate random mutation libraries of the ebh gene. Manganese and/or reduced dATP concentration is used to control the mutagenesis frequency of the Taq polymerase. The plasmid pCRscript-ebh was digested with NotI to linearize the plasmid. The Polymerase buffer was prepared with 0.166 M $(NH_4)_2SO_4$, 0.67M Tris-HCl pH 8.8, 61 mM $MgCl_2$, 67 µM EDTA pH8.0, 1.7 mg/ml Bovine Serum Albumin). The PCR reaction was prepared with 10 µl of Not I digested pCRscript-ebh (0.1 ng/µl), 10 µl of polymerase buffer, 1.0 µl of 1M β-mercaptoethanol, 10.0 µl of DMSO, 1.0 µl of NPB29-6f (SEQ ID NO:28) primer (100 pmole/µl), 1.0 µl of NPB29-7r (SEQ ID NO:29) primer (100 pmole/µl), 10 µl of 5 mM $MnCl_2$, 10.0 µl 10 mM dGTP, 10.0 µl 2 mM dATP, 10 mM dTTp, 10.0 µl Taq polymerase. $dH_2O$ was added to 100 µl. Reactions were also prepared as described above but without $MnCl_2$. The cycling reactions were performed a GeneAmp® PCR system with the following protocol: 95° C. for 1 minute, 55° C. for 30 seconds, 72° C. for 4 minutes), 72° C. for 7 minutes. The PCR reactions were separated on an agarose gel using a Qiagen spin column. The fragments were then digested with BglII and HindIII and purified using a Qiagen spin column. The purified fragments were then ligated to BglII and HindIII digested pANT849 plasmids. Screening of mutants was performed in S. lividans and S. rimousus.

Table of Characterized Mutants

| Mutant | Position | Substitution | Wild-type |
|---|---|---|---|
| ebh24-16 | 92 | Valine | Isoleucine |
|  | 237 | Alanine | Phenylalanine |
| ebh25-1 | 195 | Serine | Asparagine |
|  | 294 | Proline | Serine |
| ebh10-53 | 190 | Tyrosine | Phenylalanine |
|  | 231 | Arginine | Glutamic acid |
| ebh24-16d8 | 92 | Valine | Isoleucine |
|  | 237 | Alanine | Phenylalanine |
|  | 67 | Glutamine | Arginine |
| ebh24-16c11 | 92 | Valine | Isoleucine |
|  | 93 | Glycine | Alanine |
|  | 237 | Alanine | Phenylalanine |
|  | 365 | Threonine | Isoleucine |
| ebh24-16-16 | 92 | Valine | Isoleucine |
|  | 106 | Alanine | Valine |
|  | 237 | Alanine | Phenylalanine |
| ebh24-16-74 | 88 | Histidine | Arginine |
|  | 92 | Valine | Isoleucine |
|  | 237 | Alanine | Phenylalanine |
| ebh-M18 | 31 | Lysine | Glutamic acid |
|  | 176 | Valine | Methionine |
| ebh24-16g8 | 92 | Valine | Isoleucine |
|  | 237 | Alanine | Phenylalanine |
|  | 67 | Glutamine | Arginine |
|  | 130 | Threonine | Isoleucine |
|  | 176 | Alanine | Methionine |
| ebh24-16b9 | 92 | Valine | Isoleucine |
|  | 237 | Alanine | Phenylalanine |
|  | 67 | Glutamine | Arginine |
|  | 140 | Threonine | Alanine |
|  | 176 | Serine | Methionine |

Example 18

Comparison of Epothilone B Transformation in Cells Expressing ebh and Mutants Thereof In these experiments, twenty ml of YEME medium in a 125 ml bi-indented flask was inoculated with 200 µl of a frozen spore preparation of S. lividans TK24, S. lividans (pANT849-ebh), S. lividans (pANT849-ebh10-53) or S. lividans (pANT849-ebh24-16) and incubated 48 hours at 230 rpm, 30° C. Thiostrepton, 10 µg/ml was added to media inoculated with S. lividans (pANT849-ebh), S. lividans (pANT849-ebh10-53) and S. lividans (pANT849-ebh24-16). Four ml of culture was transferred to 20 ml of R5 medium in a 125 ml Erlenmeyer flask and incubated 18 hrs at 230 rpm, 30° C. Epothilone B in 100% EtOH was added to each culture to a final concentration of 0.05% weight/volume. Samples were taken at 0, 24, 48 and 72 hours with the exception of the S. lividans (pANT849-ebh24-16) culture, in which the epothilone B had been completely converted to epothilone F at 48 hours. The samples were analyzed by HPLC. Results were calculated as a percentage of the epothilone B at time 0 hours.

Epothilone B:

| Time (hours) | TK24 | pANT849-ebh | pANT849-ebh10-53 | pANT849-ebh24-16 |
|---|---|---|---|---|
| 0 | 100% | 100% | 100% | 100% |
| 24 | 99% | 78% | 69% | 56% |
| 48 | 87% | 19% | 39% | 0% |
| 72 | 87% | 0% | 3% | — |

Epothilone F:

| Time (hours) | TK24 | pANT849-ebh | pANT849-ebh10-53 | pANT849-ebh24-16 |
|---|---|---|---|---|
| 0 | 0% | 0% | 0% | 0% |
| 24 | 0% | 4% | 9% | 23% |
| 48 | 0% | 21% | 29% | 52% |
| 72 | 0% | 14% | 41% | — |

Alternatively, the bioconversion of epothilone B to epothilone F was performed in S. rimosus host cells transformed with expression plasmids containing the ebh gene and its variants or mutants. One-hundred µl of a frozen S. rimosus transformant culture was inoculated to 20 ml CRM media with 10 µg/ml thiostrepton 10 and cultivated 16–24 hr, 30° C., 230–300 rpm. Epothilone B in 100% ethanol was added to each culture to a final concentration of 0.05% weight/volume. The reaction was typically incubated 20–40 hrs at 30° C., 230–300 rpm. The concentration of epothilones B and F was determined by HPLC analysis.

Evaluation of Mutants in S. rimosus

| Mutant | Epothilone F yield |
|---|---|
| ebh-M18 | 55% |
| ebh24-16d8 | 75% |
| ebh24-16c11 | 75% |
| ebh24-16-16 | 75% |
| ebh24-16-74 | 75% |

-continued

| Mutant | Epothilone F yield |
|---|---|
| ebh24-16b9 | 80% |
| ebh24-16g8 | 85% |

Example 19

Biotransformation of Compactin to Pravastatin

Twenty ml of R2YE media with 10 µg/ml thiostrepton in a 125 ml flask was inoculated with 200 µl of a frozen spore preparation of *S. lividans* (pANT849), *S. lividans* (pANT849-ebh) and incubated 72 hours at 230 rpm, 28° C. Four ml of culture was inoculated to 20 ml of R2YE media and grown 24 hours at 230 rpm, 28° C. One ml of culture was transferred to a 15 ml polypropylene culture tube, 10 µl of compactin (40 mg/ml) was added to each culture and incubated for 24 hours, 28° C., 250 rpm. Five hundred µl of the culture broth was transferred to a fresh 15 ml polypropylene culture tube. Five hundred µl of 50 mM sodium hydroxide was added and vortexed. Three ml of methanol was added and vortexed, the tube was centrifuged 10 minutes at 3000 rpm in a TJ-6 table-top centrifuge. The organic phase was analyzed by HPLC. Compactin and pravastatin values were assessed relative to the control *S. lividans* (pANT849) culture.

Compactin and Pravastatin as a Percentage of Starting Compactin Concentration:

|  | *S. lividans* (pANT849) | *S. lividans* (pANT849-ebh) |
|---|---|---|
| Compactin | 36% | 11% |
| Pravastatin | 11% | 53% |

Example 20

High Performance Liquid Chromatography Method for Compactin and Pravastatin Detection The liquid chromatography separation was performed using a Hewlett Packard 1090 Series Separation system (Agilent Technologies, Palo Alto, Calif., USA) and a column, 50×46 mm, filled with Spherisorb ODS2, particle size 5 µM (Keystone Scientific, Inc, Bellefonte, Pa., USA). The gradient mobile phase programming was used with a flow rate of 2.0 ml/minute. Eluent A was water, 10 mM ammonium acetate and 0.05% Phosphoric Acid. Eluent B was acetonitrile. The mobile phase was a linear gradient from 20% B to 90% B over 4 minutes.

Example 21

Structure Determination of the Biotransformation Product of Mutant ebh25-1

Analytical HPLC was performed using a Hewlett Packard 1100 Series Liquid Chromatograph with a YMC Packed ODS-AQ column, 4.6 mm i.d.×15 cm 1. A gradient system of water (solvent A) and acetonitrile (solvent B) was used: 20% to 90% B linear gradient, 10 minutes; 90% to 20% linear gradient, 2 minutes. The flow rate was 1 ml/minute and UV detection was at 254 nm.

Preparative HPLC was performed using the following equipment and conditions:
Pump: Varian ProStar Solvent Delivery Module (Varian Inc., Palo Alto, Calif., USA). Detector: Gynkotek UVD340S.
Column: YMC ODS-A column (30 mmID×100 mm length, 5µ particle size).
Elution flow rate: 30 ml/minute
Elution gradient: (solvent A: water; solvent B: acetonitrile), 20% B, 2 minutes; 20% to 60% B linear gradient, 18 minutes; 60% B, 2 minutes; 60% to 90% B linear gradient, 1 minute; 90% B, 3 minutes; 90% to 20% B linear gradient, 2 minutes.
Detection: UV, 210 nm.

LC/NMR was performed as follows: 40 µl of sample was injected onto a YMC Packed ODS-AQ column (4.6 mm i.d.×15 cm 1). The column was eluted at 1 ml/minute flow rate with a gradient system of $D_2O$ (solvent A) and acetonitrile-$d_3$ (solvent B): 30% B, 1 minute; 30% to 80% B linear gradient, 11 minutes. The eluent passed a UV detection cell (monitored at 254 nm) before flowing through a F19/$H_1$NMR probe (60 µl active volume) in Varian AS-600 NMR spectrometer. The biotransformation product was eluted at around 7.5 minutes and the flow was stopped manually to allow the eluent to remain in the NMR probe for NMR data acquisition.

Isolation and analysis was performed as follows. The butanol/methanol extract (about 10 ml) was evaporated to dryness under nitrogen stream. One ml methanol was added to the residue (38 mg) and insoluble material was removed by centrifugation (13000 rpm, 2 min). 0.1 ml of the supernatant was used for LC/NMR study and the rest of 0.9 ml was subjected to the preparative HPLC (0.2–0.4 ml per injection). Two major peaks were observed and collected: peak A was eluted between 14 and 15 minutes, while peak B was eluted between 16.5 and 17.5 minutes. Analytical HPLC analysis indicated that peak B was the parent compound, epothilone B (Rt 8.5 minutes), and peak A was the biotransformation product (Rt 7.3 minutes). The peak A fractions were pooled and MS analysis data was obtained with the pooled fractions. The pooled fraction was evaporated to a small volume, then was lyophilized to give 3 mg of white solid. NMR and HPLC analysis of the white solid (dissolved in methanol) revealed that the biotransformation product was partially decomposed during the drying process.

APPENDIX 1

| Atom No. | Residue | Atom Name | X-coord | Y-coord | Z-coord |
|---|---|---|---|---|---|
| 1 | ALA9 | N | −39.918 | −4.913 | −1.651 |
| 2 | ALA9 | CA | −38.454 | −5.033 | −1.537 |
| 3 | ALA9 | C | −37.953 | −4.886 | −0.099 |
| 4 | ALA9 | O | −38.625 | −4.31 | 0.765 |
| 5 | ALA9 | CB | −37.809 | −3.967 | −2.415 |
| 6 | THR10 | N | −36.781 | −5.447 | 0.146 |
| 7 | THR10 | CA | −36.187 | −5.437 | 1.49 |
| 8 | THR10 | C | −34.916 | −4.585 | 1.553 |
| 9 | THR10 | O | −34.016 | −4.735 | 0.72 |
| 10 | THR10 | CB | −35.871 | −6.887 | 1.846 |
| 11 | THR10 | OG1 | −37.075 | −7.631 | 1.717 |
| 12 | THR10 | CG2 | −35.355 | −7.053 | 3.271 |
| 13 | LEU11 | N | −34.858 | −3.699 | 2.536 |
| 14 | LEU11 | CA | −33.669 | −2.853 | 2.745 |
| 15 | LEU11 | C | −32.511 | −3.649 | 3.353 |
| 16 | LEU11 | O | −32.706 | −4.468 | 4.259 |
| 17 | LEU11 | CB | −34.033 | −1.707 | 3.687 |
| 18 | LEU11 | CG | −35.079 | −0.78 | 3.078 |

APPENDIX 1-continued

| Atom No. | Residue | Atom Name | X-coord | Y-coord | Z-coord |
|---|---|---|---|---|---|
| 19 | LEU11 | CD1 | −35.53 | 0.265 | 4.091 |
| 20 | LEU11 | CD2 | −34.555 | −0.111 | 1.81 |
| 21 | PRO12 | N | −31.32 | −3.422 | 2.823 |
| 22 | PRO12 | CA | −30.121 | −4.119 | 3.302 |
| 23 | PRO12 | C | −29.652 | −3.606 | 4.663 |
| 24 | PRO12 | O | −29.656 | −2.397 | 4.918 |
| 25 | PRO12 | CB | −29.081 | −3.842 | 2.259 |
| 26 | PRO12 | CG | −29.597 | −2.771 | 1.309 |
| 27 | PRO12 | CD | −31.031 | −2.493 | 1.729 |
| 28 | LEU13 | N | −29.278 | −4.522 | 5.54 |
| 29 | LEU13 | CA | −28.676 | −4.118 | 6.819 |
| 30 | LEU13 | C | −27.183 | −3.88 | 6.627 |
| 31 | LEU13 | O | −26.449 | −4.806 | 6.267 |
| 32 | LEU13 | CB | −28.898 | −5.196 | 7.872 |
| 33 | LEU13 | CG | −30.374 | −5.354 | 8.217 |
| 34 | LEU13 | CD1 | −30.587 | −6.516 | 9.181 |
| 35 | LEU13 | CD2 | −30.945 | −4.067 | 8.802 |
| 36 | ALA14 | N | −26.72 | −2.741 | 7.112 |
| 37 | ALA14 | CA | −25.355 | −2.266 | 6.825 |
| 38 | ALA14 | C | −24.244 | −2.941 | 7.634 |
| 39 | ALA14 | O | −23.058 | −2.719 | 7.372 |
| 40 | ALA14 | CB | −25.311 | −0.764 | 7.075 |
| 41 | ARG15 | N | −24.628 | −3.792 | 8.569 |
| 42 | ARG15 | CA | −23.664 | −4.537 | 9.379 |
| 43 | ARG15 | C | −23.478 | −5.983 | 8.91 |
| 44 | ARG15 | O | −22.815 | −6.767 | 9.599 |
| 45 | ARG15 | CB | −24.174 | −4.519 | 10.81 |
| 46 | ARG15 | CG | −25.655 | −4.879 | 10.84 |
| 47 | ARG15 | CD | −26.2 | −4.843 | 12.26 |
| 48 | ARG15 | NE | −27.657 | −5.039 | 12.256 |
| 49 | ARG15 | CZ | −28.358 | −5.301 | 13.36 |
| 50 | ARG15 | NH1 | −29.69 | −5.376 | 13.3 |
| 51 | ARG15 | NH2 | −27.735 | −5.412 | 14.536 |
| 52 | LYS16 | N | −24.096 | −6.351 | 7.798 |
| 53 | LYS16 | CA | −24.016 | −7.741 | 7.335 |
| 54 | LYS16 | C | −22.639 | −8.128 | 6.807 |
| 55 | LYS16 | O | −21.959 | −7.359 | 6.115 |
| 56 | LYS16 | CB | −25.061 | −7.977 | 6.252 |
| 57 | LYS16 | CG | −26.466 | −7.985 | 6.839 |
| 58 | LYS16 | CD | −26.605 | −9.079 | 7.892 |
| 59 | LYS16 | CE | −28.002 | −9.092 | 8.499 |
| 60 | LYS16 | NZ | −28.113 | −10.128 | 9.537 |
| 61 | CYS17 | N | −22.317 | −9.392 | 7.036 |
| 62 | CYS17 | CA | −21.061 | −10.004 | 6.56 |
| 63 | CYS17 | C | −20.737 | −9.771 | 5.066 |
| 64 | CYS17 | O | −19.662 | −9.205 | 4.833 |
| 65 | CYS17 | CB | −21.096 | −11.501 | 6.864 |
| 66 | CYS17 | SG | −21.33 | −11.937 | 8.602 |
| 67 | PRO18 | N | −21.635 | −10.003 | 4.1 |
| 68 | PRO18 | CA | −21.293 | −9.756 | 2.683 |
| 69 | PRO18 | C | −21.123 | −8.291 | 2.246 |
| 70 | PRO18 | O | −21.013 | −8.061 | 1.036 |
| 71 | PRO18 | CB | −22.388 | −10.383 | 1.878 |
| 72 | PRO18 | CG | −23.509 | −10.812 | 2.802 |
| 73 | PRO18 | CD | −23.002 | −10.554 | 4.207 |
| 74 | PHE19 | N | −21.137 | −7.33 | 3.162 |
| 75 | PHE19 | CA | −20.792 | −5.947 | 2.834 |
| 76 | PHE19 | C | −19.279 | −5.777 | 2.788 |
| 77 | PHE19 | O | −18.789 | −4.92 | 2.036 |
| 78 | PHE19 | CB | −21.36 | −5.007 | 3.894 |
| 79 | PHE19 | CG | −22.8 | −4.568 | 3.654 |
| 80 | PHE19 | CD1 | −23.051 | −3.27 | 3.232 |
| 81 | PHE19 | CD2 | −23.856 | −5.444 | 3.867 |
| 82 | PHE19 | CE1 | −24.355 | −2.853 | 3.003 |
| 83 | PHE19 | CE2 | −25.159 | −5.03 | 3.629 |
| 84 | PHE19 | CZ | −25.409 | −3.735 | 3.197 |
| 85 | SER20 | N | −18.573 | −6.687 | 3.449 |
| 86 | SER20 | CA | −17.102 | −6.717 | 3.446 |
| 87 | SER20 | C | −16.569 | −7.839 | 4.342 |
| 88 | SER20 | O | −16.632 | −7.723 | 5.573 |
| 89 | SER20 | CB | −16.557 | −5.371 | 3.929 |
| 90 | SER20 | OG | −17.236 | −5.019 | 5.129 |
| 91 | PRO21 | N | −15.974 | −8.867 | 3.753 |
| 92 | PRO21 | CA | −15.978 | −9.134 | 2.304 |
| 93 | PRO21 | C | −17.267 | −9.836 | 1.856 |
| 94 | PRO21 | O | −18.026 | −10.327 | 2.702 |
| 95 | PRO21 | CB | −14.8 | −10.047 | 2.111 |
| 96 | PRO21 | CG | −14.442 | −10.669 | 3.455 |
| 97 | PRO21 | CD | −15.306 | −9.949 | 4.481 |
| 98 | PRO22 | N | −17.551 | −9.859 | 0.561 |
| 99 | PRO22 | CA | −16.897 | −9.007 | −0.445 |
| 100 | PRO22 | C | −17.4 | −7.575 | −0.296 |
| 101 | PRO22 | O | −18.341 | −7.371 | 0.469 |
| 102 | PRO22 | CB | −17.32 | −9.591 | −1.762 |
| 103 | PRO22 | CG | −18.478 | −10.549 | −1.528 |
| 104 | PRO22 | CD | −18.669 | −10.604 | −0.021 |
| 105 | PRO23 | N | −16.687 | −6.605 | −0.842 |
| 106 | PRO23 | CA | −17.224 | −5.241 | −0.897 |
| 107 | PRO23 | C | −18.525 | −5.21 | −1.693 |
| 108 | PRO23 | O | −18.524 | −5.083 | −2.925 |
| 109 | PRO23 | CB | −16.159 | −4.417 | −1.547 |
| 110 | PRO23 | CG | −15.004 | −5.321 | −1.95 |
| 111 | PRO23 | CD | −15.388 | −6.725 | −1.509 |
| 112 | GLU24 | N | −19.62 | −5.122 | −0.956 |
| 113 | GLU24 | CA | −20.963 | −5.192 | −1.547 |
| 114 | GLU24 | C | −21.415 | −3.843 | −2.088 |
| 115 | GLU24 | O | −22.323 | −3.794 | −2.93 |
| 116 | GLU24 | CB | −21.934 | −5.68 | −0.48 |
| 117 | GLU24 | CG | −23.27 | −6.137 | −1.052 |
| 118 | GLU24 | CD | −23.982 | −7.017 | −0.024 |
| 119 | GLU24 | OE1 | −24.613 | −7.981 | −0.433 |
| 120 | GLU24 | OE2 | −23.833 | −6.745 | 1.158 |
| 121 | TYR25 | N | −20.573 | −2.843 | −1.878 |
| 122 | TYR25 | CA | −20.842 | −1.47 | −2.303 |
| 123 | TYR25 | C | −20.704 | −1.311 | −3.816 |
| 124 | TYR25 | O | −21.364 | −0.436 | −4.385 |
| 125 | TYR25 | CB | −19.828 | −0.568 | −1.608 |
| 126 | TYR25 | CG | −19.616 | −0.882 | −0.128 |
| 127 | TYR25 | CD1 | −20.662 | −0.753 | 0.779 |
| 128 | TYR25 | CD2 | −18.364 | −1.298 | 0.311 |
| 129 | TYR25 | CE1 | −20.461 | −1.062 | 2.119 |
| 130 | TYR25 | CE2 | −18.163 | −1.605 | 1.65 |
| 131 | TYR25 | CZ | −19.213 | −1.492 | 2.55 |
| 132 | TYR25 | OH | −19.026 | −1.859 | 3.866 |
| 133 | GLU26 | N | −20.1 | −2.296 | −4.468 |
| 134 | GLU26 | CA | −20.009 | −2.293 | −5.928 |
| 135 | GLU26 | C | −21.404 | −2.483 | −6.52 |
| 136 | GLU26 | O | −21.92 | −1.572 | −7.177 |
| 137 | GLU26 | CB | −19.129 | −3.454 | −6.39 |
| 138 | GLU26 | CG | −17.813 | −3.593 | −5.628 |
| 139 | GLU26 | CD | −16.94 | −2.342 | −5.707 |
| 140 | GLU26 | OE1 | −16.345 | −2.12 | −6.749 |
| 141 | GLU26 | OE2 | −16.773 | −1.731 | −4.657 |
| 142 | ARG27 | N | −22.105 | −3.488 | −6.017 |
| 143 | ARG27 | CA | −23.437 | −3.805 | −6.538 |
| 144 | ARG27 | C | −24.504 | −2.909 | −5.921 |
| 145 | ARG27 | O | −25.496 | −2.591 | −6.59 |
| 146 | ARG27 | CB | −23.752 | −5.26 | −6.22 |
| 147 | ARG27 | CG | −22.7 | −6.189 | −6.812 |
| 148 | ARG27 | CD | −23.031 | −7.653 | −6.55 |
| 149 | ARG27 | NE | −23.146 | −7.926 | −5.108 |
| 150 | ARG27 | CZ | −22.251 | −8.648 | −4.428 |
| 151 | ARG27 | NH1 | −21.16 | −9.11 | −5.043 |
| 152 | ARG27 | NH2 | −22.428 | −8.879 | −3.126 |
| 153 | LEU28 | N | −24.197 | −2.331 | −4.771 |
| 154 | LEU28 | CA | −25.11 | −1.358 | −4.168 |
| 155 | LEU28 | C | −25.131 | −0.079 | −4.987 |
| 156 | LEU28 | O | −26.214 | 0.286 | −5.45 |
| 157 | LEU28 | CB | −24.67 | −1.039 | −2.746 |
| 158 | LEU28 | CG | −24.868 | −2.224 | −1.81 |
| 159 | LEU28 | CD1 | −24.303 | −1.916 | −0.43 |
| 160 | LEU28 | CD2 | −26.34 | −2.609 | −1.716 |
| 161 | ARG29 | N | −23.969 | 0.307 | −5.49 |
| 162 | ARG29 | CA | −23.835 | 1.502 | −6.327 |
| 163 | ARG29 | C | −24.521 | 1.334 | −7.677 |
| 164 | ARG29 | O | −25.271 | 2.226 | −8.096 |
| 165 | ARG29 | CB | −22.345 | 1.682 | −6.568 |
| 166 | ARG29 | CG | −21.997 | 2.947 | −7.336 |
| 167 | ARG29 | CD | −20.519 | 2.941 | −7.711 |
| 168 | ARG29 | NE | −19.696 | 2.563 | −6.551 |
| 169 | ARG29 | CZ | −18.945 | 1.459 | −6.523 |
| 170 | ARG29 | NH1 | −18.872 | 0.673 | −7.6 |
| 171 | ARG29 | NH2 | −18.265 | 1.145 | −5.421 |
| 172 | ARG30 | N | −24.494 | 0.109 | −8.182 |

APPENDIX 1-continued

| Atom No. | Residue | Atom Name | X-coord | Y-coord | Z-coord |
|---|---|---|---|---|---|
| 173 | ARG30 | CA | −25.112 | −0.208 | −9.475 |
| 174 | ARG30 | C | −26.629 | −0.386 | −9.407 |
| 175 | ARG30 | O | −27.282 | −0.429 | −10.455 |
| 176 | ARG30 | CB | −24.503 | −1.512 | −9.971 |
| 177 | ARG30 | CG | −22.992 | −1.401 | −10.1 |
| 178 | ARG30 | CD | −22.376 | −2.745 | −10.463 |
| 179 | ARG30 | NE | −20.909 | −2.659 | −10.479 |
| 180 | ARG30 | CZ | −20.12 | −3.648 | −10.054 |
| 181 | ARG30 | NH1 | −20.658 | −4.772 | −9.576 |
| 182 | ARG30 | NH2 | −18.793 | −3.508 | −10.099 |
| 183 | GLU31 | N | −27.194 | −0.493 | −8.215 |
| 184 | GLU31 | CA | −28.653 | −0.576 | −8.109 |
| 185 | GLU31 | C | −29.207 | 0.713 | −7.51 |
| 186 | GLU31 | O | −30.393 | 1.032 | −7.656 |
| 187 | GLU31 | CB | −29.025 | −1.746 | −7.203 |
| 188 | GLU31 | CG | −28.381 | −3.055 | −7.65 |
| 189 | GLU31 | CD | −28.814 | −3.443 | −9.061 |
| 190 | GLU31 | OE1 | −30.013 | −3.448 | −9.301 |
| 191 | GLU31 | OE2 | −27.961 | −3.944 | −9.782 |
| 192 | SER32 | N | −28.319 | 1.439 | −6.855 |
| 193 | SER32 | CA | −28.652 | 2.672 | −6.147 |
| 194 | SER32 | C | −27.386 | 3.393 | −5.683 |
| 195 | SER32 | O | −26.706 | 2.984 | −4.731 |
| 196 | SER32 | CB | −29.509 | 2.309 | −4.939 |
| 197 | SER32 | OG | −28.842 | 1.268 | −4.234 |
| 198 | PRO33 | N | −27.148 | 4.543 | −6.292 |
| 199 | PRO33 | CA | −26.039 | 5.408 | −5.869 |
| 200 | PRO33 | C | −26.227 | 5.972 | −4.454 |
| 201 | PRO33 | O | −25.241 | 6.254 | −3.758 |
| 202 | PRO33 | CB | −26.023 | 6.511 | −6.879 |
| 203 | PRO33 | CG | −27.203 | 6.364 | −7.829 |
| 204 | PRO33 | CD | −27.933 | 5.107 | −7.394 |
| 205 | VAL34 | N | −27.478 | 6.094 | −4.033 |
| 206 | VAL34 | CA | −27.83 | 6.472 | −2.661 |
| 207 | VAL34 | C | −28.828 | 5.447 | −2.122 |
| 208 | VAL34 | O | −30.01 | 5.467 | −2.487 |
| 209 | VAL34 | CB | −28.483 | 7.85 | −2.686 |
| 210 | VAL34 | CG1 | −28.789 | 8.339 | −1.275 |
| 211 | VAL34 | CG2 | −27.616 | 8.865 | −3.42 |
| 212 | SER35 | N | −28.344 | 4.546 | −1.286 |
| 213 | SER35 | CA | −29.186 | 3.438 | −0.802 |
| 214 | SER35 | C | −29.512 | 3.536 | 0.688 |
| 215 | SER35 | O | −28.615 | 3.692 | 1.521 |
| 216 | SER35 | CB | −28.456 | 2.126 | −1.077 |
| 217 | SER35 | OG | −27.19 | 2.169 | −0.43 |
| 218 | ARG36 | N | −30.785 | 3.413 | 1.025 |
| 219 | ARG36 | CA | −31.168 | 3.431 | 2.443 |
| 220 | ARG36 | C | −30.894 | 2.072 | 3.082 |
| 221 | ARG36 | O | −31.516 | 1.059 | 2.741 |
| 222 | ARG36 | CB | −32.645 | 3.779 | 2.597 |
| 223 | ARG36 | CG | −33.016 | 3.857 | 4.076 |
| 224 | ARG36 | CD | −34.513 | 4.047 | 4.295 |
| 225 | ARG36 | NE | −34.987 | 5.35 | 3.804 |
| 226 | ARG36 | CZ | −36.272 | 5.582 | 3.523 |
| 227 | ARG36 | NH1 | −37.16 | 4.59 | 3.609 |
| 228 | ARG36 | NH2 | −36.662 | 6.791 | 3.113 |
| 229 | VAL37 | N | −29.921 | 2.067 | 3.974 |
| 230 | VAL37 | CA | −29.543 | 0.855 | 4.695 |
| 231 | VAL37 | C | −29.982 | 0.926 | 6.152 |
| 232 | VAL37 | O | −30.313 | 1.995 | 6.684 |
| 233 | VAL37 | CB | −28.03 | 0.681 | 4.608 |
| 234 | VAL37 | CG1 | −27.591 | 0.391 | 3.177 |
| 235 | VAL37 | CG2 | −27.298 | 1.898 | 5.163 |
| 236 | GLY38 | N | −30.064 | −0.24 | 6.71 |
| 237 | GLY38 | CA | −30.404 | −0.332 | 8.18 |
| 238 | GLY38 | C | −29.151 | −0.563 | 9.016 |
| 239 | GLY38 | O | −28.562 | −1.652 | 9.003 |
| 240 | LEU39 | N | −28.764 | 0.463 | 9.75 |
| 241 | LEU39 | CA | −27.607 | 0.399 | 10.656 |
| 242 | LEU39 | C | −27.911 | −0.554 | 11.817 |
| 243 | LEU39 | O | −29.028 | −1.085 | 11.882 |
| 244 | LEU39 | CB | −27.353 | 1.814 | 11.187 |
| 245 | LEU39 | CG | −26.198 | 2.546 | 10.5 |
| 246 | LEU39 | CD1 | −26.368 | 2.665 | 8.988 |
| 247 | LEU39 | CD2 | −26.011 | 3.925 | 11.12 |
| 248 | PRO40 | N | −26.919 | −0.869 | 12.643 |
| 249 | PRO40 | CA | −27.183 | −1.62 | 13.875 |
| 250 | PRO40 | C | −28.423 | −1.116 | 14.614 |
| 251 | PRO40 | O | −28.771 | 0.073 | 14.574 |
| 252 | PRO40 | CB | −25.933 | −1.51 | 14.691 |
| 253 | PRO40 | CG | −24.84 | −0.886 | 13.837 |
| 254 | PRO40 | CD | −25.497 | −0.52 | 12.516 |
| 255 | SER41 | N | −29.188 | −2.109 | 15.042 |
| 256 | SER41 | CA | −30.511 | −1.986 | 15.686 |
| 257 | SER41 | C | −31.548 | −1.213 | 14.856 |
| 258 | SER41 | O | −32.379 | −0.492 | 15.419 |
| 259 | SER41 | CB | −30.387 | −1.382 | 17.087 |
| 260 | SER41 | OG | −30.036 | −0.008 | 17.001 |
| 261 | GLY42 | N | −31.474 | −1.34 | 13.539 |
| 262 | GLY42 | CA | −32.521 | −0.831 | 12.644 |
| 263 | GLY42 | C | −32.557 | 0.686 | 12.434 |
| 264 | GLY42 | O | −33.59 | 1.208 | 11.997 |
| 265 | GLN43 | N | −31.471 | 1.392 | 12.713 |
| 266 | GLN43 | CA | −31.501 | 2.847 | 12.494 |
| 267 | GLN43 | C | −31.201 | 3.16 | 11.025 |
| 268 | GLN43 | O | −30.079 | 2.955 | 10.551 |
| 269 | GLN43 | CB | −30.507 | 3.53 | 13.437 |
| 270 | GLN43 | CG | −30.681 | 5.05 | 13.439 |
| 271 | GLN43 | CD | −29.873 | 5.699 | 14.567 |
| 272 | GLN43 | OE1 | −30.31 | 6.682 | 15.184 |
| 273 | GLN43 | NE2 | −28.723 | 5.116 | 14.852 |
| 274 | THR44 | N | −32.227 | 3.582 | 10.304 |
| 275 | THR44 | CA | −32.096 | 3.832 | 8.859 |
| 276 | THR44 | C | −31.194 | 5.02 | 8.534 |
| 277 | THR44 | O | −31.231 | 6.071 | 9.187 |
| 278 | THR44 | CB | −33.475 | 4.077 | 8.258 |
| 279 | THR44 | OG1 | −34.009 | 5.268 | 8.823 |
| 280 | THR44 | CG2 | −34.428 | 2.923 | 8.551 |
| 281 | ALA45 | N | −30.35 | 4.799 | 7.541 |
| 282 | ALA45 | CA | −29.426 | 5.833 | 7.07 |
| 283 | ALA45 | C | −29.16 | 5.718 | 5.572 |
| 284 | ALA45 | O | −29.105 | 4.619 | 5.009 |
| 285 | ALA45 | CB | −28.115 | 5.705 | 7.836 |
| 286 | TRP46 | N | −28.989 | 6.859 | 4.931 |
| 287 | TRP46 | CA | −28.702 | 6.865 | 3.492 |
| 288 | TRP46 | C | −27.212 | 6.698 | 3.221 |
| 289 | TRP46 | O | −26.408 | 7.589 | 3.517 |
| 290 | TRP46 | CB | −29.185 | 8.173 | 2.881 |
| 291 | TRP46 | CG | −30.693 | 8.309 | 2.805 |
| 292 | TRP46 | CD1 | −31.509 | 9.009 | 3.665 |
| 293 | TRP46 | CD2 | −31.552 | 7.723 | 1.804 |
| 294 | TRP46 | NE1 | −32.788 | 8.894 | 3.228 |
| 295 | TRP46 | CE2 | −32.862 | 8.146 | 2.116 |
| 296 | TRP46 | CE3 | −31.324 | 6.922 | 0.701 |
| 297 | TRP46 | CZ2 | −33.913 | 7.774 | 1.295 |
| 298 | TRP46 | CZ3 | −32.389 | 6.538 | −0.105 |
| 299 | TRP46 | CH2 | −33.68 | 6.967 | 0.19 |
| 300 | ALA47 | N | −26.863 | 5.559 | 2.652 |
| 301 | ALA47 | CA | −25.475 | 5.257 | 2.302 |
| 302 | ALA47 | C | −25.153 | 5.708 | 0.882 |
| 303 | ALA47 | O | −25.772 | 5.272 | −0.1 |
| 304 | ALA47 | CB | −25.248 | 3.756 | 2.427 |
| 305 | LEU48 | N | −24.185 | 6.602 | 0.797 |
| 306 | LEU48 | CA | −23.751 | 7.129 | −0.501 |
| 307 | LEU48 | C | −22.648 | 6.252 | −1.067 |
| 308 | LEU48 | O | −21.546 | 6.197 | −0.511 |
| 309 | LEU48 | CB | −23.222 | 8.543 | −0.317 |
| 310 | LEU48 | CG | −24.27 | 9.464 | 0.289 |
| 311 | LEU48 | CD1 | −23.707 | 10.863 | 0.454 |
| 312 | LEU48 | CD2 | −25.524 | 9.515 | −0.569 |
| 313 | THR49 | N | −22.948 | 5.601 | −2.176 |
| 314 | THR49 | CA | −22.01 | 4.636 | −2.75 |
| 315 | THR49 | C | −21.197 | 5.214 | −3.907 |
| 316 | THR49 | O | −20.047 | 4.803 | −4.09 |
| 317 | THR49 | CB | −22.774 | 3.391 | −3.196 |
| 318 | THR49 | OG1 | −23.783 | 3.769 | −4.125 |
| 319 | THR49 | CG2 | −23.458 | 2.703 | −2.02 |
| 320 | ARG50 | N | −21.724 | 6.2 | −4.616 |
| 321 | ARG50 | CA | −20.899 | 6.838 | −5.665 |
| 322 | ARG50 | C | −20.007 | 7.927 | −5.081 |
| 323 | ARG50 | O | −20.456 | 8.712 | −4.234 |
| 324 | ARG50 | CB | −21.737 | 7.467 | −6.758 |
| 325 | ARG50 | CG | −22.426 | 6.441 | −7.639 |
| 326 | ARG50 | CD | −22.852 | 7.085 | −8.951 |

APPENDIX 1-continued

| Atom No. | Residue | Atom Name | X-coord | Y-coord | Z-coord |
|---|---|---|---|---|---|
| 327 | ARG50 | NE | −23.597 | 8.327 | −8.704 |
| 328 | ARG50 | CZ | −23.779 | 9.27 | −9.629 |
| 329 | ARG50 | NH1 | −24.462 | 10.375 | −9.326 |
| 330 | ARG50 | NH2 | −23.274 | 9.111 | −10.854 |
| 331 | LEU51 | N | −18.92 | 8.175 | −5.797 |
| 332 | LEU51 | CA | −17.931 | 9.19 | −5.399 |
| 333 | LEU51 | C | −18.52 | 10.584 | −5.583 |
| 334 | LEU51 | O | −18.42 | 11.426 | −4.682 |
| 335 | LEU51 | CB | −16.726 | 9.066 | −6.33 |
| 336 | LEU51 | CG | −15.377 | 9.193 | −5.621 |
| 337 | LEU51 | CD1 | −14.233 | 9.154 | −6.628 |
| 338 | LEU51 | CD2 | −15.267 | 10.433 | −4.746 |
| 339 | GLU52 | N | −19.404 | 10.68 | −6.562 |
| 340 | GLU52 | CA | −20.088 | 11.93 | −6.891 |
| 341 | GLU52 | C | −21.101 | 12.314 | −5.811 |
| 342 | GLU52 | O | −21.114 | 13.477 | −5.389 |
| 343 | GLU52 | CB | −20.821 | 11.759 | −8.229 |
| 344 | GLU52 | CG | −19.897 | 11.56 | −9.439 |
| 345 | GLU52 | CD | −19.749 | 10.09 | −9.853 |
| 346 | GLU52 | OE1 | −19.796 | 9.24 | −8.971 |
| 347 | GLU52 | OE2 | −19.502 | 9.849 | −11.025 |
| 348 | ASP53 | N | −21.659 | 11.313 | −5.146 |
| 349 | ASP53 | CA | −22.646 | 11.572 | −4.096 |
| 350 | ASP53 | C | −21.953 | 11.905 | −2.783 |
| 351 | ASP53 | O | −22.4 | 12.804 | −2.063 |
| 352 | ASP53 | CB | −23.493 | 10.322 | −3.876 |
| 353 | ASP53 | CG | −24.263 | 9.94 | −5.133 |
| 354 | ASP53 | OD1 | −24.319 | 8.749 | −5.405 |
| 355 | ASP53 | OD2 | −24.633 | 10.838 | −5.878 |
| 356 | ILE54 | N | −20.75 | 11.382 | −2.614 |
| 357 | ILE54 | CA | −19.991 | 11.62 | −1.387 |
| 358 | ILE54 | C | −19.301 | 12.976 | −1.41 |
| 359 | ILE54 | O | −19.36 | 13.7 | −0.409 |
| 360 | ILE54 | CB | −18.963 | 10.509 | −1.269 |
| 361 | ILE54 | CG1 | −19.674 | 9.167 | −1.252 |
| 362 | ILE54 | CG2 | −18.113 | 10.671 | −0.015 |
| 363 | ILE54 | CD1 | −18.677 | 8.03 | −1.365 |
| 364 | ARG55 | N | −18.916 | 13.43 | −2.592 |
| 365 | ARG55 | CA | −18.346 | 14.776 | −2.704 |
| 366 | ARG55 | C | −19.44 | 15.836 | −2.679 |
| 367 | ARG55 | O | −19.252 | 16.893 | −2.065 |
| 368 | ARG55 | CB | −17.551 | 14.883 | −3.998 |
| 369 | ARG55 | CG | −16.293 | 14.028 | −3.94 |
| 370 | ARG55 | CD | −15.498 | 14.133 | −5.235 |
| 371 | ARG55 | NE | −16.277 | 13.61 | −6.367 |
| 372 | ARG55 | CZ | −15.712 | 13.028 | −7.427 |
| 373 | ARG55 | NH1 | −14.383 | 12.947 | −7.513 |
| 374 | ARG55 | NH2 | −16.475 | 12.553 | −8.413 |
| 375 | GLU56 | N | −20.64 | 15.438 | −3.068 |
| 376 | GLU56 | CA | −21.795 | 16.331 | −2.984 |
| 377 | GLU56 | C | −22.287 | 16.444 | −1.539 |
| 378 | GLU56 | O | −22.628 | 17.546 | −1.095 |
| 379 | GLU56 | CB | −22.875 | 15.722 | −3.866 |
| 380 | GLU56 | CG | −24.103 | 16.605 | −4.028 |
| 381 | GLU56 | CD | −25.112 | 15.838 | −4.874 |
| 382 | GLU56 | OE1 | −25.906 | 16.463 | −5.56 |
| 383 | GLU56 | OE2 | −25.055 | 14.616 | −4.834 |
| 384 | MET57 | N | −22.065 | 15.392 | −0.767 |
| 385 | MET57 | CA | −22.379 | 15.386 | 0.665 |
| 386 | MET57 | C | −21.4 | 16.241 | 1.459 |
| 387 | MET57 | O | −21.827 | 17.091 | 2.248 |
| 388 | MET57 | CB | −22.242 | 13.948 | 1.141 |
| 389 | MET57 | CG | −22.423 | 13.805 | 2.646 |
| 390 | MET57 | SD | −21.979 | 12.184 | 3.306 |
| 391 | MET57 | CE | −20.221 | 12.196 | 2.89 |
| 392 | LEU58 | N | −20.14 | 16.197 | 1.056 |
| 393 | LEU58 | CA | −19.089 | 16.973 | 1.726 |
| 394 | LEU58 | C | −19.07 | 18.444 | 1.307 |
| 395 | LEU58 | O | −18.398 | 19.263 | 1.946 |
| 396 | LEU58 | CB | −17.751 | 16.327 | 1.389 |
| 397 | LEU58 | CG | −17.638 | 14.941 | 2.013 |
| 398 | LEU58 | CD1 | −16.504 | 14.133 | 1.394 |
| 399 | LEU58 | CD2 | −17.49 | 15.03 | 3.528 |
| 400 | SER59 | N | −19.807 | 18.776 | 0.261 |
| 401 | SER59 | CA | −19.959 | 20.171 | −0.144 |
| 402 | SER59 | C | −21.305 | 20.739 | 0.304 |
| 403 | SER59 | O | −21.531 | 21.951 | 0.204 |
| 404 | SER59 | CB | −19.852 | 20.24 | −1.661 |
| 405 | SER59 | OG | −18.59 | 19.697 | −2.022 |
| 406 | SER60 | N | −22.175 | 19.879 | 0.807 |
| 407 | SER60 | CA | −23.5 | 20.318 | 1.246 |
| 408 | SER60 | C | −23.505 | 20.806 | 2.685 |
| 409 | SER60 | O | −23.464 | 19.996 | 3.62 |
| 410 | SER60 | CB | −24.477 | 19.156 | 1.138 |
| 411 | SER60 | OG | −25.689 | 19.581 | 1.749 |
| 412 | PRO61 | N | −23.91 | 22.058 | 2.835 |
| 413 | PRO61 | CA | −24.023 | 22.695 | 4.154 |
| 414 | PRO61 | C | −25.231 | 22.233 | 4.983 |
| 415 | PRO61 | O | −25.41 | 22.7 | 6.113 |
| 416 | PRO61 | CB | −24.145 | 24.157 | 3.853 |
| 417 | PRO61 | CG | −24.401 | 24.343 | 2.364 |
| 418 | PRO61 | CD | −24.301 | 22.959 | 1.747 |
| 419 | HIS62 | N | −26.044 | 21.333 | 4.451 |
| 420 | HIS62 | CA | −27.21 | 20.856 | 5.18 |
| 421 | HIS62 | C | −26.949 | 19.497 | 5.813 |
| 422 | HIS62 | O | −27.863 | 18.935 | 6.427 |
| 423 | HIS62 | CB | −28.379 | 20.764 | 4.214 |
| 424 | HIS62 | CG | −28.703 | 22.084 | 3.55 |
| 425 | HIS62 | ND1 | −28.955 | 23.252 | 4.171 |
| 426 | HIS62 | CD2 | −28.796 | 22.32 | 2.198 |
| 427 | HIS62 | CE1 | −29.197 | 24.205 | 3.248 |
| 428 | HIS62 | NE2 | −29.098 | 23.627 | 2.029 |
| 429 | PHE63 | N | −25.765 | 18.945 | 5.596 |
| 430 | PHE63 | CA | −25.385 | 17.693 | 6.258 |
| 431 | PHE63 | C | −24.492 | 17.977 | 7.456 |
| 432 | PHE63 | O | −23.261 | 17.885 | 7.396 |
| 433 | PHE63 | CB | −24.686 | 16.783 | 5.262 |
| 434 | PHE63 | CG | −25.651 | 16.13 | 4.284 |
| 435 | PHE63 | CD1 | −26.92 | 15.76 | 4.71 |
| 436 | PHE63 | CD2 | −25.265 | 15.901 | 2.972 |
| 437 | PHE63 | CE1 | −27.804 | 15.161 | 3.824 |
| 438 | PHE63 | CE2 | −26.147 | 15.298 | 2.087 |
| 439 | PHE63 | CZ | −27.415 | 14.928 | 2.512 |
| 440 | SER64 | N | −25.159 | 18.211 | 8.569 |
| 441 | SER64 | CA | −24.502 | 18.656 | 9.795 |
| 442 | SER64 | C | −23.765 | 17.525 | 10.507 |
| 443 | SER64 | O | −24.07 | 16.34 | 10.339 |
| 444 | SER64 | CB | −25.587 | 19.225 | 10.7 |
| 445 | SER64 | OG | −24.96 | 19.785 | 11.84 |
| 446 | SER65 | N | −22.719 | 17.898 | 11.218 |
| 447 | SER65 | CA | −22.006 | 16.938 | 12.053 |
| 448 | SER65 | C | −22.463 | 17.032 | 13.513 |
| 449 | SER65 | O | −22.031 | 16.247 | 14.365 |
| 450 | SER65 | CB | −20.522 | 17.234 | 11.936 |
| 451 | SER65 | OG | −20.167 | 17.174 | 10.564 |
| 452 | ASP66 | N | −23.368 | 17.961 | 13.782 |
| 453 | ASP66 | CA | −23.901 | 18.186 | 15.122 |
| 454 | ASP66 | C | −25.388 | 18.496 | 14.919 |
| 455 | ASP66 | O | −25.978 | 18.026 | 13.938 |
| 456 | ASP66 | CB | −23.149 | 19.393 | 15.69 |
| 457 | ASP66 | CG | −22.904 | 19.311 | 17.192 |
| 458 | ASP66 | OD1 | −21.835 | 19.724 | 17.618 |
| 459 | ASP66 | OD2 | −23.871 | 19.048 | 17.899 |
| 460 | ARG67 | N | −25.972 | 19.246 | 15.842 |
| 461 | ARG67 | CA | −27.32 | 19.831 | 15.692 |
| 462 | ARG67 | C | −28.423 | 18.78 | 15.619 |
| 463 | ARG67 | O | −28.768 | 18.296 | 14.533 |
| 464 | ARG67 | CB | −27.384 | 20.684 | 14.423 |
| 465 | ARG67 | CG | −26.263 | 21.716 | 14.336 |
| 466 | ARG67 | CD | −26.329 | 22.778 | 15.428 |
| 467 | ARG67 | NE | −25.137 | 23.64 | 15.358 |
| 468 | ARG67 | CZ | −25.091 | 24.799 | 14.695 |
| 469 | ARG67 | NH1 | −26.189 | 25.28 | 14.107 |
| 470 | ARG67 | NH2 | −23.957 | 25.503 | 14.663 |
| 471 | GLN68 | N | −28.983 | 18.45 | 16.768 |
| 472 | GLN68 | CA | −30.127 | 17.538 | 16.79 |
| 473 | GLN68 | C | −31.414 | 18.348 | 16.65 |
| 474 | GLN68 | O | −31.728 | 19.187 | 17.503 |
| 475 | GLN68 | CB | −30.116 | 16.757 | 18.1 |
| 476 | GLN68 | CG | −31.207 | 15.692 | 18.12 |
| 477 | GLN68 | CD | −31.109 | 14.852 | 19.389 |
| 478 | GLN68 | OE1 | −31.941 | 14.973 | 20.296 |
| 479 | GLN68 | NE2 | −30.137 | 13.955 | 19.406 |
| 480 | SER69 | N | −32.129 | 18.102 | 15.565 |

APPENDIX 1-continued

| Atom No. | Residue | Atom Name | X-coord | Y-coord | Z-coord |
|---|---|---|---|---|---|
| 481 | SER69 | CA | −33.37 | 18.833 | 15.272 |
| 482 | SER69 | C | −34.444 | 18.558 | 16.32 |
| 483 | SER69 | O | −34.447 | 17.495 | 16.958 |
| 484 | SER69 | CB | −33.885 | 18.387 | 13.91 |
| 485 | SER69 | OG | −34.261 | 17.025 | 14.033 |
| 486 | PRO70 | N | −35.332 | 19.526 | 16.499 |
| 487 | PRO70 | CA | −36.438 | 19.385 | 17.447 |
| 488 | PRO70 | C | −37.244 | 18.122 | 17.171 |
| 489 | PRO70 | O | −37.547 | 17.795 | 16.018 |
| 490 | PRO70 | CB | −37.267 | 20.622 | 17.291 |
| 491 | PRO70 | CG | −36.6 | 21.547 | 16.285 |
| 492 | PRO70 | CD | −35.348 | 20.824 | 15.815 |
| 493 | SER71 | N | −37.424 | 17.369 | 18.245 |
| 494 | SER71 | CA | −38.115 | 16.065 | 18.289 |
| 495 | SER71 | C | −37.589 | 15.02 | 17.298 |
| 496 | SER71 | O | −38.378 | 14.228 | 16.769 |
| 497 | SER71 | CB | −39.625 | 16.244 | 18.111 |
| 498 | SER71 | OG | −39.919 | 16.638 | 16.777 |
| 499 | PHE72 | N | −36.282 | 14.985 | 17.081 |
| 500 | PHE72 | CA | −35.679 | 13.876 | 16.321 |
| 501 | PHE72 | C | −34.364 | 13.43 | 16.957 |
| 502 | PHE72 | O | −33.281 | 13.768 | 16.458 |
| 503 | PHE72 | CB | −35.428 | 14.283 | 14.872 |
| 504 | PHE72 | CG | −36.682 | 14.456 | 14.018 |
| 505 | PHE72 | CD1 | −37.097 | 15.724 | 13.63 |
| 506 | PHE72 | CD2 | −37.402 | 13.339 | 13.617 |
| 507 | PHE72 | CE1 | −38.238 | 15.875 | 12.853 |
| 508 | PHE72 | CE2 | −38.544 | 13.489 | 12.84 |
| 509 | PHE72 | CZ | −38.962 | 14.758 | 12.459 |
| 510 | PRO73 | N | −34.469 | 12.59 | 17.979 |
| 511 | PRO73 | CA | −33.31 | 12.19 | 18.786 |
| 512 | PRO73 | C | −32.522 | 11.027 | 18.18 |
| 513 | PRO73 | O | −32.606 | 9.895 | 18.668 |
| 514 | PRO73 | CB | −33.898 | 11.776 | 20.099 |
| 515 | PRO73 | CG | −35.392 | 11.555 | 19.917 |
| 516 | PRO73 | CD | −35.708 | 12.004 | 18.5 |
| 517 | LEU74 | N | −31.772 | 11.304 | 17.127 |
| 518 | LEU74 | CA | −30.933 | 10.263 | 16.521 |
| 519 | LEU74 | C | −29.707 | 9.976 | 17.375 |
| 520 | LEU74 | O | −29.08 | 10.892 | 17.926 |
| 521 | LEU74 | CB | −30.474 | 10.697 | 15.135 |
| 522 | LEU74 | CG | −31.627 | 10.794 | 14.146 |
| 523 | LEU74 | CD1 | −31.094 | 11.194 | 12.776 |
| 524 | LEU74 | CD2 | −32.381 | 9.471 | 14.05 |
| 525 | MET75 | N | −29.359 | 8.705 | 17.454 |
| 526 | MET75 | CA | −28.167 | 8.306 | 18.208 |
| 527 | MET75 | C | −27.099 | 7.808 | 17.243 |
| 528 | MET75 | O | −27.166 | 6.675 | 16.746 |
| 529 | MET75 | CB | −28.539 | 7.208 | 19.198 |
| 530 | MET75 | CG | −27.367 | 6.867 | 20.114 |
| 531 | MET75 | SD | −27.678 | 5.549 | 21.31 |
| 532 | MET75 | CE | −28.002 | 4.197 | 20.154 |
| 533 | VAL76 | N | −26.117 | 8.657 | 16.992 |
| 534 | VAL76 | CA | −25.071 | 8.327 | 16.017 |
| 535 | VAL76 | C | −24.274 | 7.103 | 16.455 |
| 536 | VAL76 | O | −23.953 | 6.925 | 17.636 |
| 537 | VAL76 | CB | −24.151 | 9.527 | 15.809 |
| 538 | VAL76 | CG1 | −24.904 | 10.676 | 15.149 |
| 539 | VAL76 | CG2 | −23.504 | 9.986 | 17.109 |
| 540 | ALA77 | N | −23.836 | 6.34 | 15.467 |
| 541 | ALA77 | CA | −23.158 | 5.062 | 15.727 |
| 542 | ALA77 | C | −21.703 | 5.203 | 16.177 |
| 543 | ALA77 | O | −21.033 | 4.194 | 16.42 |
| 544 | ALA77 | CB | −23.22 | 4.212 | 14.465 |
| 545 | ARG78 | N | −21.218 | 6.431 | 16.271 |
| 546 | ARG78 | CA | −19.868 | 6.689 | 16.762 |
| 547 | ARG78 | C | −19.868 | 7.178 | 18.215 |
| 548 | ARG78 | O | −18.816 | 7.163 | 18.865 |
| 549 | ARG78 | CB | −19.274 | 7.772 | 15.874 |
| 550 | ARG78 | CG | −19.445 | 7.436 | 14.398 |
| 551 | ARG78 | CD | −19.068 | 8.629 | 13.528 |
| 552 | ARG78 | NE | −19.848 | 9.81 | 13.932 |
| 553 | ARG78 | CZ | −19.36 | 11.053 | 13.921 |
| 554 | ARG78 | NH1 | −18.114 | 11.278 | 13.497 |
| 555 | ARG78 | NH2 | −20.12 | 12.072 | 14.33 |
| 556 | GLN79 | N | −21.028 | 7.577 | 18.722 |
| 557 | GLN79 | CA | −21.128 | 8.129 | 20.088 |
| 558 | GLN79 | C | −22.484 | 7.818 | 20.715 |
| 559 | GLN79 | O | −23.48 | 8.503 | 20.45 |
| 560 | GLN79 | CB | −20.937 | 9.651 | 20.09 |
| 561 | GLN79 | CG | −19.486 | 10.085 | 19.884 |
| 562 | GLN79 | CD | −19.353 | 11.607 | 19.931 |
| 563 | GLN79 | OE1 | −19.071 | 12.193 | 20.986 |
| 564 | GLN79 | NE2 | −19.508 | 12.226 | 18.773 |
| 565 | ILE80 | N | −22.504 | 6.806 | 21.562 |
| 566 | ILE80 | CA | −23.733 | 6.44 | 22.273 |
| 567 | ILE80 | C | −23.732 | 7.034 | 23.679 |
| 568 | ILE80 | O | −22.666 | 7.316 | 24.24 |
| 569 | ILE80 | CB | −23.847 | 4.919 | 22.333 |
| 570 | ILE80 | CG1 | −22.684 | 4.305 | 23.109 |
| 571 | ILE80 | CG2 | −23.905 | 4.35 | 20.92 |
| 572 | ILE80 | CD1 | −22.794 | 2.788 | 23.191 |
| 573 | ARG81 | N | −24.932 | 7.278 | 24.188 |
| 574 | ARG81 | CA | −25.15 | 7.84 | 25.535 |
| 575 | ARG81 | C | −24.657 | 9.276 | 25.691 |
| 576 | ARG81 | O | −23.493 | 9.571 | 25.411 |
| 577 | ARG81 | CB | −24.51 | 6.964 | 26.603 |
| 578 | ARG81 | CG | −25.437 | 5.843 | 27.046 |
| 579 | ARG81 | CD | −25.685 | 5.92 | 28.555 |
| 580 | ARG81 | NE | −26.269 | 7.22 | 28.93 |
| 581 | ARG81 | CZ | −25.651 | 8.095 | 29.722 |
| 582 | ARG81 | NH1 | −24.439 | 7.82 | 30.204 |
| 583 | ARG81 | NH2 | −26.234 | 9.257 | 30.008 |
| 584 | ARG82 | N | −25.448 | 10.076 | 26.389 |
| 585 | ARG82 | CA | −25.192 | 11.523 | 26.511 |
| 586 | ARG82 | C | −23.872 | 11.866 | 27.204 |
| 587 | ARG82 | O | −23.108 | 12.684 | 26.682 |
| 588 | ARG82 | CB | −26.32 | 12.122 | 27.333 |
| 589 | ARG82 | CG | −27.683 | 11.796 | 26.74 |
| 590 | ARG82 | CD | −28.801 | 12.301 | 27.643 |
| 591 | ARG82 | NE | −28.71 | 11.659 | 28.967 |
| 592 | ARG82 | CZ | −28.623 | 12.34 | 30.114 |
| 593 | ARG82 | NH1 | −28.477 | 11.689 | 31.271 |
| 594 | ARG82 | NH2 | −28.606 | 13.675 | 30.096 |
| 595 | GLU83 | N | −23.495 | 11.077 | 28.198 |
| 596 | GLU83 | CA | −22.237 | 11.334 | 28.909 |
| 597 | GLU83 | C | −21.03 | 10.69 | 28.227 |
| 598 | GLU83 | O | −19.894 | 10.902 | 28.657 |
| 599 | GLU83 | CB | −22.361 | 10.828 | 30.338 |
| 600 | GLU83 | CG | −23.385 | 11.651 | 31.114 |
| 601 | GLU83 | CD | −23.478 | 11.172 | 32.56 |
| 602 | GLU83 | OE1 | −23.428 | 9.967 | 32.761 |
| 603 | GLU83 | OE2 | −23.71 | 12.011 | 33.418 |
| 604 | ASP84 | N | −21.274 | 9.941 | 27.165 |
| 605 | ASP84 | CA | −20.201 | 9.327 | 26.386 |
| 606 | ASP84 | C | −20.095 | 10.012 | 25.024 |
| 607 | ASP84 | O | −19.257 | 9.646 | 24.19 |
| 608 | ASP84 | CB | −20.481 | 7.841 | 26.237 |
| 609 | ASP84 | CG | −20.585 | 7.191 | 27.613 |
| 610 | ASP84 | OD1 | −19.547 | 6.906 | 28.193 |
| 611 | ASP84 | OD2 | −21.704 | 7.048 | 28.092 |
| 612 | LYS85 | N | −20.939 | 11.017 | 24.831 |
| 613 | LYS85 | CA | −20.846 | 11.928 | 23.681 |
| 614 | LYS85 | C | −19.997 | 13.228 | 23.804 |
| 615 | LYS85 | O | −20.236 | 14.084 | 22.942 |
| 616 | LYS85 | CB | −22.27 | 12.347 | 23.327 |
| 617 | LYS85 | CG | −23.107 | 11.173 | 22.832 |
| 618 | LYS85 | CD | −24.573 | 11.567 | 22.679 |
| 619 | LYS85 | CE | −25.408 | 10.408 | 22.148 |
| 620 | LYS85 | NZ | −26.824 | 10.785 | 22.036 |
| 621 | PRO86 | N | −19.054 | 13.455 | 24.73 |
| 622 | PRO86 | CA | −18.316 | 14.731 | 24.698 |
| 623 | PRO86 | C | −17.168 | 14.8 | 23.679 |
| 624 | PRO86 | O | −16.339 | 15.713 | 23.772 |
| 625 | PRO86 | CB | −17.779 | 14.922 | 26.08 |
| 626 | PRO86 | CG | −17.866 | 13.6 | 26.815 |
| 627 | PRO86 | CD | −18.543 | 12.646 | 25.852 |
| 628 | PHE87 | N | −17.14 | 13.906 | 22.701 |
| 629 | PHE87 | CA | −16.12 | 13.963 | 21.653 |
| 630 | PHE87 | C | −16.67 | 14.817 | 20.51 |
| 631 | PHE87 | O | −15.963 | 15.16 | 19.559 |
| 632 | PHE87 | CB | −15.848 | 12.556 | 21.128 |
| 633 | PHE87 | CG | −15.724 | 11.449 | 22.174 |
| 634 | PHE87 | CD1 | −16.447 | 10.277 | 21.996 |

APPENDIX 1-continued

| Atom No. | Residue | Atom Name | X-coord | Y-coord | Z-coord |
|---|---|---|---|---|---|
| 635 | PHE87 | CD2 | −14.904 | 11.591 | 23.286 |
| 636 | PHE87 | CE1 | −16.358 | 9.254 | 22.93 |
| 637 | PHE87 | CE2 | −14.817 | 10.567 | 24.22 |
| 638 | PHE87 | CZ | −15.544 | 9.399 | 24.044 |
| 639 | ARG88 | N | −17.948 | 15.143 | 20.627 |
| 640 | ARG88 | CA | −18.629 | 16.037 | 19.686 |
| 641 | ARG88 | C | −18.178 | 17.519 | 19.7 |
| 642 | ARG88 | O | −18.118 | 18.064 | 18.59 |
| 643 | ARG88 | CB | −20.122 | 15.915 | 19.965 |
| 644 | ARG88 | CG | −20.964 | 16.678 | 18.953 |
| 645 | ARG88 | CD | −22.429 | 16.294 | 19.089 |
| 646 | ARG88 | NE | −22.593 | 14.851 | 18.868 |
| 647 | ARG88 | CZ | −23.307 | 14.07 | 19.679 |
| 648 | ARG88 | NH1 | −23.373 | 12.757 | 19.45 |
| 649 | ARG88 | NH2 | −23.922 | 14.598 | 20.739 |
| 650 | PRO89 | N | −17.919 | 18.194 | 20.826 |
| 651 | PRO89 | CA | −17.186 | 19.48 | 20.763 |
| 652 | PRO89 | C | −15.737 | 19.333 | 20.277 |
| 653 | PRO89 | O | −14.786 | 19.454 | 21.057 |
| 654 | PRO89 | CB | −17.206 | 20.033 | 22.154 |
| 655 | PRO89 | CG | −17.798 | 19.004 | 23.096 |
| 656 | PRO89 | CD | −18.208 | 17.832 | 22.224 |
| 657 | SER90 | N | −15.606 | 19.29 | 18.963 |
| 658 | SER90 | CA | −14.334 | 19.04 | 18.296 |
| 659 | SER90 | C | −14.43 | 19.413 | 16.824 |
| 660 | SER90 | O | −15.534 | 19.592 | 16.293 |
| 661 | SER90 | CB | −14.069 | 17.55 | 18.375 |
| 662 | SER90 | OG | −15.095 | 16.928 | 17.609 |
| 663 | LEU91 | N | −13.326 | 19.173 | 16.14 |
| 664 | LEU91 | CA | −13.154 | 19.564 | 14.737 |
| 665 | LEU91 | C | −14.042 | 18.804 | 13.745 |
| 666 | LEU91 | O | −14.491 | 19.39 | 12.754 |
| 667 | LEU91 | CB | −11.702 | 19.238 | 14.405 |
| 668 | LEU91 | CG | −11.325 | 19.637 | 12.988 |
| 669 | LEU91 | CD1 | −11.253 | 21.153 | 12.877 |
| 670 | LEU91 | CD2 | −9.989 | 19.012 | 12.606 |
| 671 | ILE92 | N | −14.422 | 17.582 | 14.076 |
| 672 | ILE92 | CA | −15.199 | 16.791 | 13.12 |
| 673 | ILE92 | C | −16.712 | 16.857 | 13.368 |
| 674 | ILE92 | O | −17.487 | 16.497 | 12.474 |
| 675 | ILE92 | CB | −14.682 | 15.351 | 13.173 |
| 676 | ILE92 | CG1 | −15.288 | 14.488 | 12.07 |
| 677 | ILE92 | CG2 | −14.932 | 14.719 | 14.539 |
| 678 | ILE92 | CD1 | −14.775 | 13.055 | 12.137 |
| 679 | ALA93 | N | −17.14 | 17.407 | 14.494 |
| 680 | ALA93 | CA | −18.578 | 17.414 | 14.759 |
| 681 | ALA93 | C | −19.15 | 18.822 | 14.872 |
| 682 | ALA93 | O | −20.335 | 19.048 | 14.589 |
| 683 | ALA93 | CB | −18.865 | 16.593 | 16.004 |
| 684 | MET94 | N | −18.294 | 19.776 | 15.191 |
| 685 | MET94 | CA | −18.739 | 21.168 | 15.216 |
| 686 | MET94 | C | −18.99 | 21.683 | 13.811 |
| 687 | MET94 | O | −18.221 | 21.436 | 12.88 |
| 688 | MET94 | CB | −17.695 | 22.042 | 15.893 |
| 689 | MET94 | CG | −17.822 | 21.982 | 17.407 |
| 690 | MET94 | SD | −16.686 | 23.058 | 18.31 |
| 691 | MET94 | CE | −17.561 | 23.095 | 19.891 |
| 692 | ASP95 | N | −20.089 | 22.398 | 13.672 |
| 693 | ASP95 | CA | −20.42 | 23.024 | 12.393 |
| 694 | ASP95 | C | −19.831 | 24.427 | 12.371 |
| 695 | ASP95 | O | −19.589 | 25.001 | 13.438 |
| 696 | ASP95 | CB | −21.938 | 23.082 | 12.258 |
| 697 | ASP95 | CG | −22.52 | 21.677 | 12.373 |
| 698 | ASP95 | OD1 | −22.276 | 20.87 | 11.484 |
| 699 | ASP95 | OD2 | −23.173 | 21.412 | 13.37 |
| 700 | PRO96 | N | −19.488 | 24.936 | 11.201 |
| 701 | PRO96 | CA | −19.076 | 26.343 | 11.099 |
| 702 | PRO96 | C | −20.177 | 27.263 | 11.641 |
| 703 | PRO96 | O | −21.353 | 26.892 | 11.581 |
| 704 | PRO96 | CB | −18.812 | 26.567 | 9.64 |
| 705 | PRO96 | CG | −19.078 | 25.278 | 8.875 |
| 706 | PRO96 | CD | −19.352 | 24.256 | 9.905 |
| 707 | PRO97 | N | −19.817 | 28.38 | 12.263 |
| 708 | PRO97 | CA | −18.428 | 28.85 | 12.436 |
| 709 | PRO97 | C | −17.649 | 28.271 | 13.631 |
| 710 | PRO97 | O | −16.462 | 28.595 | 13.772 |
| 711 | PRO97 | CB | −18.567 | 30.329 | 12.615 |
| 712 | PRO97 | CG | −20.013 | 30.649 | 12.964 |
| 713 | PRO97 | CD | −20.777 | 29.345 | 12.804 |
| 714 | GLU98 | N | −18.233 | 27.353 | 14.389 |
| 715 | GLU98 | CA | −17.555 | 26.761 | 15.556 |
| 716 | GLU98 | C | −16.353 | 25.946 | 15.099 |
| 717 | GLU98 | O | −15.224 | 26.174 | 15.555 |
| 718 | GLU98 | CB | −18.513 | 25.782 | 16.223 |
| 719 | GLU98 | CG | −19.894 | 26.372 | 16.474 |
| 720 | GLU98 | CD | −20.857 | 25.236 | 16.811 |
| 721 | GLU98 | OE1 | −20.697 | 24.171 | 16.227 |
| 722 | GLU98 | OE2 | −21.799 | 25.49 | 17.544 |
| 723 | HIS99 | N | −16.575 | 25.223 | 14.013 |
| 724 | HIS99 | CA | −15.52 | 24.448 | 13.359 |
| 725 | HIS99 | C | −14.43 | 25.323 | 12.743 |
| 726 | HIS99 | O | −13.249 | 24.993 | 12.887 |
| 727 | HIS99 | CB | −16.19 | 23.646 | 12.252 |
| 728 | HIS99 | CG | −15.238 | 23.09 | 11.22 |
| 729 | HIS99 | ND1 | −14.522 | 21.957 | 11.317 |
| 730 | HIS99 | CD2 | −14.946 | 23.649 | 9.998 |
| 731 | HIS99 | CE1 | −13.779 | 21.805 | 10.203 |
| 732 | HIS99 | NE2 | −14.042 | 22.852 | 9.39 |
| 733 | GLY100 | N | −14.792 | 26.524 | 12.322 |
| 734 | GLY100 | CA | −13.832 | 27.439 | 11.702 |
| 735 | GLY100 | C | −12.859 | 27.944 | 12.756 |
| 736 | GLY100 | O | −11.648 | 27.716 | 12.64 |
| 737 | LYS101 | N | −13.419 | 28.385 | 13.872 |
| 738 | LYS101 | CA | −12.626 | 28.895 | 14.993 |
| 739 | LYS101 | C | −11.711 | 27.823 | 15.579 |
| 740 | LYS101 | O | −10.485 | 28.02 | 15.622 |
| 741 | LYS101 | CB | −13.608 | 29.33 | 16.07 |
| 742 | LYS101 | CG | −12.893 | 29.892 | 17.291 |
| 743 | LYS101 | CD | −13.829 | 29.939 | 18.492 |
| 744 | LYS101 | CE | −14.189 | 28.531 | 18.955 |
| 745 | LYS101 | NZ | −12.986 | 27.796 | 19.381 |
| 746 | ALA102 | N | −12.251 | 26.624 | 15.738 |
| 747 | ALA102 | CA | −11.474 | 25.523 | 16.313 |
| 748 | ALA102 | C | −10.381 | 25.022 | 15.373 |
| 749 | ALA102 | O | −9.243 | 24.859 | 15.828 |
| 750 | ALA102 | CB | −12.425 | 24.379 | 16.645 |
| 751 | ARG103 | N | −10.622 | 25.091 | 14.074 |
| 752 | ARG103 | CA | −9.63 | 24.64 | 13.097 |
| 753 | ARG103 | C | −8.492 | 25.644 | 12.958 |
| 754 | ARG103 | O | −7.325 | 25.236 | 13.033 |
| 755 | ARG103 | CB | −10.347 | 24.476 | 11.762 |
| 756 | ARG103 | CG | −9.496 | 23.785 | 10.705 |
| 757 | ARG103 | CD | −10.366 | 23.455 | 9.496 |
| 758 | ARG103 | NE | −9.651 | 22.682 | 8.467 |
| 759 | ARG103 | CZ | −9.807 | 21.367 | 8.287 |
| 760 | ARG103 | NH1 | −10.493 | 20.645 | 9.175 |
| 761 | ARG103 | NH2 | −9.174 | 20.755 | 7.285 |
| 762 | ARG104 | N | −8.811 | 26.923 | 13.087 |
| 763 | ARG104 | CA | −7.775 | 27.957 | 13.006 |
| 764 | ARG104 | C | −6.906 | 27.966 | 14.256 |
| 765 | ARG104 | O | −5.675 | 28.083 | 14.149 |
| 766 | ARG104 | CB | −8.442 | 29.316 | 12.84 |
| 767 | ARG104 | CG | −9.166 | 29.412 | 11.502 |
| 768 | ARG104 | CD | −9.828 | 30.772 | 11.319 |
| 769 | ARG104 | NE | −10.874 | 30.999 | 12.329 |
| 770 | ARG104 | CZ | −11.061 | 32.171 | 12.941 |
| 771 | ARG104 | NH1 | −10.231 | 33.188 | 12.701 |
| 772 | ARG104 | NH2 | −12.048 | 32.31 | 13.829 |
| 773 | ASP105 | N | −7.5 | 27.625 | 15.388 |
| 774 | ASP105 | CA | −6.718 | 27.493 | 16.616 |
| 775 | ASP105 | C | −5.828 | 26.253 | 16.594 |
| 776 | ASP105 | O | −4.602 | 26.392 | 16.716 |
| 777 | ASP105 | CB | −7.67 | 27.427 | 17.806 |
| 778 | ASP105 | CG | −8.198 | 28.814 | 18.165 |
| 779 | ASP105 | OD1 | −7.389 | 29.588 | 18.666 |
| 780 | ASP105 | OD2 | −9.411 | 28.938 | 18.257 |
| 781 | VAL106 | N | −6.379 | 25.125 | 16.173 |
| 782 | VAL106 | CA | −5.636 | 23.86 | 16.236 |
| 783 | VAL106 | C | −4.51 | 23.761 | 15.214 |
| 784 | VAL106 | O | −3.414 | 23.348 | 15.612 |
| 785 | VAL106 | CB | −6.611 | 22.703 | 16.046 |
| 786 | VAL106 | CG1 | −5.886 | 21.37 | 15.89 |
| 787 | VAL106 | CG2 | −7.587 | 22.637 | 17.212 |
| 788 | VAL107 | N | −4.641 | 24.427 | 14.075 |

APPENDIX 1-continued

| Atom No. | Residue | Atom Name | X-coord | Y-coord | Z-coord |
|---|---|---|---|---|---|
| 789 | VAL107 | CA | -3.565 | 24.397 | 13.071 |
| 790 | VAL107 | C | -2.362 | 25.259 | 13.474 |
| 791 | VAL107 | O | -1.225 | 24.918 | 13.123 |
| 792 | VAL107 | CB | -4.142 | 24.869 | 11.737 |
| 793 | VAL107 | CG1 | -3.06 | 25.104 | 10.687 |
| 794 | VAL107 | CG2 | -5.175 | 23.879 | 11.213 |
| 795 | GLY108 | N | -2.576 | 26.155 | 14.426 |
| 796 | GLY108 | CA | -1.49 | 26.985 | 14.953 |
| 797 | GLY108 | C | -0.511 | 26.183 | 15.813 |
| 798 | GLY108 | O | 0.685 | 26.491 | 15.837 |
| 799 | GLU109 | N | -1.006 | 25.191 | 16.537 |
| 800 | GLU109 | CA | -0.109 | 24.388 | 17.376 |
| 801 | GLU109 | C | 0.121 | 22.976 | 16.836 |
| 802 | GLU109 | O | 1.086 | 22.311 | 17.229 |
| 803 | GLU109 | CB | -0.677 | 24.35 | 18.784 |
| 804 | GLU109 | CG | -0.577 | 25.728 | 19.424 |
| 805 | GLU109 | CD | 0.886 | 26.1 | 19.659 |
| 806 | GLU109 | OE1 | 1.612 | 25.244 | 20.147 |
| 807 | GLU109 | OE2 | 1.22 | 27.255 | 19.442 |
| 808 | PHE110 | N | -0.686 | 22.572 | 15.873 |
| 809 | PHE110 | CA | -0.511 | 21.269 | 15.221 |
| 810 | PHE110 | C | 0.017 | 21.468 | 13.798 |
| 811 | PHE110 | O | -0.547 | 20.963 | 12.819 |
| 812 | PHE110 | CB | -1.866 | 20.568 | 15.206 |
| 813 | PHE110 | CG | -1.834 | 19.088 | 14.838 |
| 814 | PHE110 | CD1 | -0.842 | 18.264 | 15.352 |
| 815 | PHE110 | CD2 | -2.808 | 18.564 | 13.998 |
| 816 | PHE110 | CE1 | -0.819 | 16.915 | 15.019 |
| 817 | PHE110 | CE2 | -2.784 | 17.216 | 13.665 |
| 818 | PHE110 | CZ | -1.79 | 16.392 | 14.176 |
| 819 | THR111 | N | 1.103 | 22.217 | 13.706 |
| 820 | THR111 | CA | 1.68 | 22.585 | 12.409 |
| 821 | THR111 | C | 2.353 | 21.411 | 11.71 |
| 822 | THR111 | O | 2.846 | 20.47 | 12.346 |
| 823 | THR111 | CB | 2.745 | 23.65 | 12.628 |
| 824 | THR111 | OG1 | 3.887 | 23.019 | 13.193 |
| 825 | THR111 | CG2 | 2.27 | 24.756 | 13.561 |
| 826 | VAL112 | N | 2.564 | 21.605 | 10.417 |
| 827 | VAL112 | CA | 3.302 | 20.63 | 9.605 |
| 828 | VAL112 | C | 4.802 | 20.712 | 9.887 |
| 829 | VAL112 | O | 5.492 | 19.689 | 9.86 |
| 830 | VAL112 | CB | 3.026 | 20.929 | 8.134 |
| 831 | VAL112 | CG1 | 3.819 | 20.01 | 7.21 |
| 832 | VAL112 | CG2 | 1.535 | 20.833 | 7.832 |
| 833 | LYS113 | N | 5.227 | 21.845 | 10.425 |
| 834 | LYS113 | CA | 6.608 | 22.003 | 10.884 |
| 835 | LYS113 | C | 6.892 | 21.096 | 12.082 |
| 836 | LYS113 | O | 7.864 | 20.332 | 12.044 |
| 837 | LYS113 | CB | 6.795 | 23.456 | 11.298 |
| 838 | LYS113 | CG | 8.168 | 23.696 | 11.914 |
| 839 | LYS113 | CD | 8.232 | 25.064 | 12.582 |
| 840 | LYS113 | CE | 7.189 | 25.184 | 13.692 |
| 841 | LYS113 | NZ | 7.407 | 24.178 | 14.747 |
| 842 | ARG114 | N | 5.945 | 21.013 | 13.008 |
| 843 | ARG114 | CA | 6.085 | 20.094 | 14.141 |
| 844 | ARG114 | C | 6.098 | 18.627 | 13.713 |
| 845 | ARG114 | O | 7.034 | 17.912 | 14.09 |
| 846 | ARG114 | CB | 4.916 | 20.313 | 15.096 |
| 847 | ARG114 | CG | 4.939 | 19.283 | 16.22 |
| 848 | ARG114 | CD | 3.721 | 19.388 | 17.131 |
| 849 | ARG114 | NE | 3.696 | 20.666 | 17.858 |
| 850 | ARG114 | CZ | 4.078 | 20.792 | 19.131 |
| 851 | ARG114 | NH1 | 3.903 | 21.953 | 19.766 |
| 852 | ARG114 | NH2 | 4.537 | 19.73 | 19.798 |
| 853 | MET115 | N | 5.28 | 18.265 | 12.737 |
| 854 | MET115 | CA | 5.23 | 16.862 | 12.311 |
| 855 | MET115 | C | 6.438 | 16.467 | 11.456 |
| 856 | MET115 | O | 6.99 | 15.378 | 11.662 |
| 857 | MET115 | CB | 3.926 | 16.642 | 11.555 |
| 858 | MET115 | CG | 2.739 | 16.915 | 12.474 |
| 859 | MET115 | SD | 1.093 | 16.637 | 11.78 |
| 860 | MET115 | CE | 1.057 | 17.94 | 10.532 |
| 861 | LYS116 | N | 7.027 | 17.445 | 10.787 |
| 862 | LYS116 | CA | 8.25 | 17.222 | 10.01 |
| 863 | LYS116 | C | 9.492 | 17.156 | 10.902 |
| 864 | LYS116 | O | 10.434 | 16.413 | 10.59 |
| 865 | LYS116 | CB | 8.372 | 18.392 | 9.042 |
| 866 | LYS116 | CG | 9.635 | 18.337 | 8.194 |
| 867 | LYS116 | CD | 9.738 | 19.592 | 7.338 |
| 868 | LYS116 | CE | 9.703 | 20.841 | 8.213 |
| 869 | LYS116 | NZ | 9.753 | 22.063 | 7.395 |
| 870 | ALA117 | N | 9.404 | 17.748 | 12.084 |
| 871 | ALA117 | CA | 10.49 | 17.663 | 13.066 |
| 872 | ALA117 | C | 10.354 | 16.43 | 13.962 |
| 873 | ALA117 | O | 11.331 | 16 | 14.587 |
| 874 | ALA117 | CB | 10.469 | 18.924 | 13.922 |
| 875 | LEU118 | N | 9.185 | 15.81 | 13.933 |
| 876 | LEU118 | CA | 8.975 | 14.544 | 14.64 |
| 877 | LEU118 | C | 9.351 | 13.359 | 13.76 |
| 878 | LEU118 | O | 9.591 | 12.26 | 14.275 |
| 879 | LEU118 | CB | 7.512 | 14.434 | 15.05 |
| 880 | LEU118 | CG | 7.153 | 15.474 | 16.104 |
| 881 | LEU118 | CD1 | 5.654 | 15.48 | 16.372 |
| 882 | LEU118 | CD2 | 7.934 | 15.246 | 17.393 |
| 883 | GLN119 | N | 9.563 | 13.632 | 12.483 |
| 884 | GLN119 | CA | 10.052 | 12.633 | 11.518 |
| 885 | GLN119 | C | 11.263 | 11.797 | 11.989 |
| 886 | GLN119 | O | 11.09 | 10.573 | 12.041 |
| 887 | GLN119 | CB | 10.378 | 13.373 | 10.227 |
| 888 | GLN119 | CG | 10.944 | 12.471 | 9.144 |
| 889 | GLN119 | CD | 11.394 | 13.351 | 7.985 |
| 890 | GLN119 | OE1 | 11.701 | 12.857 | 6.894 |
| 891 | GLN119 | NE2 | 11.444 | 14.647 | 8.243 |
| 892 | PRO120 | N | 12.388 | 12.361 | 12.439 |
| 893 | PRO120 | CA | 13.485 | 11.486 | 12.885 |
| 894 | PRO120 | C | 13.211 | 10.732 | 14.195 |
| 895 | PRO120 | O | 13.761 | 9.639 | 14.381 |
| 896 | PRO120 | CB | 14.672 | 12.386 | 13.05 |
| 897 | PRO120 | CG | 14.237 | 13.832 | 12.892 |
| 898 | PRO120 | CD | 12.764 | 13.785 | 12.533 |
| 899 | ARG121 | N | 12.229 | 11.159 | 14.974 |
| 900 | ARG121 | CA | 11.917 | 10.438 | 16.203 |
| 901 | ARG121 | C | 11.02 | 9.25 | 15.868 |
| 902 | ARG121 | O | 11.331 | 8.136 | 16.303 |
| 903 | ARG121 | CB | 11.218 | 11.385 | 17.174 |
| 904 | ARG121 | CG | 11.741 | 11.209 | 18.597 |
| 905 | ARG121 | CD | 11.481 | 9.812 | 19.149 |
| 906 | ARG121 | NE | 12.184 | 9.613 | 20.424 |
| 907 | ARG121 | CZ | 12.714 | 8.443 | 20.784 |
| 908 | ARG121 | NH1 | 13.415 | 8.346 | 21.915 |
| 909 | ARG121 | NH2 | 12.601 | 7.386 | 19.977 |
| 910 | ILE122 | N | 10.18 | 9.421 | 14.857 |
| 911 | ILE122 | CA | 9.316 | 8.332 | 14.381 |
| 912 | ILE122 | C | 10.135 | 7.27 | 13.656 |
| 913 | ILE122 | O | 9.975 | 6.073 | 13.928 |
| 914 | ILE122 | CB | 8.309 | 8.918 | 13.396 |
| 915 | ILE122 | CG1 | 7.456 | 9.995 | 14.052 |
| 916 | ILE122 | CG2 | 7.422 | 7.825 | 12.807 |
| 917 | ILE122 | CD1 | 6.509 | 10.636 | 13.044 |
| 918 | GLN123 | N | 11.179 | 7.724 | 12.982 |
| 919 | GLN123 | CA | 12.088 | 6.827 | 12.269 |
| 920 | GLN123 | C | 12.914 | 5.997 | 13.245 |
| 921 | GLN123 | O | 12.897 | 4.76 | 13.156 |
| 922 | GLN123 | CB | 12.989 | 7.717 | 11.423 |
| 923 | GLN123 | CG | 13.978 | 6.941 | 10.567 |
| 924 | GLN123 | CD | 14.72 | 7.939 | 9.684 |
| 925 | GLN123 | OE1 | 15.954 | 7.96 | 9.626 |
| 926 | GLN123 | NE2 | 13.946 | 8.8 | 9.044 |
| 927 | GLN124 | N | 13.295 | 6.633 | 14.34 |
| 928 | GLN124 | CA | 14.049 | 5.959 | 15.394 |
| 929 | GLN124 | C | 13.184 | 4.947 | 16.144 |
| 930 | GLN124 | O | 13.621 | 3.798 | 16.284 |
| 931 | GLN124 | CB | 14.544 | 7.04 | 16.345 |
| 932 | GLN124 | CG | 15.429 | 6.495 | 17.455 |
| 933 | GLN124 | CD | 15.912 | 7.668 | 18.3 |
| 934 | GLN124 | OE1 | 16.786 | 7.524 | 19.162 |
| 935 | GLN124 | NE2 | 15.357 | 8.832 | 18.008 |
| 936 | ILE125 | N | 11.904 | 5.252 | 16.299 |
| 937 | ILE125 | CA | 10.961 | 4.328 | 16.947 |
| 938 | ILE125 | C | 10.716 | 3.072 | 16.112 |
| 939 | ILE125 | O | 10.861 | 1.961 | 16.642 |
| 940 | ILE125 | CB | 9.638 | 5.064 | 17.148 |
| 941 | ILE125 | CG1 | 9.792 | 6.214 | 18.13 |
| 942 | ILE125 | CG2 | 8.543 | 4.122 | 17.628 |

APPENDIX 1-continued

| Atom No. | Residue | Atom Name | X-coord | Y-coord | Z-coord |
|---|---|---|---|---|---|
| 943 | ILE125 | CD1 | 8.487 | 6.984 | 18.275 |
| 944 | VAL126 | N | 10.649 | 3.229 | 14.797 |
| 945 | VAL126 | CA | 10.44 | 2.064 | 13.928 |
| 946 | VAL126 | C | 11.693 | 1.2 | 13.87 |
| 947 | VAL126 | O | 11.603 | −0.021 | 14.062 |
| 948 | VAL126 | CB | 10.119 | 2.529 | 12.513 |
| 949 | VAL126 | CG1 | 9.754 | 1.334 | 11.641 |
| 950 | VAL126 | CG2 | 8.988 | 3.544 | 12.503 |
| 951 | ASP127 | N | 12.843 | 1.855 | 13.909 |
| 952 | ASP127 | CA | 14.121 | 1.141 | 13.889 |
| 953 | ASP127 | C | 14.314 | 0.34 | 15.17 |
| 954 | ASP127 | O | 14.537 | −0.876 | 15.088 |
| 955 | ASP127 | CB | 15.258 | 2.153 | 13.769 |
| 956 | ASP127 | CG | 15.158 | 2.967 | 12.481 |
| 957 | ASP127 | OD1 | 15.632 | 4.097 | 12.49 |
| 958 | ASP127 | OD2 | 14.686 | 2.426 | 11.489 |
| 959 | GLU128 | N | 13.903 | 0.919 | 16.288 |
| 960 | GLU128 | CA | 14.048 | 0.26 | 17.589 |
| 961 | GLU128 | C | 13.094 | −0.915 | 17.762 |
| 962 | GLU128 | O | 13.527 | −1.952 | 18.281 |
| 963 | GLU128 | CB | 13.764 | 1.281 | 18.684 |
| 964 | GLU128 | CG | 14.807 | 2.39 | 18.707 |
| 965 | GLU128 | CD | 14.367 | 3.489 | 19.668 |
| 966 | GLU128 | OE1 | 13.584 | 4.333 | 19.247 |
| 967 | GLU128 | OE2 | 14.794 | 3.452 | 20.812 |
| 968 | HIS129 | N | 11.934 | −0.861 | 17.128 |
| 969 | HIS129 | CA | 11.002 | −1.985 | 17.237 |
| 970 | HIS129 | C | 11.411 | −3.142 | 16.333 |
| 971 | HIS129 | O | 11.344 | −4.297 | 16.772 |
| 972 | HIS129 | CB | 9.592 | −1.533 | 16.885 |
| 973 | HIS129 | CG | 8.963 | −0.57 | 17.87 |
| 974 | HIS129 | ND1 | 7.942 | 0.266 | 17.612 |
| 975 | HIS129 | CD2 | 9.3 | −0.394 | 19.192 |
| 976 | HIS129 | CE1 | 7.647 | 0.969 | 18.724 |
| 977 | HIS129 | NE2 | 8.488 | 0.561 | 19.701 |
| 978 | ILE130 | N | 12.061 | −2.848 | 15.218 |
| 979 | ILE130 | CA | 12.564 | −3.95 | 14.394 |
| 980 | ILE130 | C | 13.768 | −4.577 | 15.089 |
| 981 | ILE130 | O | 13.69 | −5.756 | 15.459 |
| 982 | ILE130 | CB | 12.968 | −3.449 | 13.012 |
| 983 | ILE130 | CG1 | 11.841 | −2.659 | 12.36 |
| 984 | ILE130 | CG2 | 13.341 | −4.632 | 12.125 |
| 985 | ILE130 | CD1 | 12.258 | −2.117 | 10.996 |
| 986 | ASP131 | N | 14.65 | −3.712 | 15.575 |
| 987 | ASP131 | CA | 15.874 | −4.12 | 16.283 |
| 988 | ASP131 | C | 15.604 | −5.033 | 17.473 |
| 989 | ASP131 | O | 15.932 | −6.226 | 17.435 |
| 990 | ASP131 | CB | 16.565 | −2.874 | 16.84 |
| 991 | ASP131 | CG | 17.175 | −1.999 | 15.749 |
| 992 | ASP131 | OD1 | 17.222 | −0.791 | 15.952 |
| 993 | ASP131 | OD2 | 17.743 | −2.564 | 14.826 |
| 994 | ALA132 | N | 14.882 | −4.505 | 18.448 |
| 995 | ALA132 | CA | 14.708 | −5.198 | 19.727 |
| 996 | ALA132 | C | 13.582 | −6.228 | 19.763 |
| 997 | ALA132 | O | 13.489 | −6.983 | 20.738 |
| 998 | ALA132 | CB | 14.465 | −4.147 | 20.803 |
| 999 | LEU133 | N | 12.752 | −6.286 | 18.736 |
| 1000 | LEU133 | CA | 11.712 | −7.311 | 18.741 |
| 1001 | LEU133 | C | 12.08 | −8.444 | 17.798 |
| 1002 | LEU133 | O | 12.567 | −9.492 | 18.239 |
| 1003 | LEU133 | CB | 10.366 | −6.697 | 18.372 |
| 1004 | LEU133 | CG | 9.925 | −5.686 | 19.427 |
| 1005 | LEU133 | CD1 | 8.679 | −4.93 | 18.987 |
| 1006 | LEU133 | CD2 | 9.698 | −6.366 | 20.773 |
| 1007 | LEU134 | N | 11.901 | −8.215 | 16.511 |
| 1008 | LEU134 | CA | 12.139 | −9.288 | 15.539 |
| 1009 | LEU134 | C | 12.895 | −8.777 | 14.32 |
| 1010 | LEU134 | O | 12.319 | −8.632 | 13.237 |
| 1011 | LEU134 | CB | 10.808 | −9.885 | 15.087 |
| 1012 | LEU134 | CG | 10.481 | −11.234 | 15.731 |
| 1013 | LEU134 | CD1 | 11.66 | −12.193 | 15.635 |
| 1014 | LEU134 | CD2 | 9.997 | −11.115 | 17.173 |
| 1015 | ALA135 | N | 14.194 | −8.586 | 14.486 |
| 1016 | ALA135 | CA | 15.038 | −8.142 | 13.371 |
| 1017 | ALA135 | C | 15.606 | −9.293 | 12.538 |
| 1018 | ALA135 | O | 16.184 | −9.051 | 11.472 |
| 1019 | ALA135 | CB | 16.193 | −7.323 | 13.935 |
| 1020 | GLY136 | N | 15.402 | −10.522 | 12.984 |
| 1021 | GLY136 | CA | 15.957 | −11.679 | 12.272 |
| 1022 | GLY136 | C | 14.865 | −12.524 | 11.62 |
| 1023 | GLY136 | O | 14.069 | −12.022 | 10.829 |
| 1024 | PRO137 | N | 14.906 | −13.813 | 11.903 |
| 1025 | PRO137 | CA | 13.938 | −14.772 | 11.353 |
| 1026 | PRO137 | C | 12.589 | −14.709 | 12.067 |
| 1027 | PRO137 | O | 12.21 | −13.679 | 12.637 |
| 1028 | PRO137 | CB | 14.573 | −16.111 | 11.568 |
| 1029 | PRO137 | CG | 15.748 | −15.953 | 12.524 |
| 1030 | PRO137 | CD | 15.899 | −14.46 | 12.763 |
| 1031 | LYS138 | N | 11.86 | −15.811 | 11.945 |
| 1032 | LYS138 | CA | 10.575 | −16.043 | 12.639 |
| 1033 | LYS138 | C | 9.412 | −15.227 | 12.069 |
| 1034 | LYS138 | O | 9.605 | −14.143 | 11.508 |
| 1035 | LYS138 | CB | 10.733 | −15.765 | 14.135 |
| 1036 | LYS138 | CG | 11.795 | −16.66 | 14.765 |
| 1037 | LYS138 | CD | 12.022 | −16.303 | 16.23 |
| 1038 | LYS138 | CE | 13.155 | −17.128 | 16.829 |
| 1039 | LYS138 | NZ | 12.859 | −18.567 | 16.746 |
| 1040 | PRO139 | N | 8.256 | −15.868 | 12.022 |
| 1041 | PRO139 | CA | 6.996 | −15.155 | 11.797 |
| 1042 | PRO139 | C | 6.612 | −14.289 | 12.995 |
| 1043 | PRO139 | O | 6.167 | −14.795 | 14.031 |
| 1044 | PRO139 | CB | 5.979 | −16.232 | 11.583 |
| 1045 | PRO139 | CG | 6.595 | −17.575 | 11.948 |
| 1046 | PRO139 | CD | 8.04 | −17.286 | 12.322 |
| 1047 | ALA140 | N | 6.749 | −12.987 | 12.824 |
| 1048 | ALA140 | CA | 6.355 | −12.036 | 13.868 |
| 1049 | ALA140 | C | 5.006 | −11.411 | 13.552 |
| 1050 | ALA140 | O | 4.591 | −11.359 | 12.391 |
| 1051 | ALA140 | CB | 7.395 | −10.931 | 13.953 |
| 1052 | ASP141 | N | 4.297 | −10.989 | 14.582 |
| 1053 | ASP141 | CA | 3.051 | −10.264 | 14.336 |
| 1054 | ASP141 | C | 3.363 | −8.779 | 14.165 |
| 1055 | ASP141 | O | 3.466 | −8.032 | 15.149 |
| 1056 | ASP141 | CB | 2.073 | −10.492 | 15.481 |
| 1057 | ASP141 | CG | 0.741 | −9.84 | 15.132 |
| 1058 | ASP141 | OD1 | 0.583 | −8.673 | 15.465 |
| 1059 | ASP141 | OD2 | 0.016 | −10.426 | 14.338 |
| 1060 | LEU142 | N | 3.261 | −8.332 | 12.923 |
| 1061 | LEU142 | CA | 3.692 | −6.983 | 12.541 |
| 1062 | LEU142 | C | 2.753 | −5.893 | 13.048 |
| 1063 | LEU142 | O | 3.232 | −4.806 | 13.4 |
| 1064 | LEU142 | CB | 3.78 | −6.96 | 11.012 |
| 1065 | LEU142 | CG | 4.336 | −5.66 | 10.428 |
| 1066 | LEU142 | CD1 | 5.227 | −5.944 | 9.225 |
| 1067 | LEU142 | CD2 | 3.241 | −4.659 | 10.063 |
| 1068 | VAL143 | N | 1.509 | −6.243 | 13.329 |
| 1069 | VAL143 | CA | 0.585 | −5.247 | 13.868 |
| 1070 | VAL143 | C | 0.992 | −4.867 | 15.287 |
| 1071 | VAL143 | O | 1.481 | −3.748 | 15.477 |
| 1072 | VAL143 | CB | −0.829 | −5.809 | 13.859 |
| 1073 | VAL143 | CG1 | −1.823 | −4.772 | 14.374 |
| 1074 | VAL143 | CG2 | −1.212 | −6.26 | 12.457 |
| 1075 | GLN144 | N | 1.184 | −5.874 | 16.119 |
| 1076 | GLN144 | CA | 1.491 | −5.656 | 17.535 |
| 1077 | GLN144 | C | 2.945 | −5.249 | 17.797 |
| 1078 | GLN144 | O | 3.212 | −4.566 | 18.791 |
| 1079 | GLN144 | CB | 1.203 | −6.982 | 18.23 |
| 1080 | GLN144 | CG | 1.485 | −6.966 | 19.726 |
| 1081 | GLN144 | CD | 1.232 | −8.364 | 20.277 |
| 1082 | GLN144 | OE1 | 1.815 | −8.777 | 21.285 |
| 1083 | GLN144 | NE2 | 0.374 | −9.091 | 19.582 |
| 1084 | ALA145 | N | 3.842 | −5.539 | 16.87 |
| 1085 | ALA145 | CA | 5.246 | −5.186 | 17.088 |
| 1086 | ALA145 | C | 5.672 | −3.884 | 16.412 |
| 1087 | ALA145 | O | 6.594 | −3.211 | 16.888 |
| 1088 | ALA145 | CB | 6.108 | −6.329 | 16.561 |
| 1089 | LEU146 | N | 4.988 | −3.499 | 15.349 |
| 1090 | LEU146 | CA | 5.424 | −2.324 | 14.588 |
| 1091 | LEU146 | C | 4.294 | −1.342 | 14.317 |
| 1092 | LEU146 | O | 4.308 | −0.207 | 14.815 |
| 1093 | LEU146 | CB | 5.964 | −2.825 | 13.252 |
| 1094 | LEU146 | CG | 7.225 | −3.659 | 13.433 |
| 1095 | LEU146 | CD1 | 7.467 | −4.589 | 12.254 |
| 1096 | LEU146 | CD2 | 8.432 | −2.772 | 13.705 |

APPENDIX 1-continued

| Atom No. | Residue | Atom Name | X-coord | Y-coord | Z-coord |
|---|---|---|---|---|---|
| 1097 | SER147 | N | 3.245 | −1.868 | 13.71 |
| 1098 | SER147 | CA | 2.169 | −1.053 | 13.134 |
| 1099 | SER147 | C | 1.274 | −0.369 | 14.164 |
| 1100 | SER147 | O | 0.727 | 0.708 | 13.911 |
| 1101 | SER147 | CB | 1.325 | −2.001 | 12.301 |
| 1102 | SER147 | OG | 0.198 | −1.277 | 11.856 |
| 1103 | LEU148 | N | 1.174 | −0.97 | 15.331 |
| 1104 | LEU148 | CA | 0.484 | −0.358 | 16.464 |
| 1105 | LEU148 | C | 1.433 | 0.51 | 17.316 |
| 1106 | LEU148 | O | 1.132 | 1.707 | 17.436 |
| 1107 | LEU148 | CB | −0.204 | −1.475 | 17.259 |
| 1108 | LEU148 | CG | −1.13 | −0.987 | 18.372 |
| 1109 | LEU148 | CD1 | −2.317 | −1.93 | 18.53 |
| 1110 | LEU148 | CD2 | −0.404 | −0.81 | 19.703 |
| 1111 | PRO149 | N | 2.553 | 0.008 | 17.848 |
| 1112 | PRO149 | CA | 3.299 | 0.829 | 18.809 |
| 1113 | PRO149 | C | 3.987 | 2.052 | 18.203 |
| 1114 | PRO149 | O | 4.043 | 3.07 | 18.9 |
| 1115 | PRO149 | CB | 4.31 | −0.075 | 19.439 |
| 1116 | PRO149 | CG | 4.261 | −1.43 | 18.764 |
| 1117 | PRO149 | CD | 3.122 | −1.352 | 17.766 |
| 1118 | VAL150 | N | 4.316 | 2.051 | 16.918 |
| 1119 | VAL150 | CA | 4.873 | 3.276 | 16.323 |
| 1120 | VAL150 | C | 3.867 | 4.442 | 16.385 |
| 1121 | VAL150 | O | 4.127 | 5.334 | 17.201 |
| 1122 | VAL150 | CB | 5.399 | 3.041 | 14.905 |
| 1123 | VAL150 | CG1 | 5.892 | 4.345 | 14.284 |
| 1124 | VAL150 | CG2 | 6.514 | 2.004 | 14.891 |
| 1125 | PRO151 | N | 2.695 | 4.396 | 15.75 |
| 1126 | PRO151 | CA | 1.816 | 5.574 | 15.799 |
| 1127 | PRO151 | C | 1.187 | 5.843 | 17.167 |
| 1128 | PRO151 | O | 1.009 | 7.014 | 17.532 |
| 1129 | PRO151 | CB | 0.742 | 5.307 | 14.799 |
| 1130 | PRO151 | CG | 0.88 | 3.895 | 14.266 |
| 1131 | PRO151 | CD | 2.136 | 3.336 | 14.896 |
| 1132 | SER152 | N | 1.059 | 4.817 | 17.993 |
| 1133 | SER152 | CA | 0.504 | 5.027 | 19.326 |
| 1134 | SER152 | C | 1.506 | 5.73 | 20.241 |
| 1135 | SER152 | O | 1.136 | 6.724 | 20.879 |
| 1136 | SER152 | CB | 0.117 | 3.671 | 19.898 |
| 1137 | SER152 | OG | −0.849 | 3.09 | 19.031 |
| 1138 | LEU153 | N | 2.785 | 5.428 | 20.079 |
| 1139 | LEU153 | CA | 3.817 | 6.088 | 20.883 |
| 1140 | LEU153 | C | 4.17 | 7.458 | 20.312 |
| 1141 | LEU153 | O | 4.34 | 8.406 | 21.091 |
| 1142 | LEU153 | CB | 5.06 | 5.206 | 20.899 |
| 1143 | LEU153 | CG | 6.168 | 5.789 | 21.769 |
| 1144 | LEU153 | CD1 | 5.708 | 5.934 | 23.216 |
| 1145 | LEU153 | CD2 | 7.424 | 4.928 | 21.689 |
| 1146 | VAL154 | N | 3.995 | 7.622 | 19.009 |
| 1147 | VAL154 | CA | 4.232 | 8.925 | 18.383 |
| 1148 | VAL154 | C | 3.185 | 9.944 | 18.813 |
| 1149 | VAL154 | O | 3.566 | 11.036 | 19.256 |
| 1150 | VAL154 | CB | 4.205 | 8.777 | 16.864 |
| 1151 | VAL154 | CG1 | 4.148 | 10.134 | 16.169 |
| 1152 | VAL154 | CG2 | 5.402 | 7.976 | 16.368 |
| 1153 | ILE155 | N | 1.945 | 9.513 | 18.977 |
| 1154 | ILE155 | CA | 0.935 | 10.467 | 19.431 |
| 1155 | ILE155 | C | 0.932 | 10.621 | 20.956 |
| 1156 | ILE155 | O | 0.6 | 11.709 | 21.446 |
| 1157 | ILE155 | CB | −0.433 | 10.065 | 18.902 |
| 1158 | ILE155 | CG1 | −1.405 | 11.218 | 19.089 |
| 1159 | ILE155 | CG2 | −0.956 | 8.814 | 19.593 |
| 1160 | ILE155 | CD1 | −0.954 | 12.46 | 18.327 |
| 1161 | CYS156 | N | 1.569 | 9.697 | 21.66 |
| 1162 | CYS156 | CA | 1.787 | 9.891 | 23.093 |
| 1163 | CYS156 | C | 2.835 | 10.973 | 23.317 |
| 1164 | CYS156 | O | 2.551 | 11.93 | 24.047 |
| 1165 | CYS156 | CB | 2.261 | 8.59 | 23.732 |
| 1166 | CYS156 | SG | 1.018 | 7.295 | 23.935 |
| 1167 | GLU157 | N | 3.838 | 11.005 | 22.454 |
| 1168 | GLU157 | CA | 4.902 | 12.011 | 22.559 |
| 1169 | GLU157 | C | 4.512 | 13.364 | 21.957 |
| 1170 | GLU157 | O | 5.08 | 14.393 | 22.339 |
| 1171 | GLU157 | CB | 6.109 | 11.474 | 21.801 |
| 1172 | GLU157 | CG | 6.57 | 10.14 | 22.372 |
| 1173 | GLU157 | CD | 7.588 | 9.499 | 21.434 |
| 1174 | GLU157 | OE1 | 8.764 | 9.522 | 21.767 |
| 1175 | GLU157 | OE2 | 7.162 | 8.932 | 20.437 |
| 1176 | LEU158 | N | 3.5 | 13.37 | 21.107 |
| 1177 | LEU158 | CA | 3.042 | 14.616 | 20.492 |
| 1178 | LEU158 | C | 2.03 | 15.308 | 21.401 |
| 1179 | LEU158 | O | 2.089 | 16.535 | 21.586 |
| 1180 | LEU158 | CB | 2.412 | 14.232 | 19.149 |
| 1181 | LEU158 | CG | 2.171 | 15.389 | 18.175 |
| 1182 | LEU158 | CD1 | 2.086 | 14.868 | 16.745 |
| 1183 | LEU158 | CD2 | 0.93 | 16.213 | 18.504 |
| 1184 | LEU159 | N | 1.211 | 14.518 | 22.072 |
| 1185 | LEU159 | CA | 0.183 | 15.099 | 22.929 |
| 1186 | LEU159 | C | 0.747 | 15.411 | 24.309 |
| 1187 | LEU159 | O | 0.832 | 16.594 | 24.66 |
| 1188 | LEU159 | CB | −0.979 | 14.12 | 23.044 |
| 1189 | LEU159 | CG | −2.24 | 14.827 | 23.524 |
| 1190 | LEU159 | CD1 | −2.637 | 15.915 | 22.535 |
| 1191 | LEU159 | CD2 | −3.385 | 13.84 | 23.707 |
| 1192 | GLY160 | N | 1.347 | 14.417 | 24.943 |
| 1193 | GLY160 | CA | 1.874 | 14.572 | 26.306 |
| 1194 | GLY160 | C | 1.433 | 13.413 | 27.2 |
| 1195 | GLY160 | O | 1.183 | 13.581 | 28.398 |
| 1196 | VAL161 | N | 1.366 | 12.238 | 26.601 |
| 1197 | VAL161 | CA | 0.869 | 11.037 | 27.284 |
| 1198 | VAL161 | C | 2.006 | 10.078 | 27.635 |
| 1199 | VAL161 | O | 2.715 | 9.58 | 26.752 |
| 1200 | VAL161 | CB | −0.111 | 10.348 | 26.338 |
| 1201 | VAL161 | CG1 | −0.763 | 9.125 | 26.976 |
| 1202 | VAL161 | CG2 | −1.175 | 11.327 | 25.866 |
| 1203 | PRO162 | N | 2.15 | 9.806 | 28.922 |
| 1204 | PRO162 | CA | 3.13 | 8.826 | 29.4 |
| 1205 | PRO162 | C | 2.838 | 7.41 | 28.901 |
| 1206 | PRO162 | O | 1.68 | 7.021 | 28.689 |
| 1207 | PRO162 | CB | 3.066 | 8.899 | 30.894 |
| 1208 | PRO162 | CG | 1.972 | 9.874 | 31.302 |
| 1209 | PRO162 | CD | 1.358 | 10.384 | 30.009 |
| 1210 | TYR163 | N | 3.882 | 6.593 | 28.912 |
| 1211 | TYR163 | CA | 3.793 | 5.209 | 28.41 |
| 1212 | TYR163 | C | 3.104 | 4.257 | 29.393 |
| 1213 | TYR163 | O | 2.72 | 3.153 | 29.002 |
| 1214 | TYR163 | CB | 5.192 | 4.684 | 28.071 |
| 1215 | TYR163 | CG | 6.111 | 4.367 | 29.254 |
| 1216 | TYR163 | CD1 | 6.895 | 5.363 | 29.826 |
| 1217 | TYR163 | CD2 | 6.181 | 3.067 | 29.743 |
| 1218 | TYR163 | CE1 | 7.726 | 5.066 | 30.898 |
| 1219 | TYR163 | CE2 | 7.011 | 2.768 | 30.815 |
| 1220 | TYR163 | CZ | 7.78 | 3.77 | 31.392 |
| 1221 | TYR163 | OH | 8.589 | 3.478 | 32.467 |
| 1222 | SER164 | N | 2.806 | 4.747 | 30.589 |
| 1223 | SER164 | CA | 2.007 | 3.992 | 31.561 |
| 1224 | SER164 | C | 0.51 | 4.158 | 31.301 |
| 1225 | SER164 | O | −0.319 | 3.566 | 32 |
| 1226 | SER164 | CB | 2.303 | 4.538 | 32.952 |
| 1227 | SER164 | OG | 1.766 | 5.854 | 33.017 |
| 1228 | ASP165 | N | 0.173 | 5.056 | 30.389 |
| 1229 | ASP165 | CA | −1.215 | 5.273 | 30.002 |
| 1230 | ASP165 | C | −1.445 | 4.619 | 28.649 |
| 1231 | ASP165 | O | −2.542 | 4.126 | 28.344 |
| 1232 | ASP165 | CB | −1.463 | 6.775 | 29.944 |
| 1233 | ASP165 | CG | −1.331 | 7.38 | 31.343 |
| 1234 | ASP165 | OD1 | −2.358 | 7.592 | 31.968 |
| 1235 | ASP165 | OD2 | −0.21 | 7.683 | 31.732 |
| 1236 | HIS166 | N | −0.343 | 4.475 | 27.929 |
| 1237 | HIS166 | CA | −0.299 | 3.666 | 26.71 |
| 1238 | HIS166 | C | −0.63 | 2.223 | 27.09 |
| 1239 | HIS166 | O | −0.515 | 1.86 | 28.266 |
| 1240 | HIS166 | CB | 1.11 | 3.792 | 26.129 |
| 1241 | HIS166 | CG | 1.387 | 3.018 | 24.856 |
| 1242 | HIS166 | ND1 | 0.916 | 3.295 | 23.626 |
| 1243 | HIS166 | CD2 | 2.174 | 1.896 | 24.741 |
| 1244 | HIS166 | CE1 | 1.378 | 2.374 | 22.756 |
| 1245 | HIS166 | NE2 | 2.156 | 1.51 | 23.445 |
| 1246 | GLU167 | N | −1.239 | 1.506 | 26.155 |
| 1247 | GLU167 | CA | −1.754 | 0.127 | 26.342 |
| 1248 | GLU167 | C | −3.12 | 0.07 | 27.045 |
| 1249 | GLU167 | O | −4.04 | −0.549 | 26.498 |
| 1250 | GLU167 | CB | −0.743 | −0.752 | 27.077 |

APPENDIX 1-continued

| Atom No. | Residue | Atom Name | X-coord | Y-coord | Z-coord |
|---|---|---|---|---|---|
| 1251 | GLU167 | CG | 0.54 | −0.919 | 26.271 |
| 1252 | GLU167 | CD | 1.593 | −1.638 | 27.107 |
| 1253 | GLU167 | OE1 | 1.207 | −2.478 | 27.907 |
| 1254 | GLU167 | OE2 | 2.766 | −1.386 | 26.875 |
| 1255 | PHE168 | N | −3.329 | 0.846 | 28.097 |
| 1256 | PHE168 | CA | −4.652 | 0.854 | 28.729 |
| 1257 | PHE168 | C | −5.586 | 1.779 | 27.954 |
| 1258 | PHE168 | O | −6.692 | 1.36 | 27.587 |
| 1259 | PHE168 | CB | −4.53 | 1.304 | 30.179 |
| 1260 | PHE168 | CG | −5.824 | 1.165 | 30.977 |
| 1261 | PHE168 | CD1 | −6.696 | 0.117 | 30.709 |
| 1262 | PHE168 | CD2 | −6.126 | 2.078 | 31.979 |
| 1263 | PHE168 | CE1 | −7.875 | −0.01 | 31.432 |
| 1264 | PHE168 | CE2 | −7.305 | 1.951 | 32.703 |
| 1265 | PHE168 | CZ | −8.18 | 0.908 | 32.428 |
| 1266 | PHE169 | N | −5.016 | 2.851 | 27.423 |
| 1267 | PHE169 | CA | −5.773 | 3.717 | 26.514 |
| 1268 | PHE169 | C | −5.944 | 3.029 | 25.162 |
| 1269 | PHE169 | O | −7.031 | 3.098 | 24.579 |
| 1270 | PHE169 | CB | −5.003 | 5.024 | 26.316 |
| 1271 | PHE169 | CG | −5.736 | 6.088 | 25.497 |
| 1272 | PHE169 | CD1 | −6.361 | 7.145 | 26.147 |
| 1273 | PHE169 | CD2 | −5.758 | 6.022 | 24.109 |
| 1274 | PHE169 | CE1 | −7.037 | 8.111 | 25.413 |
| 1275 | PHE169 | CE2 | −6.436 | 6.985 | 23.375 |
| 1276 | PHE169 | CZ | −7.082 | 8.028 | 24.027 |
| 1277 | GLN170 | N | −5.019 | 2.134 | 24.851 |
| 1278 | GLN170 | CA | −5.042 | 1.407 | 23.584 |
| 1279 | GLN170 | C | −6.148 | 0.359 | 23.564 |
| 1280 | GLN170 | O | −6.903 | 0.281 | 22.588 |
| 1281 | GLN170 | CB | −3.705 | 0.693 | 23.444 |
| 1282 | GLN170 | CG | −3.611 | −0.121 | 22.163 |
| 1283 | GLN170 | CD | −3.411 | 0.818 | 20.985 |
| 1284 | GLN170 | OE1 | −2.392 | 1.516 | 20.917 |
| 1285 | GLN170 | NE2 | −4.408 | 0.885 | 20.125 |
| 1286 | SER171 | N | −6.372 | −0.281 | 24.698 |
| 1287 | SER171 | CA | −7.424 | −1.295 | 24.769 |
| 1288 | SER171 | C | −8.811 | −0.665 | 24.856 |
| 1289 | SER171 | O | −9.706 | −1.107 | 24.125 |
| 1290 | SER171 | CB | −7.171 | −2.209 | 25.967 |
| 1291 | SER171 | OG | −7.132 | −1.427 | 27.155 |
| 1292 | CYS172 | N | −8.906 | 0.511 | 25.457 |
| 1293 | CYS172 | CA | −10.204 | 1.184 | 25.525 |
| 1294 | CYS172 | C | −10.569 | 1.806 | 24.18 |
| 1295 | CYS172 | O | −11.691 | 1.593 | 23.703 |
| 1296 | CYS172 | CB | −10.149 | 2.266 | 26.593 |
| 1297 | CYS172 | SG | −9.817 | 1.701 | 28.277 |
| 1298 | SER173 | N | −9.559 | 2.253 | 23.453 |
| 1299 | SER173 | CA | −9.781 | 2.826 | 22.121 |
| 1300 | SER173 | C | −9.949 | 1.765 | 21.033 |
| 1301 | SER173 | O | −10.363 | 2.096 | 19.916 |
| 1302 | SER173 | CB | −8.612 | 3.741 | 21.775 |
| 1303 | SER173 | OG | −7.418 | 2.972 | 21.747 |
| 1304 | SER174 | N | −9.687 | 0.509 | 21.356 |
| 1305 | SER174 | CA | −10.001 | −0.575 | 20.427 |
| 1306 | SER174 | C | −11.395 | −1.133 | 20.713 |
| 1307 | SER174 | O | −12.128 | −1.464 | 19.771 |
| 1308 | SER174 | CB | −8.949 | −1.668 | 20.566 |
| 1309 | SER174 | OG | −7.691 | −1.099 | 20.225 |
| 1310 | ARG175 | N | −11.85 | −0.974 | 21.949 |
| 1311 | ARG175 | CA | −13.224 | −1.373 | 22.294 |
| 1312 | ARG175 | C | −14.226 | −0.342 | 21.787 |
| 1313 | ARG175 | O | −15.298 | −0.72 | 21.298 |
| 1314 | ARG175 | CB | −13.371 | −1.514 | 23.805 |
| 1315 | ARG175 | CG | −12.486 | −2.622 | 24.36 |
| 1316 | ARG175 | CD | −12.761 | −2.871 | 25.837 |
| 1317 | ARG175 | NE | −12.544 | −1.662 | 26.646 |
| 1318 | ARG175 | CZ | −13.06 | −1.512 | 27.869 |
| 1319 | ARG175 | NH1 | −12.78 | −0.421 | 28.584 |
| 1320 | ARG175 | NH2 | −13.816 | −2.478 | 28.397 |
| 1321 | MET176 | N | −13.739 | 0.876 | 21.611 |
| 1322 | MET176 | CA | −14.516 | 1.951 | 20.985 |
| 1323 | MET176 | C | −14.649 | 1.843 | 19.467 |
| 1324 | MET176 | O | −15.284 | 2.71 | 18.855 |
| 1325 | MET176 | CB | −13.806 | 3.259 | 21.259 |
| 1326 | MET176 | CG | −13.86 | 3.657 | 22.721 |
| 1327 | MET176 | SD | −13.036 | 5.228 | 23.009 |
| 1328 | MET176 | CE | −13.493 | 5.972 | 21.425 |
| 1329 | LEU177 | N | −14.036 | 0.846 | 18.853 |
| 1330 | LEU177 | CA | −14.184 | 0.676 | 17.411 |
| 1331 | LEU177 | C | −15.219 | −0.388 | 17.059 |
| 1332 | LEU177 | O | −15.593 | −0.533 | 15.886 |
| 1333 | LEU177 | CB | −12.836 | 0.29 | 16.827 |
| 1334 | LEU177 | CG | −11.824 | 1.426 | 16.9 |
| 1335 | LEU177 | CD1 | −10.568 | 1.035 | 16.135 |
| 1336 | LEU177 | CD2 | −12.4 | 2.713 | 16.32 |
| 1337 | SER178 | N | −15.706 | −1.099 | 18.062 |
| 1338 | SER178 | CA | −16.693 | −2.149 | 17.793 |
| 1339 | SER178 | C | −18.117 | −1.673 | 18.08 |
| 1340 | SER178 | O | −18.628 | −1.797 | 19.2 |
| 1341 | SER178 | CB | −16.344 | −3.402 | 18.599 |
| 1342 | SER178 | OG | −16.323 | −3.095 | 19.988 |
| 1343 | ARG179 | N | −18.765 | −1.209 | 17.022 |
| 1344 | ARG179 | CA | −20.148 | −0.697 | 17.082 |
| 1345 | ARG179 | C | −21.17 | −1.832 | 17.192 |
| 1346 | ARG179 | O | −21.743 | −2.266 | 16.187 |
| 1347 | ARG179 | CB | −20.4 | 0.027 | 15.768 |
| 1348 | ARG179 | CG | −19.286 | 1.01 | 15.431 |
| 1349 | ARG179 | CD | −19.098 | 1.114 | 13.922 |
| 1350 | ARG179 | NE | −18.628 | −0.179 | 13.39 |
| 1351 | ARG179 | CZ | −19.337 | −0.967 | 12.576 |
| 1352 | ARG179 | NH1 | −18.903 | −2.2 | 12.307 |
| 1353 | ARG179 | NH2 | −20.546 | −0.583 | 12.156 |
| 1354 | GLU180 | N | −21.375 | −2.313 | 18.405 |
| 1355 | GLU180 | CA | −22.261 | −3.454 | 18.627 |
| 1356 | GLU180 | C | −23.553 | −3.038 | 19.318 |
| 1357 | GLU180 | O | −23.676 | −1.923 | 19.833 |
| 1358 | GLU180 | CB | −21.517 | −4.449 | 19.508 |
| 1359 | GLU180 | CG | −20.175 | −4.838 | 18.899 |
| 1360 | GLU180 | CD | −19.442 | −5.795 | 19.828 |
| 1361 | GLU180 | OE1 | −20.124 | −6.592 | 20.457 |
| 1362 | GLU180 | OE2 | −18.219 | −5.763 | 19.834 |
| 1363 | VAL181 | N | −24.492 | −3.969 | 19.374 |
| 1364 | VAL181 | CA | −25.72 | −3.744 | 20.147 |
| 1365 | VAL181 | C | −25.463 | −4.084 | 21.616 |
| 1366 | VAL181 | O | −26.012 | −3.452 | 22.525 |
| 1367 | VAL181 | CB | −26.823 | −4.627 | 19.569 |
| 1368 | VAL181 | CG1 | −28.119 | −4.498 | 20.362 |
| 1369 | VAL181 | CG2 | −27.062 | −4.297 | 18.099 |
| 1370 | THR182 | N | −24.438 | −4.897 | 21.822 |
| 1371 | THR182 | CA | −23.936 | −5.215 | 23.166 |
| 1372 | THR182 | C | −22.767 | −4.302 | 23.547 |
| 1373 | THR182 | O | −21.827 | −4.739 | 24.222 |
| 1374 | THR182 | CB | −23.459 | −6.664 | 23.183 |
| 1375 | THR182 | OG1 | −22.348 | −6.789 | 22.302 |
| 1376 | THR182 | CG2 | −24.551 | −7.622 | 22.719 |
| 1377 | ALA183 | N | −22.882 | −3.025 | 23.214 |
| 1378 | ALA183 | CA | −21.777 | −2.062 | 23.352 |
| 1379 | ALA183 | C | −21.585 | −1.459 | 24.748 |
| 1380 | ALA183 | O | −21.031 | −0.36 | 24.855 |
| 1381 | ALA183 | CB | −21.993 | −0.933 | 22.352 |
| 1382 | GLU184 | N | −21.832 | −2.224 | 25.799 |
| 1383 | GLU184 | CA | −21.706 | −1.688 | 27.158 |
| 1384 | GLU184 | C | −20.242 | −1.537 | 27.568 |
| 1385 | GLU184 | O | −19.888 | −0.536 | 28.199 |
| 1386 | GLU184 | CB | −22.415 | −2.636 | 28.117 |
| 1387 | GLU184 | CG | −22.387 | −2.118 | 29.551 |
| 1388 | GLU184 | CD | −23.145 | −3.086 | 30.454 |
| 1389 | GLU184 | OE1 | −22.924 | −3.047 | 31.655 |
| 1390 | GLU184 | OE2 | −23.953 | −3.832 | 29.917 |
| 1391 | GLU185 | N | −19.374 | −2.344 | 26.978 |
| 1392 | GLU185 | CA | −17.936 | −2.201 | 27.244 |
| 1393 | GLU185 | C | −17.307 | −1.143 | 26.337 |
| 1394 | GLU185 | O | −16.294 | −0.542 | 26.708 |
| 1395 | GLU185 | CB | −17.216 | −3.541 | 27.073 |
| 1396 | GLU185 | CG | −17.189 | −4.388 | 28.351 |
| 1397 | GLU185 | CD | −18.561 | −4.959 | 28.705 |
| 1398 | GLU185 | OE1 | −19.308 | −5.237 | 27.774 |
| 1399 | GLU185 | OE2 | −18.899 | −4.953 | 29.879 |
| 1400 | ARG186 | N | −18.044 | −0.74 | 25.316 |
| 1401 | ARG186 | CA | −17.607 | 0.339 | 24.434 |
| 1402 | ARG186 | C | −18.008 | 1.676 | 25.049 |
| 1403 | ARG186 | O | −17.213 | 2.624 | 25.056 |
| 1404 | ARG186 | CB | −18.317 | 0.135 | 23.103 |

APPENDIX 1-continued

| Atom No. | Residue | Atom Name | X-coord | Y-coord | Z-coord |
|---|---|---|---|---|---|
| 1405 | ARG186 | CG | −17.936 | 1.175 | 22.064 |
| 1406 | ARG186 | CD | −18.718 | 0.942 | 20.779 |
| 1407 | ARG186 | NE | −18.234 | 1.82 | 19.708 |
| 1408 | ARG186 | CZ | −19.002 | 2.705 | 19.073 |
| 1409 | ARG186 | NH1 | −20.296 | 2.816 | 19.386 |
| 1410 | ARG186 | NH2 | −18.474 | 3.477 | 18.122 |
| 1411 | MET187 | N | −19.086 | 1.627 | 25.817 |
| 1412 | MET187 | CA | −19.545 | 2.775 | 26.601 |
| 1413 | MET187 | C | −18.651 | 2.978 | 27.82 |
| 1414 | MET187 | O | −18.251 | 4.113 | 28.111 |
| 1415 | MET187 | CB | −20.958 | 2.459 | 27.07 |
| 1416 | MET187 | CG | −21.569 | 3.594 | 27.88 |
| 1417 | MET187 | SD | −23.104 | 3.161 | 28.726 |
| 1418 | MET187 | CE | −23.995 | 2.43 | 27.333 |
| 1419 | THR188 | N | −18.13 | 1.874 | 28.332 |
| 1420 | THR188 | CA | −17.174 | 1.925 | 29.44 |
| 1421 | THR188 | C | −15.819 | 2.442 | 28.969 |
| 1422 | THR188 | O | −15.237 | 3.307 | 29.634 |
| 1423 | THR188 | CB | −17.013 | 0.516 | 30 |
| 1424 | THR188 | OG1 | −18.274 | 0.091 | 30.499 |
| 1425 | THR188 | CG2 | −16.011 | 0.473 | 31.149 |
| 1426 | ALA189 | N | −15.477 | 2.139 | 27.726 |
| 1427 | ALA189 | CA | −14.243 | 2.652 | 27.133 |
| 1428 | ALA189 | C | −14.333 | 4.147 | 26.838 |
| 1429 | ALA189 | O | −13.403 | 4.884 | 27.192 |
| 1430 | ALA189 | CB | −13.996 | 1.884 | 25.844 |
| 1431 | PHE190 | N | −15.518 | 4.605 | 26.461 |
| 1432 | PHE190 | CA | −15.762 | 6.042 | 26.26 |
| 1433 | PHE190 | C | −15.632 | 6.81 | 27.572 |
| 1434 | PHE190 | O | −14.815 | 7.736 | 27.678 |
| 1435 | PHE190 | CB | −17.194 | 6.258 | 25.773 |
| 1436 | PHE190 | CG | −17.566 | 5.772 | 24.375 |
| 1437 | PHE190 | CD1 | −16.652 | 5.837 | 23.334 |
| 1438 | PHE190 | CD2 | −18.848 | 5.293 | 24.139 |
| 1439 | PHE190 | CE1 | −17.013 | 5.406 | 22.063 |
| 1440 | PHE190 | CE2 | −19.208 | 4.861 | 22.871 |
| 1441 | PHE190 | CZ | −18.291 | 4.917 | 21.832 |
| 1442 | GLU191 | N | −16.281 | 6.297 | 28.605 |
| 1443 | GLU191 | CA | −16.292 | 6.969 | 29.908 |
| 1444 | GLU191 | C | −14.921 | 6.971 | 30.575 |
| 1445 | GLU191 | O | −14.432 | 8.05 | 30.936 |
| 1446 | GLU191 | CB | −17.28 | 6.233 | 30.802 |
| 1447 | GLU191 | CG | −17.348 | 6.853 | 32.193 |
| 1448 | GLU191 | CD | −18.28 | 6.023 | 33.069 |
| 1449 | GLU191 | OE1 | −18.424 | 4.843 | 32.777 |
| 1450 | GLU191 | OE2 | −18.894 | 6.597 | 33.957 |
| 1451 | SER192 | N | −14.202 | 5.866 | 30.453 |
| 1452 | SER192 | CA | −12.877 | 5.76 | 31.071 |
| 1453 | SER192 | C | −11.82 | 6.545 | 30.301 |
| 1454 | SER192 | O | −10.892 | 7.077 | 30.921 |
| 1455 | SER192 | CB | −12.467 | 4.291 | 31.126 |
| 1456 | SER192 | OG | −12.37 | 3.801 | 29.792 |
| 1457 | LEU193 | N | −12.082 | 6.827 | 29.036 |
| 1458 | LEU193 | CA | −11.152 | 7.64 | 28.256 |
| 1459 | LEU193 | C | −11.441 | 9.127 | 28.435 |
| 1460 | LEU193 | O | −10.514 | 9.943 | 28.377 |
| 1461 | LEU193 | CB | −11.243 | 7.218 | 26.798 |
| 1462 | LEU193 | CG | −9.95 | 6.547 | 26.343 |
| 1463 | LEU193 | CD1 | −9.372 | 5.603 | 27.391 |
| 1464 | LEU193 | CD2 | −10.117 | 5.842 | 25.003 |
| 1465 | GLU194 | N | −12.63 | 9.438 | 28.923 |
| 1466 | GLU194 | CA | −12.93 | 10.811 | 29.327 |
| 1467 | GLU194 | C | −12.368 | 11.096 | 30.711 |
| 1468 | GLU194 | O | −11.82 | 12.182 | 30.938 |
| 1469 | GLU194 | CB | −14.437 | 11.017 | 29.337 |
| 1470 | GLU194 | CG | −14.97 | 11.164 | 27.922 |
| 1471 | GLU194 | CD | −14.35 | 12.405 | 27.287 |
| 1472 | GLU194 | OE1 | −13.524 | 12.27 | 26.403 |
| 1473 | GLU194 | OE2 | −14.826 | 13.487 | 27.596 |
| 1474 | ASN195 | N | −12.26 | 10.058 | 31.523 |
| 1475 | ASN195 | CA | −11.645 | 10.215 | 32.844 |
| 1476 | ASN195 | C | −10.126 | 10.268 | 32.715 |
| 1477 | ASN195 | O | −9.479 | 11.112 | 33.356 |
| 1478 | ASN195 | CB | −12.076 | 9.054 | 33.736 |
| 1479 | ASN195 | CG | −13.582 | 9.104 | 34.008 |
| 1480 | ASN195 | OD1 | −14.272 | 8.076 | 33.958 |
| 1481 | ASN195 | ND2 | −14.076 | 10.3 | 34.287 |
| 1482 | TYR196 | N | −9.64 | 9.613 | 31.673 |
| 1483 | TYR196 | CA | −8.236 | 9.692 | 31.267 |
| 1484 | TYR196 | C | −7.88 | 11.104 | 30.817 |
| 1485 | TYR196 | O | −6.953 | 11.707 | 31.371 |
| 1486 | TYR196 | CB | −8.065 | 8.757 | 30.078 |
| 1487 | TYR196 | CG | −7.054 | 7.633 | 30.253 |
| 1488 | TYR196 | CD1 | −5.806 | 7.739 | 29.658 |
| 1489 | TYR196 | CD2 | −7.39 | 6.5 | 30.982 |
| 1490 | TYR196 | CE1 | −4.884 | 6.711 | 29.799 |
| 1491 | TYR196 | CE2 | −6.466 | 5.472 | 31.126 |
| 1492 | TYR196 | CZ | −5.216 | 5.581 | 30.532 |
| 1493 | TYR196 | OH | −4.301 | 4.56 | 30.661 |
| 1494 | LEU197 | N | −8.76 | 11.708 | 30.032 |
| 1495 | LEU197 | CA | −8.543 | 13.084 | 29.57 |
| 1496 | LEU197 | C | −8.718 | 14.131 | 30.663 |
| 1497 | LEU197 | O | −7.966 | 15.11 | 30.658 |
| 1498 | LEU197 | CB | −9.53 | 13.394 | 28.458 |
| 1499 | LEU197 | CG | −9.196 | 12.63 | 27.188 |
| 1500 | LEU197 | CD1 | −10.305 | 12.816 | 26.168 |
| 1501 | LEU197 | CD2 | −7.852 | 13.072 | 26.619 |
| 1502 | ASP198 | N | −9.49 | 13.83 | 31.695 |
| 1503 | ASP198 | CA | −9.6 | 14.749 | 32.834 |
| 1504 | ASP198 | C | −8.257 | 14.841 | 33.551 |
| 1505 | ASP198 | O | −7.698 | 15.938 | 33.694 |
| 1506 | ASP198 | CB | −10.627 | 14.209 | 33.829 |
| 1507 | ASP198 | CG | −12.016 | 14.052 | 33.214 |
| 1508 | ASP198 | OD1 | −12.428 | 14.949 | 32.492 |
| 1509 | ASP198 | OD2 | −12.706 | 13.123 | 33.627 |
| 1510 | GLU199 | N | −7.629 | 13.685 | 33.696 |
| 1511 | GLU199 | CA | −6.334 | 13.598 | 34.368 |
| 1512 | GLU199 | C | −5.221 | 14.182 | 33.506 |
| 1513 | GLU199 | O | −4.521 | 15.091 | 33.965 |
| 1514 | GLU199 | CB | −6.053 | 12.121 | 34.608 |
| 1515 | GLU199 | CG | −7.157 | 11.486 | 35.444 |
| 1516 | GLU199 | CD | −7.084 | 9.966 | 35.341 |
| 1517 | GLU199 | OE1 | −7.502 | 9.312 | 36.287 |
| 1518 | GLU199 | OE2 | −6.717 | 9.484 | 34.277 |
| 1519 | LEU200 | N | −5.26 | 13.885 | 32.219 |
| 1520 | LEU200 | CA | −4.209 | 14.315 | 31.289 |
| 1521 | LEU200 | C | −4.22 | 15.821 | 31.02 |
| 1522 | LEU200 | O | −3.168 | 16.467 | 31.128 |
| 1523 | LEU200 | CB | −4.459 | 13.57 | 29.982 |
| 1524 | LEU200 | CG | −3.421 | 13.888 | 28.914 |
| 1525 | LEU200 | CD1 | −2.036 | 13.415 | 29.338 |
| 1526 | LEU200 | CD2 | −3.815 | 13.251 | 27.587 |
| 1527 | VAL201 | N | −5.406 | 16.402 | 30.938 |
| 1528 | VAL201 | CA | −5.521 | 17.832 | 30.642 |
| 1529 | VAL201 | C | −5.196 | 18.69 | 31.859 |
| 1530 | VAL201 | O | −4.491 | 19.7 | 31.709 |
| 1531 | VAL201 | CB | −6.945 | 18.094 | 30.153 |
| 1532 | VAL201 | CG1 | −7.324 | 19.57 | 30.184 |
| 1533 | VAL201 | CG2 | −7.159 | 17.508 | 28.761 |
| 1534 | THR202 | N | −5.431 | 18.149 | 33.045 |
| 1535 | THR202 | CA | −5.103 | 18.884 | 34.267 |
| 1536 | THR202 | C | −3.643 | 18.677 | 34.654 |
| 1537 | THR202 | O | −2.981 | 19.624 | 35.101 |
| 1538 | THR202 | CB | −6.02 | 18.391 | 35.378 |
| 1539 | THR202 | OG1 | −7.359 | 18.589 | 34.945 |
| 1540 | THR202 | CG2 | −5.814 | 19.173 | 36.671 |
| 1541 | LYS203 | N | −3.08 | 17.579 | 34.182 |
| 1542 | LYS203 | CA | −1.672 | 17.284 | 34.434 |
| 1543 | LYS203 | C | −0.755 | 18.113 | 33.539 |
| 1544 | LYS203 | O | 0.305 | 18.539 | 34.015 |
| 1545 | LYS203 | CB | −1.474 | 15.79 | 34.209 |
| 1546 | LYS203 | CG | −0.041 | 15.331 | 34.439 |
| 1547 | LYS203 | CD | 0.025 | 13.812 | 34.569 |
| 1548 | LYS203 | CE | −0.557 | 13.099 | 33.352 |
| 1549 | LYS203 | NZ | 0.265 | 13.325 | 32.154 |
| 1550 | LYS204 | N | −1.256 | 18.545 | 32.391 |
| 1551 | LYS204 | CA | −0.505 | 19.493 | 31.553 |
| 1552 | LYS204 | C | −0.788 | 20.954 | 31.896 |
| 1553 | LYS204 | O | −0.031 | 21.846 | 31.499 |
| 1554 | LYS204 | CB | −0.821 | 19.218 | 30.092 |
| 1555 | LYS204 | CG | −0.076 | 17.965 | 29.664 |
| 1556 | LYS204 | CD | 1.425 | 18.213 | 29.729 |
| 1557 | LYS204 | CE | 2.202 | 16.906 | 29.69 |
| 1558 | LYS204 | NZ | 1.918 | 16.115 | 30.896 |

APPENDIX 1-continued

| Atom No. | Residue | Atom Name | X-coord | Y-coord | Z-coord |
|---|---|---|---|---|---|
| 1559 | GLU205 | N | −1.781 | 21.179 | 32.741 |
| 1560 | GLU205 | CA | −2.033 | 22.524 | 33.264 |
| 1561 | GLU205 | C | −1.215 | 22.777 | 34.526 |
| 1562 | GLU205 | O | −1.027 | 23.931 | 34.927 |
| 1563 | GLU205 | CB | −3.518 | 22.66 | 33.57 |
| 1564 | GLU205 | CG | −4.309 | 22.726 | 32.273 |
| 1565 | GLU205 | CD | −5.788 | 22.444 | 32.51 |
| 1566 | GLU205 | OE1 | −6.547 | 22.661 | 31.573 |
| 1567 | GLU205 | OE2 | −6.093 | 21.798 | 33.504 |
| 1568 | ALA206 | N | −0.712 | 21.707 | 35.12 |
| 1569 | ALA206 | CA | 0.208 | 21.844 | 36.249 |
| 1570 | ALA206 | C | 1.649 | 21.772 | 35.756 |
| 1571 | ALA206 | O | 2.464 | 22.661 | 36.034 |
| 1572 | ALA206 | CB | −0.059 | 20.711 | 37.233 |
| 1573 | ASN207 | N | 1.92 | 20.765 | 34.945 |
| 1574 | ASN207 | CA | 3.253 | 20.587 | 34.366 |
| 1575 | ASN207 | C | 3.307 | 21.204 | 32.976 |
| 1576 | ASN207 | O | 2.922 | 20.574 | 31.982 |
| 1577 | ASN207 | CB | 3.568 | 19.096 | 34.27 |
| 1578 | ASN207 | CG | 3.565 | 18.441 | 35.65 |
| 1579 | ASN207 | OD1 | 4.361 | 18.793 | 36.527 |
| 1580 | ASN207 | ND2 | 2.641 | 17.515 | 35.835 |
| 1581 | ALA208 | N | 3.786 | 22.435 | 32.932 |
| 1582 | ALA208 | CA | 3.924 | 23.166 | 31.668 |
| 1583 | ALA208 | C | 5.045 | 22.601 | 30.795 |
| 1584 | ALA208 | O | 6.235 | 22.809 | 31.052 |
| 1585 | ALA208 | CB | 4.202 | 24.631 | 31.982 |
| 1586 | THR209 | N | 4.636 | 21.874 | 29.77 |
| 1587 | THR209 | CA | 5.581 | 21.251 | 28.834 |
| 1588 | THR209 | C | 5.499 | 21.873 | 27.446 |
| 1589 | THR209 | O | 4.665 | 22.737 | 27.168 |
| 1590 | THR209 | CB | 5.253 | 19.774 | 28.706 |
| 1591 | THR209 | OG1 | 3.938 | 19.693 | 28.18 |
| 1592 | THR209 | CG2 | 5.296 | 19.059 | 30.052 |
| 1593 | GLU210 | N | 6.34 | 21.363 | 26.562 |
| 1594 | GLU210 | CA | 6.411 | 21.861 | 25.18 |
| 1595 | GLU210 | C | 5.542 | 21.076 | 24.19 |
| 1596 | GLU210 | O | 5.586 | 21.361 | 22.989 |
| 1597 | GLU210 | CB | 7.861 | 21.818 | 24.692 |
| 1598 | GLU210 | CG | 8.791 | 22.752 | 25.467 |
| 1599 | GLU210 | CD | 9.689 | 21.967 | 26.424 |
| 1600 | GLU210 | OE1 | 9.258 | 20.906 | 26.861 |
| 1601 | GLU210 | OE2 | 10.778 | 22.442 | 26.707 |
| 1602 | ASP211 | N | 4.786 | 20.097 | 24.662 |
| 1603 | ASP211 | CA | 3.977 | 19.273 | 23.746 |
| 1604 | ASP211 | C | 2.732 | 20.003 | 23.249 |
| 1605 | ASP211 | O | 2.331 | 21.027 | 23.817 |
| 1606 | ASP211 | CB | 3.605 | 17.956 | 24.418 |
| 1607 | ASP211 | CG | 2.942 | 18.154 | 25.781 |
| 1608 | ASP211 | OD1 | 2.12 | 19.054 | 25.925 |
| 1609 | ASP211 | OD2 | 3.336 | 17.427 | 26.681 |
| 1610 | ASP212 | N | 2.034 | 19.382 | 22.309 |
| 1611 | ASP212 | CA | 0.906 | 20.044 | 21.64 |
| 1612 | ASP212 | C | −0.365 | 20.067 | 22.496 |
| 1613 | ASP212 | O | −1.223 | 20.928 | 22.262 |
| 1614 | ASP212 | CB | 0.653 | 19.331 | 20.312 |
| 1615 | ASP212 | CG | −0.355 | 20.078 | 19.435 |
| 1616 | ASP212 | OD1 | −0.505 | 21.277 | 19.623 |
| 1617 | ASP212 | OD2 | −1.022 | 19.415 | 18.653 |
| 1618 | LEU213 | N | −0.398 | 19.318 | 23.589 |
| 1619 | LEU213 | CA | −1.529 | 19.451 | 24.508 |
| 1620 | LEU213 | C | −1.474 | 20.819 | 25.18 |
| 1621 | LEU213 | O | −2.372 | 21.628 | 24.907 |
| 1622 | LEU213 | CB | −1.498 | 18.346 | 25.557 |
| 1623 | LEU213 | CG | −2.75 | 18.365 | 26.427 |
| 1624 | LEU213 | CD1 | −4.011 | 18.334 | 25.574 |
| 1625 | LEU213 | CD2 | −2.751 | 17.202 | 27.41 |
| 1626 | LEU214 | N | −0.306 | 21.193 | 25.691 |
| 1627 | LEU214 | CA | −0.187 | 22.52 | 26.307 |
| 1628 | LEU214 | C | −0.094 | 23.607 | 25.241 |
| 1629 | LEU214 | O | −0.613 | 24.711 | 25.445 |
| 1630 | LEU214 | CB | 1.034 | 22.608 | 27.21 |
| 1631 | LEU214 | CG | 0.987 | 23.94 | 27.954 |
| 1632 | LEU214 | CD1 | −0.18 | 23.972 | 28.934 |
| 1633 | LEU214 | CD2 | 2.288 | 24.25 | 28.671 |
| 1634 | GLY215 | N | 0.35 | 23.222 | 24.056 |
| 1635 | GLY215 | CA | 0.292 | 24.093 | 22.882 |
| 1636 | GLY215 | C | −1.121 | 24.618 | 22.629 |
| 1637 | GLY215 | O | −1.327 | 25.838 | 22.586 |
| 1638 | ARG216 | N | −2.103 | 23.733 | 22.582 |
| 1639 | ARG216 | CA | −3.473 | 24.198 | 22.351 |
| 1640 | ARG216 | C | −4.154 | 24.727 | 23.616 |
| 1641 | ARG216 | O | −5.077 | 25.542 | 23.506 |
| 1642 | ARG216 | CB | −4.3 | 23.068 | 21.765 |
| 1643 | ARG216 | CG | −3.636 | 22.456 | 20.539 |
| 1644 | ARG216 | CD | −4.555 | 21.415 | 19.912 |
| 1645 | ARG216 | NE | −5.402 | 20.812 | 20.953 |
| 1646 | ARG216 | CZ | −5.073 | 19.756 | 21.699 |
| 1647 | ARG216 | NH1 | −3.937 | 19.093 | 21.471 |
| 1648 | ARG216 | NH2 | −5.905 | 19.342 | 22.652 |
| 1649 | GLN217 | N | −3.583 | 24.445 | 24.776 |
| 1650 | GLN217 | CA | −4.102 | 25.002 | 26.031 |
| 1651 | GLN217 | C | −3.624 | 26.435 | 26.28 |
| 1652 | GLN217 | O | −4.198 | 27.131 | 27.125 |
| 1653 | GLN217 | CB | −3.648 | 24.109 | 27.181 |
| 1654 | GLN217 | CG | −4.235 | 22.711 | 27.043 |
| 1655 | GLN217 | CD | −3.691 | 21.772 | 28.114 |
| 1656 | GLN217 | OE1 | −2.544 | 21.311 | 28.052 |
| 1657 | GLN217 | NE2 | −4.552 | 21.446 | 29.059 |
| 1658 | ILE218 | N | −2.608 | 26.875 | 25.551 |
| 1659 | ILE218 | CA | −2.179 | 28.276 | 25.625 |
| 1660 | ILE218 | C | −2.638 | 29.086 | 24.409 |
| 1661 | ILE218 | O | −2.242 | 30.25 | 24.267 |
| 1662 | ILE218 | CB | −0.66 | 28.352 | 25.774 |
| 1663 | ILE218 | CG1 | 0.061 | 27.755 | 24.572 |
| 1664 | ILE218 | CG2 | −0.211 | 27.665 | 27.059 |
| 1665 | ILE218 | CD1 | 1.574 | 27.781 | 24.754 |
| 1666 | LEU219 | N | −3.431 | 28.478 | 23.538 |
| 1667 | LEU219 | CA | −3.953 | 29.194 | 22.365 |
| 1668 | LEU219 | C | −4.858 | 30.352 | 22.75 |
| 1669 | LEU219 | O | −5.716 | 30.229 | 23.629 |
| 1670 | LEU219 | CB | −4.756 | 28.24 | 21.493 |
| 1671 | LEU219 | CG | −3.859 | 27.411 | 20.59 |
| 1672 | LEU219 | CD1 | −4.674 | 26.345 | 19.873 |
| 1673 | LEU219 | CD2 | −3.135 | 28.304 | 19.588 |
| 1674 | LYS220 | N | −4.667 | 31.454 | 22.047 |
| 1675 | LYS220 | CA | −5.484 | 32.654 | 22.234 |
| 1676 | LYS220 | C | −5.341 | 33.562 | 21.012 |
| 1677 | LYS220 | O | −4.556 | 34.519 | 21.016 |
| 1678 | LYS220 | CB | −5.01 | 33.38 | 23.489 |
| 1679 | LYS220 | CG | −5.91 | 34.56 | 23.842 |
| 1680 | LYS220 | CD | −5.389 | 35.289 | 25.074 |
| 1681 | LYS220 | CE | −6.258 | 36.494 | 25.418 |
| 1682 | LYS220 | NZ | −5.74 | 37.191 | 26.607 |
| 1683 | GLN221 | N | −6.048 | 33.217 | 19.951 |
| 1684 | GLN221 | CA | −5.987 | 34.031 | 18.732 |
| 1685 | GLN221 | C | −6.904 | 35.234 | 18.892 |
| 1686 | GLN221 | O | −7.981 | 35.112 | 19.48 |
| 1687 | GLN221 | CB | −6.389 | 33.179 | 17.535 |
| 1688 | GLN221 | CG | −5.417 | 32.015 | 17.369 |
| 1689 | GLN221 | CD | −5.828 | 31.088 | 16.227 |
| 1690 | GLN221 | OE1 | −7.019 | 30.872 | 15.966 |
| 1691 | GLN221 | NE2 | −4.823 | 30.508 | 15.595 |
| 1692 | ARG222 | N | −6.553 | 36.345 | 18.268 |
| 1693 | ARG222 | CA | −7.309 | 37.589 | 18.486 |
| 1694 | ARG222 | C | −8.774 | 37.467 | 18.066 |
| 1695 | ARG222 | O | −9.669 | 37.72 | 18.877 |
| 1696 | ARG222 | CB | −6.649 | 38.705 | 17.685 |
| 1697 | ARG222 | CG | −7.362 | 40.034 | 17.911 |
| 1698 | ARG222 | CD | −6.787 | 41.134 | 17.026 |
| 1699 | ARG222 | NE | −7.505 | 42.401 | 17.232 |
| 1700 | ARG222 | CZ | −8.368 | 42.909 | 16.349 |
| 1701 | ARG222 | NH1 | −8.626 | 42.255 | 15.213 |
| 1702 | ARG222 | NH2 | −8.98 | 44.068 | 16.604 |
| 1703 | GLU223 | N | −9.009 | 36.864 | 16.912 |
| 1704 | GLU223 | CA | −10.382 | 36.702 | 16.426 |
| 1705 | GLU223 | C | −10.985 | 35.329 | 16.735 |
| 1706 | GLU223 | O | −12.083 | 35.029 | 16.257 |
| 1707 | GLU223 | CB | −10.395 | 36.959 | 14.926 |
| 1708 | GLU223 | CG | −9.977 | 38.396 | 14.634 |
| 1709 | GLU223 | CD | −9.946 | 38.649 | 13.13 |
| 1710 | GLU223 | OE1 | −9.041 | 39.35 | 12.701 |
| 1711 | GLU223 | OE2 | −10.749 | 38.047 | 12.434 |
| 1712 | SER224 | N | −10.28 | 34.5 | 17.488 |

APPENDIX 1-continued

| Atom No. | Residue | Atom Name | X-coord | Y-coord | Z-coord |
|---|---|---|---|---|---|
| 1713 | SER224 | CA | −10.803 | 33.162 | 17.775 |
| 1714 | SER224 | C | −11.036 | 32.957 | 19.266 |
| 1715 | SER224 | O | −11.791 | 32.067 | 19.67 |
| 1716 | SER224 | CB | −9.789 | 32.13 | 17.308 |
| 1717 | SER224 | OG | −9.509 | 32.374 | 15.941 |
| 1718 | GLY225 | N | −10.409 | 33.796 | 20.069 |
| 1719 | GLY225 | CA | −10.436 | 33.613 | 21.517 |
| 1720 | GLY225 | C | −9.539 | 32.435 | 21.884 |
| 1721 | GLY225 | O | −8.577 | 32.109 | 21.174 |
| 1722 | GLU226 | N | −9.863 | 31.807 | 22.998 |
| 1723 | GLU226 | CA | −9.128 | 30.613 | 23.422 |
| 1724 | GLU226 | C | −10.067 | 29.417 | 23.535 |
| 1725 | GLU226 | O | −11.22 | 29.553 | 23.963 |
| 1726 | GLU226 | CB | −8.424 | 30.894 | 24.745 |
| 1727 | GLU226 | CG | −9.368 | 31.316 | 25.86 |
| 1728 | GLU226 | CD | −8.548 | 31.714 | 27.084 |
| 1729 | GLU226 | OE1 | −8.364 | 30.873 | 27.952 |
| 1730 | GLU226 | OE2 | −8.166 | 32.875 | 27.147 |
| 1731 | ALA227 | N | −9.567 | 28.262 | 23.127 |
| 1732 | ALA227 | CA | −10.372 | 27.035 | 23.163 |
| 1733 | ALA227 | C | −10.725 | 26.657 | 24.598 |
| 1734 | ALA227 | O | −9.859 | 26.603 | 25.477 |
| 1735 | ALA227 | CB | −9.587 | 25.904 | 22.508 |
| 1736 | ASP228 | N | −12.009 | 26.456 | 24.833 |
| 1737 | ASP228 | CA | −12.471 | 26.085 | 26.175 |
| 1738 | ASP228 | C | −12.163 | 24.618 | 26.455 |
| 1739 | ASP228 | O | −11.944 | 23.836 | 25.52 |
| 1740 | ASP228 | CB | −13.961 | 26.399 | 26.323 |
| 1741 | ASP228 | CG | −14.816 | 25.698 | 25.268 |
| 1742 | ASP228 | OD1 | −14.745 | 24.475 | 25.201 |
| 1743 | ASP228 | OD2 | −15.656 | 26.364 | 24.686 |
| 1744 | HIS229 | N | −12.329 | 24.215 | 27.704 |
| 1745 | HIS229 | CA | −11.958 | 22.854 | 28.129 |
| 1746 | HIS229 | C | −12.84 | 21.733 | 27.559 |
| 1747 | HIS229 | O | −12.334 | 20.622 | 27.37 |
| 1748 | HIS229 | CB | −11.971 | 22.807 | 29.658 |
| 1749 | HIS229 | CG | −13.265 | 23.255 | 30.319 |
| 1750 | HIS229 | ND1 | −14.34 | 22.487 | 30.584 |
| 1751 | HIS229 | CD2 | −13.557 | 24.519 | 30.78 |
| 1752 | HIS229 | CE1 | −15.293 | 23.238 | 31.171 |
| 1753 | HIS229 | NE2 | −14.808 | 24.494 | 31.292 |
| 1754 | GLY230 | N | −14.024 | 22.066 | 27.068 |
| 1755 | GLY230 | CA | −14.88 | 21.073 | 26.412 |
| 1756 | GLY230 | C | −14.27 | 20.684 | 25.07 |
| 1757 | GLY230 | O | −13.958 | 19.508 | 24.84 |
| 1758 | GLU231 | N | −13.866 | 21.704 | 24.329 |
| 1759 | GLU231 | CA | −13.239 | 21.508 | 23.021 |
| 1760 | GLU231 | C | −11.809 | 21.001 | 23.152 |
| 1761 | GLU231 | O | −11.365 | 20.21 | 22.315 |
| 1762 | GLU231 | CB | −13.196 | 22.856 | 22.318 |
| 1763 | GLU231 | CG | −14.589 | 23.417 | 22.086 |
| 1764 | GLU231 | CD | −14.471 | 24.888 | 21.707 |
| 1765 | GLU231 | OE1 | −15.12 | 25.296 | 20.756 |
| 1766 | GLU231 | OE2 | −13.758 | 25.592 | 22.418 |
| 1767 | LEU232 | N | −11.181 | 21.28 | 24.281 |
| 1768 | LEU232 | CA | −9.822 | 20.803 | 24.524 |
| 1769 | LEU232 | C | −9.841 | 19.292 | 24.755 |
| 1770 | LEU232 | O | −9.061 | 18.578 | 24.112 |
| 1771 | LEU232 | CB | −9.297 | 21.541 | 25.756 |
| 1772 | LEU232 | CG | −7.777 | 21.685 | 25.784 |
| 1773 | LEU232 | CD1 | −7.057 | 20.385 | 26.124 |
| 1774 | LEU232 | CD2 | −7.256 | 22.293 | 24.486 |
| 1775 | VAL233 | N | −10.877 | 18.804 | 25.419 |
| 1776 | VAL233 | CA | −11.016 | 17.36 | 25.627 |
| 1777 | VAL233 | C | −11.406 | 16.646 | 24.331 |
| 1778 | VAL233 | O | −10.729 | 15.676 | 23.963 |
| 1779 | VAL233 | CB | −12.066 | 17.13 | 26.71 |
| 1780 | VAL233 | CG1 | −12.478 | 15.667 | 26.802 |
| 1781 | VAL233 | CG2 | −11.571 | 17.632 | 28.062 |
| 1782 | GLY234 | N | −12.258 | 17.278 | 23.536 |
| 1783 | GLY234 | CA | −12.641 | 16.729 | 22.227 |
| 1784 | GLY234 | C | −11.443 | 16.59 | 21.287 |
| 1785 | GLY234 | O | −11.116 | 15.477 | 20.849 |
| 1786 | LEU235 | N | −10.687 | 17.668 | 21.146 |
| 1787 | LEU235 | CA | −9.532 | 17.691 | 20.238 |
| 1788 | LEU235 | C | −8.375 | 16.809 | 20.702 |
| 1789 | LEU235 | O | −7.846 | 16.046 | 19.882 |
| 1790 | LEU235 | CB | −9.04 | 19.13 | 20.146 |
| 1791 | LEU235 | CG | −10.08 | 20.034 | 19.495 |
| 1792 | LEU235 | CD1 | −9.781 | 21.505 | 19.761 |
| 1793 | LEU235 | CD2 | −10.2 | 19.75 | 18.003 |
| 1794 | ALA236 | N | −8.162 | 16.713 | 22.006 |
| 1795 | ALA236 | CA | −7.065 | 15.885 | 22.523 |
| 1796 | ALA236 | C | −7.38 | 14.407 | 22.375 |
| 1797 | ALA236 | O | −6.525 | 13.633 | 21.922 |
| 1798 | ALA236 | CB | −6.861 | 16.193 | 24.002 |
| 1799 | PHE237 | N | −8.66 | 14.095 | 22.475 |
| 1800 | PHE237 | CA | −9.11 | 12.723 | 22.306 |
| 1801 | PHE237 | C | −8.956 | 12.273 | 20.864 |
| 1802 | PHE237 | O | −8.27 | 11.274 | 20.617 |
| 1803 | PHE237 | CB | −10.58 | 12.657 | 22.682 |
| 1804 | PHE237 | CG | −11.12 | 11.24 | 22.674 |
| 1805 | PHE237 | CD1 | −10.824 | 10.394 | 23.733 |
| 1806 | PHE237 | CD2 | −11.885 | 10.786 | 21.608 |
| 1807 | PHE237 | CE1 | −11.305 | 9.095 | 23.736 |
| 1808 | PHE237 | CE2 | −12.366 | 9.486 | 21.61 |
| 1809 | PHE237 | CZ | −12.076 | 8.644 | 22.676 |
| 1810 | LEU238 | N | −9.329 | 13.135 | 19.931 |
| 1811 | LEU238 | CA | −9.272 | 12.754 | 18.516 |
| 1812 | LEU238 | C | −7.845 | 12.681 | 17.984 |
| 1813 | LEU238 | O | −7.532 | 11.745 | 17.236 |
| 1814 | LEU238 | CB | −10.056 | 13.766 | 17.695 |
| 1815 | LEU238 | CG | −11.539 | 13.75 | 18.042 |
| 1816 | LEU238 | CD1 | −12.279 | 14.795 | 17.221 |
| 1817 | LEU238 | CD2 | −12.145 | 12.369 | 17.814 |
| 1818 | LEU239 | N | −6.947 | 13.467 | 18.554 |
| 1819 | LEU239 | CA | −5.551 | 13.397 | 18.122 |
| 1820 | LEU239 | C | −4.861 | 12.158 | 18.68 |
| 1821 | LEU239 | O | −4.202 | 11.444 | 17.913 |
| 1822 | LEU239 | CB | −4.821 | 14.652 | 18.586 |
| 1823 | LEU239 | CG | −5.364 | 15.898 | 17.894 |
| 1824 | LEU239 | CD1 | −4.722 | 17.162 | 18.454 |
| 1825 | LEU239 | CD2 | −5.169 | 15.82 | 16.384 |
| 1826 | LEU240 | N | −5.275 | 11.736 | 19.864 |
| 1827 | LEU240 | CA | −4.667 | 10.56 | 20.485 |
| 1828 | LEU240 | C | −5.217 | 9.265 | 19.877 |
| 1829 | LEU240 | O | −4.445 | 8.316 | 19.674 |
| 1830 | LEU240 | CB | −4.952 | 10.634 | 21.981 |
| 1831 | LEU240 | CG | −3.966 | 9.808 | 22.798 |
| 1832 | LEU240 | CD1 | −2.53 | 10.2 | 22.479 |
| 1833 | LEU240 | CD2 | −4.227 | 9.976 | 24.289 |
| 1834 | ILE241 | N | −6.425 | 9.337 | 19.333 |
| 1835 | ILE241 | CA | −7.027 | 8.197 | 18.621 |
| 1836 | ILE241 | C | −6.509 | 8.091 | 17.184 |
| 1837 | ILE241 | O | −6.406 | 6.98 | 16.64 |
| 1838 | ILE241 | CB | −8.544 | 8.391 | 18.599 |
| 1839 | ILE241 | CG1 | −9.122 | 8.403 | 20.008 |
| 1840 | ILE241 | CG2 | −9.233 | 7.311 | 17.771 |
| 1841 | ILE241 | CD1 | −8.939 | 7.06 | 20.699 |
| 1842 | ALA242 | N | −5.959 | 9.182 | 16.676 |
| 1843 | ALA242 | CA | −5.353 | 9.154 | 15.345 |
| 1844 | ALA242 | C | −4.049 | 8.363 | 15.361 |
| 1845 | ALA242 | O | −3.842 | 7.511 | 14.487 |
| 1846 | ALA242 | CB | −5.09 | 10.583 | 14.884 |
| 1847 | GLY243 | N | −3.34 | 8.426 | 16.473 |
| 1848 | GLY243 | CA | −2.135 | 7.612 | 16.614 |
| 1849 | GLY243 | C | −2.461 | 6.175 | 17.012 |
| 1850 | GLY243 | O | −2.095 | 5.238 | 16.289 |
| 1851 | HIS244 | N | −3.274 | 6.021 | 18.047 |
| 1852 | HIS244 | CA | −3.556 | 4.687 | 18.603 |
| 1853 | HIS244 | C | −4.424 | 3.78 | 17.729 |
| 1854 | HIS244 | O | −4.288 | 2.555 | 17.808 |
| 1855 | HIS244 | CB | −4.271 | 4.846 | 19.946 |
| 1856 | HIS244 | CG | −3.394 | 5.206 | 21.132 |
| 1857 | HIS244 | ND1 | −2.995 | 6.436 | 21.502 |
| 1858 | HIS244 | CD2 | −2.87 | 4.327 | 22.051 |
| 1859 | HIS244 | CE1 | −2.232 | 6.348 | 22.61 |
| 1860 | HIS244 | NE2 | −2.156 | 5.042 | 22.95 |
| 1861 | GLU245 | N | −5.298 | 4.33 | 16.905 |
| 1862 | GLU245 | CA | −6.157 | 3.454 | 16.101 |
| 1863 | GLU245 | C | −6.041 | 3.723 | 14.61 |
| 1864 | GLU245 | O | −5.883 | 2.788 | 13.812 |
| 1865 | GLU245 | CB | −7.616 | 3.66 | 16.504 |
| 1866 | GLU245 | CG | −7.895 | 3.313 | 17.963 |

APPENDIX 1-continued

| Atom No. | Residue | Atom Name | X-coord | Y-coord | Z-coord |
|---|---|---|---|---|---|
| 1867 | GLU245 | CD | −7.613 | 1.839 | 18.255 |
| 1868 | GLU245 | OE1 | −7.721 | 1.028 | 17.348 |
| 1869 | GLU245 | OE2 | −7.228 | 1.562 | 19.381 |
| 1870 | THR246 | N | −5.987 | 4.996 | 14.26 |
| 1871 | THR246 | CA | −6.101 | 5.374 | 12.849 |
| 1872 | THR246 | C | −4.863 | 4.962 | 12.066 |
| 1873 | THR246 | O | −4.949 | 4.04 | 11.244 |
| 1874 | THR246 | CB | −6.314 | 6.88 | 12.759 |
| 1875 | THR246 | OG1 | −7.415 | 7.225 | 13.59 |
| 1876 | THR246 | CG2 | −6.614 | 7.344 | 11.338 |
| 1877 | THR247 | N | −3.702 | 5.384 | 12.532 |
| 1878 | THR247 | CA | −2.48 | 5.072 | 11.792 |
| 1879 | THR247 | C | −2.013 | 3.634 | 12.044 |
| 1880 | THR247 | O | −1.437 | 3.032 | 11.132 |
| 1881 | THR247 | CB | −1.4 | 6.078 | 12.171 |
| 1882 | THR247 | OG1 | −1.937 | 7.39 | 12.062 |
| 1883 | THR247 | CG2 | −0.192 | 5.981 | 11.246 |
| 1884 | ALA248 | N | −2.533 | 3.007 | 13.09 |
| 1885 | ALA248 | CA | −2.225 | 1.596 | 13.35 |
| 1886 | ALA248 | C | −2.915 | 0.676 | 12.342 |
| 1887 | ALA248 | O | −2.236 | −0.089 | 11.643 |
| 1888 | ALA248 | CB | −2.678 | 1.25 | 14.763 |
| 1889 | ASN249 | N | −4.175 | 0.958 | 12.049 |
| 1890 | ASN249 | CA | −4.878 | 0.157 | 11.042 |
| 1891 | ASN249 | C | −4.453 | 0.517 | 9.624 |
| 1892 | ASN249 | O | −4.313 | −0.39 | 8.791 |
| 1893 | ASN249 | CB | −6.377 | 0.361 | 11.199 |
| 1894 | ASN249 | CG | −6.902 | −0.561 | 12.291 |
| 1895 | ASN249 | OD1 | −6.261 | −1.569 | 12.613 |
| 1896 | ASN249 | ND2 | −8.133 | −0.32 | 12.703 |
| 1897 | MET250 | N | −3.945 | 1.727 | 9.463 |
| 1898 | MET250 | CA | −3.472 | 2.183 | 8.159 |
| 1899 | MET250 | C | −2.137 | 1.529 | 7.787 |
| 1900 | MET250 | O | −2.018 | 1.009 | 6.669 |
| 1901 | MET250 | CB | −3.231 | 3.702 | 8.255 |
| 1902 | MET250 | CG | −3.343 | 4.33 | 6.851 |
| 1903 | MET250 | SD | −2.234 | 5.768 | 6.665 |
| 1904 | MET250 | CE | −1.954 | 6.241 | 8.406 |
| 1905 | ILE251 | N | −1.267 | 1.317 | 8.764 |
| 1906 | ILE251 | CA | 0.019 | 0.667 | 8.477 |
| 1907 | ILE251 | C | −0.132 | −0.844 | 8.328 |
| 1908 | ILE251 | O | 0.449 | −1.427 | 7.402 |
| 1909 | ILE251 | CB | 1.001 | 0.949 | 9.613 |
| 1910 | ILE251 | CG1 | 1.293 | 2.434 | 9.757 |
| 1911 | ILE251 | CG2 | 2.305 | 0.188 | 9.404 |
| 1912 | ILE251 | CD1 | 2.264 | 2.698 | 10.902 |
| 1913 | SER252 | N | −1.081 | −1.421 | 9.047 |
| 1914 | SER252 | CA | −1.254 | −2.875 | 8.973 |
| 1915 | SER252 | C | −1.947 | −3.301 | 7.679 |
| 1916 | SER252 | O | −1.444 | −4.204 | 6.998 |
| 1917 | SER252 | CB | −2.03 | −3.36 | 10.197 |
| 1918 | SER252 | OG | −3.28 | −2.684 | 10.279 |
| 1919 | LEU253 | N | −2.85 | −2.465 | 7.194 |
| 1920 | LEU253 | CA | −3.558 | −2.762 | 5.948 |
| 1921 | LEU253 | C | −2.699 | −2.386 | 4.739 |
| 1922 | LEU253 | O | −2.665 | −3.129 | 3.748 |
| 1923 | LEU253 | CB | −4.857 | −1.963 | 5.994 |
| 1924 | LEU253 | CG | −5.781 | −2.185 | 4.804 |
| 1925 | LEU253 | CD1 | −6.009 | −3.665 | 4.521 |
| 1926 | LEU253 | CD2 | −7.109 | −1.479 | 5.058 |
| 1927 | GLY254 | N | −1.818 | −1.42 | 4.948 |
| 1928 | GLY254 | CA | −0.841 | −1.031 | 3.933 |
| 1929 | GLY254 | C | 0.161 | −2.148 | 3.671 |
| 1930 | GLY254 | O | 0.267 | −2.62 | 2.531 |
| 1931 | THR255 | N | 0.707 | −2.706 | 4.742 |
| 1932 | THR255 | CA | 1.711 | −3.772 | 4.62 |
| 1933 | THR255 | C | 1.123 | −5.042 | 4.017 |
| 1934 | THR255 | O | 1.715 | −5.592 | 3.079 |
| 1935 | THR255 | CB | 2.255 | −4.105 | 6.007 |
| 1936 | THR255 | OG1 | 2.837 | −2.935 | 6.563 |
| 1937 | THR255 | CG2 | 3.334 | −5.18 | 5.938 |
| 1938 | VAL256 | N | −0.133 | −5.321 | 4.331 |
| 1939 | VAL256 | CA | −0.797 | −6.505 | 3.781 |
| 1940 | VAL256 | C | −1.11 | −6.37 | 2.291 |
| 1941 | VAL256 | O | −0.832 | −7.307 | 1.531 |
| 1942 | VAL256 | CB | −2.083 | −6.706 | 4.571 |
| 1943 | VAL256 | CG1 | −3.028 | −7.693 | 3.905 |
| 1944 | VAL256 | CG2 | −1.774 | −7.144 | 5.993 |
| 1945 | THR257 | N | −1.372 | −5.158 | 1.833 |
| 1946 | THR257 | CA | −1.675 | −4.982 | 0.413 |
| 1947 | THR257 | C | −0.401 | −4.902 | −0.427 |
| 1948 | THR257 | O | −0.357 | −5.499 | −1.512 |
| 1949 | THR257 | CB | −2.502 | −3.717 | 0.248 |
| 1950 | THR257 | OG1 | −3.63 | −3.818 | 1.106 |
| 1951 | THR257 | CG2 | −3.002 | −3.558 | −1.183 |
| 1952 | LEU258 | N | 0.69 | −4.465 | 0.185 |
| 1953 | LEU258 | CA | 1.976 | −4.434 | −0.526 |
| 1954 | LEU258 | C | 2.588 | −5.828 | −0.61 |
| 1955 | LEU258 | O | 3.147 | −6.205 | −1.648 |
| 1956 | LEU258 | CB | 2.936 | −3.524 | 0.233 |
| 1957 | LEU258 | CG | 2.45 | −2.08 | 0.263 |
| 1958 | LEU258 | CD1 | 3.329 | −1.229 | 1.172 |
| 1959 | LEU258 | CD2 | 2.391 | −1.492 | −1.141 |
| 1960 | LEU259 | N | 2.248 | −6.652 | 0.368 |
| 1961 | LEU259 | CA | 2.721 | −8.034 | 0.407 |
| 1962 | LEU259 | C | 1.818 | −8.965 | −0.407 |
| 1963 | LEU259 | O | 2.223 | −10.083 | −0.747 |
| 1964 | LEU259 | CB | 2.742 | −8.462 | 1.869 |
| 1965 | LEU259 | CG | 3.979 | −9.291 | 2.183 |
| 1966 | LEU259 | CD1 | 5.235 | −8.559 | 1.727 |
| 1967 | LEU259 | CD2 | 4.05 | −9.61 | 3.672 |
| 1968 | GLU260 | N | 0.649 | −8.473 | −0.791 |
| 1969 | GLU260 | CA | −0.221 | −9.215 | −1.707 |
| 1970 | GLU260 | C | 0.163 | −8.932 | −3.151 |
| 1971 | GLU260 | O | 0.033 | −9.804 | −4.019 |
| 1972 | GLU260 | CB | −1.67 | −8.773 | −1.531 |
| 1973 | GLU260 | CG | −2.53 | −9.85 | −0.883 |
| 1974 | GLU260 | CD | −2.442 | −9.78 | 0.637 |
| 1975 | GLU260 | OE1 | −1.632 | −10.498 | 1.204 |
| 1976 | GLU260 | OE2 | −3.287 | −9.103 | 1.202 |
| 1977 | ASN261 | N | 0.693 | −7.743 | −3.382 |
| 1978 | ASN261 | CA | 1.158 | −7.381 | −4.723 |
| 1979 | ASN261 | C | 2.669 | −7.181 | −4.742 |
| 1980 | ASN261 | O | 3.134 | −6.032 | −4.804 |
| 1981 | ASN261 | CB | 0.468 | −6.089 | −5.161 |
| 1982 | ASN261 | CG | −0.986 | −6.311 | −5.586 |
| 1983 | ASN261 | OD1 | −1.784 | −6.942 | −4.881 |
| 1984 | ASN261 | ND2 | −1.339 | −5.701 | −6.705 |
| 1985 | PRO262 | N | 3.404 | −8.259 | −4.986 |
| 1986 | PRO262 | CA | 4.864 | −8.219 | −4.846 |
| 1987 | PRO262 | C | 5.563 | −7.432 | −5.958 |
| 1988 | PRO262 | O | 6.612 | −6.834 | −5.706 |
| 1989 | PRO262 | CB | 5.298 | −9.652 | −4.871 |
| 1990 | PRO262 | CG | 4.108 | −10.533 | −5.223 |
| 1991 | PRO262 | CD | 2.912 | −9.601 | −5.319 |
| 1992 | ASP263 | N | 4.884 | −7.222 | −7.077 |
| 1993 | ASP263 | CA | 5.442 | −6.411 | −8.166 |
| 1994 | ASP263 | C | 5.27 | −4.909 | −7.918 |
| 1995 | ASP263 | O | 6.133 | −4.124 | −8.327 |
| 1996 | ASP263 | CB | 4.783 | −6.822 | −9.488 |
| 1997 | ASP263 | CG | 3.253 | −6.778 | −9.42 |
| 1998 | ASP263 | OD1 | 2.69 | −5.734 | −9.721 |
| 1999 | ASP263 | OD2 | 2.673 | −7.766 | −8.992 |
| 2000 | GLN264 | N | 4.358 | −4.558 | −7.024 |
| 2001 | GLN264 | CA | 4.149 | −3.154 | −6.675 |
| 2002 | GLN264 | C | 5.104 | −2.803 | −5.545 |
| 2003 | GLN264 | O | 5.782 | −1.769 | −5.59 |
| 2004 | GLN264 | CB | 2.709 | −3.002 | −6.206 |
| 2005 | GLN264 | CG | 1.723 | −3.483 | −7.265 |
| 2006 | GLN264 | CD | 1.637 | −2.485 | −8.412 |
| 2007 | GLN264 | OE1 | 1.631 | −1.274 | −8.178 |
| 2008 | GLN264 | NE2 | 1.592 | −2.991 | −9.63 |
| 2009 | LEU265 | N | 5.398 | −3.825 | −4.758 |
| 2010 | LEU265 | CA | 6.389 | −3.701 | −3.693 |
| 2011 | LEU265 | C | 7.808 | −3.677 | −4.263 |
| 2012 | LEU265 | O | 8.639 | −2.888 | −3.798 |
| 2013 | LEU265 | CB | 6.218 | −4.903 | −2.775 |
| 2014 | LEU265 | CG | 7.134 | −4.809 | −1.565 |
| 2015 | LEU265 | CD1 | 6.869 | −3.518 | −0.802 |
| 2016 | LEU265 | CD2 | 6.958 | −6.023 | −0.662 |
| 2017 | ALA266 | N | 7.993 | −4.309 | −5.411 |
| 2018 | ALA266 | CA | 9.286 | −4.267 | −6.093 |
| 2019 | ALA266 | C | 9.528 | −2.929 | −6.785 |
| 2020 | ALA266 | O | 10.66 | −2.434 | −6.737 |

APPENDIX 1-continued

| Atom No. | Residue | Atom Name | X-coord | Y-coord | Z-coord |
|---|---|---|---|---|---|
| 2021 | ALA266 | CB | 9.333 | −5.39 | −7.123 |
| 2022 | LYS267 | N | 8.466 | −2.235 | −7.167 |
| 2023 | LYS267 | CA | 8.641 | −0.891 | −7.725 |
| 2024 | LYS267 | C | 8.887 | 0.136 | −6.625 |
| 2025 | LYS267 | O | 9.706 | 1.042 | −6.818 |
| 2026 | LYS267 | CB | 7.406 | −0.501 | −8.523 |
| 2027 | LYS267 | CG | 7.223 | −1.394 | −9.742 |
| 2028 | LYS267 | CD | 6.072 | −0.894 | −10.604 |
| 2029 | LYS267 | CE | 4.779 | −0.825 | −9.803 |
| 2030 | LYS267 | NZ | 3.688 | −0.267 | −10.615 |
| 2031 | ILE268 | N | 8.413 | −0.162 | −5.427 |
| 2032 | ILE268 | CA | 8.717 | 0.664 | −4.254 |
| 2033 | ILE268 | C | 10.181 | 0.531 | −3.84 |
| 2034 | ILE268 | O | 10.879 | 1.544 | −3.697 |
| 2035 | ILE268 | CB | 7.827 | 0.171 | −3.117 |
| 2036 | ILE268 | CG1 | 6.38 | 0.576 | −3.335 |
| 2037 | ILE268 | CG2 | 8.311 | 0.638 | −1.75 |
| 2038 | ILE268 | CD1 | 5.504 | 0.057 | −2.205 |
| 2039 | LYS269 | N | 10.693 | −0.688 | −3.902 |
| 2040 | LYS269 | CA | 12.068 | −0.95 | −3.463 |
| 2041 | LYS269 | C | 13.116 | −0.675 | −4.542 |
| 2042 | LYS269 | O | 14.306 | −0.554 | −4.228 |
| 2043 | LYS269 | CB | 12.126 | −2.405 | −3.021 |
| 2044 | LYS269 | CG | 11.167 | −2.628 | −1.858 |
| 2045 | LYS269 | CD | 10.997 | −4.107 | −1.542 |
| 2046 | LYS269 | CE | 12.315 | −4.756 | −1.148 |
| 2047 | LYS269 | NZ | 12.106 | −6.181 | −0.856 |
| 2048 | ALA270 | N | 12.679 | −0.53 | −5.782 |
| 2049 | ALA270 | CA | 13.585 | −0.106 | −6.851 |
| 2050 | ALA270 | C | 13.478 | 1.396 | −7.101 |
| 2051 | ALA270 | O | 14.286 | 1.974 | −7.838 |
| 2052 | ALA270 | CB | 13.233 | −0.863 | −8.125 |
| 2053 | ASP271 | N | 12.486 | 2.017 | −6.486 |
| 2054 | ASP271 | CA | 12.271 | 3.453 | −6.649 |
| 2055 | ASP271 | C | 11.505 | 4.006 | −5.448 |
| 2056 | ASP271 | O | 10.267 | 4.02 | −5.445 |
| 2057 | ASP271 | CB | 11.48 | 3.653 | −7.944 |
| 2058 | ASP271 | CG | 11.354 | 5.125 | −8.337 |
| 2059 | ASP271 | OD1 | 10.975 | 5.919 | −7.482 |
| 2060 | ASP271 | OD2 | 11.493 | 5.405 | −9.517 |
| 2061 | PRO272 | N | 12.238 | 4.705 | −4.592 |
| 2062 | PRO272 | CA | 11.686 | 5.248 | −3.337 |
| 2063 | PRO272 | C | 10.72 | 6.438 | −3.497 |
| 2064 | PRO272 | O | 9.973 | 6.74 | −2.558 |
| 2065 | PRO272 | CB | 12.887 | 5.657 | −2.54 |
| 2066 | PRO272 | CG | 14.133 | 5.544 | −3.406 |
| 2067 | PRO272 | CD | 13.674 | 4.968 | −4.734 |
| 2068 | GLY273 | N | 10.586 | 6.971 | −4.702 |
| 2069 | GLY273 | CA | 9.607 | 8.03 | −4.968 |
| 2070 | GLY273 | C | 8.207 | 7.423 | −5.037 |
| 2071 | GLY273 | O | 7.257 | 7.968 | −4.456 |
| 2072 | LYS274 | N | 8.167 | 6.171 | −5.473 |
| 2073 | LYS274 | CA | 6.916 | 5.418 | −5.566 |
| 2074 | LYS274 | C | 6.39 | 4.954 | −4.21 |
| 2075 | LYS274 | O | 5.225 | 4.55 | −4.144 |
| 2076 | LYS274 | CB | 7.138 | 4.184 | −6.431 |
| 2077 | LYS274 | CG | 7.528 | 4.547 | −7.856 |
| 2078 | LYS274 | CD | 7.755 | 3.287 | −8.681 |
| 2079 | LYS274 | CE | 8.177 | 3.615 | −10.107 |
| 2080 | LYS274 | NZ | 8.465 | 2.383 | −10.858 |
| 2081 | THR275 | N | 7.12 | 5.182 | −3.127 |
| 2082 | THR275 | CA | 6.593 | 4.814 | −1.813 |
| 2083 | THR275 | C | 5.522 | 5.804 | −1.352 |
| 2084 | THR275 | O | 4.516 | 5.354 | −0.798 |
| 2085 | THR275 | CB | 7.725 | 4.76 | −0.789 |
| 2086 | THR275 | OG1 | 8.169 | 6.074 | −0.485 |
| 2087 | THR275 | CG2 | 8.912 | 3.963 | −1.305 |
| 2088 | LEU276 | N | 5.564 | 7.036 | −1.844 |
| 2089 | LEU276 | CA | 4.543 | 8.012 | −1.446 |
| 2090 | LEU276 | C | 3.312 | 7.905 | −2.346 |
| 2091 | LEU276 | O | 2.175 | 8.051 | −1.876 |
| 2092 | LEU276 | CB | 5.14 | 9.411 | −1.538 |
| 2093 | LEU276 | CG | 4.182 | 10.462 | −0.987 |
| 2094 | LEU276 | CD1 | 3.836 | 10.177 | 0.472 |
| 2095 | LEU276 | CD2 | 4.77 | 11.861 | −1.133 |
| 2096 | ALA277 | N | 3.53 | 7.375 | −3.539 |
| 2097 | ALA277 | CA | 2.417 | 7.126 | −4.451 |
| 2098 | ALA277 | C | 1.711 | 5.836 | −4.052 |
| 2099 | ALA277 | O | 0.475 | 5.796 | −4.026 |
| 2100 | ALA277 | CB | 2.963 | 7.021 | −5.869 |
| 2101 | ALA278 | N | 2.472 | 4.947 | −3.431 |
| 2102 | ALA278 | CA | 1.909 | 3.727 | −2.859 |
| 2103 | ALA278 | C | 1.12 | 4.01 | −1.591 |
| 2104 | ALA278 | O | 0.051 | 3.416 | −1.427 |
| 2105 | ALA278 | CB | 3.048 | 2.773 | −2.523 |
| 2106 | ILE279 | N | 1.472 | 5.064 | −0.867 |
| 2107 | ILE279 | CA | 0.698 | 5.447 | 0.324 |
| 2108 | ILE279 | C | −0.692 | 5.926 | −0.078 |
| 2109 | ILE279 | O | −1.691 | 5.368 | 0.396 |
| 2110 | ILE279 | CB | 1.401 | 6.588 | 1.063 |
| 2111 | ILE279 | CG1 | 2.806 | 6.209 | 1.513 |
| 2112 | ILE279 | CG2 | 0.577 | 7.041 | 2.264 |
| 2113 | ILE279 | CD1 | 2.805 | 4.984 | 2.416 |
| 2114 | GLU280 | N | −0.748 | 6.688 | −1.159 |
| 2115 | GLU280 | CA | −2.037 | 7.217 | −1.616 |
| 2116 | GLU280 | C | −2.849 | 6.159 | −2.358 |
| 2117 | GLU280 | O | −4.075 | 6.123 | −2.217 |
| 2118 | GLU280 | CB | −1.784 | 8.404 | −2.537 |
| 2119 | GLU280 | CG | −0.943 | 9.484 | −1.862 |
| 2120 | GLU280 | CD | −1.616 | 9.992 | −0.587 |
| 2121 | GLU280 | OE1 | −2.453 | 10.875 | −0.699 |
| 2122 | GLU280 | OE2 | −1.19 | 9.569 | 0.479 |
| 2123 | GLU281 | N | −2.169 | 5.173 | −2.916 |
| 2124 | GLU281 | CA | −2.857 | 4.083 | −3.604 |
| 2125 | GLU281 | C | −3.402 | 3.048 | −2.616 |
| 2126 | GLU281 | O | −4.497 | 2.514 | −2.842 |
| 2127 | GLU281 | CB | −1.846 | 3.441 | −4.546 |
| 2128 | GLU281 | CG | −2.451 | 2.329 | −5.39 |
| 2129 | GLU281 | CD | −3.395 | 2.862 | −6.465 |
| 2130 | GLU281 | OE1 | −3.893 | 2.017 | −7.199 |
| 2131 | GLU281 | OE2 | −3.446 | 4.068 | −6.653 |
| 2132 | LEU282 | N | −2.776 | 2.957 | −1.452 |
| 2133 | LEU282 | CA | −3.272 | 2.102 | −0.369 |
| 2134 | LEU282 | C | −4.527 | 2.703 | 0.232 |
| 2135 | LEU282 | O | −5.563 | 2.03 | 0.269 |
| 2136 | LEU282 | CB | −2.212 | 2.019 | 0.727 |
| 2137 | LEU282 | CG | −1.025 | 1.151 | 0.332 |
| 2138 | LEU282 | CD1 | 0.163 | 1.385 | 1.256 |
| 2139 | LEU282 | CD2 | −1.415 | −0.319 | 0.305 |
| 2140 | LEU283 | N | −4.511 | 4.018 | 0.378 |
| 2141 | LEU283 | CA | −5.666 | 4.738 | 0.922 |
| 2142 | LEU283 | C | −6.823 | 4.808 | −0.066 |
| 2143 | LEU283 | O | −7.989 | 4.766 | 0.346 |
| 2144 | LEU283 | CB | −5.202 | 6.145 | 1.257 |
| 2145 | LEU283 | CG | −4.178 | 6.103 | 2.379 |
| 2146 | LEU283 | CD1 | −3.386 | 7.399 | 2.461 |
| 2147 | LEU283 | CD2 | −4.848 | 5.766 | 3.706 |
| 2148 | ARG284 | N | −6.512 | 4.723 | −1.346 |
| 2149 | ARG284 | CA | −7.561 | 4.67 | −2.355 |
| 2150 | ARG284 | C | −8.306 | 3.337 | −2.3 |
| 2151 | ARG284 | O | −9.482 | 3.316 | −1.923 |
| 2152 | ARG284 | CB | −6.921 | 4.824 | −3.726 |
| 2153 | ARG284 | CG | −7.99 | 4.956 | −4.798 |
| 2154 | ARG284 | CD | −7.417 | 4.674 | −6.18 |
| 2155 | ARG284 | NE | −6.879 | 3.305 | −6.258 |
| 2156 | ARG284 | CZ | −7.603 | 2.231 | −6.583 |
| 2157 | ARG284 | NH1 | −8.911 | 2.35 | −6.816 |
| 2158 | ARG284 | NH2 | −7.021 | 1.032 | −6.658 |
| 2159 | ILE285 | N | −7.588 | 2.233 | −2.423 |
| 2160 | ILE285 | CA | −8.284 | 0.942 | −2.519 |
| 2161 | ILE285 | C | −8.742 | 0.397 | −1.155 |
| 2162 | ILE285 | O | −9.703 | −0.385 | −1.087 |
| 2163 | ILE285 | CB | −7.36 | −0.039 | −3.247 |
| 2164 | ILE285 | CG1 | −8.033 | −1.383 | −3.499 |
| 2165 | ILE285 | CG2 | −6.045 | −0.238 | −2.501 |
| 2166 | ILE285 | CD1 | −7.119 | −2.327 | −4.272 |
| 2167 | PHE286 | N | −8.188 | 0.934 | −0.082 |
| 2168 | PHE286 | CA | −8.543 | 0.5 | 1.268 |
| 2169 | PHE286 | C | −8.451 | 1.645 | 2.27 |
| 2170 | PHE286 | O | −7.544 | 1.66 | 3.115 |
| 2171 | PHE286 | CB | −7.575 | −0.594 | 1.708 |
| 2172 | PHE286 | CG | −7.737 | −1.948 | 1.025 |
| 2173 | PHE286 | CD1 | −6.675 | −2.503 | 0.323 |
| 2174 | PHE286 | CD2 | −8.943 | −2.632 | 1.117 |

APPENDIX 1-continued

| Atom No. | Residue | Atom Name | X-coord | Y-coord | Z-coord |
|---|---|---|---|---|---|
| 2175 | PHE286 | CE1 | −6.822 | −3.736 | −0.298 |
| 2176 | PHE286 | CE2 | −9.09 | −3.865 | 0.495 |
| 2177 | PHE286 | CZ | −8.03 | −4.417 | −0.213 |
| 2178 | THR287 | N | −9.377 | 2.584 | 2.193 |
| 2179 | THR287 | CA | −9.413 | 3.636 | 3.212 |
| 2180 | THR287 | C | −9.931 | 3.053 | 4.519 |
| 2181 | THR287 | O | −10.843 | 2.216 | 4.543 |
| 2182 | THR287 | CB | −10.294 | 4.801 | 2.77 |
| 2183 | THR287 | OG1 | −10.207 | 5.833 | 3.745 |
| 2184 | THR287 | CG2 | −11.759 | 4.423 | 2.643 |
| 2185 | ILE288 | N | −9.305 | 3.459 | 5.609 |
| 2186 | ILE288 | CA | −9.745 | 2.966 | 6.911 |
| 2187 | ILE288 | C | −10.966 | 3.747 | 7.391 |
| 2188 | ILE288 | O | −11.856 | 3.155 | 8.014 |
| 2189 | ILE288 | CB | −8.584 | 3.044 | 7.894 |
| 2190 | ILE288 | CG1 | −8.04 | 4.459 | 8.013 |
| 2191 | ILE288 | CG2 | −7.469 | 2.097 | 7.461 |
| 2192 | ILE288 | CD1 | −6.938 | 4.507 | 9.052 |
| 2193 | ALA289 | N | −11.116 | 4.965 | 6.89 |
| 2194 | ALA289 | CA | −12.34 | 5.743 | 7.09 |
| 2195 | ALA289 | C | −13.315 | 5.37 | 5.982 |
| 2196 | ALA289 | O | −13.433 | 6.062 | 4.964 |
| 2197 | ALA289 | CB | −12.003 | 7.228 | 7.013 |
| 2198 | GLU290 | N | −13.969 | 4.239 | 6.174 |
| 2199 | GLU290 | CA | −14.796 | 3.652 | 5.128 |
| 2200 | GLU290 | C | −16.223 | 4.179 | 5.178 |
| 2201 | GLU290 | O | −16.891 | 4.234 | 4.138 |
| 2202 | GLU290 | CB | −14.766 | 2.14 | 5.34 |
| 2203 | GLU290 | CG | −15.669 | 1.375 | 4.381 |
| 2204 | GLU290 | CD | −15.736 | −0.091 | 4.802 |
| 2205 | GLU290 | OE1 | −16.751 | −0.475 | 5.367 |
| 2206 | GLU290 | OE2 | −14.809 | −0.819 | 4.472 |
| 2207 | THR291 | N | −16.659 | 4.619 | 6.347 |
| 2208 | THR291 | CA | −17.992 | 5.216 | 6.481 |
| 2209 | THR291 | C | −17.983 | 6.47 | 7.349 |
| 2210 | THR291 | O | −17.68 | 6.437 | 8.55 |
| 2211 | THR291 | CB | −18.978 | 4.219 | 7.094 |
| 2212 | THR291 | OG1 | −18.522 | 3.832 | 8.382 |
| 2213 | THR291 | CG2 | −19.168 | 2.961 | 6.257 |
| 2214 | ALA292 | N | −18.397 | 7.562 | 6.734 |
| 2215 | ALA292 | CA | −18.676 | 8.799 | 7.471 |
| 2216 | ALA292 | C | −20.103 | 8.704 | 8.001 |
| 2217 | ALA292 | O | −21.051 | 9.169 | 7.355 |
| 2218 | ALA292 | CB | −18.552 | 9.986 | 6.521 |
| 2219 | THR293 | N | −20.231 | 8.1 | 9.172 |
| 2220 | THR293 | CA | −21.535 | 7.709 | 9.721 |
| 2221 | THR293 | C | −22.161 | 8.802 | 10.585 |
| 2222 | THR293 | O | −22.152 | 8.733 | 11.82 |
| 2223 | THR293 | CB | −21.308 | 6.447 | 10.546 |
| 2224 | THR293 | OG1 | −20.564 | 5.523 | 9.756 |
| 2225 | THR293 | CG2 | −22.617 | 5.788 | 10.962 |
| 2226 | SER294 | N | −22.703 | 9.805 | 9.913 |
| 2227 | SER294 | CA | −23.293 | 10.956 | 10.601 |
| 2228 | SER294 | C | −24.198 | 11.766 | 9.675 |
| 2229 | SER294 | O | −25.386 | 11.443 | 9.529 |
| 2230 | SER294 | CB | −22.167 | 11.822 | 11.164 |
| 2231 | SER294 | OG | −20.976 | 11.559 | 10.426 |
| 2232 | ARG295 | N | −23.598 | 12.789 | 9.076 |
| 2233 | ARG295 | CA | −24.233 | 13.782 | 8.187 |
| 2234 | ARG295 | C | −25.738 | 13.903 | 8.366 |
| 2235 | ARG295 | O | −26.524 | 13.3 | 7.627 |
| 2236 | ARG295 | CB | −23.905 | 13.424 | 6.747 |
| 2237 | ARG295 | CG | −22.4 | 13.455 | 6.518 |
| 2238 | ARG295 | CD | −21.819 | 14.841 | 6.786 |
| 2239 | ARG295 | NE | −20.362 | 14.859 | 6.577 |
| 2240 | ARG295 | CZ | −19.475 | 14.679 | 7.56 |
| 2241 | ARG295 | NH1 | −19.892 | 14.437 | 8.805 |
| 2242 | ARG295 | NH2 | −18.167 | 14.719 | 7.293 |
| 2243 | PHE296 | N | −26.119 | 14.646 | 9.387 |
| 2244 | PHE296 | GA | −27.528 | 14.825 | 9.712 |
| 2245 | PHE296 | C | −28.176 | 15.754 | 8.701 |
| 2246 | PHE296 | O | −27.736 | 16.899 | 8.529 |
| 2247 | PHE296 | CB | −27.623 | 15.428 | 11.11 |
| 2248 | PHE296 | CG | −29.052 | 15.695 | 11.562 |
| 2249 | PHE296 | CD1 | −29.564 | 16.985 | 11.533 |
| 2250 | PHE296 | CD2 | −29.843 | 14.643 | 12.002 |
| 2251 | PHE296 | CE1 | −30.871 | 17.221 | 11.936 |
| 2252 | PHE296 | CE2 | −31.149 | 14.879 | 12.406 |
| 2253 | PHE296 | CZ | −31.663 | 16.167 | 12.37 |
| 2254 | ALA297 | N | −29.2 | 15.255 | 8.032 |
| 2255 | ALA297 | CA | −29.931 | 16.073 | 7.065 |
| 2256 | ALA297 | C | −30.783 | 17.111 | 7.781 |
| 2257 | ALA297 | O | −31.769 | 16.781 | 8.45 |
| 2258 | ALA297 | CB | −30.819 | 15.165 | 6.224 |
| 2259 | THR298 | N | −30.369 | 18.361 | 7.668 |
| 2260 | THR298 | CA | −31.129 | 19.47 | 8.255 |
| 2261 | THR298 | C | −32.139 | 20.005 | 7.246 |
| 2262 | THR298 | O | −33.087 | 20.712 | 7.603 |
| 2263 | THR298 | CB | −30.17 | 20.586 | 8.659 |
| 2264 | THR298 | OG1 | −29.565 | 21.12 | 7.488 |
| 2265 | THR298 | CG2 | −29.068 | 20.082 | 9.582 |
| 2266 | ALA299 | N | −31.926 | 19.649 | 5.992 |
| 2267 | ALA299 | CA | −32.881 | 19.968 | 4.932 |
| 2268 | ALA299 | C | −33.091 | 18.734 | 4.068 |
| 2269 | ALA299 | O | −32.427 | 17.712 | 4.27 |
| 2270 | ALA299 | CB | −32.331 | 21.11 | 4.086 |
| 2271 | ASP300 | N | −34.041 | 18.817 | 3.151 |
| 2272 | ASP300 | CA | −34.256 | 17.727 | 2.191 |
| 2273 | ASP300 | C | −33.253 | 17.852 | 1.048 |
| 2274 | ASP300 | O | −33.498 | 18.545 | 0.053 |
| 2275 | ASP300 | CB | −35.679 | 17.801 | 1.648 |
| 2276 | ASP300 | CG | −36.682 | 17.714 | 2.793 |
| 2277 | ASP300 | OD1 | −36.686 | 16.69 | 3.463 |
| 2278 | ASP300 | OD2 | −37.289 | 18.733 | 3.09 |
| 2279 | VAL301 | N | −32.128 | 17.177 | 1.199 |
| 2280 | VAL301 | CA | −31.029 | 17.337 | 0.244 |
| 2281 | VAL301 | C | −31.065 | 16.261 | −0.833 |
| 2282 | VAL301 | O | −30.956 | 15.02 | −0.55 |
| 2283 | VAL301 | CB | −29.711 | 17.263 | 1.007 |
| 2284 | VAL301 | CG1 | −28.543 | 17.673 | 0.118 |
| 2285 | VAL301 | CG2 | −29.756 | 18.154 | 2.24 |
| 2286 | GLU302 | N | −31.242 | 16.695 | −2.067 |
| 2287 | GLU302 | CA | −31.23 | 15.75 | −3.184 |
| 2288 | GLU302 | C | −29.799 | 15.413 | −3.603 |
| 2289 | GLU302 | O | −29.141 | 16.178 | −4.318 |
| 2290 | GLU302 | CB | −31.98 | 16.355 | −4.363 |
| 2291 | GLU302 | CG | −32.053 | 15.344 | −5.497 |
| 2292 | GLU302 | CD | −32.662 | 15.959 | −6.75 |
| 2293 | GLU302 | OE1 | −33.484 | 16.852 | −6.606 |
| 2294 | GLU302 | OE2 | −32.169 | 15.628 | −7.82 |
| 2295 | ILE303 | N | −29.365 | 14.227 | −3.222 |
| 2296 | ILE303 | CA | −28.014 | 13.766 | −3.539 |
| 2297 | ILE303 | C | −28.053 | 12.812 | −4.726 |
| 2298 | ILE303 | O | −28.452 | 11.647 | −4.6 |
| 2299 | ILE303 | CB | −27.438 | 13.076 | −2.307 |
| 2300 | ILE303 | CG1 | −27.329 | 14.056 | −1.148 |
| 2301 | ILE303 | CG2 | −26.066 | 12.49 | −2.608 |
| 2302 | ILE303 | CD1 | −26.305 | 15.146 | −1.441 |
| 2303 | GLY304 | N | −27.715 | 13.356 | −5.885 |
| 2304 | GLY304 | CA | −27.705 | 12.592 | −7.139 |
| 2305 | GLY304 | C | −29.056 | 11.935 | −7.402 |
| 2306 | GLY304 | O | −29.187 | 10.708 | −7.311 |
| 2307 | GLY305 | N | −30.079 | 12.757 | −7.573 |
| 2308 | GLY305 | CA | −31.432 | 12.229 | −7.805 |
| 2309 | GLY305 | C | −32.226 | 11.982 | −6.517 |
| 2310 | GLY305 | O | −33.289 | 12.584 | −6.314 |
| 2311 | THR306 | N | −31.694 | 11.132 | −5.653 |
| 2312 | THR306 | CA | −32.399 | 10.717 | −4.431 |
| 2313 | THR306 | C | −32.569 | 11.859 | −3.43 |
| 2314 | THR306 | O | −31.597 | 12.497 | −3.015 |
| 2315 | THR306 | CB | −31.591 | 9.598 | −3.782 |
| 2316 | THR306 | OG1 | −31.461 | 8.534 | −4.716 |
| 2317 | THR306 | CG2 | −32.278 | 9.051 | −2.537 |
| 2318 | LEU307 | N | −33.811 | 12.127 | −3.066 |
| 2319 | LEU307 | CA | −34.093 | 13.162 | −2.068 |
| 2320 | LEU307 | C | −33.971 | 12.6 | −0.652 |
| 2321 | LEU307 | O | −34.803 | 11.799 | −0.209 |
| 2322 | LEU307 | CB | −35.513 | 13.67 | −2.295 |
| 2323 | LEU307 | CG | −35.845 | 14.852 | −1.391 |
| 2324 | LEU307 | CD1 | −34.946 | 16.039 | −1.71 |
| 2325 | LEU307 | CD2 | −37.31 | 15.248 | −1.534 |
| 2326 | ILE308 | N | −32.93 | 13.021 | 0.045 |
| 2327 | ILE308 | CA | −32.738 | 12.616 | 1.439 |
| 2328 | ILE308 | C | −33.586 | 13.486 | 2.362 |

APPENDIX 1-continued

| Atom No. | Residue | Atom Name | X-coord | Y-coord | Z-coord |
|---|---|---|---|---|---|
| 2329 | ILE308 | O | −33.481 | 14.719 | 2.356 |
| 2330 | ILE308 | CB | −31.253 | 12.742 | 1.764 |
| 2331 | ILE308 | CG1 | −30.456 | 11.77 | 0.901 |
| 2332 | ILE308 | CG2 | −30.976 | 12.507 | 3.245 |
| 2333 | ILE308 | CD1 | −28.974 | 11.794 | 1.246 |
| 2334 | ARG309 | N | −34.466 | 12.834 | 3.101 |
| 2335 | ARG309 | CA | −35.386 | 13.543 | 3.993 |
| 2336 | ARG309 | C | −34.674 | 14.125 | 5.209 |
| 2337 | ARG309 | O | −33.807 | 13.486 | 5.824 |
| 2338 | ARG309 | CB | −36.447 | 12.563 | 4.474 |
| 2339 | ARG309 | CG | −37.117 | 11.841 | 3.312 |
| 2340 | ARG309 | CD | −38.079 | 10.778 | 3.83 |
| 2341 | ARG309 | NE | −38.721 | 10.055 | 2.721 |
| 2342 | ARG309 | CZ | −40.046 | 9.951 | 2.594 |
| 2343 | ARG309 | NH1 | −40.85 | 10.528 | 3.49 |
| 2344 | ARG309 | NH2 | −40.566 | 9.278 | 1.566 |
| 2345 | ALA310 | N | −35.099 | 15.325 | 5.566 |
| 2346 | ALA310 | CA | −34.597 | 15.999 | 6.763 |
| 2347 | ALA310 | C | −34.952 | 15.189 | 8.003 |
| 2348 | ALA310 | O | −36.005 | 14.542 | 8.07 |
| 2349 | ALA310 | CB | −35.223 | 17.386 | 6.853 |
| 2350 | GLY311 | N | −34 | 15.115 | 8.913 |
| 2351 | GLY311 | CA | −34.172 | 14.325 | 10.13 |
| 2352 | GLY311 | C | −33.475 | 12.968 | 10.042 |
| 2353 | GLY311 | O | −33.472 | 12.217 | 11.023 |
| 2354 | GLU312 | N | −32.982 | 12.611 | 8.866 |
| 2355 | GLU312 | CA | −32.294 | 11.322 | 8.719 |
| 2356 | GLU312 | C | −30.776 | 11.471 | 8.737 |
| 2357 | GLU312 | O | −30.236 | 12.577 | 8.599 |
| 2358 | GLU312 | CB | −32.743 | 10.651 | 7.429 |
| 2359 | GLU312 | CG | −34.243 | 10.386 | 7.453 |
| 2360 | GLU312 | CD | −34.639 | 9.537 | 6.252 |
| 2361 | GLU312 | OE1 | −34.686 | 10.083 | 5.156 |
| 2362 | GLU312 | OE2 | −34.723 | 8.33 | 6.419 |
| 2363 | GLY313 | N | −30.107 | 10.356 | 8.981 |
| 2364 | GLY313 | CA | −28.64 | 10.335 | 8.994 |
| 2365 | GLY313 | C | −28.079 | 9.813 | 7.673 |
| 2366 | GLY313 | O | −28.674 | 8.944 | 7.02 |
| 2367 | VAL314 | N | −26.996 | 10.429 | 7.237 |
| 2368 | VAL314 | CA | −26.33 | 10.028 | 5.994 |
| 2369 | VAL314 | C | −24.93 | 9.467 | 6.267 |
| 2370 | VAL314 | O | −24.127 | 10.02 | 7.033 |
| 2371 | VAL314 | CB | −26.28 | 11.246 | 5.073 |
| 2372 | VAL314 | CG1 | −25.639 | 10.942 | 3.724 |
| 2373 | VAL314 | CG2 | −27.681 | 11.804 | 4.861 |
| 2374 | VAL315 | N | −24.674 | 8.328 | 5.649 |
| 2375 | VAL315 | CA | −23.386 | 7.646 | 5.773 |
| 2376 | VAL315 | C | −22.647 | 7.666 | 4.435 |
| 2377 | VAL315 | O | −23.025 | 6.975 | 3.479 |
| 2378 | VAL315 | CB | −23.634 | 6.207 | 6.213 |
| 2379 | VAL315 | CG1 | −22.325 | 5.437 | 6.347 |
| 2380 | VAL315 | CG2 | −24.404 | 6.163 | 7.528 |
| 2381 | GLY316 | N | −21.6 | 8.467 | 4.374 |
| 2382 | GLY316 | CA | −20.789 | 8.539 | 3.152 |
| 2383 | GLY316 | C | −19.797 | 7.382 | 3.096 |
| 2384 | GLY316 | O | −18.903 | 7.28 | 3.946 |
| 2385 | LEU317 | N | −19.978 | 6.508 | 2.121 |
| 2386 | LEU317 | CA | −19.102 | 5.343 | 1.978 |
| 2387 | LEU317 | C | −17.841 | 5.722 | 1.218 |
| 2388 | LEU317 | O | −17.758 | 5.485 | 0.009 |
| 2389 | LEU317 | CB | −19.835 | 4.256 | 1.199 |
| 2390 | LEU317 | CG | −20.312 | 3.094 | 2.064 |
| 2391 | LEU317 | CD1 | −19.129 | 2.374 | 2.697 |
| 2392 | LEU317 | CD2 | −21.328 | 3.519 | 3.121 |
| 2393 | SER318 | N | −16.794 | 6.056 | 1.951 |
| 2394 | SER318 | CA | −15.563 | 6.559 | 1.34 |
| 2395 | SER318 | C | −14.789 | 5.483 | 0.588 |
| 2396 | SER318 | O | −14.286 | 5.777 | −0.503 |
| 2397 | SER318 | CB | −14.689 | 7.158 | 2.434 |
| 2398 | SER318 | OG | −13.375 | 7.32 | 1.915 |
| 2399 | ASN319 | N | −14.954 | 4.222 | 0.954 |
| 2400 | ASN319 | CA | −14.267 | 3.196 | 0.162 |
| 2401 | ASN319 | C | −15.089 | 2.774 | −1.058 |
| 2402 | ASN319 | O | −14.498 | 2.343 | −2.052 |
| 2403 | ASN319 | CB | −13.899 | 1.982 | 1.004 |
| 2404 | ASN319 | CG | −12.531 | 1.507 | 0.516 |
| 2405 | ASN319 | OD1 | −11.628 | 2.333 | 0.321 |
| 2406 | ASN319 | ND2 | −12.378 | 0.209 | 0.332 |
| 2407 | ALA320 | N | −16.362 | 3.139 | −1.091 |
| 2408 | ALA320 | CA | −17.181 | 2.889 | −2.283 |
| 2409 | ALA320 | C | −17.001 | 4.055 | −3.248 |
| 2410 | ALA320 | O | −16.897 | 3.856 | −4.464 |
| 2411 | ALA320 | CB | −18.642 | 2.78 | −1.875 |
| 2412 | GLY321 | N | −16.68 | 5.197 | −2.666 |
| 2413 | GLY321 | CA | −16.233 | 6.36 | −3.426 |
| 2414 | GLY321 | C | −14.942 | 6.045 | −4.17 |
| 2415 | GLY321 | O | −14.924 | 6.106 | −5.404 |
| 2416 | ASN322 | N | −13.958 | 5.508 | −3.466 |
| 2417 | ASN322 | CA | −12.683 | 5.172 | −4.113 |
| 2418 | ASN322 | C | −12.765 | 3.924 | −5.006 |
| 2419 | ASN322 | O | −11.954 | 3.769 | −5.927 |
| 2420 | ASN322 | CB | −11.651 | 4.902 | −3.035 |
| 2421 | ASN322 | CG | −11.54 | 6.013 | −1.994 |
| 2422 | ASN322 | OD1 | −11.701 | 7.211 | −2.278 |
| 2423 | ASN322 | ND2 | −11.095 | 5.595 | −0.824 |
| 2424 | HIS323 | N | −13.785 | 3.103 | −4.807 |
| 2425 | HIS323 | CA | −14.068 | 1.985 | −5.716 |
| 2426 | HIS323 | C | −15.037 | 2.337 | −6.846 |
| 2427 | HIS323 | O | −15.541 | 1.435 | −7.525 |
| 2428 | HIS323 | CB | −14.625 | 0.804 | −4.939 |
| 2429 | HIS323 | CG | −13.581 | 0.008 | −4.19 |
| 2430 | HIS323 | ND1 | −13.802 | −0.807 | −3.144 |
| 2431 | HIS323 | CD2 | −12.233 | −0.04 | −4.46 |
| 2432 | HIS323 | CE1 | −12.634 | −1.351 | −2.748 |
| 2433 | HIS323 | NE2 | −11.664 | −0.875 | −3.563 |
| 2434 | ASP324 | N | −15.353 | 3.608 | −7.007 |
| 2435 | ASP324 | CA | −16.209 | 4.041 | −8.109 |
| 2436 | ASP324 | C | −15.409 | 4.076 | −9.411 |
| 2437 | ASP324 | O | −14.628 | 5.012 | −9.642 |
| 2438 | ASP324 | CB | −16.72 | 5.431 | −7.737 |
| 2439 | ASP324 | CG | −17.711 | 6.002 | −8.74 |
| 2440 | ASP324 | OD1 | −18.738 | 6.476 | −8.275 |
| 2441 | ASP324 | OD2 | −17.28 | 6.257 | −9.859 |
| 2442 | PRO325 | N | −15.831 | 3.237 | −10.349 |
| 2443 | PRO325 | CA | −15.082 | 2.989 | −11.595 |
| 2444 | PRO325 | C | −15.201 | 4.099 | −12.648 |
| 2445 | PRO325 | O | −14.504 | 4.065 | −13.667 |
| 2446 | PRO325 | CB | −15.653 | 1.713 | −12.134 |
| 2447 | PRO325 | CG | −16.9 | 1.346 | −11.345 |
| 2448 | PRO325 | CD | −17.01 | 2.374 | −10.232 |
| 2449 | ASP326 | N | −16.008 | 5.11 | −12.361 |
| 2450 | ASP326 | CA | −16.206 | 6.248 | −13.259 |
| 2451 | ASP326 | C | −15.146 | 7.312 | −12.983 |
| 2452 | ASP326 | O | −14.924 | 8.216 | −13.797 |
| 2453 | ASP326 | CB | −17.597 | 6.826 | −12.994 |
| 2454 | ASP326 | CG | −18.675 | 5.753 | −13.155 |
| 2455 | ASP326 | OD1 | −19.125 | 5.571 | −14.277 |
| 2456 | ASP326 | OD2 | −18.963 | 5.068 | −12.179 |
| 2457 | GLY327 | N | −14.468 | 7.162 | −11.857 |
| 2458 | GLY327 | CA | −13.318 | 8.005 | −11.542 |
| 2459 | GLY327 | C | −12.061 | 7.145 | −11.594 |
| 2460 | GLY327 | O | −11.166 | 7.366 | −12.418 |
| 2461 | PHE328 | N | −12.046 | 6.12 | −10.76 |
| 2462 | PHE328 | CA | −10.893 | 5.218 | −10.705 |
| 2463 | PHE328 | C | −11.119 | 4.009 | −11.602 |
| 2464 | PHE328 | O | −11.92 | 3.114 | −11.3 |
| 2465 | PHE328 | CB | −10.653 | 4.81 | −9.257 |
| 2466 | PHE328 | CG | −10.261 | 5.995 | −8.376 |
| 2467 | PHE328 | CD1 | −9.098 | 6.702 | −8.651 |
| 2468 | PHE328 | CD2 | −11.07 | 6.379 | −7.314 |
| 2469 | PHE328 | CE1 | −8.737 | 7.784 | −7.858 |
| 2470 | PHE328 | CE2 | −10.709 | 7.459 | −6.519 |
| 2471 | PHE328 | CZ | −9.542 | 8.161 | −6.791 |
| 2472 | GLU329 | N | −10.377 | 4.006 | −12.696 |
| 2473 | GLU329 | CA | −10.511 | 2.993 | −13.752 |
| 2474 | GLU329 | C | −10.048 | 1.63 | −13.253 |
| 2475 | GLU329 | O | −8.847 | 1.399 | −13.092 |
| 2476 | GLU329 | CB | −9.673 | 3.409 | −14.962 |
| 2477 | GLU329 | CG | −10.104 | 4.752 | −15.557 |
| 2478 | GLU329 | CD | −9.106 | 5.864 | −15.215 |
| 2479 | GLU329 | OE1 | −8.54 | 5.804 | −14.132 |
| 2480 | GLU329 | OE2 | −8.904 | 6.724 | −16.059 |
| 2481 | ASN330 | N | −10.987 | 0.698 | −13.249 |
| 2482 | ASN330 | CA | −10.826 | −0.597 | −12.566 |

APPENDIX 1-continued

| Atom No. | Residue | Atom Name | X-coord | Y-coord | Z-coord |
|---|---|---|---|---|---|
| 2483 | ASN330 | C | −10.252 | −0.375 | −11.171 |
| 2484 | ASN330 | O | −9.065 | −0.629 | −10.929 |
| 2485 | ASN330 | CB | −9.925 | −1.547 | −13.355 |
| 2486 | ASN330 | CG | −9.943 | −2.959 | −12.75 |
| 2487 | ASN330 | OD1 | −9.958 | −3.151 | −11.523 |
| 2488 | ASN330 | ND2 | −9.893 | −3.939 | −13.632 |
| 2489 | PRO331 | N | −11.157 | −0.201 | −10.224 |
| 2490 | PRO331 | CA | −10.787 | 0.129 | −8.843 |
| 2491 | PRO331 | C | −10.287 | −1.061 | −8.012 |
| 2492 | PRO331 | O | −9.994 | −0.904 | −6.822 |
| 2493 | PRO331 | CB | −12.044 | 0.673 | −8.25 |
| 2494 | PRO331 | CG | −13.21 | 0.356 | −9.172 |
| 2495 | PRO331 | CD | −12.608 | −0.26 | −10.416 |
| 2496 | ASP332 | N | −10.198 | −2.236 | −8.615 |
| 2497 | ASP332 | CA | −9.742 | −3.417 | −7.889 |
| 2498 | ASP332 | C | −8.267 | −3.667 | −8.179 |
| 2499 | ASP332 | O | −7.609 | −4.447 | −7.478 |
| 2500 | ASP332 | CB | −10.557 | −4.617 | −8.358 |
| 2501 | ASP332 | CG | −12.048 | −4.356 | −8.173 |
| 2502 | ASP332 | OD1 | −12.43 | −3.961 | −7.08 |
| 2503 | ASP332 | OD2 | −12.784 | −4.566 | −9.127 |
| 2504 | THR333 | N | −7.744 | −2.97 | −9.173 |
| 2505 | THR333 | CA | −6.339 | −3.153 | −9.535 |
| 2506 | THR333 | C | −5.433 | −2.224 | −8.735 |
| 2507 | THR333 | O | −5.283 | −1.042 | −9.06 |
| 2508 | THR333 | CB | −6.189 | −2.877 | −11.026 |
| 2509 | THR333 | OG1 | −7.072 | −3.748 | −11.718 |
| 2510 | THR333 | CG2 | −4.769 | −3.147 | −11.514 |
| 2511 | PHE334 | N | −4.84 | −2.772 | −7.688 |
| 2512 | PHE334 | CA | −3.868 | −2.017 | −6.89 |
| 2513 | PHE334 | C | −2.589 | −1.762 | −7.684 |
| 2514 | PHE334 | O | −1.817 | −2.686 | −7.979 |
| 2515 | PHE334 | CB | −3.543 | −2.812 | −5.63 |
| 2516 | PHE334 | CG | −2.485 | −2.162 | −4.744 |
| 2517 | PHE334 | CD1 | −2.784 | −1 | −4.047 |
| 2518 | PHE334 | CD2 | −1.221 | −2.728 | −4.638 |
| 2519 | PHE334 | CE1 | −1.82 | −0.404 | −3.246 |
| 2520 | PHE334 | CE2 | −0.256 | −2.132 | −3.837 |
| 2521 | PHE334 | CZ | −0.556 | −0.969 | −3.142 |
| 2522 | ASP335 | N | −2.407 | −0.509 | −8.064 |
| 2523 | ASP335 | CA | −1.206 | −0.106 | −8.794 |
| 2524 | ASP335 | C | −0.697 | 1.24 | −8.283 |
| 2525 | ASP335 | O | −1.322 | 2.277 | −8.525 |
| 2526 | ASP335 | CB | −1.55 | −0.019 | −10.277 |
| 2527 | ASP335 | CG | −0.276 | 0.2 | −11.084 |
| 2528 | ASP335 | OD1 | 0.34 | −0.792 | −11.448 |
| 2529 | ASP335 | OD2 | 0.15 | 1.347 | −11.159 |
| 2530 | ILE336 | N | 0.532 | 1.249 | −7.794 |
| 2531 | ILE336 | CA | 1.118 | 2.426 | −7.127 |
| 2532 | ILE336 | C | 1.596 | 3.552 | −8.058 |
| 2533 | ILE336 | O | 2.207 | 4.512 | −7.579 |
| 2534 | ILE336 | CB | 2.303 | 1.948 | −6.301 |
| 2535 | ILE336 | CG1 | 3.437 | 1.48 | −7.203 |
| 2536 | ILE336 | CG2 | 1.873 | 0.817 | −5.375 |
| 2537 | ILE336 | CD1 | 4.676 | 1.131 | −6.396 |
| 2538 | GLU337 | N | 1.41 | 3.407 | −9.361 |
| 2539 | GLU337 | CA | 1.712 | 4.496 | −10.291 |
| 2540 | GLU337 | C | 0.434 | 5.236 | −10.681 |
| 2541 | GLU337 | O | 0.487 | 6.246 | −11.393 |
| 2542 | GLU337 | CB | 2.393 | 3.936 | −11.533 |
| 2543 | GLU337 | CG | 3.788 | 3.412 | −11.213 |
| 2544 | GLU337 | CD | 4.442 | 2.871 | −12.481 |
| 2545 | GLU337 | OE1 | 3.934 | 3.167 | −13.552 |
| 2546 | GLU337 | OE2 | 5.372 | 2.089 | −12.348 |
| 2547 | ARG338 | N | −0.697 | 4.719 | −10.229 |
| 2548 | ARG338 | CA | −1.982 | 5.376 | −10.464 |
| 2549 | ARG338 | C | −2.095 | 6.636 | −9.615 |
| 2550 | ARG338 | O | −1.809 | 6.625 | −8.412 |
| 2551 | ARG338 | CB | −3.085 | 4.393 | −10.082 |
| 2552 | ARG338 | CG | −4.484 | 4.977 | −10.234 |
| 2553 | ARG338 | CD | −5.532 | 3.961 | −9.809 |
| 2554 | ARG338 | NE | −5.375 | 2.729 | −10.591 |
| 2555 | ARG338 | CZ | −6.357 | 1.847 | −10.77 |
| 2556 | ARG338 | NH1 | −7.549 | 2.056 | −10.207 |
| 2557 | ARG338 | NH2 | −6.143 | 0.757 | −11.509 |
| 2558 | GLY339 | N | −2.423 | 7.735 | −10.271 |
| 2559 | GLY339 | CA | −2.685 | 8.98 | −9.55 |
| 2560 | GLY339 | C | −4.038 | 8.895 | −8.852 |
| 2561 | GLY339 | O | −5.086 | 9.045 | −9.489 |
| 2562 | ALA340 | N | −3.994 | 8.767 | −7.534 |
| 2563 | ALA340 | CA | −5.202 | 8.646 | −6.691 |
| 2564 | ALA340 | C | −5.871 | 9.982 | −6.335 |
| 2565 | ALA340 | O | −6.419 | 10.145 | −5.237 |
| 2566 | ALA340 | CB | −4.817 | 7.907 | −5.414 |
| 2567 | ARG341 | N | −5.844 | 10.917 | −7.27 |
| 2568 | ARG341 | CA | −6.395 | 12.25 | −7.043 |
| 2569 | ARG341 | C | −7.904 | 12.179 | −6.87 |
| 2570 | ARG341 | O | −8.571 | 11.307 | −7.436 |
| 2571 | ARG341 | CB | −6.045 | 13.131 | −8.235 |
| 2572 | ARG341 | CG | −4.535 | 13.264 | −8.387 |
| 2573 | ARG341 | CD | −4.175 | 14.135 | −9.583 |
| 2574 | ARG341 | NE | −2.718 | 14.303 | −9.691 |
| 2575 | ARG341 | CZ | −2.142 | 15.463 | −10.016 |
| 2576 | ARG341 | NH1 | −2.898 | 16.534 | −10.271 |
| 2577 | ARG341 | NH2 | −0.813 | 15.551 | −10.092 |
| 2578 | HIS342 | N | −8.378 | 13.009 | −5.954 |
| 2579 | HIS342 | CA | −9.801 | 13.12 | −5.603 |
| 2580 | HIS342 | C | −10.342 | 11.888 | −4.88 |
| 2581 | HIS342 | O | −11.547 | 11.621 | −4.961 |
| 2582 | HIS342 | CB | −10.644 | 13.367 | −6.855 |
| 2583 | HIS342 | CG | −10.32 | 14.641 | −7.606 |
| 2584 | HIS342 | ND1 | −10.757 | 15.877 | −7.303 |
| 2585 | HIS342 | CD2 | −9.536 | 14.758 | −8.731 |
| 2586 | HIS342 | CE1 | −10.259 | 16.758 | −8.195 |
| 2587 | HIS342 | NE2 | −9.504 | 16.064 | −9.078 |
| 2588 | HIS343 | N | −9.49 | 11.15 | −4.184 |
| 2589 | HIS343 | CA | −10.02 | 10.075 | −3.346 |
| 2590 | HIS343 | C | −10.572 | 10.661 | −2.053 |
| 2591 | HIS343 | O | −9.984 | 11.572 | −1.455 |
| 2592 | HIS343 | CB | −8.988 | 8.965 | −3.085 |
| 2593 | HIS343 | CG | −7.691 | 9.253 | −2.333 |
| 2594 | HIS343 | ND1 | −7.374 | 10.313 | −1.562 |
| 2595 | HIS343 | CD2 | −6.597 | 8.421 | −2.319 |
| 2596 | HIS343 | CE1 | −6.125 | 10.166 | −1.079 |
| 2597 | HIS343 | NE2 | −5.643 | 8.993 | −1.549 |
| 2598 | VAL344 | N | −11.634 | 10.052 | −1.563 |
| 2599 | VAL344 | CA | −12.278 | 10.521 | −0.331 |
| 2600 | VAL344 | C | −11.732 | 9.82 | 0.915 |
| 2601 | VAL344 | O | −12.271 | 9.998 | 2.015 |
| 2602 | VAL344 | CB | −13.787 | 10.343 | −0.45 |
| 2603 | VAL344 | CG1 | −14.412 | 11.457 | −1.282 |
| 2604 | VAL344 | CG2 | −14.141 | 8.977 | −1.019 |
| 2605 | ALA345 | N | −10.581 | 9.178 | 0.768 |
| 2606 | ALA345 | CA | −9.947 | 8.411 | 1.849 |
| 2607 | ALA345 | C | −9.419 | 9.24 | 3.02 |
| 2608 | ALA345 | O | −9.242 | 8.703 | 4.12 |
| 2609 | ALA345 | CB | −8.757 | 7.686 | 1.237 |
| 2610 | PHE346 | N | −9.169 | 10.518 | 2.787 |
| 2611 | PHE346 | CA | −8.763 | 11.424 | 3.867 |
| 2612 | PHE346 | C | −9.885 | 12.363 | 4.291 |
| 2613 | PHE346 | O | −9.652 | 13.29 | 5.083 |
| 2614 | PHE346 | CB | −7.571 | 12.253 | 3.409 |
| 2615 | PHE346 | CG | −6.223 | 11.583 | 3.635 |
| 2616 | PHE346 | CD1 | −5.295 | 11.513 | 2.605 |
| 2617 | PHE346 | CD2 | −5.921 | 11.048 | 4.881 |
| 2618 | PHE346 | CE1 | −4.061 | 10.916 | 2.825 |
| 2619 | PHE346 | CE2 | −4.687 | 10.451 | 5.101 |
| 2620 | PHE346 | CZ | −3.756 | 10.388 | 4.073 |
| 2621 | GLY347 | N | −11.068 | 12.169 | 3.731 |
| 2622 | GLY347 | CA | −12.177 | 13.091 | 3.979 |
| 2623 | GLY347 | C | −12.007 | 14.367 | 3.158 |
| 2624 | GLY347 | O | −10.882 | 14.764 | 2.825 |
| 2625 | PHE348 | N | −13.123 | 14.988 | 2.822 |
| 2626 | PHE348 | CA | −13.084 | 16.264 | 2.097 |
| 2627 | PHE348 | C | −13.98 | 17.307 | 2.752 |
| 2628 | PHE348 | O | −14.185 | 17.307 | 3.976 |
| 2629 | PHE348 | CB | −13.497 | 16.085 | 0.64 |
| 2630 | PHE348 | CG | −12.375 | 15.613 | −0.285 |
| 2631 | PHE348 | CD1 | −12.654 | 14.749 | −1.333 |
| 2632 | PHE348 | CD2 | −11.075 | 16.06 | −0.081 |
| 2633 | PHE348 | CE1 | −11.633 | 14.322 | −2.172 |
| 2634 | PHE348 | CE2 | −10.054 | 15.633 | −0.918 |
| 2635 | PHE348 | CZ | −10.332 | 14.763 | −1.963 |
| 2636 | GLY349 | N | −14.438 | 18.227 | 1.918 |

APPENDIX 1-continued

| Atom No. | Residue | Atom Name | X-coord | Y-coord | Z-coord |
|---|---|---|---|---|---|
| 2637 | GLY349 | CA | −15.269 | 19.339 | 2.376 |
| 2638 | GLY349 | C | −14.484 | 20.194 | 3.353 |
| 2639 | GLY349 | O | −13.286 | 20.433 | 3.165 |
| 2640 | VAL350 | N | −15.121 | 20.525 | 4.458 |
| 2641 | VAL350 | CA | −14.426 | 21.29 | 5.493 |
| 2642 | VAL350 | C | −13.865 | 20.408 | 6.613 |
| 2643 | VAL350 | O | −12.964 | 20.854 | 7.327 |
| 2644 | VAL350 | CB | −15.384 | 22.334 | 6.062 |
| 2645 | VAL350 | CG1 | −15.675 | 23.433 | 5.047 |
| 2646 | VAL350 | CG2 | −16.682 | 21.709 | 6.561 |
| 2647 | HIS351 | N | −14.217 | 19.133 | 6.631 |
| 2648 | HIS351 | CA | −13.875 | 18.287 | 7.784 |
| 2649 | HIS351 | C | −12.75 | 17.284 | 7.532 |
| 2650 | HIS351 | O | −12.711 | 16.259 | 8.223 |
| 2651 | HIS351 | CB | −15.113 | 17.514 | 8.23 |
| 2652 | HIS351 | CG | −16.205 | 18.349 | 8.87 |
| 2653 | HIS351 | ND1 | −16.137 | 18.987 | 10.054 |
| 2654 | HIS351 | CD2 | −17.46 | 18.588 | 8.36 |
| 2655 | HIS351 | CE1 | −17.304 | 19.619 | 10.29 |
| 2656 | HIS351 | NE2 | −18.122 | 19.372 | 9.242 |
| 2657 | GLN352 | N | −11.876 | 17.53 | 6.568 |
| 2658 | GLN352 | CA | −10.852 | 16.518 | 6.26 |
| 2659 | GLN352 | C | −9.793 | 16.385 | 7.357 |
| 2660 | GLN352 | O | −9.716 | 17.193 | 8.291 |
| 2661 | GLN352 | CB | −10.178 | 16.785 | 4.923 |
| 2662 | GLN352 | CG | −9.244 | 17.98 | 4.902 |
| 2663 | GLN352 | CD | −8.308 | 17.803 | 3.712 |
| 2664 | GLN352 | OE1 | −7.316 | 18.528 | 3.568 |
| 2665 | GLN352 | NE2 | −8.572 | 16.766 | 2.934 |
| 2666 | CYS353 | N | −9.049 | 15.296 | 7.271 |
| 2667 | CYS353 | CA | −8.044 | 14.964 | 8.287 |
| 2668 | CYS353 | C | −6.883 | 15.962 | 8.319 |
| 2669 | CYS353 | O | −6.101 | 16.072 | 7.366 |
| 2670 | CYS353 | CB | −7.524 | 13.567 | 7.961 |
| 2671 | CYS353 | SG | −6.412 | 12.816 | 9.17 |
| 2672 | LEU354 | N | −6.724 | 16.61 | 9.464 |
| 2673 | LEU354 | CA | −5.607 | 17.549 | 9.666 |
| 2674 | LEU354 | C | −4.308 | 16.852 | 10.059 |
| 2675 | LEU354 | O | −3.224 | 17.358 | 9.747 |
| 2676 | LEU354 | CB | −5.967 | 18.561 | 10.748 |
| 2677 | LEU354 | CG | −6.805 | 19.7 | 10.188 |
| 2678 | LEU354 | CD1 | −7.148 | 20.701 | 11.284 |
| 2679 | LEU354 | CD2 | −6.054 | 20.396 | 9.057 |
| 2680 | GLY355 | N | −4.414 | 15.6 | 10.478 |
| 2681 | GLY355 | CA | −3.223 | 14.791 | 10.772 |
| 2682 | GLY355 | C | −2.835 | 13.936 | 9.566 |
| 2683 | GLY355 | O | −2.119 | 12.936 | 9.702 |
| 2684 | GLN356 | N | −3.078 | 14.499 | 8.393 |
| 2685 | GLN356 | CA | −2.896 | 13.81 | 7.119 |
| 2686 | GLN356 | C | −1.414 | 13.677 | 6.799 |
| 2687 | GLN356 | O | −0.939 | 12.562 | 6.544 |
| 2688 | GLN356 | CB | −3.598 | 14.696 | 6.094 |
| 2689 | GLN356 | CG | −3.657 | 14.117 | 4.691 |
| 2690 | GLN356 | CD | −4.524 | 15.024 | 3.818 |
| 2691 | GLN356 | OE1 | −4.609 | 14.834 | 2.599 |
| 2692 | GLN356 | NE2 | −5.231 | 15.939 | 4.463 |
| 2693 | ASN357 | N | −0.67 | 14.7 | 7.191 |
| 2694 | ASN357 | CA | 0.781 | 14.7 | 7.005 |
| 2695 | ASN357 | C | 1.476 | 13.761 | 7.989 |
| 2696 | ASN357 | O | 2.328 | 12.977 | 7.554 |
| 2697 | ASN357 | CB | 1.258 | 16.137 | 7.203 |
| 2698 | ASN357 | CG | 2.78 | 16.244 | 7.261 |
| 2699 | ASN357 | OD1 | 3.324 | 16.808 | 8.217 |
| 2700 | ASN357 | ND2 | 3.444 | 15.745 | 6.233 |
| 2701 | LEU358 | N | 0.896 | 13.592 | 9.166 |
| 2702 | LEU358 | CA | 1.515 | 12.727 | 10.168 |
| 2703 | LEU358 | C | 1.271 | 11.264 | 9.826 |
| 2704 | LEU358 | O | 2.234 | 10.487 | 9.791 |
| 2705 | LEU358 | CB | 0.908 | 13.034 | 11.53 |
| 2706 | LEU358 | CG | 1.612 | 12.261 | 12.639 |
| 2707 | LEU358 | CD1 | 3.089 | 12.639 | 12.712 |
| 2708 | LEU358 | CD2 | 0.931 | 12.493 | 13.982 |
| 2709 | ALA359 | N | 0.102 | 10.986 | 9.272 |
| 2710 | ALA359 | CA | −0.235 | 9.616 | 8.887 |
| 2711 | ALA359 | C | 0.571 | 9.151 | 7.679 |
| 2712 | ALA359 | O | 1.204 | 8.089 | 7.756 |
| 2713 | ALA359 | CB | −1.723 | 9.558 | 8.566 |
| 2714 | ARG360 | N | 0.794 | 10.045 | 6.728 |
| 2715 | ARG360 | CA | 1.585 | 9.681 | 5.546 |
| 2716 | ARG360 | C | 3.078 | 9.603 | 5.853 |
| 2717 | ARG360 | O | 3.747 | 8.677 | 5.374 |
| 2718 | ARG360 | CB | 1.354 | 10.721 | 4.459 |
| 2719 | ARG360 | CG | −0.081 | 10.681 | 3.954 |
| 2720 | ARG360 | CD | −0.325 | 11.752 | 2.898 |
| 2721 | ARG360 | NE | −0.144 | 13.097 | 3.463 |
| 2722 | ARG360 | CZ | 0.509 | 14.076 | 2.833 |
| 2723 | ARG360 | NH1 | 0.602 | 15.283 | 3.393 |
| 2724 | ARG360 | NH2 | 1.045 | 13.853 | 1.631 |
| 2725 | LEU361 | N | 3.518 | 10.379 | 6.83 |
| 2726 | LEU361 | CA | 4.921 | 10.356 | 7.239 |
| 2727 | LEU361 | C | 5.238 | 9.078 | 8.005 |
| 2728 | LEU361 | O | 6.174 | 8.36 | 7.628 |
| 2729 | LEU361 | CB | 5.159 | 11.566 | 8.133 |
| 2730 | LEU361 | CG | 6.612 | 11.69 | 8.572 |
| 2731 | LEU361 | CD1 | 7.537 | 11.811 | 7.365 |
| 2732 | LEU361 | CD2 | 6.778 | 12.888 | 9.498 |
| 2733 | GLU362 | N | 4.306 | 8.658 | 8.846 |
| 2734 | GLU362 | CA | 4.499 | 7.431 | 9.622 |
| 2735 | GLU362 | C | 4.413 | 6.2 | 8.73 |
| 2736 | GLU362 | O | 5.31 | 5.352 | 8.793 |
| 2737 | GLU362 | CB | 3.418 | 7.347 | 10.694 |
| 2738 | GLU362 | CG | 3.519 | 8.493 | 11.693 |
| 2739 | GLU362 | CD | 2.341 | 8.447 | 12.662 |
| 2740 | GLU362 | OE1 | 1.268 | 8.901 | 12.284 |
| 2741 | GLU362 | OE2 | 2.517 | 7.891 | 13.736 |
| 2742 | LEU363 | N | 3.541 | 6.253 | 7.736 |
| 2743 | LEU363 | CA | 3.389 | 5.125 | 6.814 |
| 2744 | LEU363 | C | 4.61 | 4.946 | 5.927 |
| 2745 | LEU363 | O | 5.174 | 3.844 | 5.889 |
| 2746 | LEU363 | CB | 2.184 | 5.364 | 5.914 |
| 2747 | LEU363 | CG | 0.977 | 4.517 | 6.298 |
| 2748 | LEU363 | CD1 | 0.35 | 4.995 | 7.601 |
| 2749 | LEU363 | CD2 | −0.056 | 4.54 | 5.179 |
| 2750 | GLN364 | N | 5.151 | 6.047 | 5.432 |
| 2751 | GLN364 | CA | 6.296 | 5.955 | 4.529 |
| 2752 | GLN364 | C | 7.559 | 5.544 | 5.276 |
| 2753 | GLN364 | O | 8.219 | 4.588 | 4.843 |
| 2754 | GLN364 | CB | 6.505 | 7.308 | 3.86 |
| 2755 | GLN364 | CG | 7.624 | 7.232 | 2.83 |
| 2756 | GLN364 | CD | 7.846 | 8.592 | 2.181 |
| 2757 | GLN364 | OE1 | 7.741 | 9.637 | 2.835 |
| 2758 | GLN364 | NE2 | 8.108 | 8.565 | 0.886 |
| 2759 | ILE365 | N | 7.707 | 6.019 | 6.503 |
| 2760 | ILE365 | CA | 8.879 | 5.644 | 7.298 |
| 2761 | ILE365 | C | 8.835 | 4.171 | 7.691 |
| 2762 | ILE365 | O | 9.772 | 3.438 | 7.339 |
| 2763 | ILE365 | CB | 8.94 | 6.511 | 8.554 |
| 2764 | ILE365 | CG1 | 9.202 | 7.973 | 8.208 |
| 2765 | ILE365 | CG2 | 10.012 | 5.996 | 9.506 |
| 2766 | ILE365 | CD1 | 10.539 | 8.151 | 7.497 |
| 2767 | VAL366 | N | 7.667 | 3.695 | 8.099 |
| 2768 | VAL366 | CA | 7.555 | 2.301 | 8.53 |
| 2769 | VAL366 | C | 7.703 | 1.335 | 7.361 |
| 2770 | VAL366 | O | 8.611 | 0.497 | 7.417 |
| 2771 | VAL366 | CB | 6.21 | 2.076 | 9.217 |
| 2772 | VAL366 | CG1 | 6.011 | 0.606 | 9.565 |
| 2773 | VAL366 | CG2 | 6.085 | 2.923 | 10.477 |
| 2774 | PHE367 | N | 7.094 | 1.641 | 6.225 |
| 2775 | PHE367 | CA | 7.145 | 0.701 | 5.097 |
| 2776 | PHE367 | C | 8.524 | 0.663 | 4.453 |
| 2777 | PHE367 | O | 9.066 | −0.434 | 4.254 |
| 2778 | PHE367 | CB | 6.125 | 1.099 | 4.034 |
| 2779 | PHE367 | CG | 4.662 | 1.012 | 4.458 |
| 2780 | PHE367 | CD1 | 3.726 | 1.83 | 3.841 |
| 2781 | PHE367 | CD2 | 4.258 | 0.112 | 5.435 |
| 2782 | PHE367 | CE1 | 2.391 | 1.767 | 4.216 |
| 2783 | PHE367 | CE2 | 2.924 | 0.052 | 5.813 |
| 2784 | PHE367 | CZ | 1.99 | 0.88 | 5.206 |
| 2785 | ASP368 | N | 9.187 | 1.808 | 4.423 |
| 2786 | ASP368 | CA | 10.522 | 1.869 | 3.83 |
| 2787 | ASP368 | C | 11.52 | 1.102 | 4.686 |
| 2788 | ASP368 | O | 12.115 | 0.138 | 4.185 |
| 2789 | ASP368 | CB | 10.964 | 3.326 | 3.707 |
| 2790 | ASP368 | CG | 10.101 | 4.09 | 2.701 |

APPENDIX 1-continued

| Atom No. | Residue | Atom Name | X-coord | Y-coord | Z-coord |
|---|---|---|---|---|---|
| 2791 | ASP368 | OD1 | 10.208 | 5.31 | 2.678 |
| 2792 | ASP368 | OD2 | 9.508 | 3.443 | 1.847 |
| 2793 | THR369 | N | 11.438 | 1.285 | 5.995 |
| 2794 | THR369 | CA | 12.381 | 0.606 | 6.892 |
| 2795 | THR369 | C | 12.07 | −0.88 | 7.076 |
| 2796 | THR369 | O | 13.004 | −1.658 | 7.287 |
| 2797 | THR369 | CB | 12.376 | 1.294 | 8.252 |
| 2798 | THR369 | OG1 | 11.058 | 1.242 | 8.778 |
| 2799 | THR369 | CG2 | 12.797 | 2.756 | 8.149 |
| 2800 | LEU370 | N | 10.848 | −1.302 | 6.793 |
| 2801 | LEU370 | CA | 10.523 | −2.729 | 6.862 |
| 2802 | LEU370 | C | 11.145 | −3.486 | 5.703 |
| 2803 | LEU370 | O | 12.038 | −4.319 | 5.916 |
| 2804 | LEU370 | CB | 9.012 | −2.919 | 6.78 |
| 2805 | LEU370 | CG | 8.302 | −2.463 | 8.044 |
| 2806 | LEU370 | CD1 | 6.792 | −2.589 | 7.882 |
| 2807 | LEU370 | CD2 | 8.79 | −3.256 | 9.248 |
| 2808 | PHE371 | N | 10.872 | −3.006 | 4.502 |
| 2809 | PHE371 | CA | 11.266 | −3.75 | 3.303 |
| 2810 | PHE371 | C | 12.728 | −3.529 | 2.918 |
| 2811 | PHE371 | O | 13.332 | −4.398 | 2.278 |
| 2812 | PHE371 | CB | 10.333 | −3.34 | 2.169 |
| 2813 | PHE371 | CG | 8.861 | −3.634 | 2.463 |
| 2814 | PHE371 | CD1 | 7.935 | −2.599 | 2.503 |
| 2815 | PHE371 | CD2 | 8.447 | −4.94 | 2.692 |
| 2816 | PHE371 | CE1 | 6.601 | −2.867 | 2.784 |
| 2817 | PHE371 | CE2 | 7.112 | −5.209 | 2.971 |
| 2818 | PHE371 | CZ | 6.19 | −4.172 | 3.019 |
| 2819 | ARG372 | N | 13.335 | −2.472 | 3.436 |
| 2820 | ARG372 | CA | 14.773 | −2.281 | 3.231 |
| 2821 | ARG372 | C | 15.606 | −2.901 | 4.353 |
| 2822 | ARG372 | O | 16.834 | −2.982 | 4.229 |
| 2823 | ARG372 | CB | 15.084 | −0.795 | 3.116 |
| 2824 | ARG372 | CG | 14.397 | −0.176 | 1.904 |
| 2825 | ARG372 | CD | 14.777 | 1.291 | 1.76 |
| 2826 | ARG372 | NE | 14.497 | 2.015 | 3.008 |
| 2827 | ARG372 | CZ | 14.919 | 3.257 | 3.251 |
| 2828 | ARG372 | NH1 | 14.646 | 3.835 | 4.423 |
| 2829 | ARG372 | NH2 | 15.631 | 3.911 | 2.331 |
| 2830 | ARG373 | N | 14.958 | −3.347 | 5.418 |
| 2831 | ARG373 | CA | 15.671 | −4.087 | 6.457 |
| 2832 | ARG373 | C | 15.659 | −5.559 | 6.09 |
| 2833 | ARG373 | O | 16.694 | −6.238 | 6.097 |
| 2834 | ARG373 | CB | 14.937 | −3.926 | 7.783 |
| 2835 | ARG373 | CG | 15.657 | −4.637 | 8.922 |
| 2836 | ARG373 | CD | 16.912 | −3.879 | 9.335 |
| 2837 | ARG373 | NE | 16.548 | −2.554 | 9.862 |
| 2838 | ARG373 | CZ | 16.405 | −2.304 | 11.165 |
| 2839 | ARG373 | NH1 | 16.663 | −3.261 | 12.059 |
| 2840 | ARG373 | NH2 | 16.046 | −1.087 | 11.576 |
| 2841 | VAL374 | N | 14.474 | −6.032 | 5.749 |
| 2842 | VAL374 | CA | 14.314 | −7.425 | 5.338 |
| 2843 | VAL374 | C | 13.644 | −7.499 | 3.971 |
| 2844 | VAL374 | O | 12.43 | −7.307 | 3.841 |
| 2845 | VAL374 | CB | 13.473 | −8.164 | 6.376 |
| 2846 | VAL374 | CG1 | 13.297 | −9.625 | 5.984 |
| 2847 | VAL374 | CG2 | 14.086 | −8.075 | 7.77 |
| 2848 | PRO375 | N | 14.432 | −7.873 | 2.976 |
| 2849 | PRO375 | CA | 13.929 | −8.036 | 1.606 |
| 2850 | PRO375 | C | 13.088 | −9.304 | 1.369 |
| 2851 | PRO375 | O | 12.539 | −9.472 | 0.275 |
| 2852 | PRO375 | CB | 15.165 | −8.072 | 0.76 |
| 2853 | PRO375 | CG | 16.384 | −8.221 | 1.658 |
| 2854 | PRO375 | CD | 15.865 | −8.159 | 3.084 |
| 2855 | GLY376 | N | 12.945 | −10.158 | 2.371 |
| 2856 | GLY376 | CA | 12.162 | −11.386 | 2.21 |
| 2857 | GLY376 | C | 11.071 | −11.52 | 3.271 |
| 2858 | GLY376 | O | 11.012 | −12.523 | 3.992 |
| 2859 | ILE377 | N | 10.225 | −10.508 | 3.367 |
| 2860 | ILE377 | CA | 9.092 | −10.568 | 4.299 |
| 2861 | ILE377 | C | 7.921 | −11.295 | 3.645 |
| 2862 | ILE377 | O | 7.217 | −10.731 | 2.801 |
| 2863 | ILE377 | CB | 8.663 | −9.148 | 4.656 |
| 2864 | ILE377 | CG1 | 9.836 | −8.352 | 5.203 |
| 2865 | ILE377 | CG2 | 7.529 | −9.169 | 5.674 |
| 2866 | ILE377 | CD1 | 9.433 | −6.919 | 5.526 |
| 2867 | ARG378 | N | 7.743 | −12.55 | 4.009 |
| 2868 | ARG378 | CA | 6.648 | −13.342 | 3.451 |
| 2869 | ARG378 | C | 5.468 | −13.417 | 4.409 |
| 2870 | ARG378 | O | 5.629 | −13.304 | 5.627 |
| 2871 | ARG378 | CB | 7.186 | −14.734 | 3.163 |
| 2872 | ARG378 | CG | 8.265 | −14.671 | 2.089 |
| 2873 | ARG378 | CD | 8.975 | −16.01 | 1.929 |
| 2874 | ARG378 | NE | 9.756 | −16.33 | 3.134 |
| 2875 | ARG378 | CZ | 9.57 | −17.431 | 3.864 |
| 2876 | ARG378 | NH1 | 8.587 | −18.28 | 3.556 |
| 2877 | ARG378 | NH2 | 10.338 | −17.659 | 4.931 |
| 2878 | ILE379 | N | 4.277 | −13.531 | 3.854 |
| 2879 | ILE379 | CA | 3.096 | −13.713 | 4.703 |
| 2880 | ILE379 | C | 3.14 | −15.13 | 5.272 |
| 2881 | ILE379 | O | 3.519 | −16.07 | 4.563 |
| 2882 | ILE379 | CB | 1.841 | −13.536 | 3.855 |
| 2883 | ILE379 | CG1 | 2.108 | −12.589 | 2.692 |
| 2884 | ILE379 | CG2 | 0.702 | −12.984 | 4.709 |
| 2885 | ILE379 | CD1 | 0.882 | −12.447 | 1.798 |
| 2886 | ALA380 | N | 2.872 | −15.267 | 6.56 |
| 2887 | ALA380 | CA | 2.895 | −16.598 | 7.174 |
| 2888 | ALA380 | C | 1.533 | −17.277 | 7.07 |
| 2889 | ALA380 | O | 1.435 | −18.51 | 7.097 |
| 2890 | ALA380 | CB | 3.306 | −16.471 | 8.635 |
| 2891 | VAL381 | N | 0.498 | −16.47 | 6.917 |
| 2892 | VAL381 | CA | −0.839 | −17.005 | 6.651 |
| 2893 | VAL381 | C | −1.231 | −16.745 | 5.2 |
| 2894 | VAL381 | O | −0.782 | −15.768 | 4.59 |
| 2895 | VAL381 | CB | −1.847 | −16.359 | 7.599 |
| 2896 | VAL381 | CG1 | −1.705 | −16.897 | 9.018 |
| 2897 | VAL381 | CG2 | −1.747 | −14.839 | 7.57 |
| 2898 | PRO382 | N | −1.999 | −17.662 | 4.635 |
| 2899 | PRO382 | CA | −2.615 | −17.424 | 3.329 |
| 2900 | PRO382 | C | −3.477 | −16.166 | 3.352 |
| 2901 | PRO382 | O | −4.045 | −15.802 | 4.391 |
| 2902 | PRO382 | CB | −3.422 | −18.651 | 3.039 |
| 2903 | PRO382 | CG | −3.29 | −19.627 | 4.198 |
| 2904 | PRO382 | CD | −2.414 | −18.938 | 5.231 |
| 2905 | VAL383 | N | −3.721 | −15.621 | 2.172 |
| 2906 | VAL383 | CA | −4.415 | −14.327 | 2.051 |
| 2907 | VAL383 | C | −5.892 | −14.388 | 2.452 |
| 2908 | VAL383 | O | −6.376 | −13.473 | 3.126 |
| 2909 | VAL383 | CB | −4.302 | −13.886 | 0.593 |
| 2910 | VAL383 | CG1 | −5.05 | −12.578 | 0.343 |
| 2911 | VAL383 | CG2 | −2.838 | −13.751 | 0.177 |
| 2912 | ASP384 | N | −6.478 | −15.572 | 2.355 |
| 2913 | ASP384 | CA | −7.876 | −15.767 | 2.759 |
| 2914 | ASP384 | C | −8.031 | −15.962 | 4.271 |
| 2915 | ASP384 | O | −9.156 | −16.094 | 4.761 |
| 2916 | ASP384 | CB | −8.42 | −17.003 | 2.048 |
| 2917 | ASP384 | CG | −8.293 | −16.849 | 0.534 |
| 2918 | ASP384 | OD1 | −9.1 | −16.128 | −0.032 |
| 2919 | ASP384 | OD2 | −7.312 | −17.346 | −0.002 |
| 2920 | GLU385 | N | −6.926 | −15.995 | 5 |
| 2921 | GLU385 | CA | −6.994 | −16.177 | 6.448 |
| 2922 | GLU385 | C | −6.674 | −14.884 | 7.194 |
| 2923 | GLU385 | O | −6.638 | −14.896 | 8.429 |
| 2924 | GLU385 | CB | −6.01 | −17.259 | 6.874 |
| 2925 | GLU385 | CG | −6.219 | −18.561 | 6.111 |
| 2926 | GLU385 | CD | −7.651 | −19.079 | 6.248 |
| 2927 | GLU385 | OE1 | −8.017 | −19.462 | 7.349 |
| 2928 | GLU385 | OE2 | −8.266 | −19.256 | 5.205 |
| 2929 | LEU386 | N | −6.406 | −13.81 | 6.463 |
| 2930 | LEU386 | CA | −6.082 | −12.519 | 7.093 |
| 2931 | LEU386 | C | −7.266 | −11.953 | 7.874 |
| 2932 | LEU386 | O | −8.342 | −11.71 | 7.315 |
| 2933 | LEU386 | CB | −5.676 | −11.542 | 5.996 |
| 2934 | LEU386 | CG | −4.348 | −11.943 | 5.365 |
| 2935 | LEU386 | CD1 | −4.081 | −11.153 | 4.091 |
| 2936 | LEU386 | CD2 | −3.204 | −11.773 | 6.357 |
| 2937 | PRO387 | N | −7.063 | −11.798 | 9.173 |
| 2938 | PRO387 | CA | −8.132 | −11.39 | 10.091 |
| 2939 | PRO387 | C | −8.419 | −9.89 | 10.047 |
| 2940 | PRO387 | O | −7.84 | −9.095 | 10.805 |
| 2941 | PRO387 | CB | −7.647 | −11.801 | 11.445 |
| 2942 | PRO387 | CG | −6.191 | −12.224 | 11.339 |
| 2943 | PRO387 | CD | −5.817 | −12.105 | 9.873 |
| 2944 | PHE388 | N | −9.314 | −9.528 | 9.143 |

APPENDIX 1-continued

| Atom No. | Residue | Atom Name | X-coord | Y-coord | Z-coord |
|---|---|---|---|---|---|
| 2945 | PHE388 | CA | −9.775 | −8.145 | 9.012 |
| 2946 | PHE388 | C | −10.688 | −7.79 | 10.176 |
| 2947 | PHE388 | O | −11.522 | −8.597 | 10.603 |
| 2948 | PHE388 | CB | −10.558 | −7.999 | 7.709 |
| 2949 | PHE388 | CG | −9.785 | −8.343 | 6.437 |
| 2950 | PHE388 | CD1 | −8.78 | −7.498 | 5.987 |
| 2951 | PHE388 | CD2 | −10.097 | −9.492 | 5.721 |
| 2952 | PHE388 | CE1 | −8.076 | −7.809 | 4.831 |
| 2953 | PHE388 | CE2 | −9.393 | −9.804 | 4.565 |
| 2954 | PHE388 | CZ | −8.381 | −8.963 | 4.121 |
| 2955 | LYS389 | N | −10.5 | −6.599 | 10.707 |
| 2956 | LYS389 | CA | −11.364 | −6.141 | 11.792 |
| 2957 | LYS389 | C | −12.626 | −5.52 | 11.203 |
| 2958 | LYS389 | O | −12.542 | −4.581 | 10.4 |
| 2959 | LYS389 | CB | −10.611 | −5.115 | 12.633 |
| 2960 | LYS389 | CG | −11.439 | −4.708 | 13.847 |
| 2961 | LYS389 | CD | −10.677 | −3.763 | 14.767 |
| 2962 | LYS389 | CE | −11.487 | −3.466 | 16.023 |
| 2963 | LYS389 | NZ | −10.719 | −2.637 | 16.96 |
| 2964 | HIS390 | N | −13.775 | −6.068 | 11.571 |
| 2965 | HIS390 | CA | −15.055 | −5.523 | 11.102 |
| 2966 | HIS390 | C | −15.385 | −4.226 | 11.836 |
| 2967 | HIS390 | O | −15.845 | −4.213 | 12.983 |
| 2968 | HIS390 | CB | −16.162 | −6.548 | 11.316 |
| 2969 | HIS390 | CG | −17.525 | −6.094 | 10.826 |
| 2970 | HIS390 | ND1 | −17.895 | −5.893 | 9.545 |
| 2971 | HIS390 | CD2 | −18.62 | −5.81 | 11.607 |
| 2972 | HIS390 | CE1 | −19.181 | −5.487 | 9.511 |
| 2973 | HIS390 | NE2 | −19.629 | −5.437 | 10.786 |
| 2974 | ASP391 | N | −15.053 | −3.138 | 11.167 |
| 2975 | ASP391 | CA | −15.269 | −1.789 | 11.683 |
| 2976 | ASP391 | C | −15.392 | −0.871 | 10.48 |
| 2977 | ASP391 | O | −14.395 | −0.539 | 9.835 |
| 2978 | ASP391 | CB | −14.068 | −1.414 | 12.553 |
| 2979 | ASP391 | CG | −14.172 | −0.02 | 13.18 |
| 2980 | ASP391 | OD1 | −14.984 | 0.771 | 12.707 |
| 2981 | ASP391 | OD2 | −13.241 | 0.324 | 13.884 |
| 2982 | SER392 | N | −16.582 | −0.335 | 10.283 |
| 2983 | SER392 | CA | −16.835 | 0.448 | 9.075 |
| 2984 | SER392 | C | −16.261 | 1.863 | 9.129 |
| 2985 | SER392 | O | −15.99 | 2.431 | 8.07 |
| 2986 | SER392 | CB | −18.342 | 0.537 | 8.868 |
| 2987 | SER392 | OG | −18.876 | 1.383 | 9.878 |
| 2988 | THR393 | N | −15.944 | 2.392 | 10.297 |
| 2989 | THR393 | CA | −15.451 | 3.768 | 10.313 |
| 2990 | THR393 | C | −13.931 | 3.822 | 10.468 |
| 2991 | THR393 | O | −13.294 | 4.722 | 9.909 |
| 2992 | THR393 | CB | −16.183 | 4.53 | 11.411 |
| 2993 | THR393 | OG1 | −17.557 | 4.561 | 11.04 |
| 2994 | THR393 | CG2 | −15.703 | 5.972 | 11.528 |
| 2995 | ILE394 | N | −13.365 | 2.816 | 11.118 |
| 2996 | ILE394 | CA | −11.899 | 2.665 | 11.203 |
| 2997 | ILE394 | C | −11.525 | 1.204 | 10.92 |
| 2998 | ILE394 | O | −11.205 | 0.419 | 11.824 |
| 2999 | ILE394 | CB | −11.37 | 3.095 | 12.577 |
| 3000 | ILE394 | CG1 | −11.744 | 4.533 | 12.921 |
| 3001 | ILE394 | CG2 | −9.847 | 2.978 | 12.624 |
| 3002 | ILE394 | CD1 | −10.977 | 5.529 | 12.055 |
| 3003 | TYR395 | N | −11.59 | 0.854 | 9.649 |
| 3004 | TYR395 | CA | −11.29 | −0.503 | 9.179 |
| 3005 | TYR395 | C | −9.792 | −0.786 | 9.302 |
| 3006 | TYR395 | O | −8.997 | 0.149 | 9.447 |
| 3007 | TYR395 | CB | −11.747 | −0.572 | 7.721 |
| 3008 | TYR395 | CG | −11.784 | −1.967 | 7.101 |
| 3009 | TYR395 | CD1 | −10.958 | −2.272 | 6.026 |
| 3010 | TYR395 | CD2 | −12.648 | −2.927 | 7.612 |
| 3011 | TYR395 | CE1 | −10.991 | −3.543 | 5.465 |
| 3012 | TYR395 | CE2 | −12.682 | −4.199 | 7.052 |
| 3013 | TYR395 | CZ | −11.852 | −4.502 | 5.982 |
| 3014 | TYR395 | OH | −11.882 | −5.763 | 5.427 |
| 3015 | GLY396 | N | −9.433 | −2.053 | 9.421 |
| 3016 | GLY396 | CA | −8.007 | −2.401 | 9.468 |
| 3017 | GLY396 | C | −7.732 | −3.871 | 9.759 |
| 3018 | GLY396 | O | −8.601 | −4.74 | 9.609 |
| 3019 | LEU397 | N | −6.493 | −4.132 | 10.134 |
| 3020 | LEU397 | CA | −6.031 | −5.497 | 10.406 |
| 3021 | LEU397 | C | −5.334 | −5.577 | 11.751 |
| 3022 | LEU397 | O | −4.297 | −4.938 | 11.961 |
| 3023 | LEU397 | CB | −5.051 | −5.894 | 9.311 |
| 3024 | LEU397 | CG | −5.773 | −6.502 | 8.12 |
| 3025 | LEU397 | CD1 | −5.037 | −6.225 | 6.822 |
| 3026 | LEU397 | CD2 | −5.979 | −7.996 | 8.325 |
| 3027 | HIS398 | N | −5.87 | −6.402 | 12.634 |
| 3028 | HIS398 | CA | −5.274 | −6.514 | 13.967 |
| 3029 | HIS398 | C | −4.348 | −7.718 | 14.107 |
| 3030 | HIS398 | O | −3.651 | −7.848 | 15.12 |
| 3031 | HIS398 | CB | −6.363 | −6.528 | 15.033 |
| 3032 | HIS398 | CG | −6.737 | −5.14 | 15.525 |
| 3033 | HIS398 | ND1 | −7.052 | −4.804 | 16.79 |
| 3034 | HIS398 | CD2 | −6.795 | −3.984 | 14.781 |
| 3035 | HIS398 | CE1 | −7.311 | −3.482 | 16.851 |
| 3036 | HIS398 | NE2 | −7.152 | −2.975 | 15.607 |
| 3037 | ALA399 | N | −4.306 | −8.567 | 13.094 |
| 3038 | ALA399 | CA | −3.343 | −9.671 | 13.12 |
| 3039 | ALA399 | C | −2.7 | −9.903 | 11.756 |
| 3040 | ALA399 | O | −3.373 | −10.014 | 10.724 |
| 3041 | ALA399 | CB | −4.014 | −10.936 | 13.633 |
| 3042 | LEU400 | N | −1.383 | −10.004 | 11.794 |
| 3043 | LEU400 | CA | −0.567 | −10.204 | 10.589 |
| 3044 | LEU400 | C | 0.772 | −10.856 | 10.935 |
| 3045 | LEU400 | O | 1.712 | −10.165 | 11.35 |
| 3046 | LEU400 | CB | −0.307 | −8.845 | 9.946 |
| 3047 | LEU400 | CG | 0.615 | −8.952 | 8.736 |
| 3048 | LEU400 | CD1 | 0.005 | −9.826 | 7.644 |
| 3049 | LEU400 | CD2 | 0.973 | −7.572 | 8.197 |
| 3050 | PRO401 | N | 0.815 | −12.178 | 10.881 |
| 3051 | PRO401 | CA | 2.084 | −12.9 | 10.974 |
| 3052 | PRO401 | C | 2.88 | −12.822 | 9.671 |
| 3053 | PRO401 | O | 2.413 | −13.242 | 8.602 |
| 3054 | PRO401 | CB | 1.686 | −14.312 | 11.269 |
| 3055 | PRO401 | CG | 0.197 | −14.466 | 10.993 |
| 3056 | PRO401 | CD | −0.308 | −13.08 | 10.625 |
| 3057 | VAL402 | N | 4.074 | −12.267 | 9.78 |
| 3058 | VAL402 | CA | 5.008 | −12.183 | 8.653 |
| 3059 | VAL402 | C | 6.358 | −12.814 | 8.998 |
| 3060 | VAL402 | O | 7.008 | −12.485 | 9.998 |
| 3061 | VAL402 | CB | 5.194 | −10.723 | 8.25 |
| 3062 | VAL402 | CG1 | 3.968 | −10.185 | 7.523 |
| 3063 | VAL402 | CG2 | 5.553 | −9.84 | 9.44 |
| 3064 | THR403 | N | 6.772 | −13.729 | 8.146 |
| 3065 | THR403 | CA | 8.039 | −14.428 | 8.342 |
| 3066 | THR403 | C | 9.135 | −13.709 | 7.571 |
| 3067 | THR403 | O | 9.102 | −13.66 | 6.335 |
| 3068 | THR403 | CB | 7.888 | −15.853 | 7.827 |
| 3069 | THR403 | OG1 | 6.715 | −16.403 | 8.406 |
| 3070 | THR403 | CG2 | 9.077 | −16.723 | 8.22 |
| 3071 | TRP404 | N | 10.089 | −13.156 | 8.298 |
| 3072 | TRP404 | CA | 11.177 | −12.406 | 7.66 |
| 3073 | TRP404 | C | 12.136 | −13.344 | 6.931 |
| 3074 | TRP404 | O | 12.984 | −12.835 | 6.21 |
| 3075 | TRP404 | CB | 11.969 | −11.654 | 8.719 |
| 3076 | TRP404 | CG | 11.163 | −10.949 | 9.79 |
| 3077 | TRP404 | CD1 | 10.886 | −11.444 | 11.043 |
| 3078 | TRP404 | CD2 | 10.559 | −9.637 | 9.729 |
| 3079 | TRP404 | NE1 | 10.155 | −10.524 | 11.721 |
| 3080 | TRP404 | CE2 | 9.943 | −9.428 | 10.972 |
| 3081 | TRP404 | CE3 | 10.506 | −8.656 | 8.749 |
| 3082 | TRP404 | CZ2 | 9.278 | −8.237 | 11.225 |
| 3083 | TRP404 | CZ3 | 9.838 | −7.468 | 9.009 |
| 3084 | TRP404 | CH2 | 9.226 | −7.257 | 10.239 |
| 3085 | TRP404 | OXT | 12.117 | −14.53 | 7.239 |
| 3086 | HEM1 | FE | −8.08 | 12.05 | 10.226 |
| 3087 | HEM1 | NA | −9.653 | 12.085 | 9.078 |
| 3088 | HEM1 | C1A | −10.7 | 13.004 | 9.077 |
| 3089 | HEM1 | C2A | −11.687 | 12.681 | 8.118 |
| 3090 | HEM1 | C3A | −11.292 | 11.525 | 7.568 |
| 3091 | HEM1 | C4A | −10.019 | 11.174 | 8.129 |
| 3092 | HEM1 | CHB | −9.224 | 10.115 | 7.699 |
| 3093 | HEM1 | C1B | −7.931 | 9.83 | 8.181 |
| 3094 | HEM1 | NB | −7.308 | 10.582 | 9.182 |
| 3095 | HEM1 | C4B | −6.086 | 9.964 | 9.364 |
| 3096 | HEM1 | C3B | −5.946 | 8.85 | 8.506 |
| 3097 | HEM1 | C2B | −7.068 | 8.771 | 7.746 |
| 3098 | HEM1 | CMB | −7.416 | 7.755 | 6.682 |

APPENDIX 1-continued

| Atom No. | Residue | Atom Name | X-coord | Y-coord | Z-coord |
|---|---|---|---|---|---|
| 3099 | HEM1 | CAB | −4.833 | 8.031 | 8.591 |
| 3100 | HEM1 | CBB | −4.44 | 7.051 | 7.74 |
| 3101 | HEM1 | CHC | −5.212 | 10.298 | 10.374 |
| 3102 | HEM1 | C1C | −5.439 | 11.223 | 11.336 |
| 3103 | HEM1 | NC | −6.519 | 12.039 | 11.384 |
| 3104 | HEM1 | C4C | −6.227 | 12.887 | 12.426 |
| 3105 | HEM1 | C3C | −4.926 | 12.636 | 13.002 |
| 3106 | HEM1 | C2C | −4.491 | 11.556 | 12.313 |
| 3107 | HEM1 | CMC | −3.265 | 10.712 | 12.532 |
| 3108 | HEM1 | CAC | −4.462 | 13.435 | 14.055 |
| 3109 | HEM1 | CBC | −3.452 | 13.231 | 14.936 |
| 3110 | HEM1 | CHD | −7.061 | 13.855 | 12.91 |
| 3111 | HEM1 | C1D | −8.237 | 14.203 | 12.292 |
| 3112 | HEM1 | ND | −8.777 | 13.572 | 11.18 |
| 3113 | HEM1 | C4D | −9.915 | 14.313 | 10.916 |
| 3114 | HEM1 | C3D | −10.045 | 15.413 | 11.808 |
| 3115 | HEM1 | C2D | −9.006 | 15.334 | 12.673 |
| 3116 | HEM1 | CMD | −8.71 | 16.241 | 13.844 |
| 3117 | HEM1 | CAD | −11.178 | 16.421 | 11.802 |
| 3118 | HEM1 | CBD | −10.91 | 17.624 | 10.918 |
| 3119 | HEM1 | CGD | −12.079 | 18.574 | 10.862 |
| 3120 | HEM1 | O1D | −13.198 | 18.167 | 11.204 |
| 3121 | HEM1 | O2D | −11.889 | 19.736 | 10.477 |
| 3122 | HEM1 | CHA | −10.849 | 14.026 | 9.961 |
| 3123 | HEM1 | CMA | −12.005 | 10.703 | 6.498 |
| 3124 | HEM1 | CAA | −12.907 | 13.51 | 7.748 |
| 3125 | HEM1 | CBA | −14.087 | 13.112 | 8.645 |
| 3126 | HEM1 | CGA | −15.442 | 13.596 | 8.14 |
| 3127 | HEM1 | O1A | −15.522 | 14.131 | 7.009 |
| 3128 | HEM1 | O2A | −16.439 | 13.4 | 8.866 |

What is claimed is:

1. An isolated nucleic acid sequence encoding epothilone B hydroxylase of SEQ ID NO: 2 or a mutant thereof, wherein said mutant comprises at least one amino acid substitution at an amino acid position seleted from the group consisting of GLU31, ARG67, ARG88, ILE92, ALA93, VAL106, ILE130, ALA140, MET176, PHE190, GLU231, SER294, PHE237, and ILE365 of SEQ ID NO: 2, and wherein said mutant has epothilone B hydroxylase activity.

2. The isolated nucleic acid sequence of claim 1 comprising a nucleic acid sequence selected from the group consisting of SEQ ID NO: 1, 30, 32, 34, 60, 62, 64, 66, 68, 72 and 74.

3. The isolated nucleic acid sequence of claim 1 wherein said at least one mutation comprises an amino acid substitution at GLU31 of SEQ ID NO:2.

4. The isolated nucleic acid sequence of claim 1 wherein said at least one mutation comprises an amino acid sequence substitution at ARG67 of SEQ ID NO:2.

5. The isolated nucleic acid sequence of claim 1 wherein said at least one mutation comprises an amino acid substitution at ARG88 of SEQ ID NO:2.

6. The isolated nucleic acid sequence of claim 1 wherein said at least one mutation comprises an amino acid substitution at ILE92 of SEQ ID NO:2.

7. The isolated nucleic acid sequence of claim 1 wherein said at least one mutation comprises an amino acid substitution at ALA93 of SEQ ID NO:2.

8. The isolated nucleic acid sequence of claim 1 wherein said at least one mutation comprises an amino acid substitution at VAL106 of SEQ ID NO:2.

9. The isolated nucleic acid sequence of claim 1 wherein said at least one mutation comprises an amino acid substitution at ILE130 of SEQ ID NO:2.

10. The isolated nucleic acid sequence of claim 1 wherein said at least one mutation comprises an amino acid substitution at ALA140 of SEQ ID NO:2.

11. The isolated nucleic avid sequence of claim 1 wherein said at least one mutation comprises an amino acid substitution at MET176 of SEQ ID NO:2.

12. The isolated nucleic acid sequence of claim 1 wherein said at least one mutation comprises an amino acid substitution at PHE190 of SEQ ID NO:2.

13. The isolated nucleic acid sequence of claim 1 wherein said at least one mutation comprises an amino acid substitution at GLU231 of SEQ ID NO:2.

14. The isolated nucleic acid sequence of claim 1 wherein said at least one mutation comprises an amino acid substitution at SER294 of SEQ ID NO:2.

15. The isolated nucleic acid sequence of claim 1 wherein said at least one mutation comprises an amino acid substitution at PHE237 of SBQ ID NO:2.

16. The isolated nucleic acid sequence of claim 1 wherein said at least one mutation comprises an amino acid substitution at ILE365 of SEQ ID NO:2.

17. A vector comprising the isolated nucleic acid sequence of claim 1.

18. An isolated host cell comprising the vector of claim 17.

19. A method for producing a recombinant microorganism which hydroxylate epothilone B, said method comprising transfecting a microorganism with the vector of claim 17.

20. A recombinant microorganism produced by the method of claim 19.

21. The recombinant microorganism of claim 20 wherein said microorganism expresses a nucleic acid sequence selected from the group consisting of SEQ ID NO: 1, 30, 32, 34, 60, 62, 64, 66, 68, 72 and 74.

* * * * *

SEQUENCE LISTING

<160> NUMBER OF SEQ ID NOS: 76

<210> SEQ ID NO 1
<211> LENGTH: 1186
<212> TYPE: DNA
<213> ORGANISM: Amycolatopsis orientalis

<400> SEQUENCE: 1

```
atgaccgacg tcgaggaaac caccgcgacc ttgccactgg cccgcaaatg cccgttttca      60
ccaccgcccg aatacgagcg gctccgccgg gaaagtccgg tttcccgggt cggtctcccc     120
tccggtcaaa ccgcttgggc gctcacccgg ctcgaagaca tccgcgaaat gctgagcagt     180
ccgcatttca gctccgaccg gcagagtccg tcgttccgc tgatggtggc gcggcagatc      240
cggcgcgagg acaagccgtt ccgcccgtcc ctcatcgcga tggacccgcc ggaacacggc     300
aaggccaggc gtgacgtcgt cggggaattc accgtcaagc gcatgaaagc gcttcagcca     360
cgtattcagc agatcgtcga cgagcatatc gacgccctgc tcgccggccc caaacccgcc     420
gatctcgtcc aggcgctttc cctgccggtt ccgtccttgg tgatctgcga actgctcggt     480 gtccctatt cggaccacga gttcttccag tcctgcagtt cccggatgct cagccgggaa      540
gtcaccgccg aagaacggat gaccgcgttc gagtcgctcg agaactatct cgacgaactc     600
gtcacgaaga aggaggcgaa cgccaccgag gacgacctcc tcggccgcca gatcctgaag     660
cagcgcgaat ccggcgaagc cgaccacggc gaactggtcg gtctggcgtt cctcctgctc     720
atcgcggggc acgagactac ggcgaacatg atctcgctcg gcacggtgac cctgctggag     780
aaccccgatc agctggcgaa gatcaaggcg gatccgggca gaccctcgc cgcgatcgag       840 gaactcctgc ggatcttcac catcgcggag acggcgacct cacgcttcgc cacggcggac     900
gtcgagatcg gcgcacgct catccgcgcg ggtgaaggcg tcgtcggcct gagcaacgcg     960
ggcaaccacg atccggacgg cttcgagaac ccggacacct tcgacatcga acgcggcgcg    1020
```

-continued

```
cggcatcacg tcgccttcgg attcggtgtg caccaatgcc tcggccagaa cttggcgagg    1080
ttggaactcc agatcgtgtt cgatacgttg ttccggcgag tgccgggcat ccggatcgcc    1140
gtaccggtcg acgaactgcc gttcaagcac gattcgacga tctacg                   1186
```

<210> SEQ ID NO 2
<211> LENGTH: 404
<212> TYPE: PRT
<213> ORGANISM: Amycolatopsis orientalis

<400> SEQUENCE: 2

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Gly Lys Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Ile Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Ser
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Ser
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Ile Phe Thr Ile
        275                 280                 285

Ala Glu Thr Ala Thr Ser Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
```

```
                340              345              350
Cys Leu Gly Gln Asn Leu Ala Arg Leu Glu Leu Gln Ile Val Phe Asp
            355              360              365

Thr Leu Phe Arg Arg Val Pro Gly Ile Arg Ile Ala Val Pro Val Asp
    370              375              380

Glu Leu Pro Phe Lys His Asp Ser Thr Ile Tyr Gly Leu His Ala Leu
385              390              395              400

Pro Val Thr Trp

<210> SEQ ID NO 3
<211> LENGTH: 195
<212> TYPE: DNA
<213> ORGANISM: Amycolatopsis orientalis

<400> SEQUENCE: 3
atgaagatca tcgcggacac cgggaagtgc gtgggggcgg gccagtgcgt gctcaccgat      60
cccgatctgt tcgaccagag cgaggacgac gggacggtcc tcctgctgaa cgccgagccc     120
gaaggcgaag aggcggagga gaacgcgcgc accgccgtgc acatctgccc ggggcaggca     180
ctttcgctcg cgtag                                                      195

<210> SEQ ID NO 4
<211> LENGTH: 64
<212> TYPE: PRT
<213> ORGANISM: Amycolatopsis orientalis

<400> SEQUENCE: 4

Met Lys Ile Ile Ala Asp Thr Gly Lys Cys Val Gly Ala Gly Gln Cys
1               5                  10                  15

Val Leu Thr Asp Pro Asp Leu Phe Asp Gln Ser Glu Asp Asp Gly Thr
                20                  25                  30

Val Leu Leu Leu Asn Ala Glu Pro Glu Gly Glu Ala Glu Glu Asn
            35                  40                  45

Ala Arg Thr Ala Val His Ile Cys Pro Gly Gln Ala Leu Ser Leu Ala
    50                  55                  60

<210> SEQ ID NO 5
<211> LENGTH: 22
<212> TYPE: DNA
<213> ORGANISM: Artificial sequence
<220> FEATURE:
<223> OTHER INFORMATION: Synthetic

<400> SEQUENCE: 5
tcctcatcgc cggccacgag ac                                               22

<210> SEQ ID NO 6
<211> LENGTH: 22
<212> TYPE: DNA
<213> ORGANISM: Artificial sequence
<220> FEATURE:
<223> OTHER INFORMATION: Synthetic

<400> SEQUENCE: 6
tgctggtcgc cggccacgag ac                                               22

<210> SEQ ID NO 7
<211> LENGTH: 22
<212> TYPE: DNA
<213> ORGANISM: Artificial sequence
<220> FEATURE:
```

<223> OTHER INFORMATION: Synthetic

<400> SEQUENCE: 7
tgctcatcac cggccaggac ac        22

<210> SEQ ID NO 8
<211> LENGTH: 20
<212> TYPE: DNA
<213> ORGANISM: Artificial sequence
<220> FEATURE:
<223> OTHER INFORMATION: Synthetic

<400> SEQUENCE: 8
ctgttcgccg ggcacgactc        20

<210> SEQ ID NO 9
<211> LENGTH: 22
<212> TYPE: DNA
<213> ORGANISM: Artificial sequence
<220> FEATURE:
<223> OTHER INFORMATION: Synthetic

<400> SEQUENCE: 9
tgctcatcgc gggccacgag ac        22

<210> SEQ ID NO 10
<211> LENGTH: 22
<212> TYPE: DNA
<213> ORGANISM: Artificial sequence
<220> FEATURE:
<223> OTHER INFORMATION: Synthetic

<400> SEQUENCE: 10
tgctggtcgc cgggcacgag ac        22

<210> SEQ ID NO 11
<211> LENGTH: 21
<212> TYPE: DNA
<213> ORGANISM: Artificial sequence
<220> FEATURE:
<223> OTHER INFORMATION: Synthetic

<400> SEQUENCE: 11
cggcgcggtg gaggaactgc t        21

<210> SEQ ID NO 12
<211> LENGTH: 21
<212> TYPE: DNA
<213> ORGANISM: Artificial sequence
<220> FEATURE:
<223> OTHER INFORMATION: Synthetic

<400> SEQUENCE: 12
gggcgccgtc gaggagctgc t        21

<210> SEQ ID NO 13
<211> LENGTH: 21
<212> TYPE: DNA
<213> ORGANISM: Artificial sequence
<220> FEATURE:
<223> OTHER INFORMATION: Synthetic

<400> SEQUENCE: 13
ccgcaccctg gaggagctgc t        21

<210> SEQ ID NO 14
<211> LENGTH: 21
<212> TYPE: DNA
<213> ORGANISM: Artificial sequence
<220> FEATURE:
<223> OTHER INFORMATION: Synthetic

<400> SEQUENCE: 14
cggcgcggtc gaggagatgc t                                              21

<210> SEQ ID NO 15
<211> LENGTH: 21
<212> TYPE: DNA
<213> ORGANISM: Artificial sequence
<220> FEATURE:
<223> OTHER INFORMATION: Synthetic

<400> SEQUENCE: 15
cgcggcggtg gaggagatgc t                                              21

<210> SEQ ID NO 16
<211> LENGTH: 21
<212> TYPE: DNA
<213> ORGANISM: Artificial sequence
<220> FEATURE:
<223> OTHER INFORMATION: Synthetic

<400> SEQUENCE: 16
cggcgcgatc gaggagaccc t                                              21

<210> SEQ ID NO 17
<211> LENGTH: 30
<212> TYPE: DNA
<213> ORGANISM: Artificial sequence
<220> FEATURE:
<223> OTHER INFORMATION: Synthetic

<400> SEQUENCE: 17
ttcggcttcg gcgtgcacca gtgcctgggc                                     30

<210> SEQ ID NO 18
<211> LENGTH: 30
<212> TYPE: DNA
<213> ORGANISM: Artificial sequence
<220> FEATURE:
<223> OTHER INFORMATION: Synthetic

<400> SEQUENCE: 18
ttcggcttcg gcgtccacca gtgcctggga                                     30

<210> SEQ ID NO 19
<211> LENGTH: 30
<212> TYPE: DNA
<213> ORGANISM: Artificial sequence
<220> FEATURE:
<223> OTHER INFORMATION: Synthetic

<400> SEQUENCE: 19
ttcggctggg gcccccacca ctgcctgggc                                     30

<210> SEQ ID NO 20
<211> LENGTH: 30
<212> TYPE: DNA
<213> ORGANISM: Artificial sequence
<220> FEATURE:
<223> OTHER INFORMATION: Synthetic

```
<400> SEQUENCE: 20
ttcggtcacg gcgtccacaa gtgtcctggc                                        30

<210> SEQ ID NO 21
<211> LENGTH: 30
<212> TYPE: DNA
<213> ORGANISM: Artificial sequence
<220> FEATURE:
<223> OTHER INFORMATION: Synthetic

<400> SEQUENCE: 21
ttcgggcacg gagcgcacca ctgcatcggc                                        30

<210> SEQ ID NO 22
<211> LENGTH: 30
<212> TYPE: DNA
<213> ORGANISM: Artificial sequence
<220> FEATURE:
<223> OTHER INFORMATION: Synthetic

<400> SEQUENCE: 22
ttcggccacg gcatccactt ctgcgtgggc                                        30

<210> SEQ ID NO 23
<211> LENGTH: 25
<212> TYPE: DNA
<213> ORGANISM: Artificial sequence
<220> FEATURE:
<223> OTHER INFORMATION: Synthetic

<400> SEQUENCE: 23
tgctgctsdt cgccggbcab gasac                                             25

<210> SEQ ID NO 24
<211> LENGTH: 25
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: n=a, c, g or t

<400> SEQUENCE: 24
tgmtssysnt cgscgsbcay gasac                                             25

<210> SEQ ID NO 25
<211> LENGTH: 24
<212> TYPE: DNA
<213> ORGANISM: Artificial sequence
<220> FEATURE:
<223> OTHER INFORMATION: Synthetic

<400> SEQUENCE: 25
cggvgcsvts gaggarmtgc tgcg                                              24

<210> SEQ ID NO 26
<211> LENGTH: 24
<212> TYPE: DNA
<213> ORGANISM: Artificial sequence
<220> FEATURE:
<223> OTHER INFORMATION: Synthetic

<400> SEQUENCE: 26
cgcagcakyt cctcsabsgc bccg                                              24
```

<210> SEQ ID NO 27
<211> LENGTH: 30
<212> TYPE: DNA
<213> ORGANISM: Artificial sequence
<220> FEATURE:
<223> OTHER INFORMATION: Synthetic

<400> SEQUENCE: 27
gcccaggcas ahcacsyvvg gcdybggctt                                          30

<210> SEQ ID NO 28
<211> LENGTH: 27
<212> TYPE: DNA
<213> ORGANISM: Artificial sequence
<220> FEATURE:
<223> OTHER INFORMATION: Synthetic

<400> SEQUENCE: 28
gcgagatcta cctggggaag gacaacc                                             27

<210> SEQ ID NO 29
<211> LENGTH: 27
<212> TYPE: DNA
<213> ORGANISM: Artificial sequence
<220> FEATURE:
<223> OTHER INFORMATION: Synthetic

<400> SEQUENCE: 29
gcgaagctta cggacttgga ccctacg                                             27

<210> SEQ ID NO 30
<211> LENGTH: 1215
<212> TYPE: DNA
<213> ORGANISM: Artificial sequence
<220> FEATURE:
<223> OTHER INFORMATION: Synthetic

<400> SEQUENCE: 30

| | | | | |
|---|---|---|---|---|
| atgaccgacg | tcgaggaaac | caccgcgacc | ttgccactgg | cccgcaaatg | cccgttttca | 60 |
| ccaccgcccg | aatacgagcg | gctccgccgg | gaaagtccgg | tttccgggt | cggtctcccc | 120 |
| tccggtcaaa | ccgcttgggc | gctcacccgg | ctcgaagaca | tccgcgaaat | gctgagcagt | 180 |
| ccgcatttca | gctccgaccg | gcagagtccg | tcgttcccgc | tgatggtggc | gcggcagatc | 240 |
| cggcgcgagg | acaagccgtt | ccgcccgtcc | ctcatcgcga | tggacccgcc | ggaacacggc | 300 |
| aaggccaggc | gtgacgtcgt | cggggaattc | accgtcaagc | gcatgaaagc | gcttcagcca | 360 |
| cgtattcagc | agatcgtcga | cgagcatatc | gacgccctgc | tcgccggccc | caaacccgcc | 420 |
| gatctcgtcc | aggcgctttc | cctgccggtt | ccgtccttgg | tgatctgcga | actgctcggt | 480 |
| gtcccctatt | cggaccacga | gttcttccag | tcctgcagtt | cccggatgct | cagccgggaa | 540 |
| gtcaccgccg | aagaacggat | gaccgcgttc | gagtcgctcg | agagctatct | cgacgaactc | 600 |
| gtcacgaaga | aggaggcgaa | cgccaccgag | gacgacctcc | tcggccgcca | gatcctgaag | 660 |
| cagcgcgaat | ccggcgaagc | cgaccacggc | gaactggtcg | gtctggcgtt | cttgctgctc | 720 |
| atcgcggggc | acgagactac | ggcgaacatg | atctcgctcg | gcacggtgac | cctgctggag | 780 |
| aaccccgatc | agctggcgaa | gatcaaggcg | atccgggca | agaccctcgc | cgcgatcgag | 840 |
| gaactcctgc | ggatcttcac | catcgcggag | acgcgacccc | acgcttcgc | cacggcggac | 900 |
| gtcgagatcg | gcggcacgct | catccgcgcg | ggtgaaggcg | tcgtcggcct | gagcaacgcg | 960 |

```
ggcaaccacg atccggacgg cttcgagaac ccggacacct tcgacatcga acgcggcgcg   1020
cggcatcacg tcgccttcgg attcggtgtg caccaatgcc tcggccagaa cttggcgagg   1080
ttggaactcc agatcgtgtt cgatacgttg ttccggcgag tgccgggcat ccggatcgcc   1140
gtaccggtcg acgaactgcc gttcaagcac gattcgacga tctacggcct ccacgccctg   1200
ccggtcacct ggtag                                                    1215
```

<210> SEQ ID NO 31
<211> LENGTH: 404
<212> TYPE: PRT
<213> ORGANISM: Artificial sequence
<220> FEATURE:
<223> OTHER INFORMATION: Synthetic

<400> SEQUENCE: 31

```
Met Thr Asp Val Glu Thr Thr Ala Thr Leu Pro Leu Ala Arg Lys
 1               5                  10                  15

Cys Pro Phe Ser Pro Pro Glu Tyr Glu Arg Leu Arg Arg Glu Ser
                20                  25                  30

Pro Val Ser Arg Val Gly Leu Pro Ser Gly Gln Thr Ala Trp Ala Leu
            35                  40                  45

Thr Arg Leu Glu Asp Ile Arg Glu Met Leu Ser Ser Pro His Phe Ser
        50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Gly Lys Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Ile Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Ser
            180                 185                 190

Leu Glu Ser Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Ser
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Ile Phe Thr Ile
        275                 280                 285

Ala Glu Thr Ala Thr Pro Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320
```

Gly Asn His Asp Pro Asp Gly Phe Glu Asn Pro Asp Thr Phe Asp Ile
             325                 330                 335

Glu Arg Gly Ala Arg His His Val Ala Phe Gly Phe Gly Val His Gln
         340                 345                 350

Cys Leu Gly Gln Asn Leu Ala Arg Leu Glu Leu Gln Ile Val Phe Asp
         355                 360                 365

Thr Leu Phe Arg Arg Val Pro Gly Ile Arg Ile Ala Val Pro Val Asp
     370                 375                 380

Glu Leu Pro Phe Lys His Asp Ser Thr Ile Tyr Gly Leu His Ala Leu
385                 390                 395                 400

Pro Val Thr Trp

<210> SEQ ID NO 32
<211> LENGTH: 1215
<212> TYPE: DNA
<213> ORGANISM: Artificial sequence
<220> FEATURE:
<223> OTHER INFORMATION: Synthetic

<400> SEQUENCE: 32

| | | | | | |
|---|---|---|---|---|---|
| atgaccgacg | tcgaggaaac | caccgcgacc | ttgccactgg | cccgcaaatg | cccgttttca | 60 |
| ccaccgcccg | aatacgagcg | gctccgccgg | gaaagtccgg | tttcccgggt | cggtctcccc | 120 |
| tccggtcaaa | ccgcttgggc | gctcacccgg | ctcgaagaca | tccgcgaaat | gctgagcagt | 180 |
| ccgcatttca | gctccgaccg | gcagagtccg | tcgttcccgc | tgatggtggc | gcggcagatc | 240 |
| cggcgcgagg | acaagccgtt | ccgcccgtcc | ctcatcgcga | tggacccgcc | ggaacacggc | 300 |
| aaggccaggc | gtgacgtcgt | cggggaattc | accgtcaagc | gcatgaaagc | gcttcagcca | 360 |
| cgtattcagc | agatcgtcga | cgagcatatc | gacgccctgc | tcgccggccc | caaacccgcc | 420 |
| gatctcgtcc | aggcgctttc | cctgccggtt | ccgtccttgg | tgatctgcga | actgctcggt | 480 |
| gtcccctatt | cggaccacga | gttcttccag | tcctgcagtt | cccggatgct | cagccgggaa | 540 |
| gtcaccgccg | aagaacggat | gaccgcgtac | gagtcgctcg | agaactatct | cgacgaactc | 600 |
| gtcacgaaga | aggaggcgaa | cgccaccgag | gacgacctcc | tcggccgcca | gatcctgaag | 660 |
| cagcgcgaat | ccggcgaagc | cgaccacggc | cgcctggtcg | gtctggcgtt | cctcctgctc | 720 |
| atcgcggggc | acgagactac | ggcgaacatg | atctcgctcg | gcacggtgac | cctgctggag | 780 |
| aaccccgatc | agctggcgaa | gatcaaggcg | gatccgggca | agaccctcgc | gcgatcgag | 840 |
| gaactcctgc | ggatcttcac | catcgcggag | acggcgacct | cacgcttcgc | cacggcggac | 900 |
| gtcgagatcg | gcggcacgct | catccgcgcg | ggtgaaggcg | tcgtcggcct | gagcaacgcg | 960 |
| ggcaaccacg | atccggacgg | cttcgagaac | ccggacacct | tcgacatcga | acgcggcgcg | 1020 |
| cggcatcacg | tcgccttcgg | attcggtgtg | caccaatgcc | tcggccagaa | cttggcgagg | 1080 |
| ttggaactcc | agatcgtgtt | cgatacgttg | ttccggcgag | tgcccgggcat | ccggatcgcc | 1140 |
| gtaccggtcg | acgaactgcc | gttcaagcac | gattcgacga | tctacggcct | ccacgccctg | 1200 |
| ccggtcacct | ggtag | | | | | 1215 |

<210> SEQ ID NO 33
<211> LENGTH: 404
<212> TYPE: PRT
<213> ORGANISM: Artificial sequence
<220> FEATURE:
<223> OTHER INFORMATION: Synthetic

<400> SEQUENCE: 33

-continued

```
Met Thr Asp Val Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
            85                  90                  95

Pro Glu His Gly Lys Ala Arg Arg Asp Val Val Gly Glu Phe Thr Val
            100                 105                 110

Lys Arg Met Lys Ala Leu Gln Pro Arg Ile Gln Gln Ile Val Asp Glu
            115                 120                 125

His Ile Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
            165                 170                 175

Leu Ser Arg Glu Val Thr Ala Glu Glu Arg Met Thr Ala Tyr Glu Ser
            180                 185                 190

Leu Glu Asn Tyr Leu Asp Glu Leu Val Thr Lys Glu Ala Asn Ala
            195                 200                 205

Thr Glu Asp Asp Leu Leu Gly Arg Gln Ile Leu Lys Gln Arg Glu Ser
    210                 215                 220

Gly Glu Ala Asp His Gly Arg Leu Val Gly Leu Ala Phe Leu Leu Leu
225                 230                 235                 240

Ile Ala Gly His Glu Thr Thr Ala Asn Met Ile Ser Leu Gly Thr Val
            245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Ile Phe Thr Ile
            275                 280                 285

Ala Glu Thr Ala Thr Ser Arg Phe Ala Thr Ala Asp Val Glu Ile Gly
            290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
            325                 330                 335

Glu Arg Gly Ala Arg His Val Ala Phe Gly Phe Gly Val His Gln
            340                 345                 350

Cys Leu Gly Gln Asn Leu Ala Arg Leu Glu Leu Gln Ile Val Phe Asp
            355                 360                 365

Thr Leu Phe Arg Arg Val Pro Gly Ile Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp
```

-continued

<210> SEQ ID NO 34
<211> LENGTH: 1215
<212> TYPE: DNA
<213> ORGANISM: Artificial sequence
<220> FEATURE:
<223> OTHER INFORMATION: Synthetic

<400> SEQUENCE: 34

| | | | |
|---|---|---|---|
| atgaccgacg tcgaggaaac caccgcgacc ttgccactgg cccgcaaatg cccgttttca | | | 60 |
| ccaccgcccg aatacgagcg gctccgccgg gaaagtccgg tttcccgggt cggtctcccc | | | 120 |
| tccggtcaaa ccgcttgggc gctcacccgg ctcgaagaca tccgcgaaat gctgagcagt | | | 180 |
| ccgcatttca gctccgaccg gcagagtccg tcgttcccgc tgatggtggc gcggcagatc | | | 240 |
| cggcgcgagg acaagccgtt ccgcccgtcc ctcgtcgcga tggacccgcc ggaacacggc | | | 300 |
| aaggccaggc gtgacgtcgt cggggaattc accgtcaagc gcatgaaagc gcttcagcca | | | 360 |
| cgtattcagc agatcgtcga cgagcatatc gacgccctgc tcgccggccc caaacccgcc | | | 420 |
| gatctcgtcc aggcgctttc cctgccggtt ccgtccttgg tgatctgcga actgctcggt | | | 480 |
| gtcccctatt cggaccacga gttcttccag tcctgcagtt cccggatgct cagccgggaa | | | 540 |
| gtcaccgccg aagaacggat gaccgcgttc gagtcgctcg agaactatct cgacgaactc | | | 600 |
| gtcacgaaga aggaggcgaa cgccaccgag gacgacctcc tcggccgcca gatcctgaag | | | 660 |
| cagcgcgaat ccggcgaagc cgaccacggc gaactggtcg gtctggcggc gctcctgctc | | | 720 |
| atcgcggggc acgagactac ggcgaacatg atctcgctcg gcacggtgac cctgctggag | | | 780 |
| aaccccgatc agctggcgaa gatcaaggcg atccgggca agaccctcgc cgcgatcgag | | | 840 |
| gaactcctgc ggatcttcac catcgcggag acggcgacct cacgcttcgc cacggcggac | | | 900 |
| gtcgagatcg gcggcacgct catccgcgcg ggtgaaggcg tcgtcggcct gagcaacgcg | | | 960 |
| ggcaaccacg atccggacgg cttcgagaac ccggacacct tcgacatcga acgcggcgcg | | | 1020 |
| cggcatcacg tcgccttcgg attcggtgtg caccaatgcc tcggccagaa cttggcgagg | | | 1080 |
| ttggaactcc agatcgtgtt cgatacgttg ttccggcgag tgccgggcat ccggatcgcc | | | 1140 |
| gtaccggtcg acgaactgcc gttcaagcac gattcgacga tctacggcct ccacgccctg | | | 1200 |
| ccggtcacct ggtag | | | 1215 |

<210> SEQ ID NO 35
<211> LENGTH: 404
<212> TYPE: PRT
<213> ORGANISM: Artificial sequence
<220> FEATURE:
<223> OTHER INFORMATION: Synthetic

<400> SEQUENCE: 35

Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Val Ala Met Asp Pro
                85                  90                  95

Pro Glu His Gly Lys Ala Arg Arg Asp Val Gly Glu Phe Thr Val
            100                 105                 110

Lys Arg Met Lys Ala Leu Gln Pro Arg Ile Gln Gln Ile Val Asp Glu
        115                 120                 125

His Ile Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Ser
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Ser
    210                 215                 220

Gly Glu Ala Asp His Gly Glu Leu Val Gly Leu Ala Ala Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Ile Phe Thr Ile
        275                 280                 285

Ala Glu Thr Ala Thr Ser Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
        355                 360                 365

Thr Leu Phe Arg Arg Val Pro Gly Ile Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp

<210> SEQ ID NO 36
<211> LENGTH: 1104
<212> TYPE: DNA
<213> ORGANISM: Amycolatopsis orientalis

<400> SEQUENCE: 36
gcgaccttgc cgctggcccg caaatgcccg ttttcaccgc cgcccgaata cgagcggctt        60
cgccgggaaa gtccggtttc ccgggtcggt ctcccgtccg gtcaaaccgc ttgggcgctc       120
acccggctcg aggacatccg cgaaatgctg agcagtccgc atttcagctc cgaccggcag       180
agtccgtcgt tcccgctgat ggtggcccgg cagatccggc gcgaggacaa gccgttccgc       240
ccgtccctca tcgcgatgga cccgccggaa cacagcaagg ccaggcgtga cgtcgtcggg       300
gaattcaccg tcaagcgcat gaaagcgctt cagccgcgta ttcagcagat cgtcgacgag       360

```
catatcgacg ccatgctcgc cggccccaaa cccgccgatc tcgtccaggc gctttccctg    420
ccggttccgt ccttggtgat ctgcgaactg ctcggtgtcc cctattcgga ccacgagttc    480
ttccagtcct gcagttcccg gatgctcagc cgggaagtca ccgccgaaga acggatgacc    540
gcgttcgagt cgctcgagaa ctatctcgac gaactcgtca cgaagaagga ggcgaacgcc    600
accgaggacg acctcctcgg ccgccagatc ctgaagcagc gcgaaacggg cgaagccgac    660
cacggcgaac tcgtcgggct ggcgttcctg ctgctcatcg cgggacacga gacgacggcg    720
aacatgatct cgctcggcac ggcgaccctg ctggagaacc ccgaccagct ggcgaagatc    780
aaggccgatc cgggcaagac cctcgccgcg atcgaggagc tcctgcgggt cttcaccatc    840
gcggagacgg cgacctcacg cttcgccacg gcggacgtcg agatcggcgg cacgctcatc    900
cgcgcgggtg aaggcgtcgt cggcctgagc aacgcgggca accacgatcc ggaaggcttc    960
gagaacccgg acgccttcga catcgaacgc ggcgcgcggc accacgtcgc cttcggattc    1020
ggtgtgcacc aatgcctcgg ccagaacttg gcgaggttgg aactccagat cgtgttcgat    1080
acgttgttcc ggcgagtgcc gggc                                            1104
```

<210> SEQ ID NO 37
<211> LENGTH: 1103
<212> TYPE: DNA
<213> ORGANISM: Amycolatopsis orientalis

<400> SEQUENCE: 37

```
gaccttgccg ctggcccgga aatgcccgtt ttcgccgccg cccgaatacg aacggcttcg     60
ccgggaaagt ccggtttccc gggtcggtct cccgtccggt caaacggctt gggcgctcac    120
ccggctcgaa gacatccgcg aaatgctgag cagcccgcat ttcagttccg accggcagag    180
cccgtcgttc ccgctgatgg tcgcgcggca gatccgccgc gaggacaagc cgttccgccc    240
ctccctcatc gcgatggatc cgccggaaca cagcccgggcc aggcgtgacg tcgtcgggga    300
attcaccgtc aagcggatga aggcgctcca gccgcgaatt cagcagatcg tcgacgaaca    360
tctcgacgcc ctgctcgcgg gccccaaacc cgccgatctc gtccaggcgc tttccctgcc    420
cgttccctcg ctggtgatct cgaactgct cggcgtcccc tattcggacc acgagttctt    480
ccagtcctgc agttccagga tgctcagccg ggaggtcacc gccgaagaac ggatgaccgc    540
gttcgagcag ctcgaaaact atctcgacga actggtcacc aagaaggagg cgaacgccac    600
cgaggacgac ctcctcggcc gtcagatcct gaaacagcgg gaaacgggcg aggccgacca    660
cggtgaactc gtcgggctgg cgttcctgct gctcatcgcc ggacacgaga ccacggcgaa    720
catgatctcg ctcggcacgg tgaccctgct ggagaatccc gatcagctcg cgaagatcaa    780
ggcagacccc ggcaagaccc tcgccgccat cgaggaactc ctgcgggtct tcacgatcgc    840
ggaaacggcg acctcacgct tcgccacggc ggacgtcgag atcggcggaa cgctgatccg    900
cgcgggggaa ggggtggtgg gcctgagcaa cgcgggcaac cacgatccgg acggcttcga    960
gaacccggac accttcgaca tcgaacgcgg cgcgcggcat cacgtcgcgt tcggattcgg    1020
ggtgcaccag tgtctcggcc agaacttggc gaggttggaa ctccagatcg tcttcgatac    1080
gttgttccgg cgagtgccgg gcc                                             1103
```

<210> SEQ ID NO 38
<211> LENGTH: 817
<212> TYPE: DNA
<213> ORGANISM: Amycolatopsis orientalis

<400> SEQUENCE: 38

```
cttcacccgc gcggatgagc gtgccgccga tctcgacgtc cgccgtggcg aagcgtgagg      60
tcgccgtctc cgcgatggtg aagatccgca ggagttcctc gatcgcggcg agggtcttgc     120
ccggatccgc cttgatcttc gccagctgat cggggttctc cagcagggtc accgtgccga     180
gcgagatcat gttcgccgta gtctcgtgcc ccgcgatgag caggaggaac gccagaccga     240
ccagttcgcc gtggtcggct cgccggatt cgcgctgctt caggatctgg cggccgagga      300
ggtcgtcctc ggtggcgttc gcctccttct tcgtgacgag ttcgtcgaga tagttctcga     360
gcgactcgaa cgcggtcatc cgttcttcgg cggtgacttc ccggctgagc atccgggaac     420
tgcaggactg gaagaactcg tggtccgaat aggggacacc gagcagttcg cagatcacca     480
aggacggaac cggcagggaa agcgcctgga cgagatcggc gggtttgggg ccggcgagca     540
gggcgtcgat atgctcgtcg acgatctgct gaatacgtgg ctgaagcgct tcatgcgct      600 tgacggtgaa ttccccgacg acgtcacgcc tggccttgcc gtgttccggc gggtccatcg     660
cgatgaggga cgggcggaac ggcttgtcct cgcgccggat ctgccgcgcc accatcagcg     720
ggaacgacgg actctgccgg tcggagctga atgcggact gctcagcatt cgcggatgt       780 cttcgagccg ggtgagcgcc caagcggttt gaccgga                              817

<210> SEQ ID NO 39
<211> LENGTH: 1105
<212> TYPE: DNA
<213> ORGANISM: Amycolatopsis orientalis

<400> SEQUENCE: 39
ccgcgacctt gccgctggcc cgcaaatgcc cgtttttcacc gccgcccgaa tacgagcggc     60
ttcgccggga aagtccggtt tcccgggtcg gtctcccgtc cggtcaaacc gcttgggcgc    120
tcacccggct cgaggacatc cgcgaaatgc tgagcagtcc gcatttcagc tccgaccggc    180
agagtccgtc gttcccgctg atggtggccc ggcagatccg gcgcgaggac aagccgttcc    240
gcccgtccct catctcgatg gacccgccgg aacacagcaa ggccaggcgt gacgtcgtcg    300
gggaattcac cgtcaagcgc atgaaagcgc ttcagccgcg tattcagcag atcgtcgacg    360
agcatatcga cgccctgctc gccggcccca aacccgccga tctcgtccag gcgcttcccc    420
tgccggttcc gtccttggtg atctgcgaac tgctcggtgt cccctattcg gaccacgagt    480
tcttccagtc ctgcagttcc cggatgctca gccgggaagt caccgccgaa gaacggatga    540
ccgcgttcga gtcgctcgag aactatctcg acgaactcgt cacgaagaag gaggcgaacg    600
ccaccgagga cgacctcctc ggccgccaga tcctgaagca gcgcgaaacg ggcgaagccg    660
accacgcgca actggtcggg ctggcgttcc tcctgctcat cgcgggacac gagacgacgg    720
cgaacatgat ctcgctcggc acggcgaccc tgctggagaa ccccgaccag ctggcgaaga    780
tcaaggccga tccgggcaag accctcgccg cgatcgagga gctcctgcgg gtcttcacca    840
tcgcggagac ggcgaccctca cgcttcgcca cggcggacgt cgagatcggc ggcacgctca    900
tccgcgcggg tgaaggcgtc gtcggcctga gtaacgcggg caaccacgat ccggaaggct    960
tcgagaaccc ggacgccttc gacatcgaac gcggcgcgcg gcaccacgtc gccttcggat   1020
tcggtgtgca ccaatgcctc ggccagaact tggcgaggtt ggaactccag atcgtgttcg   1080
atacgttgtt ccggcgagtg ccggg                                          1105

<210> SEQ ID NO 40
<211> LENGTH: 1304
<212> TYPE: DNA
```

<213> ORGANISM: Amycolatopsis orientalis

<400> SEQUENCE: 40

```
ccttgccact ggcccgcaaa tgcccgtttt caccaccgcc cgaatacgag cggctccgcc      60
gggaaagtcc ggtttccggg gtcggtctcc cctccggtca aaccgcttgg gcgctcaccc     120
ggctcgaaga catccgcgaa atgctgagca gtccgcattt cagctccgac cggcagagtc     180
cgtcgttccc gctgatggtg gcgcggcaga tccggcgcga ggacaagccg ttccgcccgt     240
ccctcatcgc gatggacccg ccggaacacg gcaaggccag gcgtgacgtc gtcggggaat     300
tcaccgtcaa gcgcatgaaa gcgcttcagc cacgtattca gcagatcgtc gacgagcata     360
tcgacgccct gctcgccggc cccaaacccg ccgatctcgt ccaggcgctt ccctgccgg      420
ttccgtcctt ggtgatctgc gaactgctcg gtgtccccta ttcggaccac gagttcttcc     480
agtcctgcag ttcccggatg ctcagccggg aagtcaccgc cgaagaacgg atgaccgcgt     540
tcgagtcgct cgagaactat ctcgacgaac tcgtcacgaa gaaggaggcg aacgccaccg     600
aggacgacct cctcggccgc cagatcctga gcagcgcga atccggcgaa gccgaccacg      660
gcgaactggt cggtctggcg ttcctcctgc tcatcgcggg gcacgagact acggcgaaca     720
tgatctcgct cggcacggtg accctgctgg agaaccccga tcagctggcg aagatcaagg     780
cggatccggg caagaccctc gccgcgatcg aggaactcct gcggatcttc accatcgcgg     840
agacggcgac ctcacgcttc gccacggcgg acgtcgagat cggcggcacg ctcatccgcg     900
cgggtgaagg cgtcgtcggc ctgagcaacg cgggcaacca cgatccggac ggcttcgaga     960
acccggacac cttcgacatc gaacgcggcg cgcggcatca cgtcgccttc ggattcggtg    1020
tgcaccaatg cctcggccag aacttggcga ggttggaact ccagatcgtg ttcgatacgt    1080
tgttccggcg agtgccgggc atccggatcg ccgtaccggt cgacgaactg ccgttcaagc    1140
acgattcgac gatctacggc ctccgcgccc tgccggtcac ctggtaggag gagccatgaa    1200
gatcatcgcg gacaccggga agtgcgtggg ggcgggccag tgcgtgctca ccgatcccga    1260
tctgttcgac cagagcgagg acgacgggac ggtcctcctg ctga                     1304
```

<210> SEQ ID NO 41
<211> LENGTH: 825
<212> TYPE: DNA
<213> ORGANISM: Amycolatopsis orientalis

<400> SEQUENCE: 41

```
ctccggtcaa accgcttggg cgctcacccg gctcgaagac atccgcgaaa tgctgagcag      60
tccgcatttc agctccgacc ggcagaatcc gtcgttcccg ctgatggtgg cgcggcagat     120
ccggcgcgag gacaagccgt tccgcccgtc cctcatcgcg atggacccgc cggaacacag     180
caaggccagg cgtgacgtcg tcggggaatt caccgtcaag gcatgaaag cgcttcagcc      240
gcgtattcag cagatcgtcg acgagcatat cgacgccctg ctcgccggcc ccaaacccgc     300
cgatctcgtc caggcgcttt ccctgccggt tccgtccttg gtgatctgcg aactgctcgg     360
tgtcccctat tcggaccacg agttcttcca gtcctgcagt tcccggatgc tcagccggga     420
agtcaccgcc gaagaacgga tgaccgcgtt cgagtcgctc gagaactatc tcgacgaact     480
cgtcacgaag aaggaggcga acgccaccga ggacgacctc ctcggccgcc agatcctgaa     540
gcagcgggaa acgggcgagg ccgaccacgg cgaactcgtc gggctggcgt tcctgctgct     600
catcgccggg cacgagacga cggcgaacat gatctcgctc ggcacggcga ccctgctgga     660
gaaccccgac cagctggcga agatcaaggc ggatccgggc aagaccctcg ccgcgatcga     720
```

```
ggaactgctg cgcgtcttca cgatcgcgga gacggcgacc tcacgcttcg ccacggcgga      780
cgtcgagatc ggcggcacgc tcatccgcgc gggtgaaggc gtcgt                     825

<210> SEQ ID NO 42
<211> LENGTH: 1103
<212> TYPE: DNA
<213> ORGANISM: Amycolatopsis orientalis

<400> SEQUENCE: 42
gcgaccttgc cactggcccg caaatgcccg ttttcaccac cgcccgaata cgagcggctc       60
cgccgggaaa gtccggtttc ccgggtcggt ctcccctccg gtcaaaccgc ttgggcgctc      120
acccggctcg aagacatccg cgaaatgctg agcagtccgc atttcagctc cgaccggcag      180
agtccgtcgt tcccgctgat ggtggcgcgg cagatccggc gcgaggacaa gccgttccgc      240
ccgtccctca tcgcgatgga cccgccggaa cacggcaagg ccaggcgtga cgtcgtcggg      300
gaattcaccg tcaagcgcat gaaagcgctt cagccacgta ttcagcagat cgtcgacgag      360
catatcgacg ccctgctcgc cggccccaaa cccgccgatc tcgtccaggc gctttccctg      420
ccggttccgt ccttggtgat ctgcgaactg ctcggtgtcc cctattcgga ccacgagttc      480
ttccagtcct gcagttcccg gatgctcagc cgggaagtca ccgccgaaga acggatgacc      540
gcgttcgagt cgctcgagaa ctatctcgac gaactcgtca cgaagaagga ggcgaacgcc      600
accgaggacg acctcctcgg ccgccagatc ctgaagcagc gcgaatccgg cgaagccgac      660
cacggcgaac tggtcggtct ggcgttcctc ctgctcatcg cggggcacga gactacggcg      720
aacatgatct cgctcggcac ggtgaccctg ctggagaacc ccgatcagct ggcgaagatc      780
aaggcggatc cgggcaagac cctcgccgcg atcgaggaac tcctgcggat cttcaccatc      840
gcggagacgg cgacctcacg cttcgccacg gcggacgtcg agatcggcgg cacgctcatc      900
cgcgcgggtg aaggcgtcgt cggcctgagc aacgcgggca accacgatcc ggacggcttc      960
gagaacccgg acaccttcga catcgaacgc ggcgcgcggc atcacgtcgc cttcggattc     1020
ggtgtgcacc aatgcctcgg ccagaacttg gcgaggttgg aactccagat cgtgttcgat     1080
acgttgttcc ggcgagtgcc ggg                                             1103

<210> SEQ ID NO 43
<211> LENGTH: 402
<212> TYPE: PRT
<213> ORGANISM: Amycolatopsis orientalis

<400> SEQUENCE: 43

Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Lys Ala Arg Arg Asp Val Val Gly Glu Phe Thr Val
            100                 105                 110
```

-continued

```
Lys Arg Met Lys Ala Leu Gln Pro Arg Ile Gln Ile Val Asp Glu
        115                 120                 125
His Ile Asp Ala Met Leu Ala Gly Pro Lys Pro Ala Asp Leu Val Gln
    130                 135                 140
Ala Leu Ser Leu Pro Val Pro Ser Leu Val Ile Cys Glu Leu Leu Gly
145                 150                 155                 160
Val Pro Tyr Ser Asp His Glu Phe Phe Gln Ser Cys Ser Ser Arg Met
                165                 170                 175
Leu Ser Arg Glu Val Thr Ala Glu Arg Met Thr Ala Phe Glu Ser
        180                 185                 190
Leu Glu Asn Tyr Leu Asp Glu Leu Val Thr Lys Lys Glu Ala Asn Ala
        195                 200                 205
Thr Glu Asp Asp Leu Leu Gly Arg Gln Ile Leu Lys Gln Arg Glu Thr
    210                 215                 220
Gly Glu Ala Asp His Gly Glu Leu Val Gly Leu Ala Phe Leu Leu Leu
225                 230                 235                 240
Ile Ala Gly His Glu Thr Thr Ala Asn Met Ile Ser Leu Gly Thr Ala
                245                 250                 255
Thr Leu Leu Glu Asn Pro Asp Gln Leu Ala Lys Ile Lys Ala Asp Pro
        260                 265                 270
Gly Lys Thr Leu Ala Ala Ile Glu Glu Leu Leu Arg Val Phe Thr Ile
        275                 280                 285
Ala Glu Thr Ala Thr Ser Arg Phe Ala Thr Ala Asp Val Glu Ile Gly
    290                 295                 300
Gly Thr Leu Ile Arg Ala Gly Glu Gly Val Val Gly Leu Ser Asn Ala
305                 310                 315                 320
Gly Asn His Asp Pro Glu Gly Phe Glu Asn Pro Asp Ala Phe Asp Ile
                325                 330                 335
Glu Arg Gly Ala Arg His His Val Ala Phe Gly Phe Gly Val His Gln
        340                 345                 350
Cys Leu Gly Gln Asn Leu Ala Arg Leu Glu Leu Gln Ile Val Phe Asp
        355                 360                 365
Thr Leu Phe Arg Arg Val Pro Gly Ile Arg Ile Ala Val Pro Val Asp
    370                 375                 380
Glu Leu Pro Phe Lys His Asp Ser Thr Ile Tyr Gly Leu His Ala Leu
385                 390                 395                 400
Pro Val

<210> SEQ ID NO 44
<211> LENGTH: 367
<212> TYPE: PRT
<213> ORGANISM: Amycolatopsis orientalis

<400> SEQUENCE: 44

Thr Leu Pro Leu Ala Arg Lys Cys Pro Phe Ser Pro Pro Pro Glu Tyr
1               5                   10                  15
Glu Arg Leu Arg Arg Glu Ser Pro Val Ser Arg Val Gly Leu Pro Ser
            20                  25                  30
Gly Gln Thr Ala Trp Ala Leu Thr Arg Leu Glu Asp Ile Arg Glu Met
        35                  40                  45
Leu Ser Ser Pro His Phe Ser Asp Arg Gln Ser Pro Ser Phe Pro
    50                  55                  60
Leu Met Val Ala Arg Gln Ile Arg Glu Asp Lys Pro Phe Arg Pro
65              70                  75                  80
```

-continued

Ser Leu Ile Ala Met Asp Pro Pro Glu His Ser Arg Ala Arg Arg Asp
              85                  90                  95

Val Val Gly Glu Phe Thr Val Lys Arg Met Lys Ala Leu Gln Pro Arg
            100                 105                 110

Ile Gln Gln Ile Val Asp Glu His Leu Asp Ala Leu Leu Ala Gly Pro
        115                 120                 125

Lys Pro Ala Asp Leu Val Gln Ala Leu Ser Leu Pro Val Pro Ser Leu
    130                 135                 140

Val Ile Cys Glu Leu Leu Gly Val Pro Tyr Ser Asp His Glu Phe Phe
145                 150                 155                 160

Gln Ser Cys Ser Ser Arg Met Leu Ser Arg Glu Val Thr Ala Glu Glu
                165                 170                 175

Arg Met Thr Ala Phe Glu Gln Leu Glu Asn Tyr Leu Asp Glu Leu Val
            180                 185                 190

Thr Lys Lys Glu Ala Asn Ala Thr Glu Asp Asp Leu Leu Gly Arg Gln
        195                 200                 205

Ile Leu Lys Gln Arg Glu Thr Gly Glu Ala Asp His Gly Glu Leu Val
    210                 215                 220

Gly Leu Ala Phe Leu Leu Leu Ile Ala Gly His Glu Thr Thr Ala Asn
225                 230                 235                 240

Met Ile Ser Leu Gly Thr Val Thr Leu Leu Glu Asn Pro Asp Gln Leu
                245                 250                 255

Ala Lys Ile Lys Ala Asp Pro Gly Lys Thr Leu Ala Ala Ile Glu Glu
            260                 265                 270

Leu Leu Arg Val Phe Thr Ile Ala Glu Thr Ala Thr Ser Arg Phe Ala
        275                 280                 285

Thr Ala Asp Val Glu Ile Gly Gly Thr Leu Ile Arg Ala Gly Glu Gly
    290                 295                 300

Val Val Gly Leu Ser Asn Ala Gly Asn His Asp Pro Asp Gly Phe Glu
305                 310                 315                 320

Asn Pro Asp Thr Phe Asp Ile Glu Arg Gly Ala Arg His His Val Ala
                325                 330                 335

Phe Gly Phe Gly Val His Gln Cys Leu Gly Gln Asn Leu Ala Arg Leu
            340                 345                 350

Glu Leu Gln Ile Val Phe Asp Thr Leu Phe Arg Arg Val Pro Gly
        355                 360                 365

<210> SEQ ID NO 45
<211> LENGTH: 272
<212> TYPE: PRT
<213> ORGANISM: Amycolatopsis orientalis

<400> SEQUENCE: 45

Ser Gly Gln Thr Ala Trp Ala Leu Thr Arg Leu Glu Asp Ile Arg Glu
1               5                  10                  15

Met Leu Ser Ser Pro His Phe Ser Ser Asp Arg Gln Ser Pro Ser Phe
            20                  25                  30

Pro Leu Met Val Ala Arg Gln Ile Arg Arg Glu Asp Lys Pro Phe Arg
        35                  40                  45

Pro Ser Leu Ile Ala Met Asp Pro Pro Glu His Gly Lys Ala Arg Arg
    50                  55                  60

Asp Val Val Gly Glu Phe Thr Val Lys Arg Met Lys Ala Leu Gln Pro
65                  70                  75                  80

Arg Ile Gln Gln Ile Val Asp Glu His Ile Asp Ala Leu Leu Ala Gly

```
                    85                  90                  95
Pro Lys Pro Ala Asp Leu Val Gln Ala Leu Ser Leu Pro Val Pro Ser
            100                 105                 110
Leu Val Ile Cys Glu Leu Leu Gly Val Pro Tyr Ser Asp His Glu Phe
            115                 120                 125
Phe Gln Ser Cys Ser Ser Arg Met Leu Ser Arg Glu Val Thr Ala Glu
            130                 135                 140
Glu Arg Met Thr Ala Phe Glu Ser Leu Glu Asn Tyr Leu Asp Glu Leu
145                 150                 155                 160
Val Thr Lys Lys Glu Ala Asn Ala Thr Glu Asp Asp Leu Leu Gly Arg
                165                 170                 175
Gln Ile Leu Lys Gln Arg Glu Ser Gly Glu Ala Asp His Gly Glu Leu
            180                 185                 190
Val Gly Leu Ala Phe Leu Leu Ile Ala Gly His Glu Thr Thr Ala
            195                 200                 205
Asn Met Ile Ser Leu Gly Thr Val Thr Leu Leu Glu Asn Pro Asp Gln
    210                 215                 220
Leu Ala Lys Ile Lys Ala Asp Pro Gly Lys Thr Leu Ala Ala Ile Glu
225                 230                 235                 240
Glu Leu Leu Arg Ile Phe Thr Ile Ala Glu Thr Ala Thr Ser Arg Phe
                245                 250                 255
Ala Thr Ala Asp Val Glu Ile Gly Gly Thr Leu Ile Arg Ala Gly Glu
            260                 265                 270

<210> SEQ ID NO 46
<211> LENGTH: 367
<212> TYPE: PRT
<213> ORGANISM: Amycolatopsis orientalis

<400> SEQUENCE: 46

Ala Thr Leu Pro Leu Ala Arg Lys Cys Pro Phe Ser Pro Pro Pro Glu
1               5                   10                  15
Tyr Glu Arg Leu Arg Arg Glu Ser Pro Val Ser Arg Val Gly Leu Pro
                20                  25                  30
Ser Gly Gln Thr Ala Trp Ala Leu Thr Arg Leu Glu Asp Ile Arg Glu
            35                  40                  45
Met Leu Ser Ser Pro His Phe Ser Ser Asp Arg Gln Ser Pro Ser Phe
    50                  55                  60
Pro Leu Met Val Ala Arg Gln Ile Arg Arg Glu Asp Lys Pro Phe Arg
65                  70                  75                  80
Pro Ser Leu Ile Ser Met Asp Pro Pro Glu His Ser Lys Ala Arg Arg
                85                  90                  95
Asp Val Val Gly Glu Phe Thr Val Lys Arg Met Lys Ala Leu Gln Pro
            100                 105                 110
Arg Ile Gln Gln Ile Val Asp Glu His Ile Asp Ala Leu Leu Ala Gly
            115                 120                 125
Pro Lys Pro Ala Asp Leu Val Gln Ala Leu Ser Leu Pro Val Pro Ser
            130                 135                 140
Leu Val Ile Cys Glu Leu Leu Gly Val Pro Tyr Ser Asp His Glu Phe
145                 150                 155                 160
Phe Gln Ser Cys Ser Ser Arg Met Leu Ser Arg Glu Val Thr Ala Glu
                165                 170                 175
Glu Arg Met Thr Ala Phe Glu Ser Leu Glu Asn Tyr Leu Asp Glu Leu
            180                 185                 190
```

```
Val Thr Lys Lys Glu Ala Asn Ala Thr Glu Asp Asp Leu Leu Gly Arg
        195                 200                 205

Gln Ile Leu Lys Gln Arg Glu Thr Gly Glu Ala Asp His Gly Glu Leu
    210                 215                 220

Val Gly Leu Ala Phe Leu Leu Ile Ala Gly His Glu Thr Thr Ala
225                 230                 235                 240

Asn Met Ile Ser Leu Gly Thr Ala Thr Leu Leu Glu Asn Pro Asp Gln
                245                 250                 255

Leu Ala Lys Ile Lys Ala Asp Pro Gly Lys Thr Leu Ala Ala Ile Glu
            260                 265                 270

Glu Leu Leu Arg Val Phe Thr Ile Ala Glu Thr Ala Thr Ser Arg Phe
            275                 280                 285

Ala Thr Ala Asp Val Glu Ile Gly Gly Thr Leu Ile Arg Ala Gly Glu
290                 295                 300

Gly Val Val Gly Leu Ser Asn Ala Gly Asn His Asp Pro Glu Gly Phe
305                 310                 315                 320

Glu Asn Pro Asp Ala Phe Asp Ile Glu Arg Gly Ala Arg His His Val
                325                 330                 335

Ala Phe Gly Phe Gly Val His Gln Cys Leu Gly Gln Asn Leu Ala Arg
            340                 345                 350

Leu Glu Leu Gln Ile Val Phe Asp Thr Leu Phe Arg Arg Val Pro
            355                 360                 365

<210> SEQ ID NO 47
<211> LENGTH: 394
<212> TYPE: PRT
<213> ORGANISM: Amycolatopsis orientalis

<400> SEQUENCE: 47

Leu Pro Leu Ala Arg Lys Cys Pro Phe Ser Pro Pro Glu Tyr Glu
1               5                   10                  15

Arg Leu Arg Arg Glu Ser Pro Val Ser Arg Val Gly Leu Pro Ser Gly
                20                  25                  30

Gln Thr Ala Trp Ala Leu Thr Arg Leu Glu Asp Ile Arg Glu Met Leu
            35                  40                  45

Ser Ser Pro His Phe Ser Ser Asp Arg Gln Ser Pro Ser Phe Pro Leu
        50                  55                  60

Met Val Ala Arg Gln Ile Arg Arg Glu Asp Lys Pro Phe Arg Pro Ser
65                  70                  75                  80

Leu Ile Ala Met Asp Pro Pro Glu His Gly Lys Ala Arg Arg Asp Val
                85                  90                  95

Val Gly Glu Phe Thr Val Lys Arg Met Lys Ala Leu Gln Pro Arg Ile
                100                 105                 110

Gln Gln Ile Val Asp Glu His Ile Asp Ala Leu Leu Ala Gly Pro Lys
            115                 120                 125

Pro Ala Asp Leu Val Gln Ala Leu Ser Leu Pro Val Pro Ser Leu Val
        130                 135                 140

Ile Cys Glu Leu Leu Gly Val Pro Tyr Ser Asp His Glu Phe Phe Gln
145                 150                 155                 160

Ser Cys Ser Ser Arg Met Leu Ser Arg Glu Val Thr Ala Glu Glu Arg
                165                 170                 175

Met Thr Ala Phe Glu Ser Leu Glu Asn Tyr Leu Asp Glu Leu Val Thr
            180                 185                 190

Lys Lys Glu Ala Asn Ala Thr Glu Asp Asp Leu Leu Gly Arg Gln Ile
        195                 200                 205
```

-continued

Leu Lys Gln Arg Glu Ser Gly Glu Ala Asp His Gly Glu Leu Val Gly
            210                 215                 220

Leu Ala Phe Leu Leu Leu Ile Ala Gly His Glu Thr Thr Ala Asn Met
225                 230                 235                 240

Ile Ser Leu Gly Thr Val Thr Leu Leu Glu Asn Pro Asp Gln Leu Ala
                245                 250                 255

Lys Ile Lys Ala Asp Pro Gly Lys Thr Leu Ala Ala Ile Glu Glu Leu
            260                 265                 270

Leu Arg Ile Phe Thr Ile Ala Glu Thr Ala Thr Ser Arg Phe Ala Thr
        275                 280                 285

Ala Asp Val Glu Ile Gly Gly Thr Leu Ile Arg Ala Gly Glu Gly Val
    290                 295                 300

Val Gly Leu Ser Asn Ala Gly Asn His Asp Pro Asp Gly Phe Glu Asn
305                 310                 315                 320

Pro Asp Thr Phe Asp Ile Glu Arg Gly Ala Arg His His Val Ala Phe
                325                 330                 335

Gly Phe Gly Val His Gln Cys Leu Gly Gln Asn Leu Ala Arg Leu Glu
            340                 345                 350

Leu Gln Ile Val Phe Asp Thr Leu Phe Arg Arg Val Pro Gly Ile Arg
        355                 360                 365

Ile Ala Val Pro Val Asp Glu Leu Pro Phe Lys His Asp Ser Thr Ile
    370                 375                 380

Tyr Gly Leu Arg Ala Leu Pro Val Thr Trp
385                 390

<210> SEQ ID NO 48
<211> LENGTH: 274
<212> TYPE: PRT
<213> ORGANISM: Amycolatopsis orientalis

<400> SEQUENCE: 48

Ser Gly Gln Thr Ala Trp Ala Leu Thr Arg Leu Glu Asp Ile Arg Glu
1               5                  10                  15

Met Leu Ser Ser Pro His Phe Ser Ser Asp Arg Gln Asn Pro Ser Phe
            20                  25                  30

Pro Leu Met Val Ala Arg Gln Ile Arg Arg Glu Asp Lys Pro Phe Arg
        35                  40                  45

Pro Ser Leu Ile Ala Met Asp Pro Pro Glu His Ser Lys Ala Arg Arg
    50                  55                  60

Asp Val Val Gly Glu Phe Thr Val Lys Arg Met Lys Ala Leu Gln Pro
65                  70                  75                  80

Arg Ile Gln Gln Ile Val Asp Glu His Ile Asp Ala Leu Leu Ala Gly
                85                  90                  95

Pro Lys Pro Ala Asp Leu Val Gln Ala Leu Ser Leu Pro Val Pro Ser
            100                 105                 110

Leu Val Ile Cys Glu Leu Leu Gly Val Pro Tyr Ser Asp His Glu Phe
        115                 120                 125

Phe Gln Ser Cys Ser Ser Arg Met Leu Ser Arg Glu Val Thr Ala Glu
    130                 135                 140

Glu Arg Met Thr Ala Phe Glu Ser Leu Glu Asn Tyr Leu Asp Glu Leu
145                 150                 155                 160

Val Thr Lys Lys Glu Ala Asn Ala Thr Glu Asp Asp Leu Leu Gly Arg
                165                 170                 175

Gln Ile Leu Lys Gln Arg Glu Thr Gly Glu Ala Asp His Gly Glu Leu

```
                180              185              190
Val Gly Leu Ala Phe Leu Leu Ile Ala Gly His Glu Thr Thr Ala
        195              200              205

Asn Met Ile Ser Leu Gly Thr Ala Thr Leu Leu Glu Asn Pro Asp Gln
        210              215              220

Leu Ala Lys Ile Lys Ala Asp Pro Gly Lys Thr Leu Ala Ala Ile Glu
225              230              235              240

Glu Leu Leu Arg Val Phe Thr Ile Ala Glu Thr Ala Thr Ser Arg Phe
                245              250              255

Ala Thr Ala Asp Val Glu Ile Gly Gly Thr Leu Ile Arg Ala Gly Glu
                260              265              270

Gly Val

<210> SEQ ID NO 49
<211> LENGTH: 367
<212> TYPE: PRT
<213> ORGANISM: Amycolatopsis orientalis

<400> SEQUENCE: 49

Ala Thr Leu Pro Leu Ala Arg Lys Cys Pro Phe Ser Pro Pro Pro Glu
1               5                  10                  15

Tyr Glu Arg Leu Arg Arg Glu Ser Pro Val Ser Arg Val Gly Leu Pro
                20                  25                  30

Ser Gly Gln Thr Ala Trp Ala Leu Thr Arg Leu Glu Asp Ile Arg Glu
            35                  40                  45

Met Leu Ser Ser Pro His Phe Ser Ser Asp Arg Gln Ser Pro Ser Phe
        50                  55                  60

Pro Leu Met Val Ala Arg Gln Ile Arg Arg Glu Asp Lys Pro Phe Arg
65                  70                  75                  80

Pro Ser Leu Ile Ala Met Asp Pro Pro Glu His Gly Lys Ala Arg Arg
                85                  90                  95

Asp Val Val Gly Glu Phe Thr Val Lys Arg Met Lys Ala Leu Gln Pro
                100                 105                 110

Arg Ile Gln Gln Ile Val Asp Glu His Ile Asp Ala Leu Leu Ala Gly
            115                 120                 125

Pro Lys Pro Ala Asp Leu Val Gln Ala Leu Ser Leu Pro Val Pro Ser
        130                 135                 140

Leu Val Ile Cys Glu Leu Leu Gly Val Pro Tyr Ser Asp His Glu Phe
145                 150                 155                 160

Phe Gln Ser Cys Ser Ser Arg Met Leu Ser Arg Glu Val Thr Ala Glu
                165                 170                 175

Glu Arg Met Thr Ala Phe Glu Ser Leu Glu Asn Tyr Leu Asp Glu Leu
                180                 185                 190

Val Thr Lys Lys Glu Ala Asn Ala Thr Glu Asp Asp Leu Leu Gly Arg
            195                 200                 205

Gln Ile Leu Lys Gln Arg Glu Ser Gly Glu Ala Asp His Gly Glu Leu
        210                 215                 220

Val Gly Leu Ala Phe Leu Leu Ile Ala Gly His Glu Thr Thr Ala
225                 230                 235                 240

Asn Met Ile Ser Leu Gly Thr Val Thr Leu Leu Glu Asn Pro Asp Gln
                245                 250                 255

Leu Ala Lys Ile Lys Ala Asp Pro Gly Lys Thr Leu Ala Ala Ile Glu
            260                 265                 270

Glu Leu Leu Arg Ile Phe Thr Ile Ala Glu Thr Ala Thr Ser Arg Phe
```

```
                275                 280                 285
Ala Thr Ala Asp Val Glu Ile Gly Gly Thr Leu Ile Arg Ala Gly Glu
        290                 295                 300

Gly Val Val Gly Leu Ser Asn Ala Gly Asn His Asp Pro Asp Gly Phe
305                 310                 315                 320

Glu Asn Pro Asp Thr Phe Asp Ile Glu Arg Gly Ala Arg His His Val
                325                 330                 335

Ala Phe Gly Phe Gly Val His Gln Cys Leu Gly Gln Asn Leu Ala Arg
            340                 345                 350

Leu Glu Leu Gln Ile Val Phe Asp Thr Leu Phe Arg Arg Val Pro
        355                 360                 365
```

<210> SEQ ID NO 50
<211> LENGTH: 25
<212> TYPE: DNA
<213> ORGANISM: Artificial sequence
<220> FEATURE:
<223> OTHER INFORMATION: Synthetic

<400> SEQUENCE: 50
aggaaaccac cgcgaccttg ccact                                    25

<210> SEQ ID NO 51
<211> LENGTH: 25
<212> TYPE: DNA
<213> ORGANISM: Artificial sequence
<220> FEATURE:
<223> OTHER INFORMATION: Synthetic

<400> SEQUENCE: 51
accgaatccg aaggcgacgt gatgc                                    25

<210> SEQ ID NO 52
<211> LENGTH: 23
<212> TYPE: DNA
<213> ORGANISM: Artificial sequence
<220> FEATURE:
<223> OTHER INFORMATION: Synthetic

<400> SEQUENCE: 52
cggaatgaat ccatccgcat acg                                      23

<210> SEQ ID NO 53
<211> LENGTH: 23
<212> TYPE: DNA
<213> ORGANISM: Artificial sequence
<220> FEATURE:
<223> OTHER INFORMATION: Synthetic

<400> SEQUENCE: 53
tgatcttcat ggctcctcct acc                                      23

<210> SEQ ID NO 54
<211> LENGTH: 35
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (18)..(20)
<223> OTHER INFORMATION: n=a, c, g or t

<400> SEQUENCE: 54
gcgaagccga ccacggcnnn ctggtcggtc tggcg                                35

<210> SEQ ID NO 55
<211> LENGTH: 35
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (16)..(18)
<223> OTHER INFORMATION: n=a, c, g or t

<400> SEQUENCE: 55
cgccagaccg accagnnngc cgtggtcggc ttcgc                                35

<210> SEQ ID NO 56
<211> LENGTH: 35
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: n=a, c, g or t

<400> SEQUENCE: 56
ggtcggtctg gcgnysctcc tgctcatcgc ggggc                                35

<210> SEQ ID NO 57
<211> LENGTH: 35
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: n=a, c, g or t

<400> SEQUENCE: 57
gccccgcgat gagcaggags rncgccagac cgacc                                35

<210> SEQ ID NO 58
<211> LENGTH: 35
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: n=a, c, g or t

<400> SEQUENCE: 58
ggtcggtctg gcgttcnysc tgctcatcgc ggggc                                35

<210> SEQ ID NO 59
<211> LENGTH: 35
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: n=a, c, g or t

<400> SEQUENCE: 59
gccccgcgat gagcagsrng aacgccagac cgacc            35

<210> SEQ ID NO 60
<211> LENGTH: 1215
<212> TYPE: DNA
<213> ORGANISM: Artificial sequence
<220> FEATURE:
<223> OTHER INFORMATION: Synthetic

<400> SEQUENCE: 60

```
atgaccgacg tcgaggaaac caccgcgacc ttgccactgg cccgcaaatg cccgttttca      60
ccaccgcccg aatacgagcg gctccgccgg gaaagtccgg tttcccgggt cggtctcccc     120
tccggtcaaa ccgcttgggc gctcacccgg ctcgaagaca tccgcgaaat gctgagcagt     180
ccgcatttca gctccgacca gcagagtccg tcgttcccgc tgatggtggc gcggcagatc     240
cggcgcgagg acaagccgtt ccgcccgtcc ctcgtcgcga tggacccgcc ggaacacggc     300
aaggccaggc gtgacgtcgt cggggaattc accgtcaagc gcatgaaagc gcttcagcca     360
cgtattcagc agatcgtcga cgagcatatc gacgccctgc tcgccggccc caaacccgcc     420
gatctcgtcc aggcgctttc cctgccggtt ccgtccttgg tgatctgcga actgctcggt     480
gtcccctatt cggaccacga gttcttccag tcctgcagtt cccggatgct cagccgggaa     540
gtcaccgccg aagaacggat gaccgcgttc gagtcgctcg agaactatct cgacgaactc     600
gtcacgaaga aggaggcgaa cgccaccgag gacgacctcc tcggccgcca gatcctgaag     660
cagcgcgaat ccggcgaagc cgaccacggc gaactggtcg gtctggcggc gctcctgctc     720
atcgcggggc acgagactac ggcgaacatg atctcgctcg gcacggtgac cctgctggag     780
aaccccgatc agctggcgaa gatcaaggcg atccgggca agaccctcgc cgcgatcgag     840
gaactcctgc ggatcttcac catcgcggag acggcgacct cacgcttcgc cacggcggac     900
gtcgagatcg gcggcacgct catccgcgcg ggtgaaggcg tcgtcggcct gagcaacgcg     960
ggcaaccacg atccggacgg cttcgagaac ccggacacct tcgacatcga acgcggcgcg    1020
cggcatcacg tcgccttcgg attcggtgtg caccaatgcc tcggccagaa cttggcgagg    1080
ttggaactcc agatcgtgtt cgatacgttg ttccggcgag tgccgggcat ccggatcgcc    1140
gtaccggtcg acgaactgcc gttcaagcac gattcgacga tctacggcct ccacgccctg    1200
ccggtcacct ggtag                                                     1215
```

<210> SEQ ID NO 61
<211> LENGTH: 404
<212> TYPE: PRT
<213> ORGANISM: Artificial sequence
<220> FEATURE:
<223> OTHER INFORMATION: Synthetic

<400> SEQUENCE: 61

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Gln Gln Ser Pro Ser Phe Pro Leu Met Val Ala Arg Gln Ile
65                  70                  75                  80
```

Arg Arg Glu Asp Lys Pro Phe Arg Pro Ser Leu Val Ala Met Asp Pro
                85                  90                  95

Pro Glu His Gly Lys Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Ile Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Ser
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Ser
    210                 215                 220

Gly Glu Ala Asp His Gly Glu Leu Val Gly Leu Ala Ala Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Ile Phe Thr Ile
        275                 280                 285

Ala Glu Thr Ala Thr Ser Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
        355                 360                 365

Thr Leu Phe Arg Arg Val Pro Gly Ile Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp

<210> SEQ ID NO 62
<211> LENGTH: 1215
<212> TYPE: DNA
<213> ORGANISM: Artificial sequence
<220> FEATURE:
<223> OTHER INFORMATION: Synthetic

<400> SEQUENCE: 62
atgaccgacg tcgaggaaac caccgcgacc ttgccactgg cccgcaaatg cccgttttca      60
ccaccgcccg aatacgagcg gctccgccgg gaaagtccgg tttcccgggt cggtctcccc     120
tccggtcaaa ccgcttgggc gctcacccgg ctcgaagaca tccgcgaaat gctgagcagt     180

-continued

```
ccgcatttca gctccgaccg gcagagtccg tcgttcccgc tgatggtggc gcggcagatc      240
cggcgcgagg acaagccgtt ccgcccgtcc ctcgtcggga tggacccgcc ggaacacggc      300
aaggccaggc gtgacgtcgt cggggaattc accgtcaagc gcatgaaagc gcttcagcca      360
cgtattcagc agatcgtcga cgagcatatc gacgccctgc tcgccggccc caaacccgcc      420
gatctcgtcc aggcgctttc cctgccggtt ccgtccttgg tgatctgcga actgctcggt      480 gtccctatt  cggaccacga gttcttccag tcctgcagtt cccggatgct cagccgggaa      540
gtcaccgccg aagaacggat gaccgcgttc gagtcgctcg agaactatct cgacgaactc      600
gtcacgaaga aggaggcgaa cgccaccgag gacgacctcc tcggccgcca gatcctgaag      660
cagcgcgaat ccggcgaagc cgaccacggc gaactggtcg gtctggcggc gctcctgctc      720
atcgcggggc acgagactac ggcgaacatg atctcgctcg gcacggtgac cctgctggag      780
aaccccgatc agctggcgaa gatcaaggcg gatccgggca agaccctcgc gcgatcgag      840 gaactcctgc ggatcttcac catcgcggag acggcgacct cacgcttcgc cacggcggac      900
gtcgagatcg gcggcacgct catccgcgcg ggtgaaggcg tcgtcggcct gagcaacgcg      960
ggcaaccacg atccggacgg cttcgagaac ccggacacct tcgacatcga acgcggcgcg     1020
cggcatcacg tcgccttcgg attcggtgtg caccaatgcc tcggccagaa cttggcgagg     1080
ttggaactcc agaccgtgtt cgatacgttg ttccggcgag tgccgggcat ccggatcgcc     1140
gtaccggtcg acgaactgcc gttcaagcac gattcgacga tctacggcct ccacgccctg     1200
ccggtcacct ggtag                                                      1215
```

<210> SEQ ID NO 63
<211> LENGTH: 404
<212> TYPE: PRT
<213> ORGANISM: Artificial sequence
<220> FEATURE:
<223> OTHER INFORMATION: Synthetic

<400> SEQUENCE: 63

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Val Gly Met Asp Pro
                85                  90                  95

Pro Glu His Gly Lys Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Ile Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175
```

```
Leu Ser Arg Glu Val Thr Ala Glu Glu Arg Met Thr Ala Phe Glu Ser
            180                 185                 190

Leu Glu Asn Tyr Leu Asp Glu Leu Val Thr Lys Lys Glu Ala Asn Ala
            195                 200                 205

Thr Glu Asp Asp Leu Leu Gly Arg Gln Ile Leu Lys Gln Arg Glu Ser
        210                 215                 220

Gly Glu Ala Asp His Gly Glu Leu Val Gly Leu Ala Ala Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Ile Phe Thr Ile
            275                 280                 285

Ala Glu Thr Ala Thr Ser Arg Phe Ala Thr Ala Asp Val Glu Ile Gly
        290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Thr Val Phe Asp
            355                 360                 365

Thr Leu Phe Arg Arg Val Pro Gly Ile Arg Ile Ala Val Pro Val Asp
        370                 375                 380

Glu Leu Pro Phe Lys His Asp Ser Thr Ile Tyr Gly Leu His Ala Leu
385                 390                 395                 400

Pro Val Thr Trp

<210> SEQ ID NO 64
<211> LENGTH: 1215
<212> TYPE: DNA
<213> ORGANISM: Artificial sequence
<220> FEATURE:
<223> OTHER INFORMATION: Synthetic

<400> SEQUENCE: 64
atgaccgacg tcgaggaaac caccgcgacc ttgccactgg cccgcaaatg cccgttttca      60
ccaccgcccg aatacgagcg gctccgccgg gaaagtccgg tttcccgggt cggtctcccc     120
tccggtcaaa ccgcttgggc gctcacccgg ctcgaagaca tccgcgaaat gctgagcagt     180
ccgcatttca gctccgaccg gcagagtccg tcgttcccgc tgatggtggc gcggcagatc     240
cggcgcgagg acaagccgtt ccgcccgtcc ctcgtcgcga tggacccgcc ggaacacggc     300
aaggccaggc gtgacgccgt cggggaattc ccgtcaagc gcatgaaagc gcttcagcca     360
cgtattcagc agatcgtcga cgagcatatc gacgccctgc tcgccggccc caaacccgcc     420
gatctcgtcc aggcgctttc cctgccggtt ccgtccttgg tgatctgcga actgctcggt     480 gtccctatt cggaccacga gttcttccag tcctgcagtt cccggatgct cagccgggaa     540
gtcaccgccg aagaacggat gaccgcgttc gagtcgctcg agaactatct cgacgaactc     600
gtcacgaaga aggaggcgaa cgccaccgag gacgacctcc tcggccgcca gatcctgaag     660
cagcgcgaat ccggcgaagc cgaccacggc gaactggtcg gtctggcggc gctcctgctc     720 atcgcgggc acgagactac ggcgaacatg atctcgctcg gcacggtgac cctgctggag     780
```

```
aaccccgatc agctggcgaa gatcaaggca gatccgggca agaccctcgc cgcgatcgag    840
gaactcctgc ggatcttcac catcgcggag acggcgacct cacgcttcgc cacggcggac    900
gtcgagatcg gcggcacgct catccgcgcg ggtgaaggcg tcgtcggcct gagcaacgcg    960
ggcaaccacg atccggacgg cttcgagaac ccggacacct tcgacatcga acgcggcgcg   1020
cggcatcacg tcgccttcgg attcggtgtg caccaatgcc tcggccagaa cttggcgagg   1080
ttggaactcc agatcgtgtt cgatacgttg ttccggcgag tgccgggcat ccggatcgcc   1140
gtaccggtcg acgaactgcc gttcaagcac gattcgacga tctacggcct ccacgccctg   1200
ccggtcacct ggtag                                                    1215
```

<210> SEQ ID NO 65
<211> LENGTH: 404
<212> TYPE: PRT
<213> ORGANISM: Artificial sequence
<220> FEATURE:
<223> OTHER INFORMATION: Synthetic

<400> SEQUENCE: 65

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Val Ala Met Asp Pro
                85                  90                  95

Pro Glu His Gly Lys Ala Arg Arg Asp Ala Val Gly Glu Phe Thr Val
            100                 105                 110

Lys Arg Met Lys Ala Leu Gln Pro Arg Ile Gln Gln Ile Val Asp Glu
        115                 120                 125

His Ile Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Ser
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Ser
    210                 215                 220

Gly Glu Ala Asp His Gly Glu Leu Val Gly Leu Ala Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Ile Phe Thr Ile
```

-continued

```
                275                 280                 285
Ala Glu Thr Ala Thr Ser Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
                340                 345                 350

Cys Leu Gly Gln Asn Leu Ala Arg Leu Glu Leu Gln Ile Val Phe Asp
            355                 360                 365

Thr Leu Phe Arg Arg Val Pro Gly Ile Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp
```

<210> SEQ ID NO 66
<211> LENGTH: 1215
<212> TYPE: DNA
<213> ORGANISM: Artificial sequence
<220> FEATURE:
<223> OTHER INFORMATION: Synthetic

<400> SEQUENCE: 66

```
atgaccgacg tcgaggaaac caccgcgacc ttgccactgg ctcgcaaatg cccgttttca      60
ccaccgcccg aatacgagcg gctccgccgg gaaagtccgg tttcccgggt cggtctcccc     120
tccggtcaaa ccgcttgggc gctcacccgg ctcgaagaca tccgcgaaat gctgagcagt     180
ccgcatttca gctccgaccg gcagagtccg tcgttcccgc tgatggtggc gcggcagatc     240
cggcgcgagg acaagccgtt ccacccgtcc ctcgtcgcga tggacccgcc ggaacacggc     300
aaggccaggc gtgacgtcgt cggggaattc accgtcaagc gcatgaaagc gcttcagcca     360
cgtattcagc agatcgtcga cgagcatatc gacgccctgc tcgccggccc caaacccgcc     420
gatctcgtcc aggcgctttc cctgccggtt ccgtccttgg tgatctgcga actgctcggt     480
gtcccctatt cggaccacga gttcttccag tcctgcagtt cccggatgct cagccgggaa     540
gtcaccgccg aagaacggat gaccgcgttc gagtcgctcg agaactatct cgacgaactc     600
gtcacgaaga aggaggcgaa cgccaccgag gacgacctcc tcggccgcca gatcctgaag     660
cagcgcgaat ccggcgaagc cgaccacggc gaactggtcg gtctggcggc gctcctgctc     720
atcgcggggc acgagactac ggcgaacatg atctcgctcg gcacggtgac cctgctggag     780
aaccccgatc agctggcgaa gatcaaggcg atccgggca  agaccctcgc cgcgatcgag     840
gaactcctgc ggatcttcac catcgcggag acggcgacct cacgcttcgc cacggcggac     900
gtcgagatcg gcggcacgct catccgcgcg ggtgaaggcg tcgtcggcct gagcaacgcg     960
ggcaaccacg atccggacgg cttcgagaac ccggacacct tcgacatcga acgcggcgcg    1020
cggcatcacg tcgccttcgg attcggtgtg caccaatgcc tcggccagaa cttggcgagg    1080
ttggaactcc agatcgtgtt cgatacgttg ttccggcgag tgccgggcat ccggatcgcc    1140
gtaccggtcg acgaactgcc gttcaagcac gattcgacga tctacggcct ccacgccctg    1200
ccggtcacct ggtag                                                    1215
```

<210> SEQ ID NO 67

-continued

```
<211> LENGTH: 404
<212> TYPE: PRT
<213> ORGANISM: Artificial sequence
<220> FEATURE:
<223> OTHER INFORMATION: Synthetic

<400> SEQUENCE: 67

Met Thr Asp Val Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe His Pro Ser Leu Val Ala Met Asp Pro
                85                  90                  95

Pro Glu His Gly Lys Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Ile Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Ser
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Ser
    210                 215                 220

Gly Glu Ala Asp His Gly Glu Leu Val Gly Leu Ala Ala Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Ile Phe Thr Ile
        275                 280                 285

Ala Glu Thr Ala Thr Ser Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
        355                 360                 365

Thr Leu Phe Arg Arg Val Pro Gly Ile Arg Ile Ala Val Pro Val Asp
    370                 375                 380
```

```
Glu Leu Pro Phe Lys His Asp Ser Thr Ile Tyr Gly Leu His Ala Leu
385                 390                 395                 400

Pro Val Thr Trp

<210> SEQ ID NO 68
<211> LENGTH: 1215
<212> TYPE: DNA
<213> ORGANISM: Artificial sequence
<220> FEATURE:
<223> OTHER INFORMATION: Synthetic

<400> SEQUENCE: 68
atgaccgacg tcgaggaaac caccgcgacc ttgccactgg cccgcaaatg cccgttttca      60
ccaccgcccg aatacgagcg gctccgccgg aaaagtccgg tttcccgggt cggtctcccc     120
tccggtcaaa ccgcttgggc gctcacccgg ctcgaagaca tccgcgaaat gctgagcagt     180
ccgcatttca gctccgaccg gcagagtccg tcgttcccgc tgatggtggc gcggcagatc     240
cggcgcgagg acaagccgtt ccgcccgtcc ctcatcgcga tggacccgcc ggaacacggc     300
aaggccaggc gtgacgtcgt cggggaattc accgtcaagc gcatgaaagc gcttcagcca     360
cgtattcagc agatcgtcga cgagcatatc gacgccctgc tcgccggccc caaacccgcc     420
gatctcgtcc aggcgctttc cctgccggtt ccgtccttgg tgatctgcga actgctcggt     480
gtcccctatt cggaccacga gttcttccag tcctgcagtt cccggatgct cagccgggaa     540
gtcaccgccg aagaacggat gaccgcgttc gagtcgctcg agaactatct cgacgaactc     600
gtcacgaaga aggaggcgaa cgccaccgag gacgacctcc tcggccgcca gatcctgaag     660
cagcgcgaat ccggcgaagc cgaccacggc gaactggtcg gtctggcgtt cctcctgctc     720 atcgcgggc acgagactac ggcgaacatg atctcgctcg gcacggtgac cctgctggag     780
aaccccgatc agctggcgaa gatcaaggcg gatccgggca agaccctcgc cgcgatcgag     840
gaactcctgc ggatcttcac catcgcggag acggcgacct cacgcttcgc cacggcggac     900
gtcgagatcg gcggcacgct catccgcgcg ggtgaaggcg tcgtcggcct gagcaacgcg     960
ggcaaccacg atccggacgg cttcgagaac ccggacacct tcgacatcga acgcggcgcg    1020
cggcatcacg tcgccttcgg attcggtgtg caccaatgcc tcggccagaa cttggcgagg    1080
ttggaactcc agatcgtgtt cgatacgttg ttccggcgag tgccgggcat ccggatcgcc    1140
gtaccggtcg acgaactgcc gttcaagcac gattcgacga tctacggcct ccacgccctg    1200
ccggtcacct ggtag                                                    1215

<210> SEQ ID NO 69
<211> LENGTH: 404
<212> TYPE: PRT
<213> ORGANISM: Artificial sequence
<220> FEATURE:
<223> OTHER INFORMATION: Synthetic

<400> SEQUENCE: 69

Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Lys Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60
```

```
Ser Asp Arg Gln Ser Pro Ser Phe Pro Leu Met Val Ala Arg Gln Ile
 65                  70                  75                  80

Arg Arg Glu Asp Lys Pro Phe Arg Pro Ser Leu Ile Ala Met Asp Pro
                 85                  90                  95

Pro Glu His Gly Lys Ala Arg Arg Asp Val Val Gly Glu Phe Thr Val
            100                 105                 110

Lys Arg Met Lys Ala Leu Gln Pro Arg Ile Gln Gln Ile Val Asp Glu
            115                 120                 125

His Ile Asp Ala Leu Leu Ala Gly Pro Lys Pro Ala Asp Leu Val Gln
130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Arg Met Thr Ala Phe Glu Ser
            180                 185                 190

Leu Glu Asn Tyr Leu Asp Glu Leu Val Thr Lys Lys Glu Ala Asn Ala
            195                 200                 205

Thr Glu Asp Asp Leu Leu Gly Arg Gln Ile Leu Lys Gln Arg Glu Ser
210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Ile Phe Thr Ile
            275                 280                 285

Ala Glu Thr Ala Thr Ser Arg Phe Ala Thr Ala Asp Val Glu Ile Gly
290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
            355                 360                 365

Thr Leu Phe Arg Arg Val Pro Gly Ile Arg Ile Ala Val Pro Val Asp
370                 375                 380

Glu Leu Pro Phe Lys His Asp Ser Thr Ile Tyr Gly Leu His Ala Leu
385                 390                 395                 400

Pro Val Thr Trp

<210> SEQ ID NO 70
<211> LENGTH: 35
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n=a, c, g or t

<400> SEQUENCE: 70
```
gttccgcccg tccctcgtcn nsatggaccc gccgg      35

<210> SEQ ID NO 71
<211> LENGTH: 35
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (15)..(16)
<223> OTHER INFORMATION: n=a, c, g or t

<400> SEQUENCE: 71
cctgcagttc ccggnnsctc agccgggaag tcacc      35

<210> SEQ ID NO 72
<211> LENGTH: 1215
<212> TYPE: DNA
<213> ORGANISM: Artificial sequence
<220> FEATURE:
<223> OTHER INFORMATION: Synthetic

<400> SEQUENCE: 72
atgaccgacg tcgaggaaac caccgcgacc ttgccactgg cccgcaaatg cccgttttca      60
ccaccgcccg aatacgagcg gctccgccgg gaaagtccgg tttcccgggt cggtctcccc     120
tccggtcaga ccgcttgggc gctcacccgg ctcgaagaca tccgcgaaat gctgagcagt     180
ccgcatttca gctccgacca gcagagtccg tcgttcccgc tgatggtggc gcggcagatc     240
cggcgcgagg acaagccgtt ccgcccgtcc ctcgtcgcga tggacccgcc ggaacacggc     300
aaggccaggc gtgacgtcgt cggggaattc accgtcaagc gcatgaaagc gcttcagcca     360
cgtattcagc agatcgtcga cgagcatacc gacgccctgc tcgccggccc caaacccgcc     420
gatctcgtcc aggcgctttc cctgccggtt ccgtccttgg tgatctgcga actgctcggt     480
gtcccctatt cggaccacga gttcttccag tcctgcagtt cccgggcgct cagccgggaa     540
gtcaccgccg aagaacggat gaccgcgttc gagtcgctcg agaactatct cgacgaactc     600
gtcacgaaga aggaggcgaa cgccaccgag gacgacctcc tcggccgcca gatcctgaag     660
cagcgcgaat ccggcgaagc cgaccacggc gaactggtcg gtctggcggc gctcctgctc     720
atcgcgggc acgagactac ggcgaacatg atctcgctcg gcacggtgac cctgctggag     780
aaccccgatc agctggcgaa gatcaaggcg gacccgggca agaccctcgc cgcgatcgag     840
gaactcctgc ggatcttcac catcgcggag acggcgacct cacgcttcgc cacggcggac     900
gtcgagatcg gcgcacgct catccgcgcg ggtgaaggcg tcgtcggcct gagcaacgcg     960
ggcaaccacg atccggacgg cttcgagaac ccggacacct tcgacatcga acgcggcgcg    1020
cggcatcacg tcgccttcgg attcggtgtg caccaatgcc tcggccagaa cttggcgagg    1080
ttggaactcc agatcgtgtt cgatacgttg ttccggcgag tgccgggcat ccggatcgcc    1140
gtaccggtcg acgaactgcc gttcaagcac gattcgacga tctacggcct ccacgccctg    1200
ccggtcacct ggtag                                                     1215

<210> SEQ ID NO 73
<211> LENGTH: 404
<212> TYPE: PRT
<213> ORGANISM: Artificial sequence
<220> FEATURE:
<223> OTHER INFORMATION: Synthetic

```
<400> SEQUENCE: 73

Met Thr Asp Val Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
                20                  25                  30

Pro Val Ser Arg Val Gly Leu Pro Ser Gly Gln Thr Ala Trp Ala Leu
                35                  40                  45

Thr Arg Leu Glu Asp Ile Arg Glu Met Leu Ser Ser Pro His Phe Ser
        50                  55                  60

Ser Asp Gln Gln Ser Pro Ser Phe Pro Leu Met Val Ala Arg Gln Ile
65                  70                  75                  80

Arg Arg Glu Asp Lys Pro Phe Arg Pro Ser Leu Val Ala Met Asp Pro
                85                  90                  95

Pro Glu His Gly Lys Ala Arg Arg Asp Val Val Gly Glu Phe Thr Val
                100                 105                 110

Lys Arg Met Lys Ala Leu Gln Pro Arg Ile Gln Ile Val Asp Glu
                115                 120                 125

His Thr Asp Ala Leu Leu Ala Gly Pro Lys Pro Ala Asp Leu Val Gln
        130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Ala
                165                 170                 175

Leu Ser Arg Glu Val Thr Ala Glu Glu Arg Met Thr Ala Phe Glu Ser
                180                 185                 190

Leu Glu Asn Tyr Leu Asp Glu Leu Val Thr Lys Lys Glu Ala Asn Ala
                195                 200                 205

Thr Glu Asp Asp Leu Leu Gly Arg Gln Ile Leu Lys Gln Arg Glu Ser
        210                 215                 220

Gly Glu Ala Asp His Gly Glu Leu Val Gly Leu Ala Ala Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
                260                 265                 270

Gly Lys Thr Leu Ala Ala Ile Glu Glu Leu Leu Arg Ile Phe Thr Ile
                275                 280                 285

Ala Glu Thr Ala Thr Ser Arg Phe Ala Thr Ala Asp Val Glu Ile Gly
                290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
                340                 345                 350

Cys Leu Gly Gln Asn Leu Ala Arg Leu Glu Leu Gln Ile Val Phe Asp
                355                 360                 365

Thr Leu Phe Arg Arg Val Pro Gly Ile Arg Ile Ala Val Pro Val Asp
        370                 375                 380

Glu Leu Pro Phe Lys His Asp Ser Thr Ile Tyr Gly Leu His Ala Leu
385                 390                 395                 400

Pro Val Thr Trp
```

<210> SEQ ID NO 74
<211> LENGTH: 1215
<212> TYPE: DNA
<213> ORGANISM: Artificial sequence
<220> FEATURE:
<223> OTHER INFORMATION: Synthetic

<400> SEQUENCE: 74

```
atgaccgacg tcgaggaaac caccgcgacc ttgccactgg cccgcaaatg cccgttttca      60
ccaccgcccg aatacgagcg gctccgccgg gaaagtccgg tttccgggt cggtctcccc      120
tccggtcaaa ccgcttgggc gctcacccgg ctcgaagaca tccgcgaaat gctgagcagt     180
ccgcatttca gctccgacca gcagagtccg tcgttcccgc tgatggtggc gcggcagatc     240
cggcgcgagg acaagccgtt ccgcccgtcc ctcgtcgcga tggacccgcc ggaacacggc     300
aaggccaggc gtgacgtcgt cggggaattc accgtcaagc gcatgaaggc gcttcagcca     360
cgtattcagc agatcgtcga cgagcatatc gacgccctgc tcgccggccc caaacccacc     420
gatctcgtcc aggcgctttc cctgccggtt ccgtccttgg tgatctgcga actgctcggt     480
gtcccctatt cggaccacga gttcttccag tcctgcagtt cccggtcgct cagccgggaa     540
gtcaccgccg aagaacggat gaccgcgttc gagtcgctcg agaactatct cgacgaactc     600
gtcacgaaga aggaggcgaa cgccaccgag gacgacctcc tcggccgcca gatcctgaag     660
cagcgcgaat ccggcgaagc cgaccacggc gaactggtcg gtctggcggc gctcctgctc     720
atcgcggggc acgagactac ggcgaacatg atctcgctcg gcacggtgac cctgctggag     780
aaccccgatc agctggcgaa gatcaaggcg gacccgggca gaccctcgc cgcgatcgag      840
gaactcctgc ggatcttcac catcgcggag acggcgacct cacgcttcgc cacggcggac     900
gtcgagatcg gcggcacgct catccgcgcg ggtgaaggcg tcgtcggcct gagcaacgcg     960
ggcaaccacg atccggacgg cttcgagaac ccggacacct tcgacatcga acgcggcgcg     1020
cggcatcacg tcgccttcgg attcggtgtg caccaatgcc tcggccagaa cttggcgagg     1080
ttggaactcc agatcgtgtt cgatacgttg ttccggcgag tgcgggcat ccggatcgcc      1140
gtaccggtcg acgaactgcc gttcaagcac gattcgacga tctacggcct ccacgccctg     1200
ccggtcacct ggtag                                                       1215
```

<210> SEQ ID NO 75
<211> LENGTH: 404
<212> TYPE: PRT
<213> ORGANISM: Artificial sequence
<220> FEATURE:
<223> OTHER INFORMATION: Synthetic

<400> SEQUENCE: 75

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Gln Gln Ser Pro Ser Phe Pro Leu Met Val Ala Arg Gln Ile
65                  70                  75                  80

Arg Arg Glu Asp Lys Pro Phe Arg Pro Ser Leu Val Ala Met Asp Pro
                85                  90                  95
```

-continued

Pro Glu His Gly Lys Ala Arg Arg Asp Val Val Gly Glu Phe Thr Val
              100                 105                 110

Lys Arg Met Lys Ala Leu Gln Pro Arg Ile Gln Gln Ile Val Asp Glu
          115                 120                 125

His Ile Asp Ala Leu Leu Ala Gly Pro Lys Pro Thr Asp Leu Val Gln
      130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Ser
                165                 170                 175

Leu Ser Arg Glu Val Thr Ala Glu Arg Met Thr Ala Phe Glu Ser
          180                 185                 190

Leu Glu Asn Tyr Leu Asp Glu Leu Val Thr Lys Lys Glu Ala Asn Ala
          195                 200                 205

Thr Glu Asp Asp Leu Leu Gly Arg Gln Ile Leu Lys Gln Arg Glu Ser
      210                 215                 220

Gly Glu Ala Asp His Gly Glu Leu Val Gly Leu Ala Ala Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
          260                 265                 270

Gly Lys Thr Leu Ala Ala Ile Glu Glu Leu Leu Arg Ile Phe Thr Ile
      275                 280                 285

Ala Glu Thr Ala Thr Ser Arg Phe Ala Thr Ala Asp Val Glu Ile Gly
      290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
          340                 345                 350

Cys Leu Gly Gln Asn Leu Ala Arg Leu Glu Leu Gln Ile Val Phe Asp
      355                 360                 365

Thr Leu Phe Arg Arg Val Pro Gly Ile Arg Ile Ala Val Pro Val Asp
      370                 375                 380

Glu Leu Pro Phe Lys His Asp Ser Thr Ile Tyr Gly Leu His Ala Leu
385                 390                 395                 400

Pro Val Thr Trp

<210> SEQ ID NO 76
<211> LENGTH: 404
<212> TYPE: PRT
<213> ORGANISM: Saccharopolyspora erythaea

<400> SEQUENCE: 76

Met Thr Thr Val Pro Asp Leu Glu Ser Asp Ser Phe His Val Asp Trp
1               5                   10                  15

Tyr Arg Thr Tyr Ala Glu Leu Arg Glu Thr Ala Pro Val Thr Pro Val
              20                  25                  30

Arg Phe Leu Gly Gln Asp Ala Trp Leu Val Thr Gly Tyr Asp Glu Ala
          35                  40                  45

Lys Ala Ala Leu Ser Asp Leu Arg Leu Ser Ser Asp Pro Lys Lys Lys
      50                  55                  60

```
Tyr Pro Gly Val Glu Val Phe Pro Ala Tyr Leu Gly Phe Pro Glu
 65                  70                  75                  80

Asp Val Arg Asn Tyr Phe Ala Thr Asn Met Gly Thr Ser Asp Pro Pro
                 85                  90                  95

Thr His Thr Arg Leu Arg Lys Leu Val Ser Gln Glu Phe Thr Val Arg
                100                 105                 110

Arg Val Glu Ala Met Arg Pro Arg Val Glu Gln Ile Thr Ala Glu Leu
            115                 120                 125

Leu Asp Glu Val Gly Asp Ser Gly Val Val Asp Ile Val Asp Arg Phe
130                 135                 140

Ala His Pro Leu Pro Ile Lys Val Ile Cys Glu Leu Leu Gly Val Asp
145                 150                 155                 160

Glu Lys Tyr Arg Gly Glu Phe Gly Arg Trp Ser Ser Glu Ile Leu Val
                165                 170                 175

Met Asp Pro Glu Arg Ala Glu Gln Arg Gly Gln Ala Ala Arg Glu Val
            180                 185                 190

Val Asn Phe Ile Leu Asp Leu Val Glu Arg Arg Thr Glu Pro Gly
            195                 200                 205

Asp Asp Leu Leu Ser Ala Leu Ile Arg Val Gln Asp Asp Asp Gly
    210                 215                 220

Arg Leu Ser Ala Asp Glu Leu Thr Ser Ile Ala Leu Val Leu Leu Leu
225                 230                 235                 240

Ala Gly Phe Glu Ala Ser Val Ser Leu Ile Gly Ile Gly Thr Tyr Leu
                245                 250                 255

Leu Leu Thr His Pro Asp Gln Leu Ala Leu Val Arg Arg Asp Pro Ser
            260                 265                 270

Ala Leu Pro Asn Ala Val Glu Glu Ile Leu Arg Tyr Ile Ala Pro Pro
            275                 280                 285

Glu Thr Thr Thr Arg Phe Ala Ala Glu Glu Val Glu Ile Gly Gly Val
290                 295                 300

Ala Ile Pro Gln Tyr Ser Thr Val Leu Val Ala Asn Gly Ala Ala Asn
305                 310                 315                 320

Arg Asp Pro Lys Gln Phe Pro Asp Pro His Arg Phe Asp Val Thr Arg
                325                 330                 335

Asp Thr Arg Gly His Leu Ser Phe Gly Gln Gly Ile His Phe Cys Met
            340                 345                 350

Gly Arg Pro Leu Ala Lys Leu Glu Gly Glu Val Ala Leu Arg Ala Leu
            355                 360                 365

Phe Gly Arg Phe Pro Ala Leu Ser Leu Gly Ile Asp Ala Asp Asp Val
370                 375                 380

Val Trp Arg Arg Ser Leu Leu Leu Arg Gly Ile Asp His Leu Pro Val
385                 390                 395                 400

Arg Leu Asp Gly
```